US011471282B2

(12) United States Patent
Argento et al.

(10) Patent No.: US 11,471,282 B2
(45) Date of Patent: Oct. 18, 2022

(54) PROSTHETIC CARDIAC VALVE DEVICES, SYSTEMS, AND METHODS

(71) Applicant: Shifamed Holdings, LLC, Campbell, CA (US)

(72) Inventors: Claudio Argento, Felton, CA (US); Andrew Backus, Campbell, CA (US); Alice Yang, Campbell, CA (US); Ali Salahieh, Saratoga, CA (US); Jasper Ellington Adamek-Bowers, San Francisco, CA (US); Connor Mulcahy, Campbell, CA (US); Ryan William Boyd, Santa Cruz, CA (US); Nicholas J. Spinelli, San Carlos, CA (US); Tom Saul, Moss Beach, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 0 days.

(21) Appl. No.: 16/824,576

(22) Filed: Mar. 19, 2020

(65) Prior Publication Data

US 2020/0297491 A1 Sep. 24, 2020

Related U.S. Application Data

(60) Provisional application No. 62/984,602, filed on Mar. 3, 2020, provisional application No. 62/968,909, filed on
(Continued)

(51) Int. Cl.
*A61F 2/24* (2006.01)
*A61F 2/82* (2013.01)

(52) U.S. Cl.
CPC .......... *A61F 2/2466* (2013.01); *A61F 2/2457* (2013.01); *A61F 2/82* (2013.01);
(Continued)

(58) Field of Classification Search
CPC .... A61F 2/2457; A61F 2/2409; A61F 2/2466; A61F 2220/0008; A61F 2/82
See application file for complete search history.

(56) References Cited

U.S. PATENT DOCUMENTS

| 5,002,563 A | 3/1991 | Pyka et al. |
| 5,327,905 A | 7/1994 | Avitall |
(Continued)

FOREIGN PATENT DOCUMENTS

| AU | 2012261727 B2 | 10/2015 |
| AU | 2019246822 B2 | 8/2020 |
(Continued)

OTHER PUBLICATIONS

Westaby et al.; Adult human valve dimensions and their surgical significance; The American Journal of Cardiology; 53(4); pp. 552-556; Feb. 1984.
(Continued)

*Primary Examiner* — Jennifer Dieterle
*Assistant Examiner* — Rebecca Lynee Zimmerman
(74) *Attorney, Agent, or Firm* — Shay Glenn LLP

(57) ABSTRACT

A system for treating a diseased native valve in a patient includes a valve prosthesis and a delivery device. The prosthesis includes an anchor and a frame. The delivery device includes an outer sheath, an inner shaft, an anchor guide, and a tether. The anchor is shaped to encircle chordae or leaflets of a native valve. The frame is configured to sit within the anchor. The inner shaft is positioned within the outer sheath and translatable and rotatable relative to the outer sheath. The anchor guide is attached to a distal end of the inner shaft and has a curved distal section. The tether is configured to detachably couple to the anchor and to longitudinally translate the anchor within the inner shaft and anchor guide. The anchor is configured to be actuated from
(Continued)

a delivery configuration to the deployed configuration when the anchor is translated out of the anchor guide.

14 Claims, 78 Drawing Sheets

Related U.S. Application Data on Jan. 31, 2020, provisional application No. 62/946,602, filed on Dec. 11, 2019, provisional application No. 62/879,979, filed on Jul. 29, 2019, provisional application No. 62/872,016, filed on Jul. 9, 2019, provisional application No. 62/833,430, filed on Apr. 12, 2019, provisional application No. 62/828,835, filed on Apr. 3, 2019, provisional application No. 62/820,570, filed on Mar. 19, 2019.

(52) U.S. Cl.
CPC ............ *A61F 2210/0014* (2013.01); *A61F 2220/0008* (2013.01); *A61F 2230/0091* (2013.01)

(56) References Cited

U.S. PATENT DOCUMENTS

| | | |
|---|---|---|
| 5,356,424 A | 10/1994 | Buzerak et al. |
| 5,370,685 A | 12/1994 | Stevens |
| 5,582,616 A | 12/1996 | Bolduc et al. |
| 5,755,601 A | 5/1998 | Jones |
| 5,779,669 A | 7/1998 | Haissaguerre et al. |
| 5,873,835 A | 2/1999 | Hastings et al. |
| 5,944,690 A | 8/1999 | Falwell et al. |
| 6,048,339 A | 4/2000 | Zirps et al. |
| 6,053,873 A | 4/2000 | Govari et al. |
| 6,254,550 B1 | 7/2001 | McNamara et al. |
| 6,419,695 B1 | 7/2002 | Gabbay |
| 6,419,696 B1 | 7/2002 | Ortiz et al. |
| 6,530,952 B2 | 3/2003 | Vesely |
| 6,533,783 B1 | 3/2003 | Töllner |
| 6,641,553 B1 | 11/2003 | Chee et al. |
| 6,752,813 B2 | 6/2004 | Goidfarb et al. |
| 6,908,478 B2 | 6/2005 | Alferness et al. |
| 6,964,684 B2 | 11/2005 | Ortiz et al. |
| 6,974,476 B2 | 12/2005 | McGuckin, Jr. et al. |
| 7,077,861 B2 | 7/2006 | Spence |
| 7,101,395 B2 | 9/2006 | Tremulis et al. |
| 7,125,421 B2 | 10/2006 | Tremulis et al. |
| 7,160,322 B2 | 1/2007 | Gabbay |
| 7,175,656 B2 | 2/2007 | Khairkhahan |
| 7,201,771 B2 | 4/2007 | Lane |
| 7,226,467 B2 | 6/2007 | Lucatero et al. |
| 7,381,219 B2 | 1/2008 | Salahieh et al. |
| 7,329,279 B2 | 2/2008 | Haug et al. |
| 7,445,631 B2 | 11/2008 | Salahieh et al. |
| 7,470,285 B2 | 12/2008 | Nugent et al. |
| 7,527,647 B2 | 5/2009 | Spence |
| 7,563,267 B2 | 7/2009 | Goldfarb et al. |
| 7,594,903 B2 | 9/2009 | Webler et al. |
| 7,604,646 B2 | 10/2009 | Goldfarb et al. |
| 7,608,091 B2 | 10/2009 | Goldfarb et al. |
| 7,618,449 B2 | 11/2009 | Tremulis et al. |
| 7,621,948 B2 | 11/2009 | Herrmann et al. |
| 7,666,204 B2 | 2/2010 | Thornton et al. |
| 7,704,269 B2 | 4/2010 | St. Goar et al. |
| 7,731,705 B2 | 6/2010 | Wardle |
| 7,748,389 B2 | 7/2010 | Salahieh et al. |
| 7,749,266 B2 | 7/2010 | Forster et al. |
| 7,780,725 B2 | 8/2010 | Haug et al. |
| 7,799,069 B2 | 9/2010 | Bailey et al. |
| 7,811,296 B2 | 10/2010 | Goldfarb et al. |
| 7,824,442 B2 | 11/2010 | Salahieh et al. |
| 7,824,443 B2 | 11/2010 | Salahieh et al. |
| 7,846,203 B2 | 12/2010 | Cribier |
| 7,947,075 B2 | 5/2011 | Goetz et al. |
| 7,951,195 B2 | 5/2011 | Antonsson et al. |
| 7,959,666 B2 | 6/2011 | Salahieh et al. |
| 7,988,724 B2 | 8/2011 | Salahieh et al. |
| 8,021,421 B2 | 9/2011 | Fogarty et al. |
| 8,052,749 B2 | 11/2011 | Salahieh et al. |
| 8,052,750 B2 | 11/2011 | Tuval et al. |
| 8,062,355 B2 | 11/2011 | Figulla et al. |
| 8,070,800 B2 | 12/2011 | Lock et al. |
| 8,075,615 B2 | 12/2011 | Eberhardt et al. |
| 8,096,985 B2 | 1/2012 | Legaspi et al. |
| 8,147,541 B2 | 4/2012 | Forster et al. |
| 8,147,542 B2 | 4/2012 | Maisano et al. |
| 8,182,528 B2 | 5/2012 | Salahieh et al. |
| 8,216,256 B2 | 7/2012 | Raschdorf et al. |
| 8,236,049 B2 | 8/2012 | Rowe et al. |
| 8,241,351 B2 | 8/2012 | Cabir |
| 8,251,977 B2 | 8/2012 | Partlett |
| 8,252,050 B2 | 8/2012 | Maisano et al. |
| 8,287,584 B2 | 10/2012 | Salahieh et al. |
| 8,313,526 B2 | 11/2012 | Hoffman et al. |
| 8,323,241 B2 | 12/2012 | Salahieh et al. |
| 8,323,336 B2 | 12/2012 | Hill et al. |
| 8,328,868 B2 | 12/2012 | Paul et al. |
| 8,343,213 B2 | 1/2013 | Salahieh et al. |
| 8,348,995 B2 | 1/2013 | Tuval et al. |
| 8,348,996 B2 | 1/2013 | Tuval et al. |
| 8,366,767 B2 | 2/2013 | Zhang |
| 8,403,981 B2 | 3/2013 | Forster et al. |
| 8,403,983 B2 | 3/2013 | Quadri et al. |
| 8,414,643 B2 | 4/2013 | Tuval et al. |
| 8,414,644 B2 | 4/2013 | Quadri et al. |
| 8,414,645 B2 | 4/2013 | Dwork et al. |
| 8,425,593 B2 | 4/2013 | Braido et al. |
| 8,449,599 B2 | 5/2013 | Chau et al. |
| 8,454,686 B2 | 6/2013 | Alkhatib |
| 8,465,541 B2 | 6/2013 | Dwork |
| 8,500,800 B2 | 8/2013 | Maisano et al. |
| 8,512,401 B2 | 8/2013 | Murray et al. |
| 8,523,881 B2 | 9/2013 | Cabiri et al. |
| 8,545,553 B2 | 10/2013 | Zipory et al. |
| 8,556,963 B2 | 10/2013 | Tremulis et al. |
| 8,562,645 B2 | 10/2013 | Stone et al. |
| 8,562,673 B2 | 10/2013 | Yeung et al. |
| 8,579,962 B2 | 11/2013 | Salahieh et al. |
| 8,603,157 B2 | 12/2013 | Seguin et al. |
| 8,603,160 B2 | 12/2013 | Salahieh et al. |
| 8,623,075 B2 | 1/2014 | Murray et al. |
| 8,628,570 B2 | 1/2014 | Seguin |
| 8,641,727 B2 | 2/2014 | Starksen et al. |
| 8,652,202 B2 | 2/2014 | Alon et al. |
| 8,652,203 B2 | 2/2014 | Quadri et al. |
| 8,657,872 B2 | 2/2014 | Seguin |
| 8,685,086 B2 | 4/2014 | Navia et al. |
| 8,696,693 B2 | 4/2014 | Najafi et al. |
| 8,715,300 B2 | 5/2014 | Najafi et al. |
| 8,715,342 B2 | 5/2014 | Zipory et al. |
| 8,740,976 B2 | 6/2014 | Tran et al. |
| 8,784,479 B2 | 7/2014 | Antonsson et al. |
| 8,790,367 B2 | 7/2014 | Nguyen et al. |
| 8,808,368 B2 | 8/2014 | Maisano et al. |
| 8,828,078 B2 | 9/2014 | Salahieh et al. |
| 8,834,564 B2 | 9/2014 | Tuval et al. |
| 8,840,663 B2 | 9/2014 | Salahieh et al. |
| 8,840,664 B2 | 9/2014 | Karapetian et al. |
| 8,845,588 B2 | 9/2014 | Bruszewski |
| 8,852,271 B2 | 10/2014 | Murray et al. |
| 8,876,893 B2 | 11/2014 | Dwork et al. |
| 8,876,894 B2 | 11/2014 | Tuval et al. |
| 8,876,895 B2 | 11/2014 | Tuval et al. |
| 8,900,294 B2 | 12/2014 | Paniagua et al. |
| 8,911,494 B2 | 12/2014 | Hammer et al. |
| 8,920,369 B2 | 12/2014 | Salahieh et al. |
| 8,926,690 B2 | 1/2015 | Kowalsky |
| 8,926,696 B2 | 1/2015 | Cabiri et al. |
| 8,926,697 B2 | 1/2015 | Gross et al. |
| 8,940,002 B2 | 1/2015 | Goertzen |
| 8,940,044 B2 | 1/2015 | Hammer et al. |
| 8,951,299 B2 | 2/2015 | Paul et al. |

(56) References Cited

U.S. PATENT DOCUMENTS

| | | |
|---|---|---|
| 8,986,371 B2 | 3/2015 | Quill et al. |
| 8,998,980 B2 | 4/2015 | Shipley et al. |
| 9,005,273 B2 | 4/2015 | Salahieh et al. |
| 9,011,515 B2 | 4/2015 | Schweich et al. |
| 9,011,523 B2 | 4/2015 | Seguin |
| 9,011,530 B2 | 4/2015 | Reich et al. |
| 9,017,408 B2 | 4/2015 | Siegal et al. |
| 9,023,100 B2 | 5/2015 | Quadri et al. |
| 9,034,032 B2 | 5/2015 | McLean et al. |
| 9,039,757 B2 | 5/2015 | McLean et al. |
| 9,056,009 B2 | 6/2015 | Keränen |
| 9,061,120 B2 | 6/2015 | Osypka et al. |
| 9,095,431 B2 | 8/2015 | Yu et al. |
| 9,119,719 B2 | 9/2015 | Zipory et al. |
| 9,125,739 B2 | 9/2015 | Paniagua et al. |
| 9,125,740 B2 | 9/2015 | Morriss et al. |
| 9,155,619 B2 | 10/2015 | Liu et al. |
| 9,168,129 B2 | 10/2015 | Valdez et al. |
| 9,168,131 B2 | 10/2015 | Yohanan et al. |
| 9,173,713 B2 | 11/2015 | Hart et al. |
| 9,173,737 B2 | 11/2015 | Hill et al. |
| 9,180,006 B2 | 11/2015 | Keränen |
| 9,226,823 B2 | 1/2016 | Dwork |
| 9,232,995 B2 | 1/2016 | Kovalsky et al. |
| 9,277,994 B2 | 3/2016 | Miller et al. |
| 9,289,297 B2 | 3/2016 | Wilson et al. |
| 9,295,547 B2 | 3/2016 | Costello et al. |
| 9,301,756 B2 | 4/2016 | Wardle |
| 9,301,836 B2 | 4/2016 | Buchbinder et al. |
| 9,320,597 B2 | 4/2016 | Savage et al. |
| 9,343,224 B2 | 5/2016 | Zilbershlag |
| 9,358,110 B2 | 6/2016 | Paul et al. |
| 9,414,915 B2 | 8/2016 | Lombardi et al. |
| 9,427,315 B2 | 8/2016 | Schweich et al. |
| 9,439,757 B2 | 9/2016 | Wallace et al. |
| 9,468,525 B2 | 10/2016 | Kovalsky |
| 9,474,606 B2 | 10/2016 | Zipory et al. |
| 9,474,840 B2 | 10/2016 | Siess |
| 9,480,559 B2 | 11/2016 | Vidlund et al. |
| 9,492,273 B2 | 11/2016 | Wallace et al. |
| 9,526,487 B2 | 12/2016 | Rahmani |
| 9,526,609 B2 | 12/2016 | Salahieh et al. |
| 9,532,868 B2 | 1/2017 | Braido |
| 9,532,870 B2 | 1/2017 | Cooper et al. |
| 9,561,102 B2 | 2/2017 | Rust et al. |
| 9,579,198 B2 | 2/2017 | Deem et al. |
| 9,636,224 B2 | 5/2017 | Zipory et al. |
| 9,636,481 B2 | 5/2017 | Campbell et al. |
| 9,662,202 B2 | 5/2017 | Quill et al. |
| 9,662,206 B2 | 5/2017 | Börtlein et al. |
| 9,662,209 B2 | 5/2017 | Gross et al. |
| 9,675,454 B2 | 6/2017 | Vidlund et al. |
| 9,681,952 B2 | 6/2017 | Hacohen et al. |
| 9,687,343 B2 | 6/2017 | Börtlein et al. |
| 9,724,192 B2 | 8/2017 | Sheps et al. |
| 9,730,790 B2 | 8/2017 | Quadri et al. |
| 9,730,793 B2 | 8/2017 | Reich et al. |
| 9,744,031 B2 | 8/2017 | Girard et al. |
| 9,744,038 B2 | 8/2017 | Dahlgren et al. |
| 9,750,605 B2 | 9/2017 | Ganesan et al. |
| 9,763,779 B2 | 9/2017 | Börtlein et al. |
| 9,763,780 B2 | 9/2017 | Morriss et al. |
| 9,814,611 B2 | 11/2017 | Cartledge et al. |
| 9,827,090 B2 | 11/2017 | Hill et al. |
| 9,861,480 B2 | 1/2018 | Zakai et al. |
| 9,867,700 B2 | 1/2018 | Bakis et al. |
| 9,867,702 B2 | 1/2018 | Keränen et al. |
| 9,877,833 B1 | 1/2018 | Bishop et al. |
| 9,883,941 B2 | 2/2018 | Hastings et al. |
| 9,889,003 B2 | 2/2018 | Börtlein et al. |
| 9,895,221 B2 | 2/2018 | Vidlund |
| 9,895,222 B2 | 2/2018 | Zeng et al. |
| 9,901,444 B2 | 2/2018 | Valdez et al. |
| 9,918,840 B2 | 3/2018 | Reich et al. |
| D815,744 S | 4/2018 | Rate et al. |
| 9,949,825 B2 | 4/2018 | Braido et al. |
| 9,949,828 B2 | 4/2018 | Sheps et al. |
| 9,950,142 B2 | 4/2018 | Eversull et al. |
| 9,968,452 B2 | 5/2018 | Sheps et al. |
| 9,974,647 B2 | 5/2018 | Ganesan et al. |
| 9,974,650 B2 | 5/2018 | Nguyen-Thien-Nhon et al. |
| 9,999,504 B2 | 6/2018 | Czyscon et al. |
| 10,004,599 B2 | 6/2018 | Rabito et al. |
| 10,016,271 B2 | 7/2018 | Morriss et al. |
| 10,016,272 B2 | 7/2018 | Spence et al. |
| 10,028,832 B2 | 7/2018 | Quill et al. |
| 10,029,037 B2 | 7/2018 | Muller et al. |
| 10,034,747 B2 | 7/2018 | Harewood |
| 10,034,749 B2 | 7/2018 | Spence et al. |
| 10,039,637 B2 | 8/2018 | Maimon et al. |
| 10,045,846 B2 | 8/2018 | Bonyuet et al. |
| 10,052,198 B2 | 8/2018 | Chau et al. |
| 10,052,199 B2 | 8/2018 | Spence et al. |
| 10,058,318 B2 | 8/2018 | Tegzes |
| 10,058,321 B2 | 8/2018 | Sampson et al. |
| 10,064,719 B2 | 9/2018 | Börtlein et al. |
| 10,070,954 B2 | 9/2018 | Braido et al. |
| 10,092,400 B2 | 10/2018 | Jimenez et al. |
| 10,098,734 B2 | 10/2018 | Hoang |
| 10,105,217 B2 | 10/2018 | Keränen |
| 10,105,224 B2 | 10/2018 | Buchbinder et al. |
| 10,130,464 B2 | 11/2018 | Meiri et al. |
| 10,130,471 B2 | 11/2018 | Keränen et al. |
| 10,143,552 B2 | 12/2018 | Wallace et al. |
| 10,149,759 B2 | 12/2018 | Naor |
| 10,172,708 B2 | 1/2019 | Anderson |
| 10,172,711 B2 | 1/2019 | Keränen |
| 10,179,042 B2 | 1/2019 | Braido et al. |
| 10,195,021 B2 | 2/2019 | Keränen et al. |
| 10,195,025 B2 | 2/2019 | Levi |
| 10,195,027 B2 | 2/2019 | Nasr |
| 10,195,028 B2 | 2/2019 | Hosmer et al. |
| 10,195,029 B2 | 2/2019 | Keränen |
| 10,201,418 B2 | 2/2019 | Biadillah et al. |
| 10,206,775 B2 | 2/2019 | Kovalsky et al. |
| 10,213,307 B2 | 2/2019 | Dwork et al. |
| 10,226,330 B2 | 3/2019 | Spence et al. |
| 10,226,334 B2 | 3/2019 | Rowe et al. |
| 10,226,339 B2 | 3/2019 | Spence et al. |
| 10,238,489 B2 | 3/2019 | Conklin |
| 10,251,749 B2 | 4/2019 | Zerkowski et al. |
| 10,258,464 B2 | 4/2019 | Delaloye et al. |
| 10,258,468 B2 | 4/2019 | Deem et al. |
| 10,265,169 B2 | 4/2019 | Desrosiers et al. |
| 10,271,950 B2 | 4/2019 | Neustadter |
| 10,299,917 B2 | 5/2019 | Morriss et al. |
| 10,299,921 B2 | 5/2019 | Dale et al. |
| 10,321,988 B2 | 6/2019 | Gorman et al. |
| 10,321,989 B2 | 6/2019 | Keränen |
| 10,327,743 B2 | 6/2019 | St. Goar et al. |
| 10,327,766 B2 | 6/2019 | Zerkowski et al. |
| 10,335,277 B2 | 7/2019 | Crisostomo et al. |
| 10,338,724 B2 | 7/2019 | Zhao |
| 10,350,066 B2 | 7/2019 | Cooper et al. |
| 10,357,351 B2 | 7/2019 | Cooper et al. |
| 10,357,634 B2 | 7/2019 | Simmons et al. |
| 10,363,130 B2 | 7/2019 | Armer et al. |
| 10,363,131 B2 | 7/2019 | Eidenschink et al. |
| 10,368,986 B2 | 8/2019 | Gosal et al. |
| 10,368,990 B2 | 8/2019 | Noe et al. |
| 10,376,266 B2 | 8/2019 | Herman et al. |
| 10,376,360 B2 | 8/2019 | Bruchman et al. |
| 10,376,363 B2 | 8/2019 | Quadri et al. |
| 10,398,547 B2 | 9/2019 | Li et al. |
| 10,426,608 B2 | 10/2019 | Salahieh et al. |
| 10,433,961 B2 | 10/2019 | McLean |
| 10,470,881 B2 | 11/2019 | Noe et al. |
| 10,500,048 B2 | 12/2019 | Khairkhahan et al. |
| 10,507,104 B2 | 12/2019 | Zhang et al. |
| 10,512,541 B2 | 12/2019 | Zerkowski et al. |
| 10,524,901 B2 | 1/2020 | Quadri et al. |
| 10,548,729 B2 | 2/2020 | Zipory et al. |
| 10,568,737 B2 | 2/2020 | Noe et al. |
| 10,575,951 B2 | 3/2020 | Johnson et al. |

(56) References Cited

U.S. PATENT DOCUMENTS

| | | |
|---|---|---|
| 10,603,165 B2 | 3/2020 | Maimon et al. |
| 10,639,154 B2 | 5/2020 | Seguin |
| 10,653,524 B2 | 5/2020 | Khairkhahan et al. |
| 10,660,753 B2 | 5/2020 | Pham et al. |
| 10,687,938 B2 | 6/2020 | Patel et al. |
| 10,695,160 B2 | 6/2020 | Lashinski et al. |
| 10,702,386 B2 | 7/2020 | Khairkhahan et al. |
| 10,716,662 B2 | 7/2020 | Delaloye et al. |
| 10,722,352 B2 | 7/2020 | Spence |
| 10,722,353 B2 | 7/2020 | Levi |
| 10,729,542 B2 | 8/2020 | Howard et al. |
| 10,743,991 B2 | 8/2020 | Brown |
| 10,751,180 B2 | 8/2020 | Schewel |
| 10,751,184 B2 | 8/2020 | Reich et al. |
| 10,765,514 B2 | 9/2020 | Iflah et al. |
| 10,813,749 B2 | 10/2020 | Nguyen et al. |
| 10,828,153 B2 | 11/2020 | Noe et al. |
| 10,856,970 B2 | 12/2020 | Tuval et al. |
| 10,869,755 B2 | 12/2020 | Granada et al. |
| 10,888,420 B2 | 1/2021 | Bateman et al. |
| 10,973,629 B2 | 4/2021 | Levi et al. |
| 10,973,630 B2 | 4/2021 | Torrianni et al. |
| 11,007,057 B2 | 5/2021 | Pham et al. |
| 11,020,221 B2 | 6/2021 | Arcaro et al. |
| 11,039,922 B2 | 6/2021 | Konno |
| 11,103,345 B2 | 8/2021 | Levi et al. |
| 2002/0173841 A1 | 11/2002 | Ortiz et al. |
| 2003/0114913 A1 | 6/2003 | Spenser et al. |
| 2004/0039442 A1 | 2/2004 | St. Goar et al. |
| 2004/0044350 A1 | 3/2004 | Martin et al. |
| 2005/0137686 A1 | 6/2005 | Salahieh et al. |
| 2005/0137687 A1 | 6/2005 | Salahieh et al. |
| 2005/0137691 A1 | 6/2005 | Salahieh et al. |
| 2005/0137694 A1 | 6/2005 | Haug et al. |
| 2005/0137696 A1 | 6/2005 | Salahieh et al. |
| 2005/0165344 A1 | 7/2005 | Dobak, III |
| 2005/0277839 A1 | 12/2005 | Aiderman et al. |
| 2006/0009841 A1 | 1/2006 | McGuckin, Jr. et al. |
| 2006/0052821 A1 | 3/2006 | Abbot et al. |
| 2006/0074484 A1 | 4/2006 | Huber |
| 2006/0178700 A1 | 8/2006 | Quinn |
| 2006/0217762 A1 | 9/2006 | Maahs et al. |
| 2006/0259136 A1 | 11/2006 | Nguyen et al. |
| 2006/0293698 A1 | 12/2006 | Douk |
| 2007/0055206 A1 | 3/2007 | To et al. |
| 2007/0118151 A1 | 5/2007 | Davidson |
| 2007/0142907 A1 | 6/2007 | Moaddeb et al. |
| 2007/0185572 A1 | 8/2007 | Solem et al. |
| 2007/0255396 A1 | 11/2007 | Douk et al. |
| 2007/0293724 A1 | 12/2007 | Saadat et al. |
| 2007/0293943 A1 | 12/2007 | Quinn |
| 2008/0004696 A1 | 1/2008 | Vesely |
| 2008/0004697 A1 | 1/2008 | Lichtenstein et al. |
| 2008/0200980 A1 | 8/2008 | Robin et al. |
| 2008/0208327 A1 | 8/2008 | Rowe |
| 2008/0275503 A1 | 11/2008 | Spence et al. |
| 2008/0275540 A1 | 11/2008 | Wen |
| 2009/0093826 A1 | 4/2009 | Warder-Gabaldon |
| 2009/0138079 A1 | 5/2009 | Tuval et al. |
| 2009/0209950 A1 | 8/2009 | Starksen |
| 2009/0276040 A1 | 11/2009 | Rowe et al. |
| 2010/0010520 A1 | 1/2010 | Takahashi et al. |
| 2010/0049239 A1 | 2/2010 | McGuckin, Jr. et al. |
| 2010/0076497 A1 | 3/2010 | Zwirkoski |
| 2010/0094406 A1 | 4/2010 | Leprince et al. |
| 2010/0185172 A1 | 7/2010 | Fabro |
| 2010/0198056 A1 | 8/2010 | Fabro et al. |
| 2010/0198192 A1 | 8/2010 | Serina et al. |
| 2010/0198208 A1 | 8/2010 | Napp et al. |
| 2010/0217385 A1 | 8/2010 | Thompson et al. |
| 2010/0312333 A1 | 12/2010 | Navia et al. |
| 2011/0022164 A1 | 1/2011 | Quinn et al. |
| 2011/0046600 A1 | 2/2011 | Crank |
| 2011/0224785 A1 | 9/2011 | Hacohen |
| 2011/0288637 A1 | 11/2011 | De Marchena |
| 2011/0313515 A1 | 12/2011 | Quadri et al. |
| 2011/0319989 A1 | 12/2011 | Lane et al. |
| 2012/0022633 A1 | 1/2012 | Olson et al. |
| 2012/0053680 A1 | 3/2012 | Bolling et al. |
| 2012/0143316 A1 | 6/2012 | Seguin et al. |
| 2012/0197388 A1 | 8/2012 | Khairkhahan et al. |
| 2012/0203333 A1 | 8/2012 | McGuckin, Jr. et al. |
| 2012/0221101 A1 | 8/2012 | Moaddeb et al. |
| 2012/0277853 A1 | 11/2012 | Rothstein |
| 2013/0006352 A1 | 1/2013 | Yaron |
| 2013/0023985 A1 | 1/2013 | Khairkhahan et al. |
| 2013/0035758 A1 | 2/2013 | Seguin et al. |
| 2013/0079873 A1 | 3/2013 | Migliazza et al. |
| 2013/0123912 A1 | 5/2013 | Tung et al. |
| 2013/0172992 A1 | 7/2013 | Gross et al. |
| 2013/0253643 A1 | 9/2013 | Rolando et al. |
| 2013/0274873 A1 | 10/2013 | Delaloye et al. |
| 2013/0325110 A1 | 12/2013 | Khalil et al. |
| 2014/0005768 A1 | 1/2014 | Thomas et al. |
| 2014/0031928 A1 | 1/2014 | Murphy et al. |
| 2014/0081154 A1 | 5/2014 | Toth |
| 2014/0200649 A1 | 7/2014 | Essinger et al. |
| 2014/0228943 A1 | 8/2014 | Stigall et al. |
| 2014/0249621 A1 | 9/2014 | Eidenschink |
| 2014/0257467 A1 | 9/2014 | Lane et al. |
| 2014/0324163 A1 | 10/2014 | Keränen et al. |
| 2015/0005764 A1 | 1/2015 | Hanson et al. |
| 2015/0018876 A1 | 1/2015 | Ewers et al. |
| 2015/0051709 A1 | 2/2015 | Vasquez et al. |
| 2015/0134055 A1 | 5/2015 | Spence et al. |
| 2015/0173897 A1 | 6/2015 | Raanani et al. |
| 2015/0250480 A1 | 9/2015 | Featherstone |
| 2015/0265403 A1 | 9/2015 | Keränen |
| 2015/0272737 A1 | 10/2015 | Dale et al. |
| 2015/0297346 A1 | 10/2015 | Duffy et al. |
| 2015/0305863 A1 | 10/2015 | Gray et al. |
| 2015/0328000 A1 | 11/2015 | Ratz et al. |
| 2015/0335290 A1 | 11/2015 | Hunter |
| 2015/0351735 A1 | 12/2015 | Keränen et al. |
| 2015/0351908 A1 | 12/2015 | Keränen et al. |
| 2015/0351911 A1 | 12/2015 | Keränen et al. |
| 2016/0089126 A1 | 3/2016 | Guo |
| 2016/0095705 A1 | 4/2016 | Keränen et al. |
| 2016/0113764 A1 | 4/2016 | Sheahan et al. |
| 2016/0143689 A1 | 5/2016 | Ditter |
| 2016/0166380 A1 | 6/2016 | Seguin et al. |
| 2016/0228247 A1 | 8/2016 | Maimon et al. |
| 2016/0235526 A1 | 8/2016 | Lashinski et al. |
| 2016/0324637 A1 | 11/2016 | Hlavka et al. |
| 2016/0324639 A1 | 11/2016 | Nguyen et al. |
| 2016/0331523 A1 | 11/2016 | Chau et al. |
| 2016/0346080 A1 | 12/2016 | Righini et al. |
| 2017/0056163 A1 | 3/2017 | Tayeb et al. |
| 2017/0079790 A1 | 3/2017 | Vidlund et al. |
| 2017/0112624 A1 | 4/2017 | Patel |
| 2017/0119524 A1 | 5/2017 | Salahieh et al. |
| 2017/0128203 A1 | 5/2017 | Zhang et al. |
| 2017/0156723 A1 | 6/2017 | Keating et al. |
| 2017/0165057 A9 | 6/2017 | Morriss et al. |
| 2017/0189177 A1 | 7/2017 | Schweich et al. |
| 2017/0216025 A1 | 8/2017 | Nitzan et al. |
| 2017/0245850 A1 | 8/2017 | Call et al. |
| 2017/0258585 A1 | 9/2017 | Marquez et al. |
| 2017/0273788 A1 | 9/2017 | O'Carroll et al. |
| 2017/0273789 A1 | 9/2017 | Yaron et al. |
| 2017/0281341 A1 | 10/2017 | Lim et al. |
| 2017/0311937 A1 | 11/2017 | Bambury et al. |
| 2017/0348099 A1 | 12/2017 | Mendelson et al. |
| 2018/0049873 A1 | 2/2018 | Manash et al. |
| 2018/0055628 A1 | 3/2018 | Patel et al. |
| 2018/0092763 A1 | 4/2018 | Dagan et al. |
| 2018/0110622 A1 | 4/2018 | Gregg et al. |
| 2018/0116790 A1 | 5/2018 | Ratz et al. |
| 2018/0133003 A1 | 5/2018 | Levi |
| 2018/0177592 A1 | 6/2018 | Benichou et al. |
| 2018/0177594 A1 | 6/2018 | Patel et al. |
| 2018/0206982 A1 | 7/2018 | Haivatov et al. |
| 2018/0206986 A1 | 7/2018 | Noe et al. |
| 2018/0206992 A1 | 7/2018 | Brown |

(56) References Cited

U.S. PATENT DOCUMENTS

| | | |
|---|---|---|
| 2018/0207395 A1 | 7/2018 | Bulman et al. |
| 2018/0214267 A1 | 8/2018 | Lally et al. |
| 2018/0214270 A1 | 8/2018 | Subramanian et al. |
| 2018/0221014 A1 | 8/2018 | Darabian |
| 2018/0228608 A1 | 8/2018 | Sheps et al. |
| 2018/0228610 A1 | 8/2018 | Lashinski et al. |
| 2018/0235443 A1 | 8/2018 | Smith et al. |
| 2018/0250126 A1 | 9/2018 | O'Connor et al. |
| 2018/0250132 A1 | 9/2018 | Ketai et al. |
| 2018/0263764 A1 | 9/2018 | Manash et al. |
| 2018/0289473 A1 | 10/2018 | Rajagopal et al. |
| 2018/0289474 A1 | 10/2018 | Rajagopal et al. |
| 2018/0289478 A1 | 10/2018 | Quill |
| 2018/0289480 A1 | 10/2018 | D'ambra et al. |
| 2018/0289485 A1 | 10/2018 | Rajagopal et al. |
| 2018/0296335 A1 | 10/2018 | Miyashiro |
| 2018/0296338 A1 | 10/2018 | Rabito et al. |
| 2018/0318079 A1* | 11/2018 | Patel ............... A61M 25/0138 |
| 2018/0333259 A1 | 11/2018 | Dibie |
| 2018/0344303 A1 | 12/2018 | Bambury et al. |
| 2018/0344454 A1 | 12/2018 | Mauch et al. |
| 2018/0344459 A1 | 12/2018 | Spence et al. |
| 2018/0360600 A1 | 12/2018 | Zhuang et al. |
| 2018/0368830 A1 | 12/2018 | O'Carroll et al. |
| 2019/0000625 A1 | 1/2019 | O'Carroll et al. |
| 2019/0008635 A1 | 1/2019 | Francis et al. |
| 2019/0008639 A1 | 1/2019 | Landon et al. |
| 2019/0008640 A1 | 1/2019 | Cooper et al. |
| 2019/0015205 A1 | 1/2019 | Rajagopal et al. |
| 2019/0021859 A1 | 1/2019 | O'Carrol et al. |
| 2019/0046315 A1 | 2/2019 | Gao et al. |
| 2019/0053894 A1 | 2/2019 | Levi et al. |
| 2019/0053895 A1 | 2/2019 | Levi |
| 2019/0053898 A1 | 2/2019 | Maimon et al. |
| 2019/0053899 A1 | 2/2019 | Levi |
| 2019/0053903 A1 | 2/2019 | Rohl et al. |
| 2019/0060068 A1 | 2/2019 | Cope et al. |
| 2019/0060069 A1 | 2/2019 | Maimon et al. |
| 2019/0060071 A1 | 2/2019 | Lane et al. |
| 2019/0076244 A1 | 3/2019 | Yohanan et al. |
| 2019/0076664 A1 | 3/2019 | Ollivier |
| 2019/0117392 A1 | 4/2019 | Quadri et al. |
| 2019/0133756 A1 | 5/2019 | Zhang et al. |
| 2019/0133757 A1 | 5/2019 | Zhang et al. |
| 2019/0142589 A1 | 5/2019 | Basude |
| 2019/0159770 A1 | 5/2019 | Rohl et al. |
| 2019/0160292 A1 | 5/2019 | Peichel et al. |
| 2019/0167425 A1 | 6/2019 | Reich et al. |
| 2019/0183649 A1 | 6/2019 | Allen et al. |
| 2019/0192296 A1 | 6/2019 | Schwartz et al. |
| 2019/0201191 A1 | 7/2019 | McLean et al. |
| 2019/0209311 A1 | 7/2019 | Zhang et al. |
| 2019/0209312 A1 | 7/2019 | Zhang et al. |
| 2019/0209313 A1 | 7/2019 | Zhang et al. |
| 2019/0209314 A1 | 7/2019 | Zhang et al. |
| 2019/0209315 A1 | 7/2019 | Zhang et al. |
| 2019/0209316 A1 | 7/2019 | Zhang et al. |
| 2019/0209317 A1 | 7/2019 | Zhang et al. |
| 2019/0209318 A1 | 7/2019 | Zhang et al. |
| 2019/0209320 A1 | 7/2019 | Drasler et al. |
| 2019/0231520 A1 | 8/2019 | Desrosiers et al. |
| 2019/0240023 A1 | 8/2019 | Spence et al. |
| 2019/0246916 A1 | 8/2019 | Kuraguntla et al. |
| 2019/0254816 A1 | 8/2019 | Anderson et al. |
| 2019/0261995 A1 | 8/2019 | Goldfarb et al. |
| 2019/0261996 A1 | 8/2019 | Goldfarb et al. |
| 2019/0261997 A1 | 8/2019 | Goldfarb et al. |
| 2019/0262129 A1 | 8/2019 | Cooper et al. |
| 2019/0282237 A1 | 9/2019 | Goldfarb et al. |
| 2019/0328518 A1 | 10/2019 | Neumann |
| 2019/0336282 A1 | 11/2019 | Christianson et al. |
| 2019/0343625 A1 | 11/2019 | Gharib et al. |
| 2019/0365530 A1 | 12/2019 | Hoang et al. |
| 2019/0374337 A1 | 12/2019 | Zamani et al. |
| 2019/0374342 A1 | 12/2019 | Gregg et al. |
| 2020/0000579 A1 | 1/2020 | Manash et al. |
| 2020/0000586 A1 | 1/2020 | Tian et al. |
| 2020/0008936 A1 | 1/2020 | Cheema et al. |
| 2020/0022811 A1 | 1/2020 | Griswold et al. |
| 2020/0054453 A1 | 2/2020 | Zerkowski et al. |
| 2020/0060813 A1 | 2/2020 | Nguyen et al. |
| 2020/0060820 A1 | 2/2020 | Ben-Zvi et al. |
| 2020/0060852 A1 | 2/2020 | Argento et al. |
| 2020/0078000 A1 | 3/2020 | Rajagopal et al. |
| 2020/0093601 A1 | 3/2020 | Neustadter |
| 2020/0107932 A1 | 4/2020 | Rabito et al. |
| 2020/0107933 A1 | 4/2020 | Oba |
| 2020/0113586 A1 | 4/2020 | Karasic et al. |
| 2020/0113685 A1 | 4/2020 | Miller et al. |
| 2020/0113696 A1 | 4/2020 | Ekvall et al. |
| 2020/0138575 A1 | 5/2020 | Tuval |
| 2020/0178977 A1 | 6/2020 | Coleman et al. |
| 2020/0188107 A1 | 6/2020 | Gloss et al. |
| 2020/0205800 A1 | 7/2020 | Gilmore et al. |
| 2020/0205969 A1 | 7/2020 | Hacohen |
| 2020/0205974 A1 | 7/2020 | Zerkowski et al. |
| 2020/0205975 A1 | 7/2020 | Khairkhahan |
| 2020/0205979 A1 | 7/2020 | O'Carroll et al. |
| 2020/0214708 A1 | 7/2020 | Sharma |
| 2020/0229806 A1 | 7/2020 | Goldfarb et al. |
| 2020/0229918 A1 | 7/2020 | Pham et al. |
| 2020/0275921 A1 | 9/2020 | Gilmore et al. |
| 2020/0297489 A1 | 9/2020 | Bishop et al. |
| 2020/0352705 A1 | 11/2020 | Heneghan et al. |
| 2020/0352706 A1 | 11/2020 | Campbell |
| 2020/0360139 A1 | 11/2020 | Hammer et al. |
| 2021/0022854 A1 | 1/2021 | Zhao et al. |
| 2021/0022860 A1 | 1/2021 | Lally et al. |
| 2021/0030536 A1 | 2/2021 | Kaleta |
| 2021/0121289 A1 | 4/2021 | Bruchman et al. |
| 2021/0128297 A1 | 5/2021 | Braido et al. |
| 2021/0145573 A1 | 5/2021 | Dasi et al. |
| 2021/0154009 A1 | 5/2021 | Argento et al. |
| 2021/0161688 A1 | 6/2021 | Shahriari |
| 2021/0177583 A1 | 6/2021 | Colavito et al. |
| 2021/0177584 A1 | 6/2021 | Levi et al. |
| 2021/0177587 A1 | 6/2021 | Braido |
| 2021/0186689 A1 | 6/2021 | Eidenschink et al. |
| 2021/0228343 A1 | 7/2021 | Scheinblum et al. |

FOREIGN PATENT DOCUMENTS

| | | |
|---|---|---|
| AU | 2020227034 A1 | 9/2020 |
| BR | PI0820603 B1 | 6/2020 |
| CA | 2979817 A1 | 9/2016 |
| CA | 2954826 C | 10/2019 |
| CN | 103764216 A | 4/2014 |
| CN | 103974670 A | 8/2014 |
| CN | 105358098 A | 2/2016 |
| CN | 111110401 A | 5/2020 |
| CN | 111110403 A | 5/2020 |
| CN | 108601655 B | 6/2020 |
| CN | 111265335 A | 6/2020 |
| CN | 111278389 A | 6/2020 |
| CN | 111329541 A | 6/2020 |
| DE | 19857887 B4 | 5/2005 |
| EP | 1432369 B1 | 2/2008 |
| EP | 2374415 A1 | 10/2011 |
| EP | 2907479 A1 | 8/2015 |
| EP | 3037064 A1 | 6/2016 |
| EP | 3342355 A1 | 7/2018 |
| EP | 3395296 A1 | 10/2018 |
| EP | 3406225 A1 | 11/2018 |
| EP | 3417831 A1 | 12/2018 |
| EP | 3476366 A1 | 5/2019 |
| EP | 3482718 A1 | 5/2019 |
| EP | 2637607 B1 | 10/2019 |
| EP | 3554424 A1 | 10/2019 |
| EP | 3244809 B1 | 2/2020 |
| EP | 3639792 A1 | 4/2020 |
| EP | 3417831 B1 | 5/2020 |
| EP | 3649963 A2 | 5/2020 |
| EP | 2072027 B1 | 6/2020 |
| EP | 3441045 B1 | 7/2020 |

(56) References Cited

FOREIGN PATENT DOCUMENTS

| | | |
|---|---|---|
| EP | 3672528 A1 | 7/2020 |
| EP | 3554423 B1 | 8/2020 |
| EP | 3107498 B1 | 9/2020 |
| EP | 3570782 B1 | 9/2020 |
| EP | 3700467 A1 | 9/2020 |
| EP | 3705090 A1 | 9/2020 |
| EP | 3782585 A1 | 2/2021 |
| JP | 2020515375 A | 5/2020 |
| JP | 2020517379 A | 6/2020 |
| JP | 2020520729 A | 7/2020 |
| JP | 6735294 B2 | 8/2020 |
| KR | 2020032237 A | 3/2020 |
| KR | 2020033349 A | 3/2020 |
| KR | 2020033350 A | 3/2020 |
| TW | 202027694 A | 8/2020 |
| WO | WO2007/081820 A1 | 7/2007 |
| WO | WO2010/141847 A1 | 12/2010 |
| WO | WO2011/025945 A1 | 3/2011 |
| WO | WO2012/145545 A1 | 10/2012 |
| WO | WO2015/127264 A1 | 8/2015 |
| WO | WO2015/195823 A1 | 12/2015 |
| WO | WO2016/183485 A1 | 11/2016 |
| WO | WO2017/121193 A1 | 7/2017 |
| WO | WO2017/151566 A1 | 9/2017 |
| WO | WO2017/214098 A1 | 12/2017 |
| WO | WO2018/039561 A1 | 3/2018 |
| WO | WO2018/039589 A1 | 3/2018 |
| WO | WO2018/119304 A1 | 6/2018 |
| WO | WO2018/178966 A1 | 10/2018 |
| WO | WO2018/178967 A1 | 10/2018 |
| WO | WO2018/187390 A1 | 10/2018 |
| WO | WO2018/192197 A1 | 10/2018 |
| WO | WO2019/010370 A1 | 1/2019 |
| WO | WO2019/036592 A1 | 2/2019 |
| WO | WO2019/062366 A1 | 4/2019 |
| WO | WO2019/081777 A1 | 5/2019 |
| WO | WO2019/086958 A1 | 5/2019 |
| WO | WO2019/102484 A1 | 5/2019 |
| WO | WO2019/116369 A1 | 6/2019 |
| WO | WO2019/118371 A1 | 6/2019 |
| WO | WO2019/135011 A1 | 7/2019 |
| WO | WO2019/135028 A1 | 7/2019 |
| WO | WO2019/144036 A1 | 7/2019 |
| WO | WO2019/147504 A1 | 8/2019 |
| WO | WO2019/147846 A2 | 8/2019 |
| WO | WO2019/154124 A1 | 8/2019 |
| WO | WO2019/164516 A1 | 8/2019 |
| WO | WO2019/195860 A2 | 10/2019 |
| WO | WO2019/209927 A1 | 10/2019 |
| WO | WO2019/222694 A1 | 11/2019 |
| WO | WO2019/241777 A1 | 12/2019 |
| WO | WO2020/051147 A1 | 3/2020 |
| WO | WO2020/051591 A1 | 3/2020 |
| WO | WO2020/072199 A1 | 4/2020 |
| WO | WO2020/072201 A1 | 4/2020 |
| WO | WO2020/073050 A1 | 4/2020 |
| WO | WO2020/082039 A1 | 4/2020 |
| WO | WO2020/123719 A1 | 6/2020 |
| WO | WO2020/157018 A1 | 8/2020 |
| WO | WO2020/163112 A1 | 8/2020 |
| WO | WO2020/210685 A8 | 10/2020 |
| WO | WO2020/236830 A1 | 11/2020 |
| WO | WO2020/247907 A1 | 12/2020 |
| WO | WO2021/034497 A1 | 2/2021 |
| WO | WO2021/086850 A1 | 5/2021 |
| WO | WO2021/087400 A1 | 5/2021 |
| WO | WO2021/091754 A1 | 5/2021 |

OTHER PUBLICATIONS

Argento et al.; U.S. Appl. No. 16/594,946 entitled "Prosthetic cardiac valve devices, systems, and methods," filed Oct. 7, 2019.
Argento et al.; U.S. Appl. No. 16/723,537 entitled "Prothetic cardiac valve devices, systems, and methods," filed Dec. 20, 2019.
Argento et al.; U.S. Appl. No. 17/286,724 entitled "Adjustable medical device," filed Apr. 19, 2021.

* cited by examiner

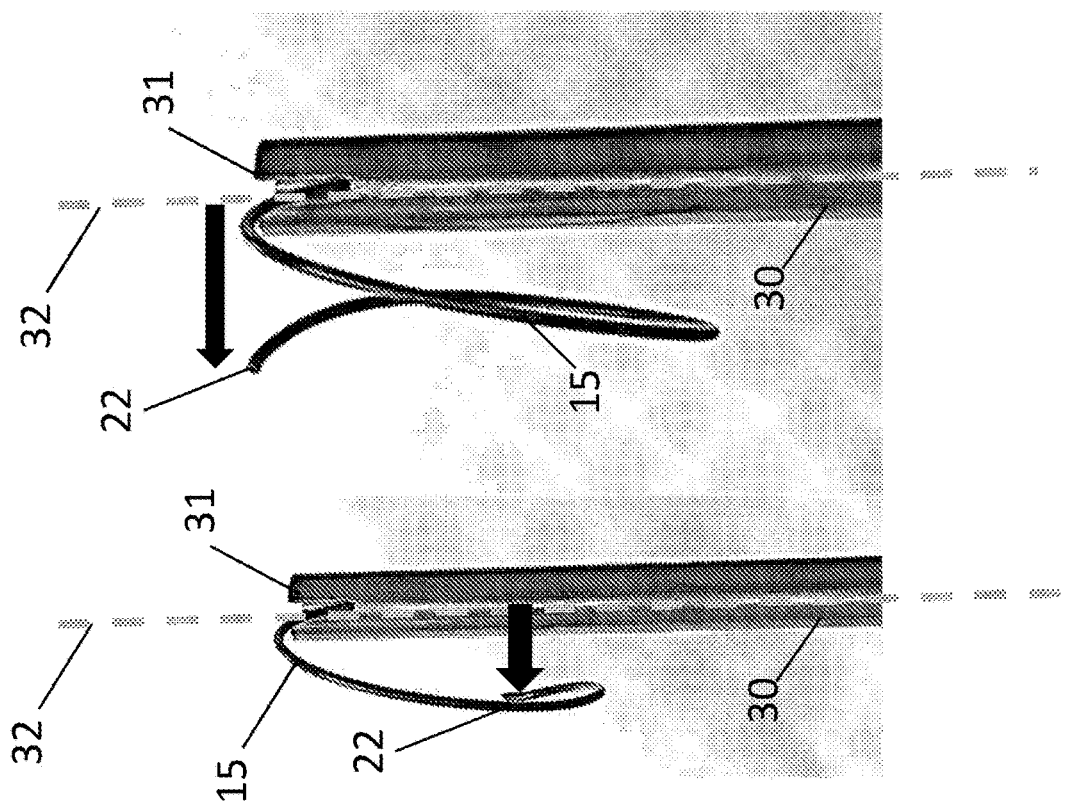
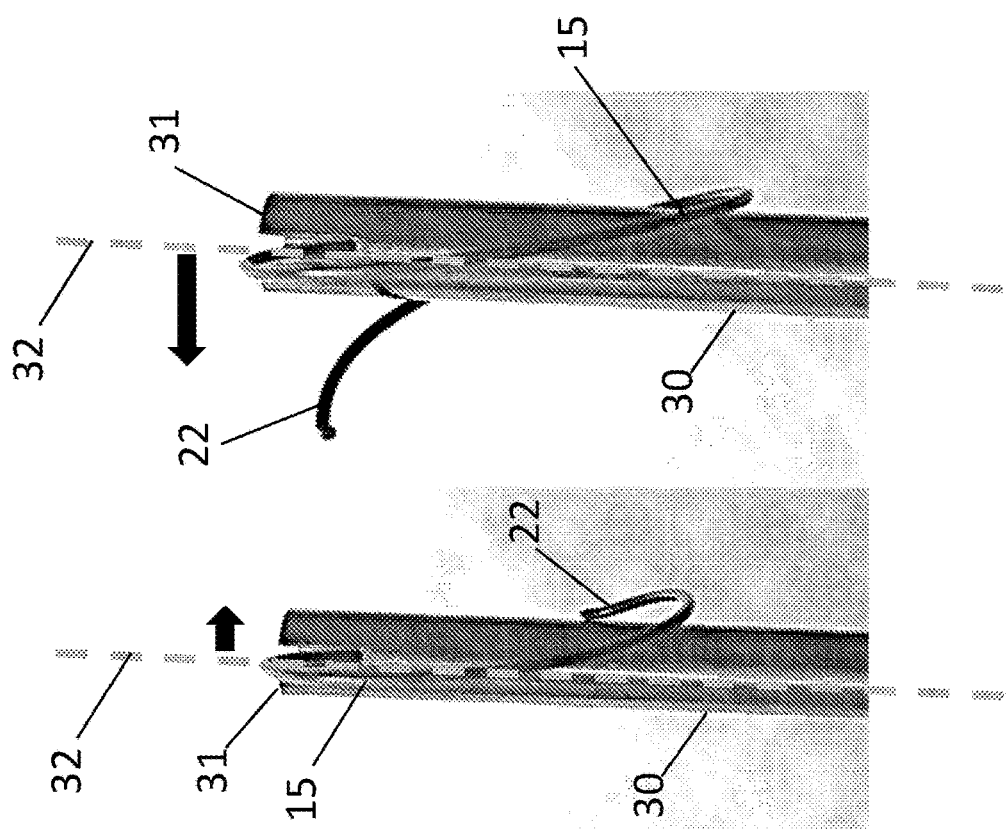

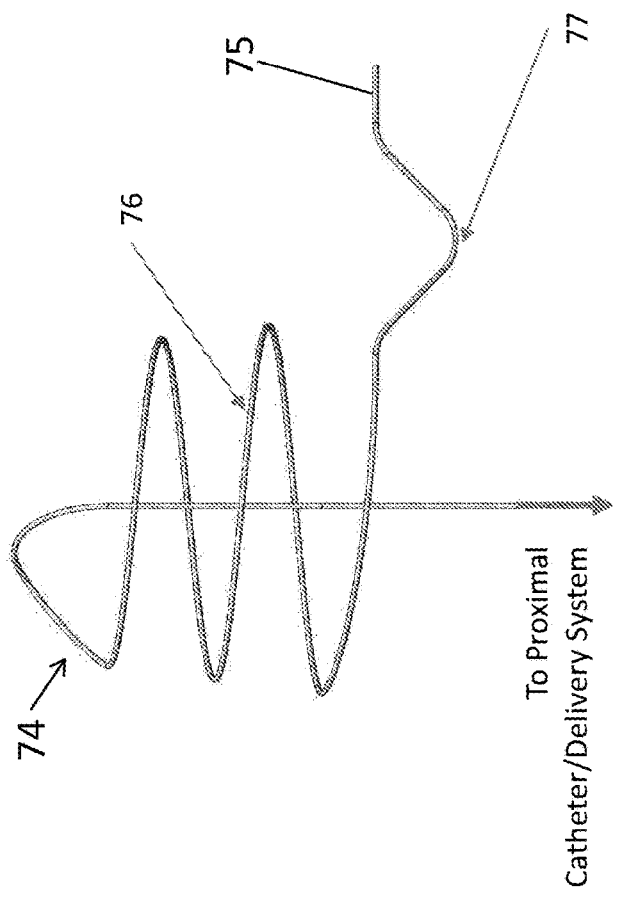
FIG. 15
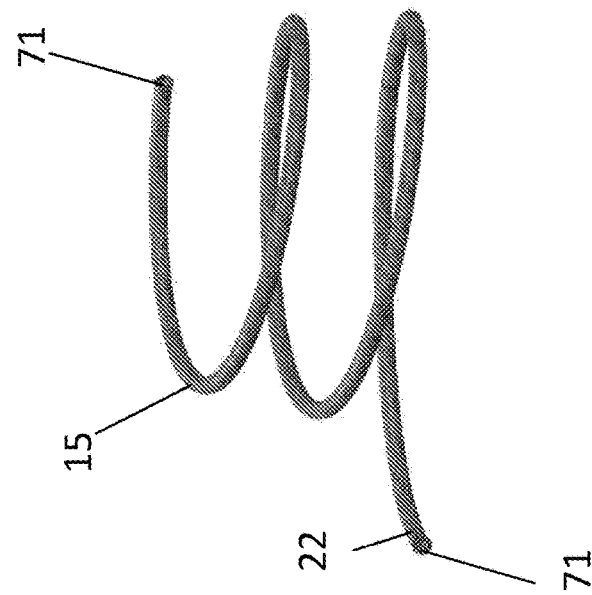
FIG. 16
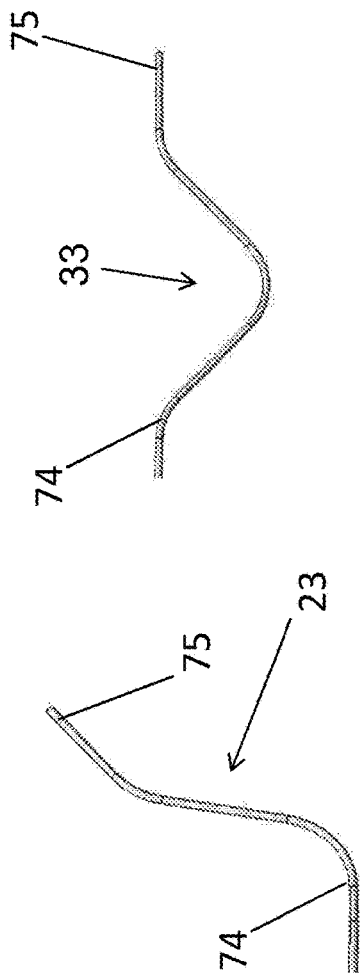
FIG. 17C
FIG. 17B
FIG. 17A

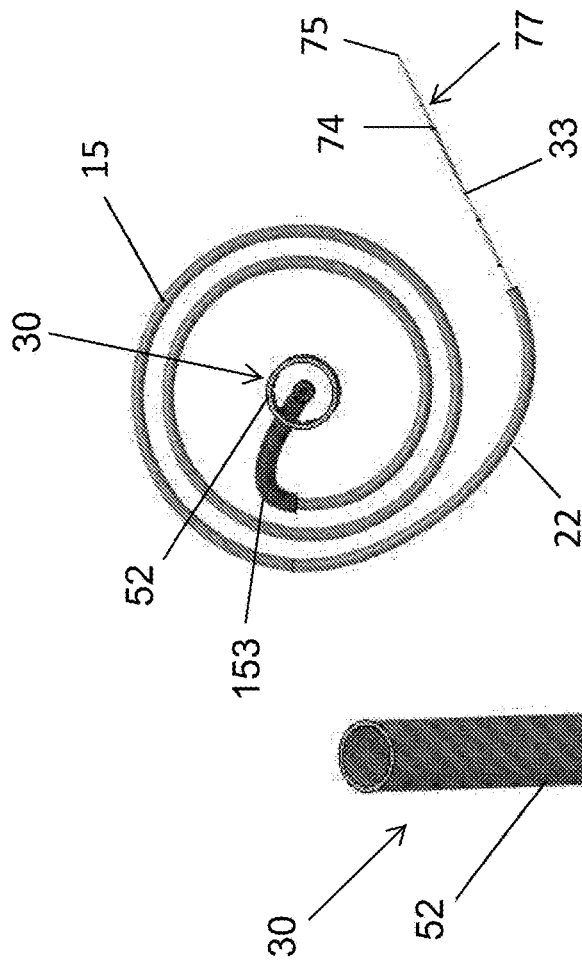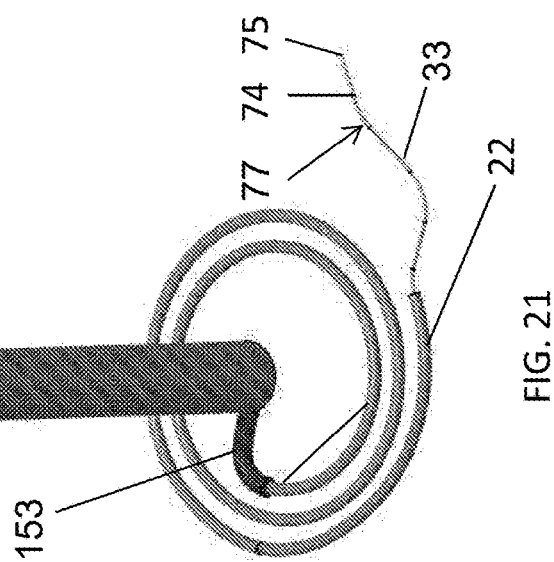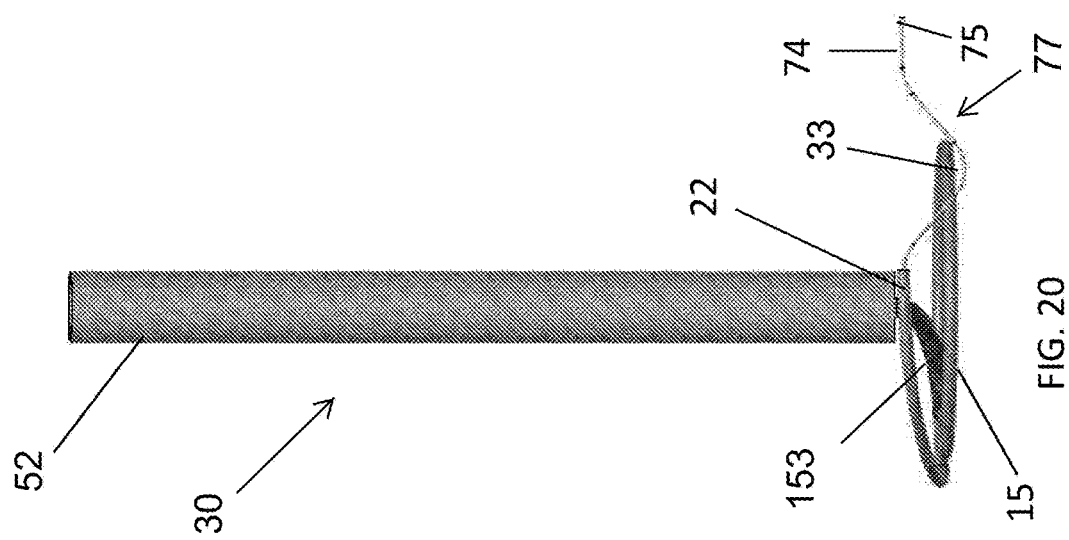

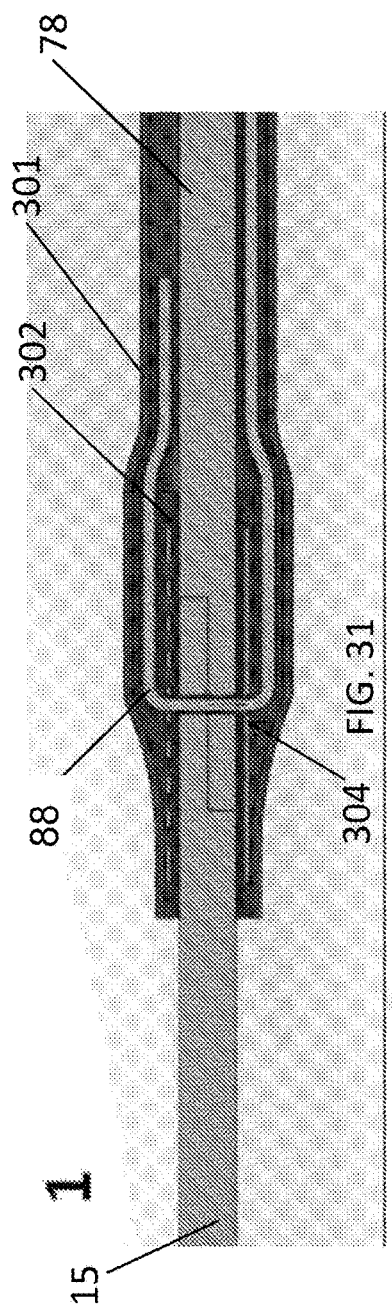
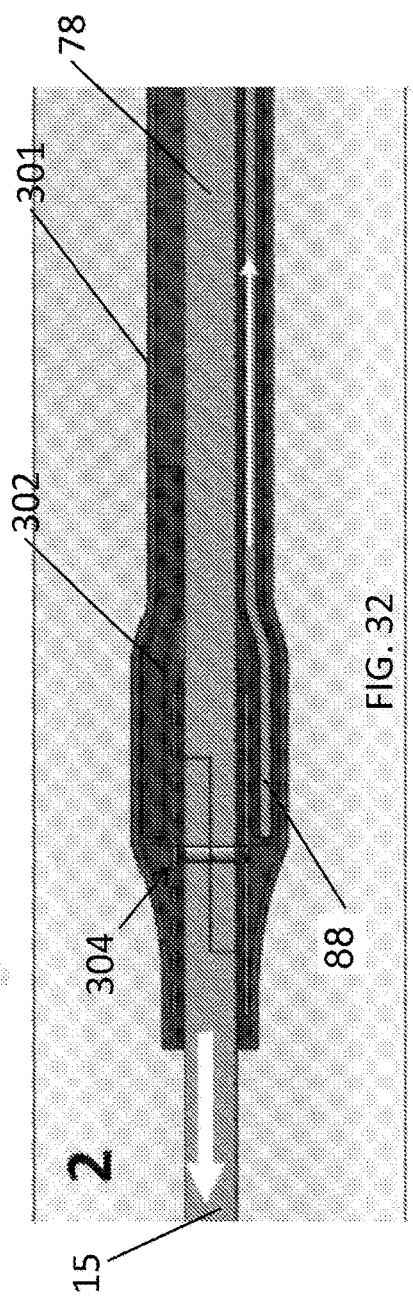
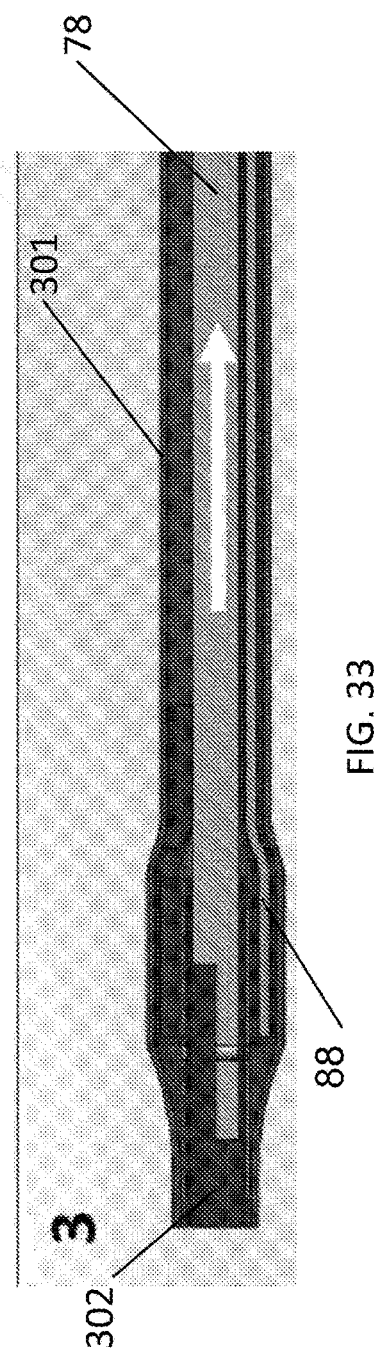

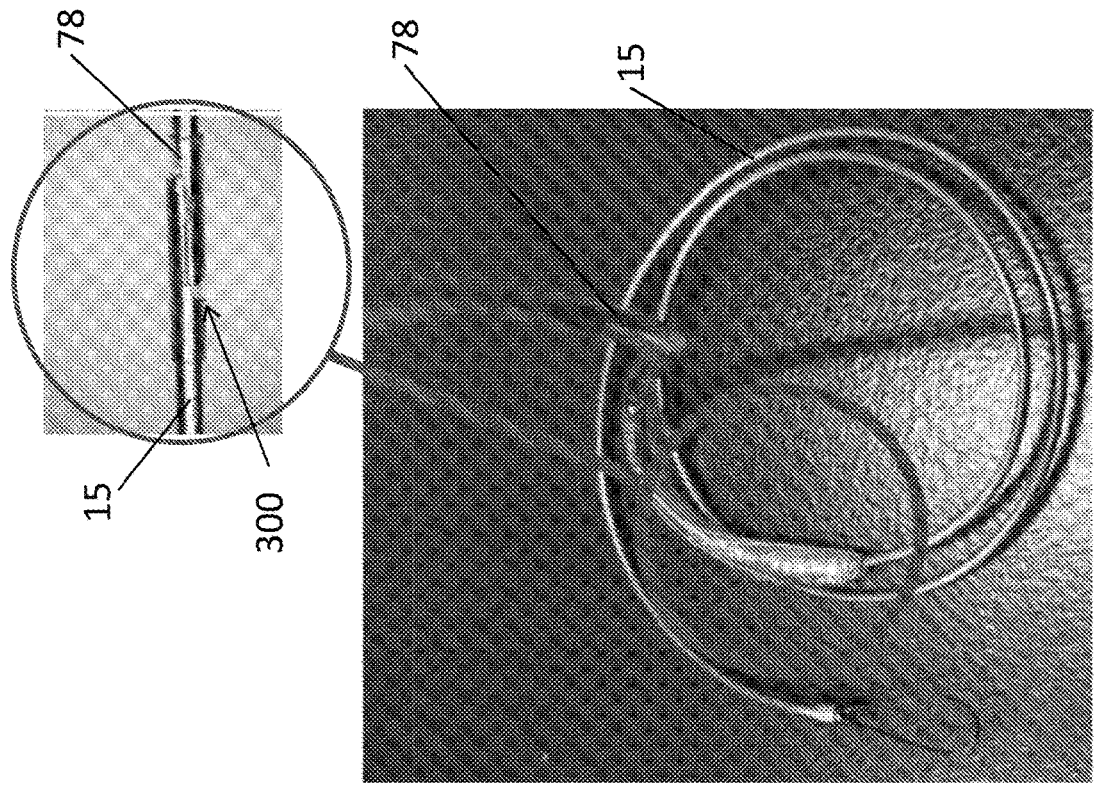
FIG. 36
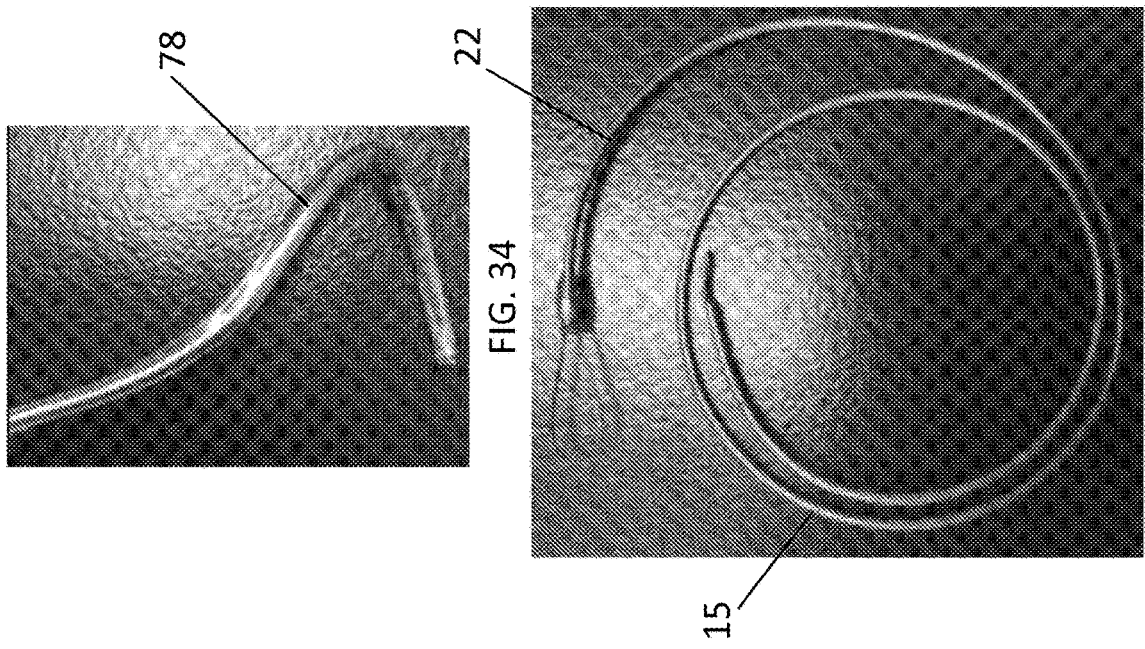
FIG. 34
FIG. 35

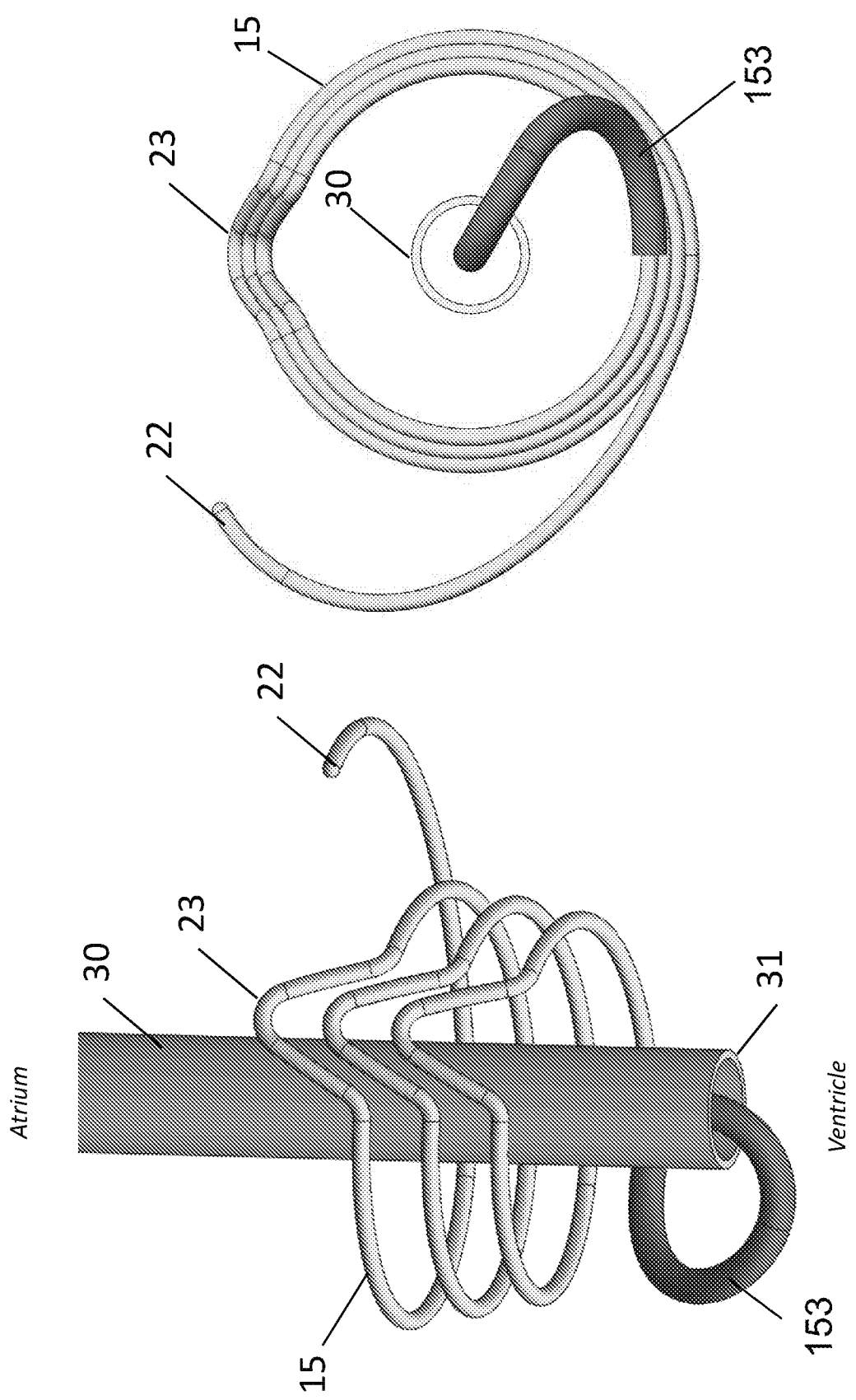

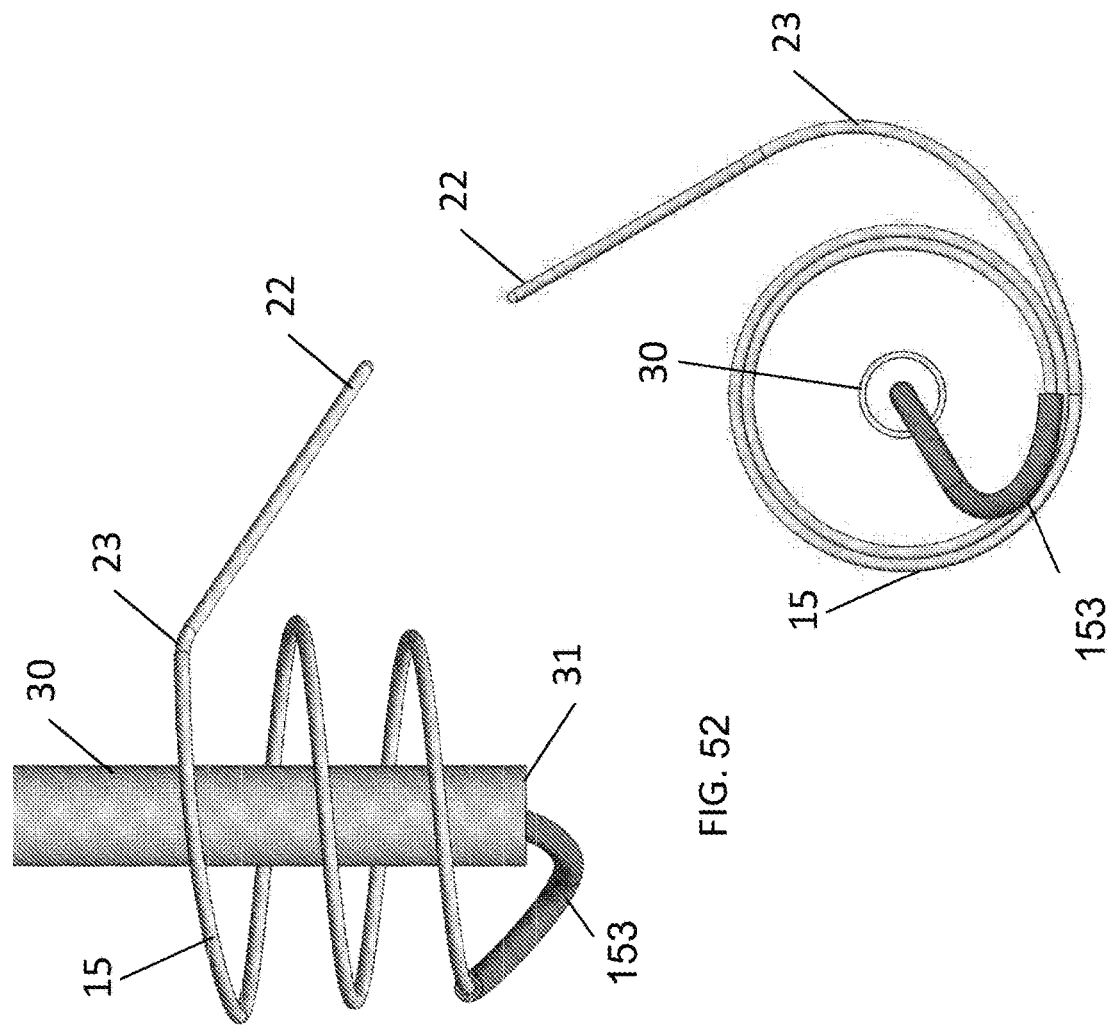
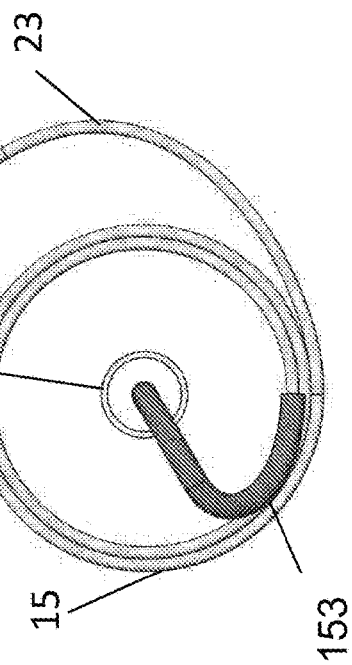
FIG. 53
FIG. 52
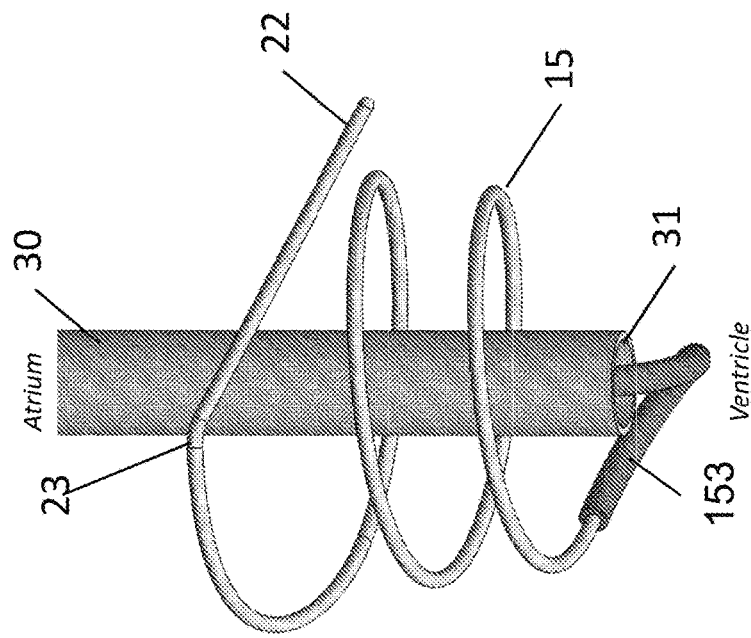
FIG. 51

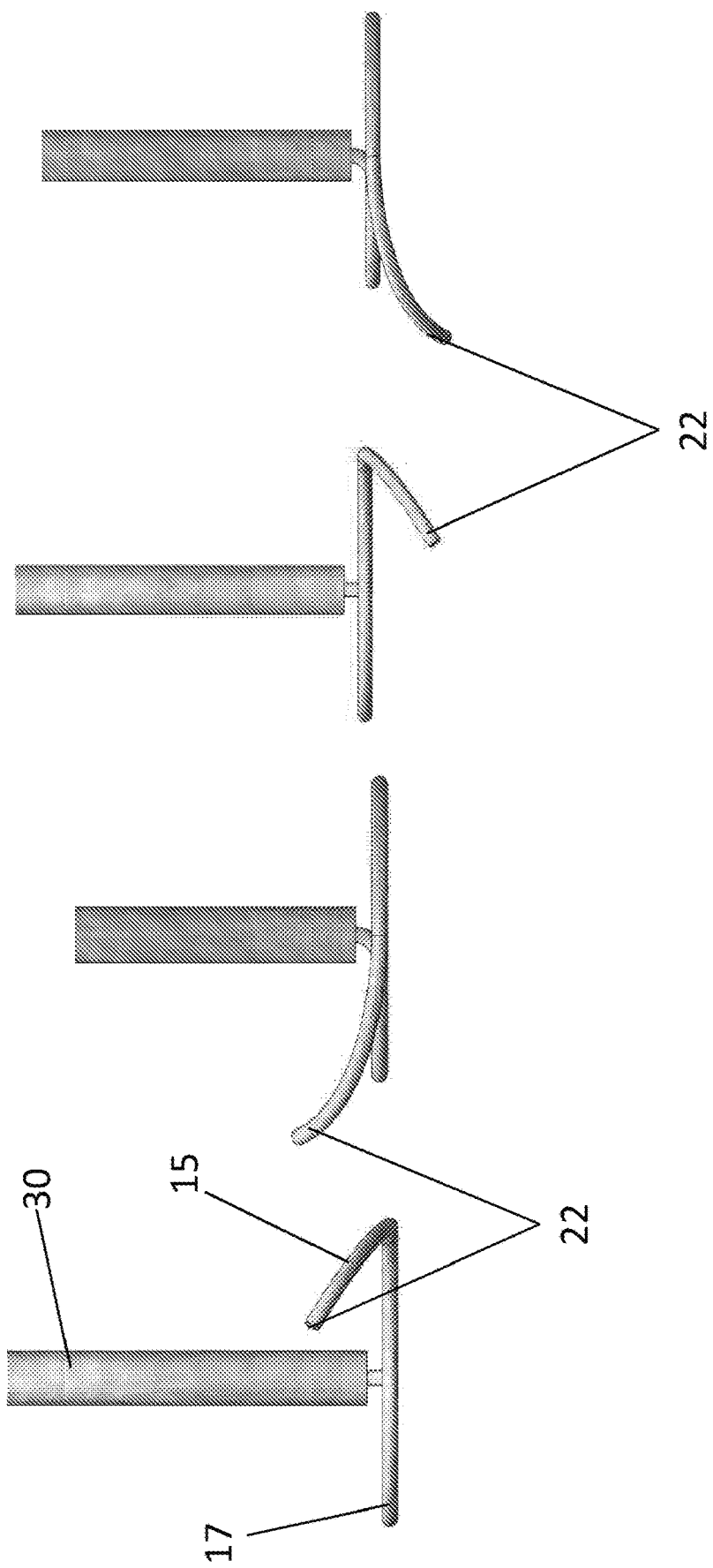

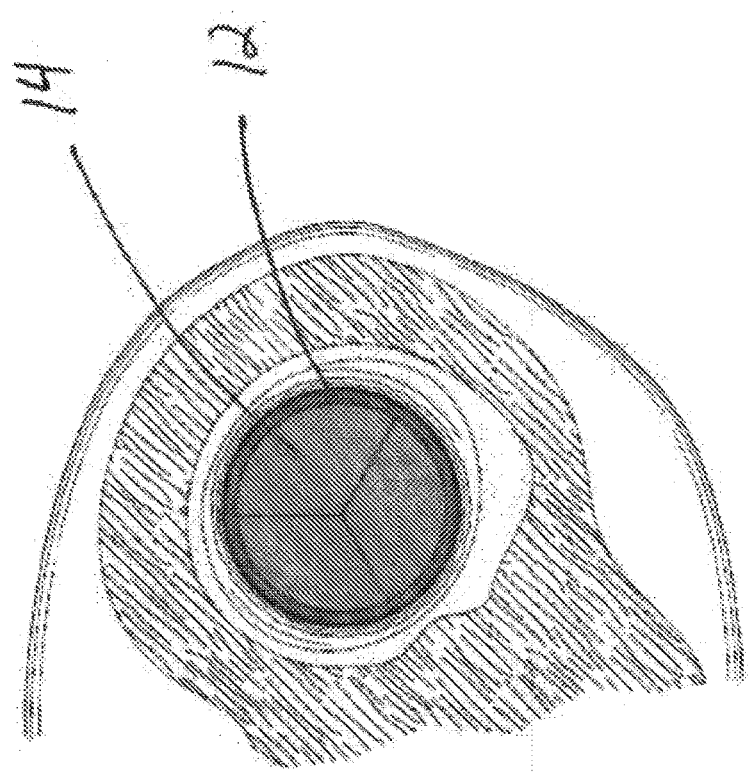
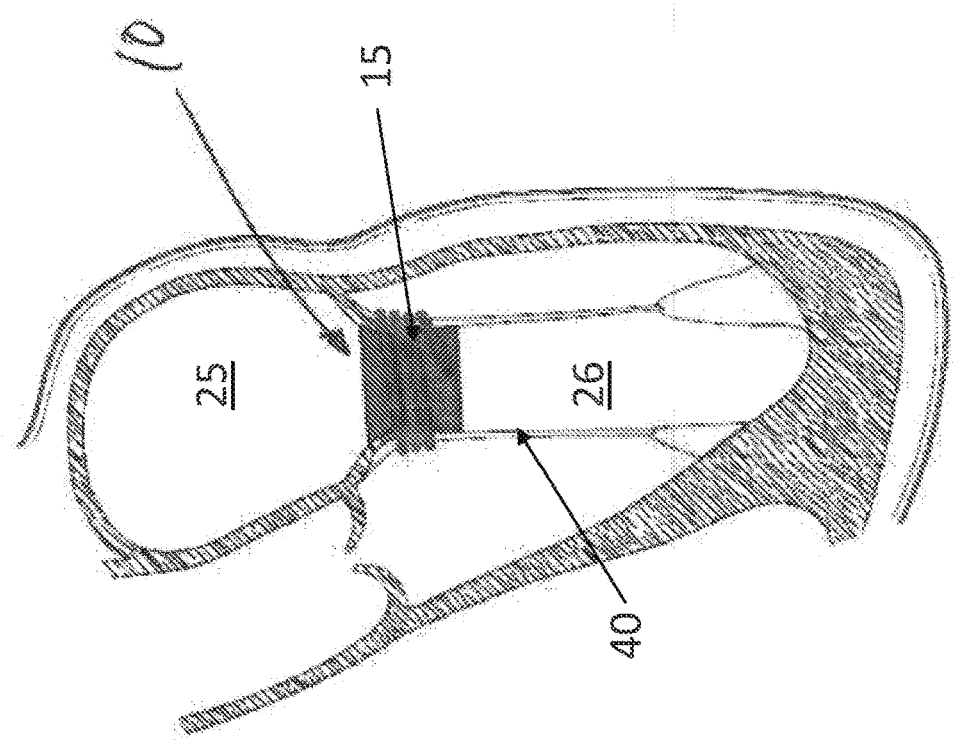
FIG. 58B
FIG. 58A

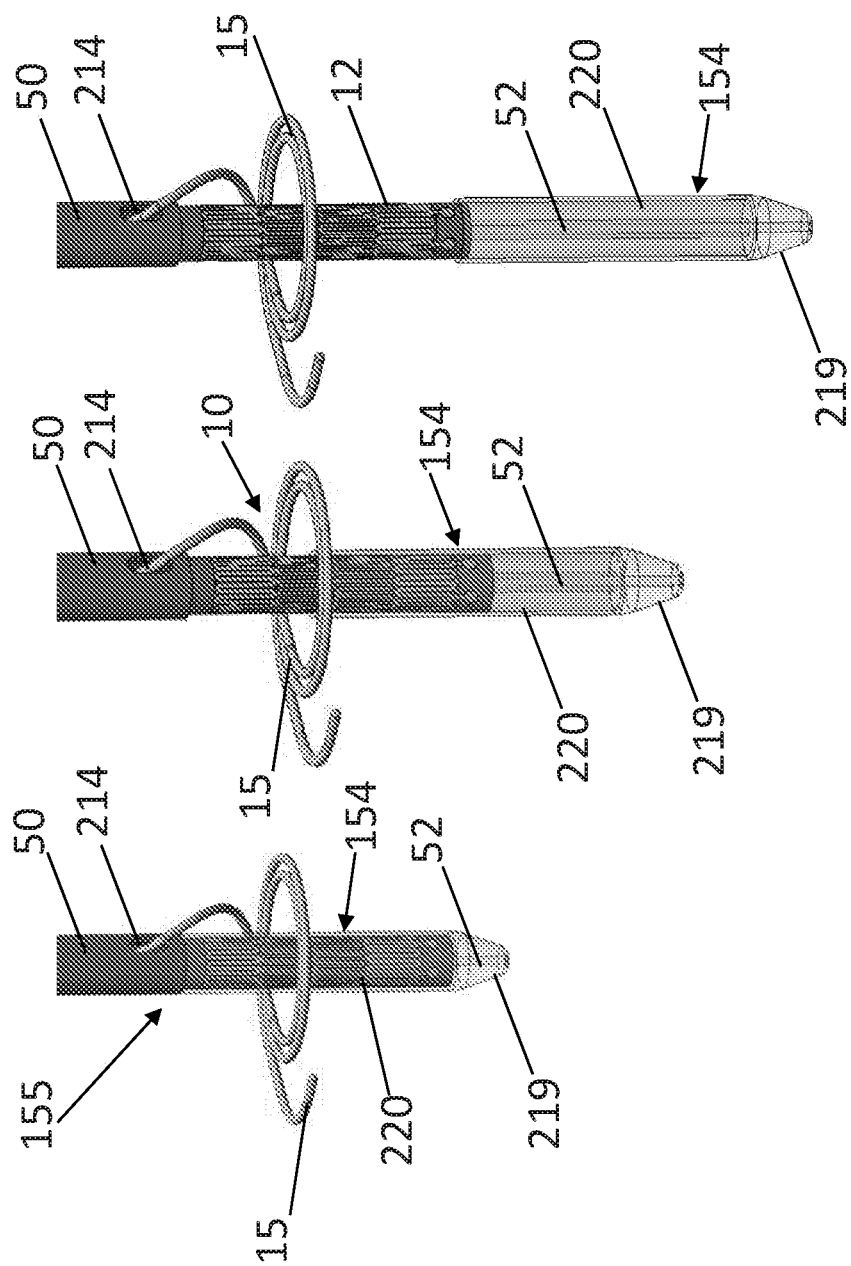

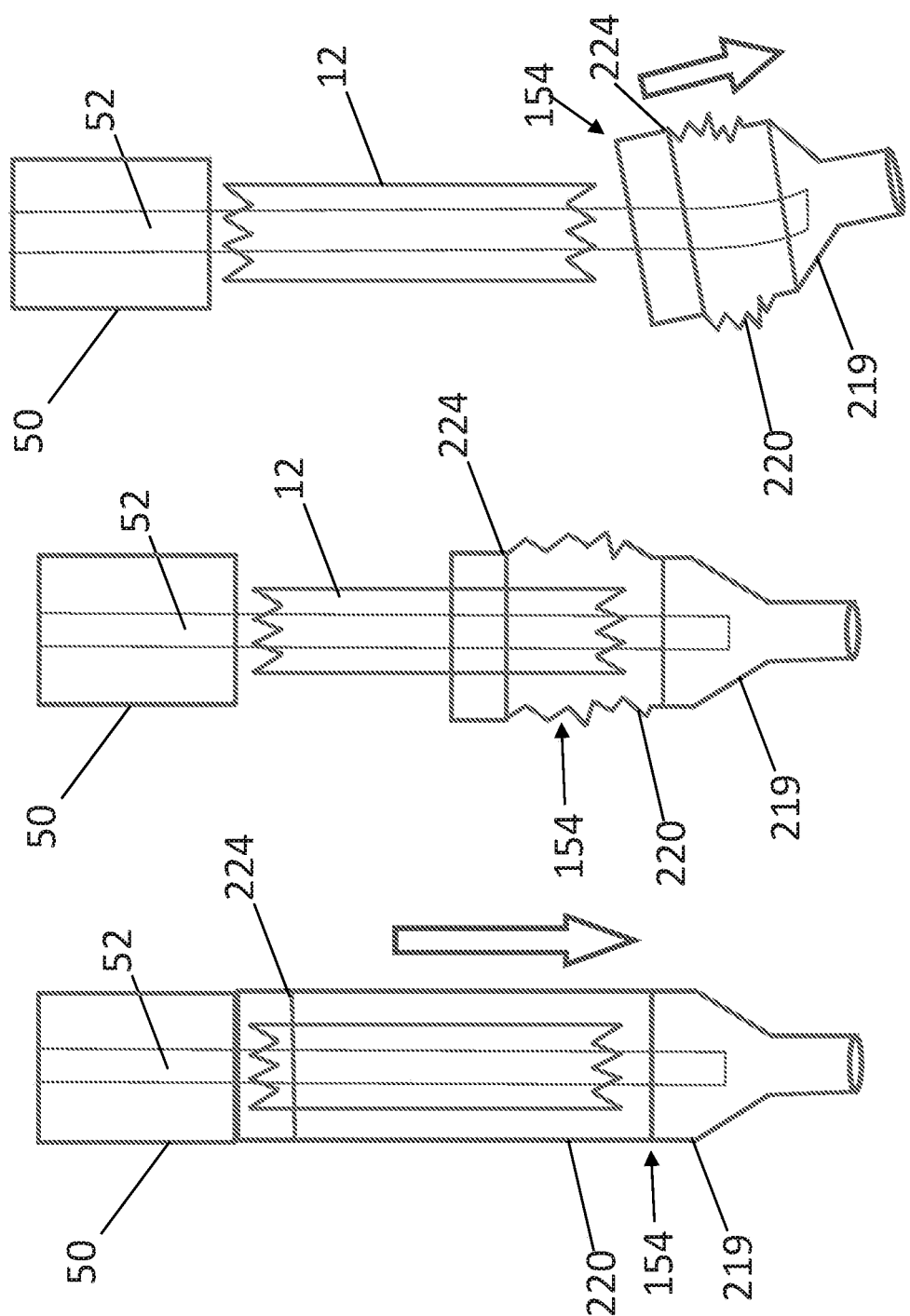

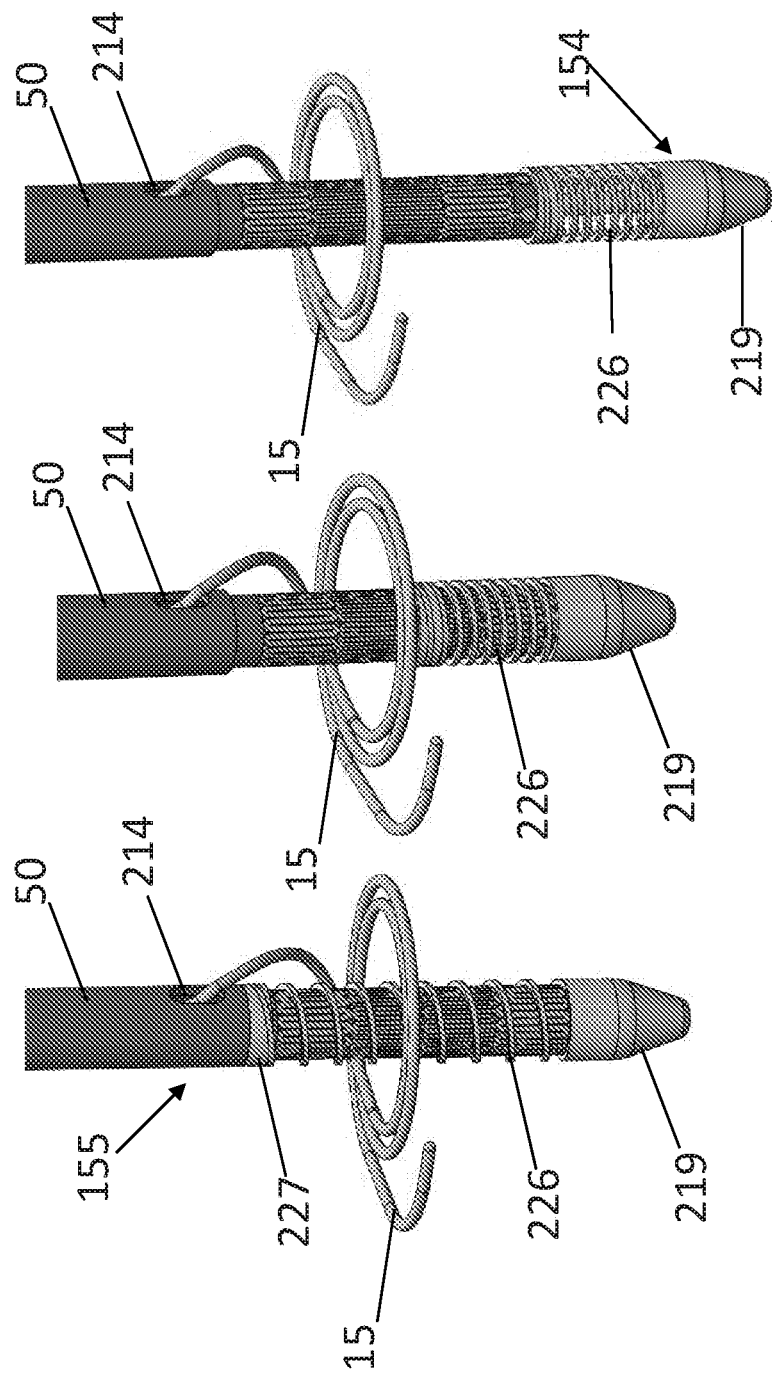

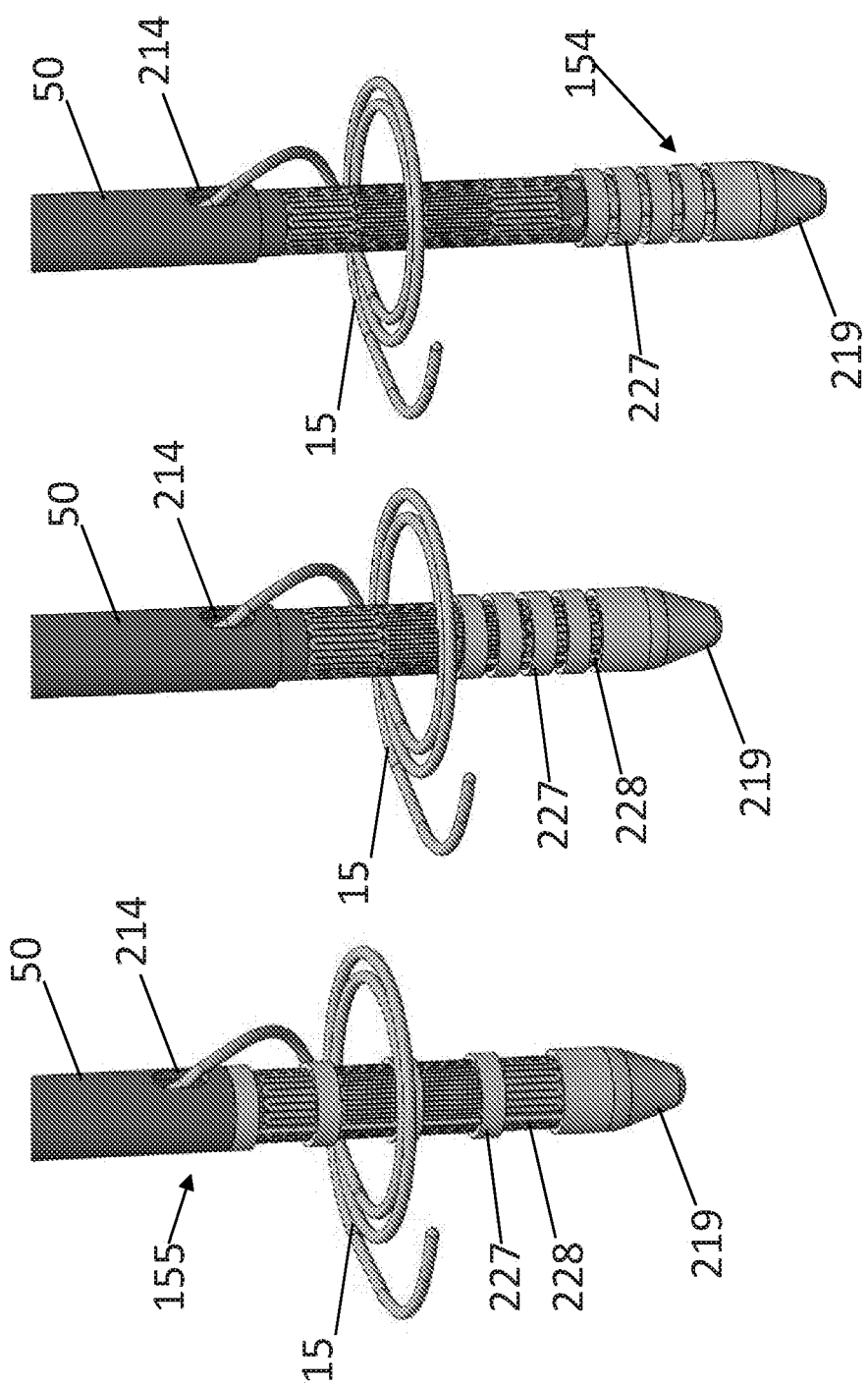

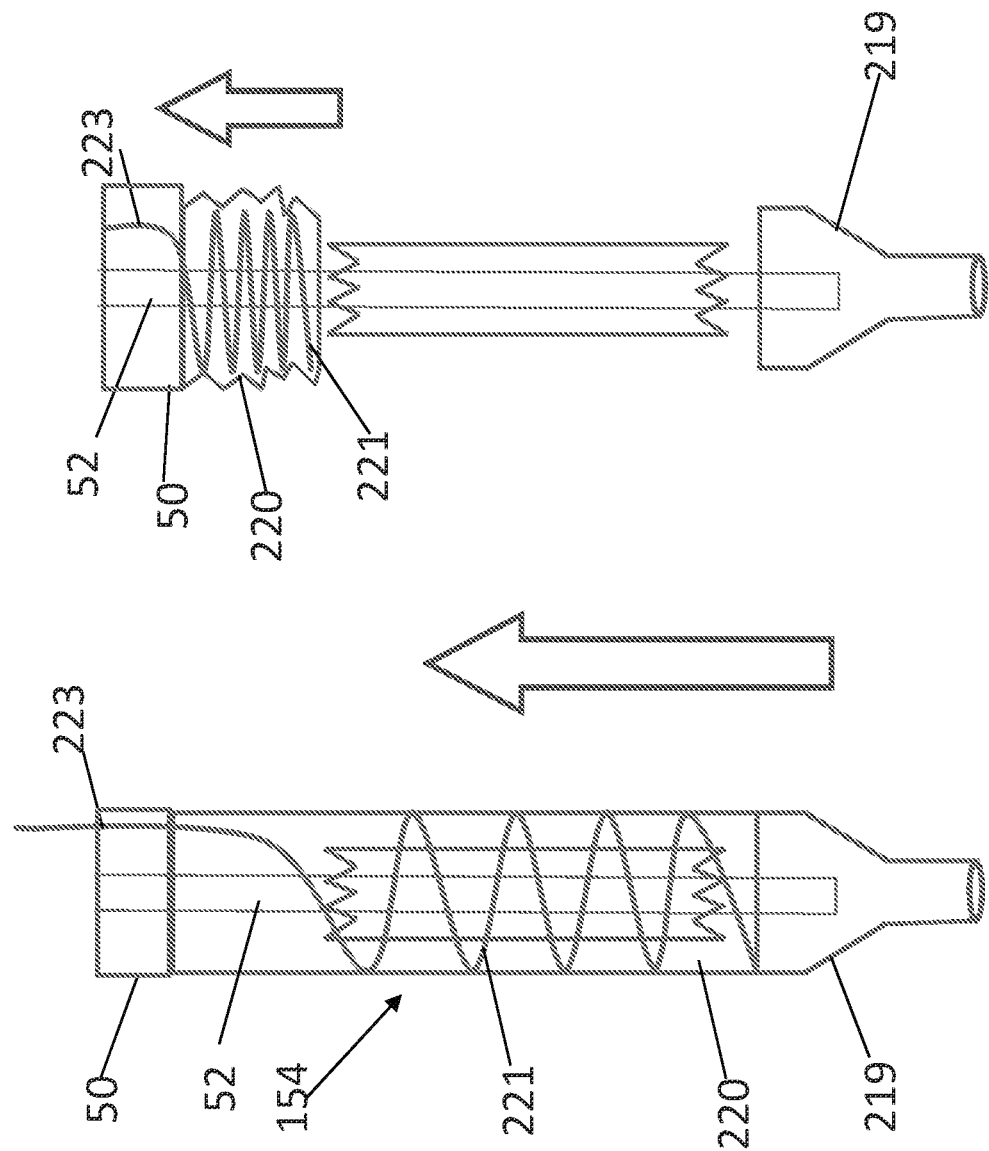

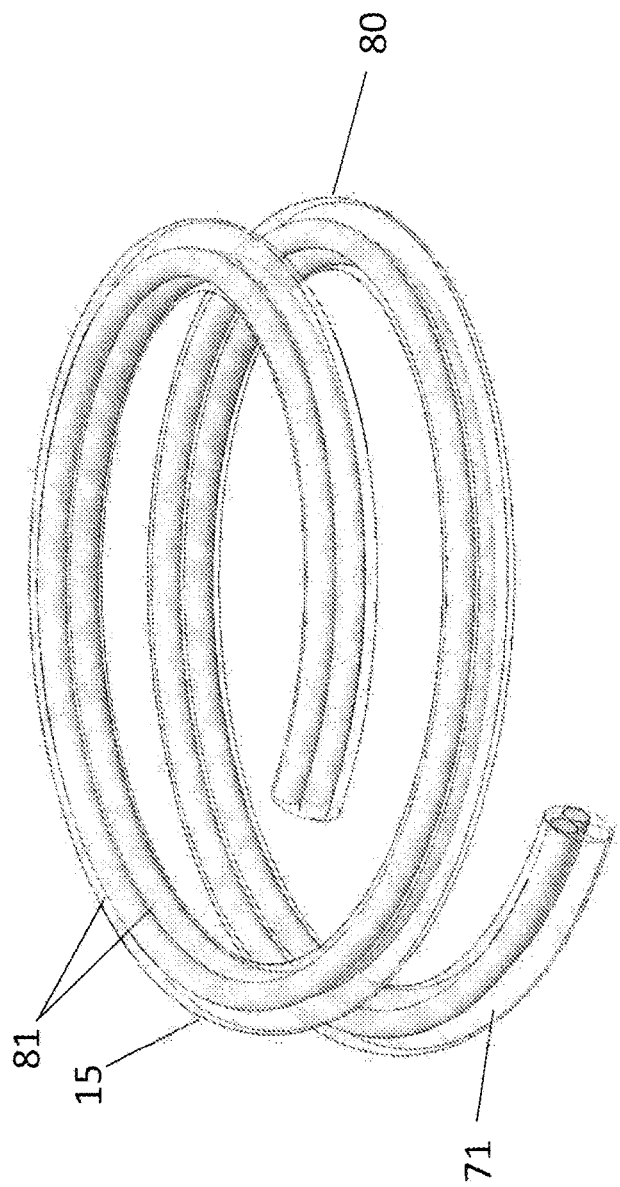
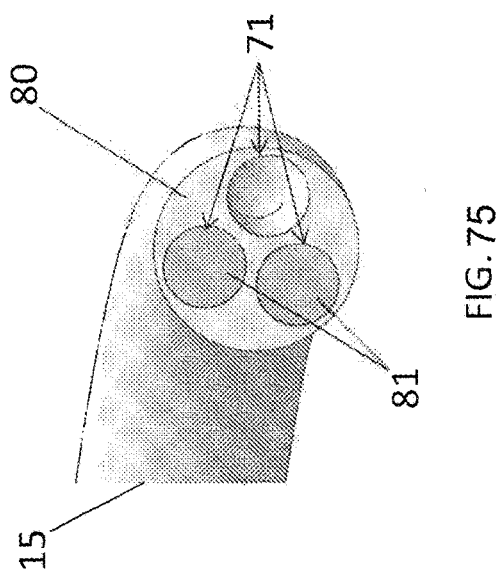
FIG. 74
FIG. 75

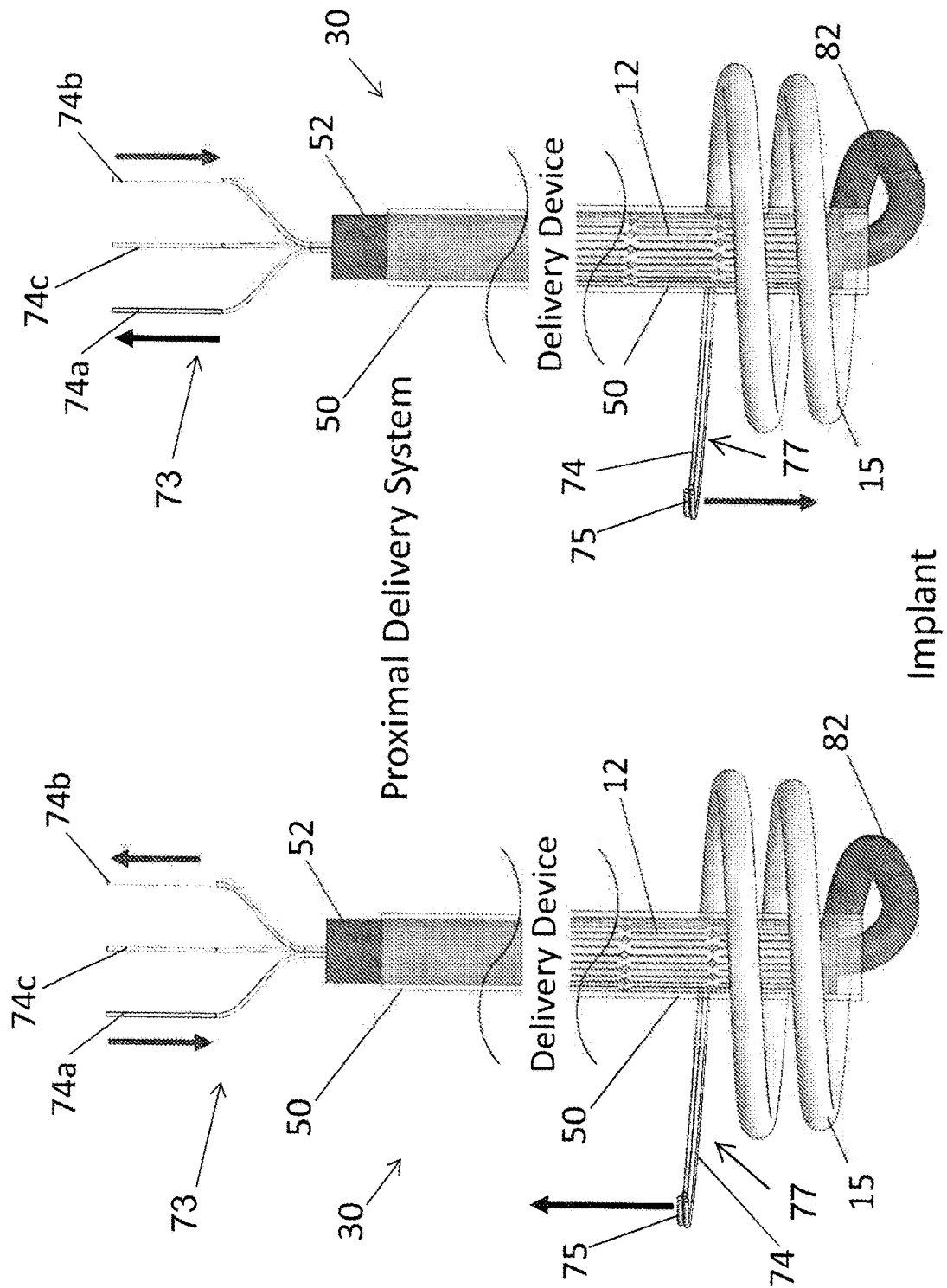

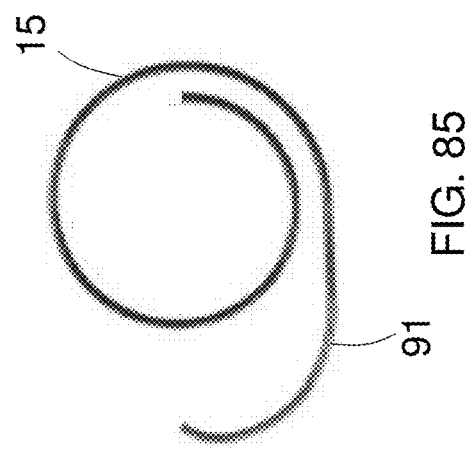
FIG. 85
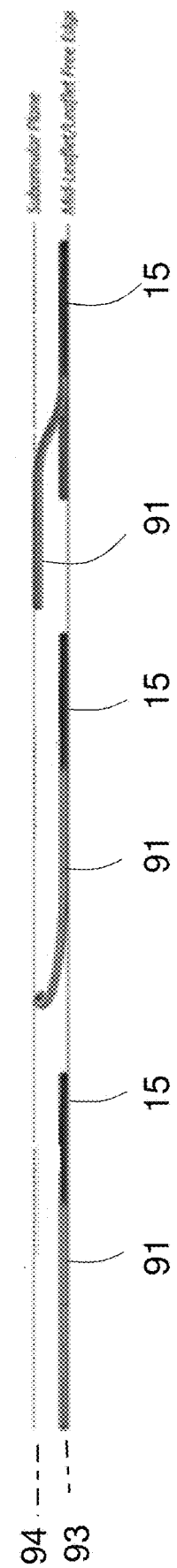
FIG. 86C
FIG. 86B
FIG. 86A

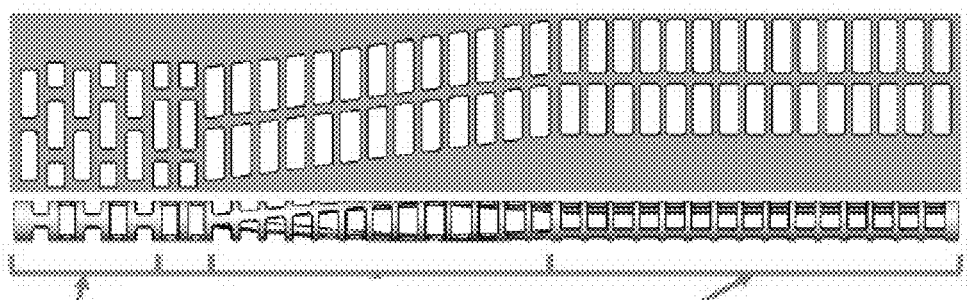
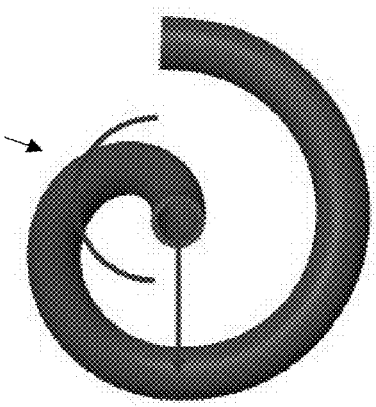
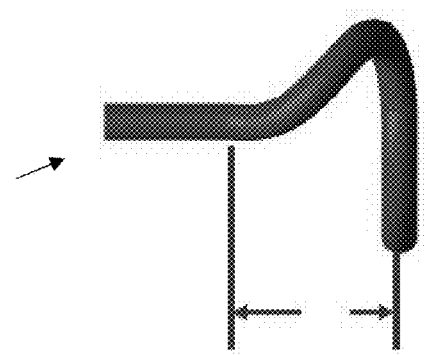
FIG. 87A  FIG. 87B  FIG. 87C  FIG. 87D

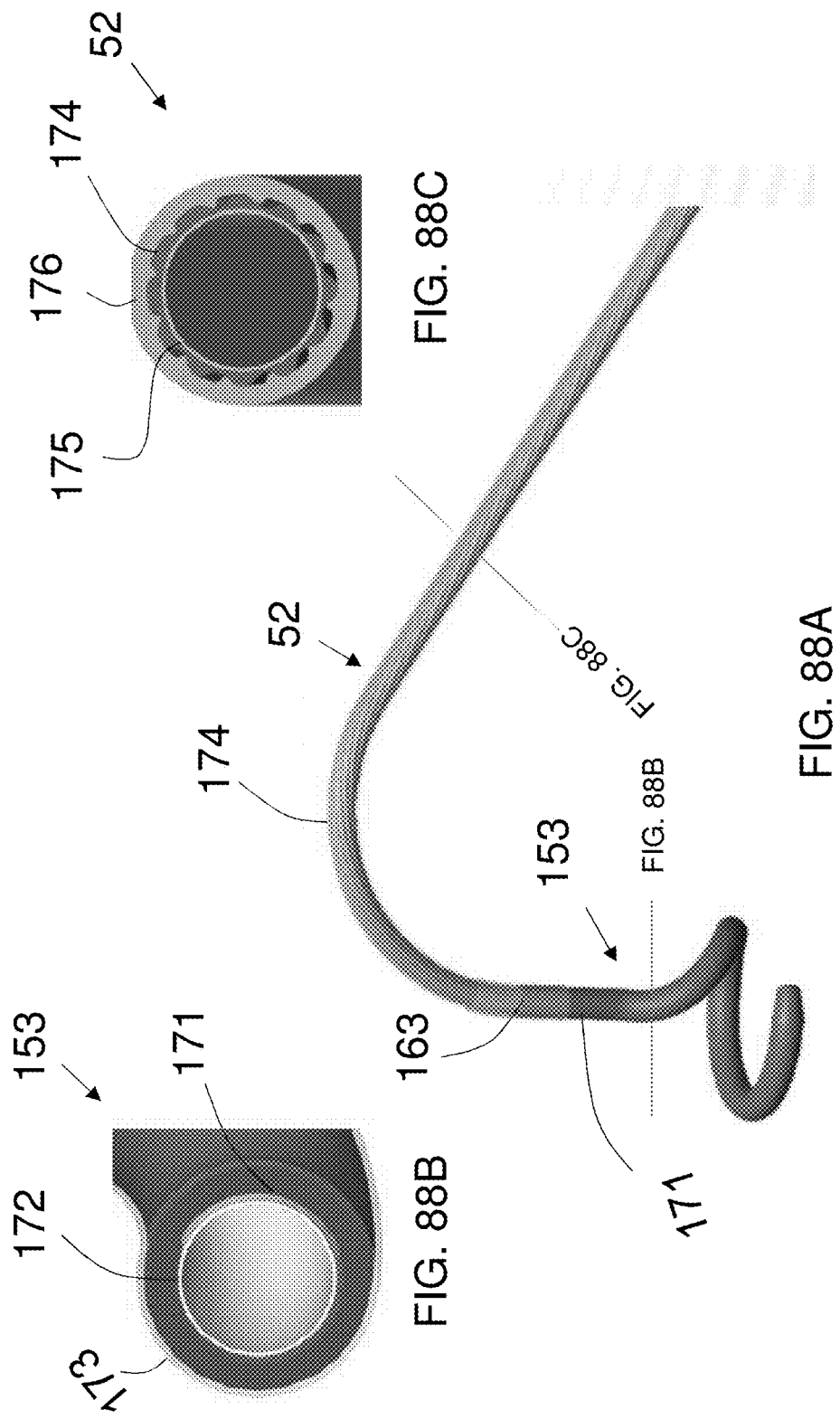

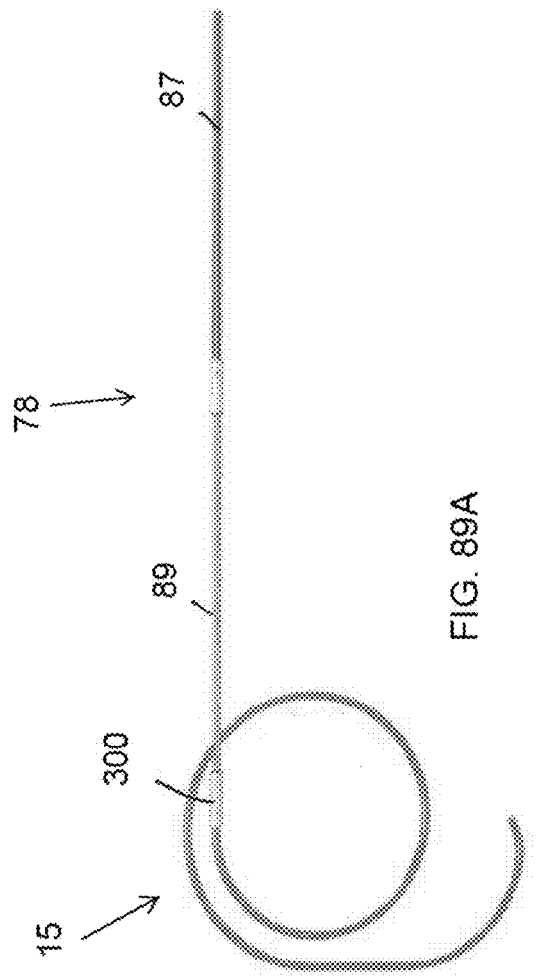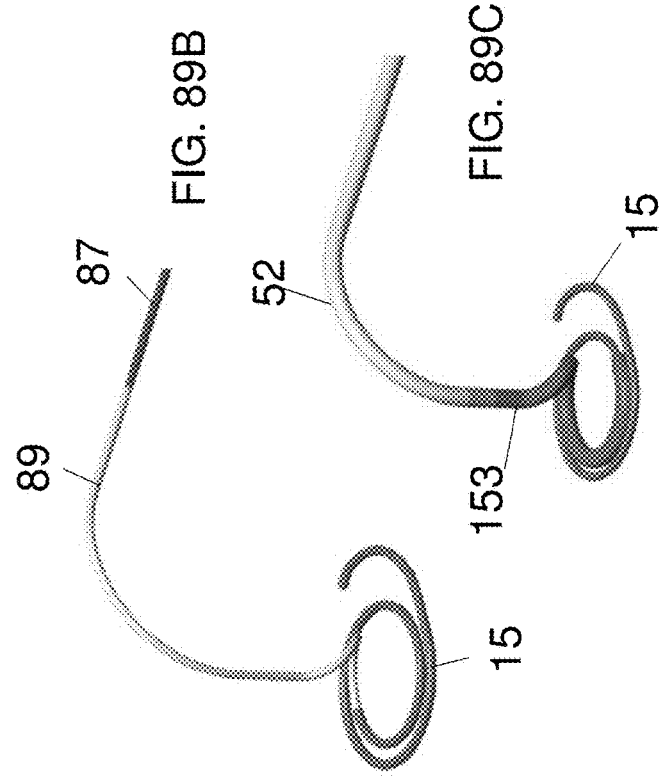

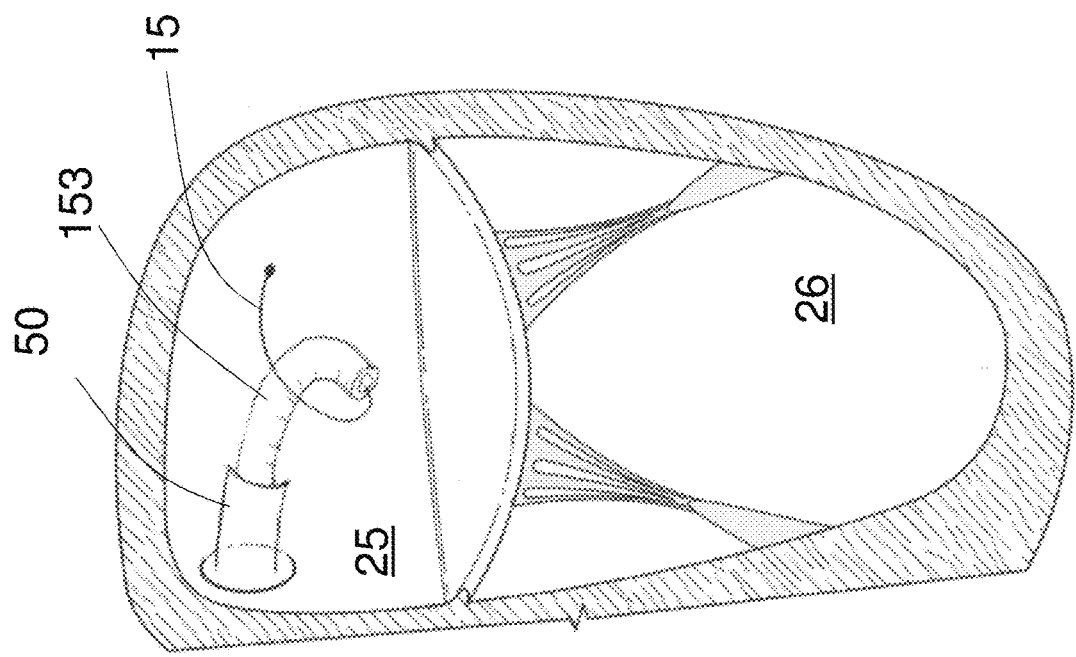
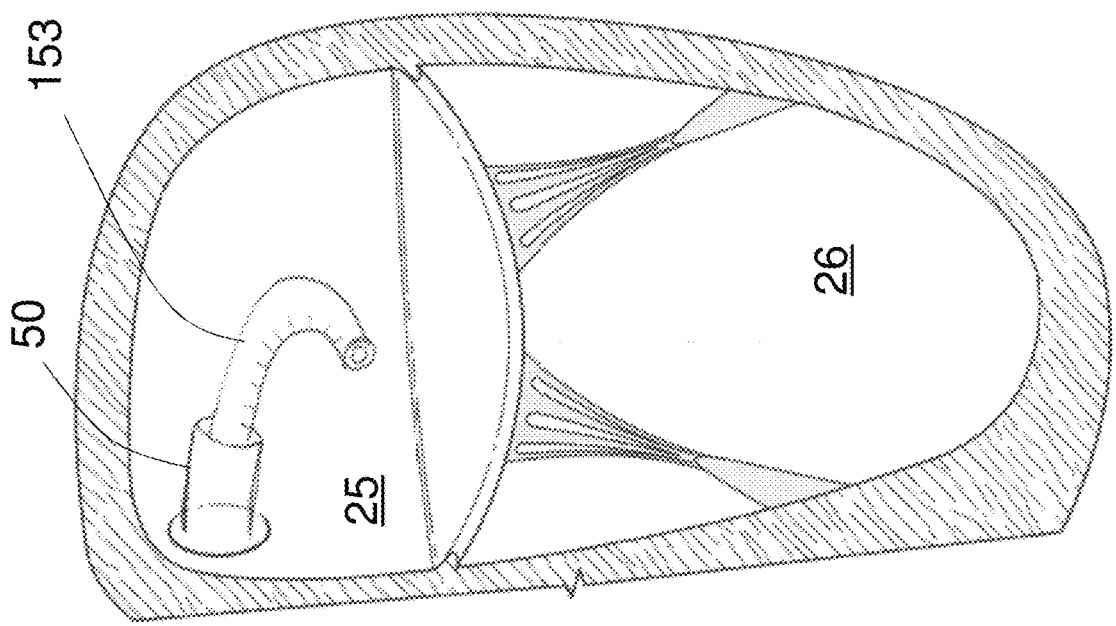
FIG. 90C
FIG. 90D

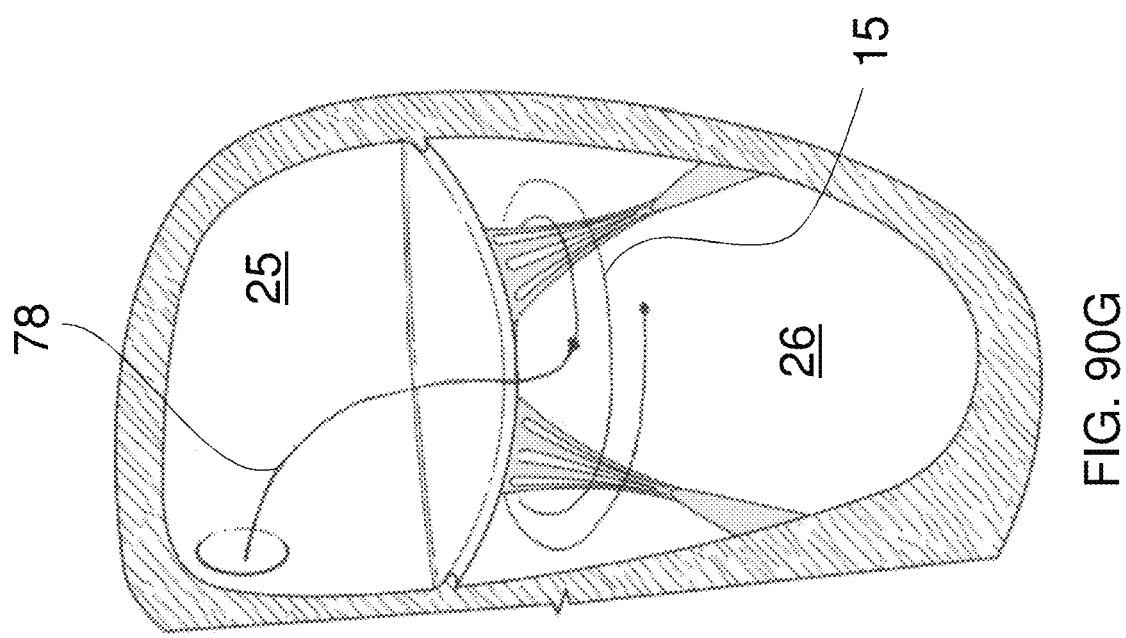

PROSTHETIC CARDIAC VALVE DEVICES, SYSTEMS, AND METHODS

CROSS-REFERENCE TO RELATED APPLICATIONS

This application claims priority to U.S. Provisional Application No. 62/820,570, filed Mar. 19, 2019, entitled "Prosthetic Cardiac Valve Delivery Devices. Systems. and Methods"; U.S. Provisional Application No. 62/828,835, filed Apr. 3, 2019, entitled "Prosthetic Cardiac Valve Devices. Systems. and Methods"; U.S. Provisional Application No. 62/946,602, filed Dec. 11, 2019, entitled "Prosthetic Cardiac Valve Devices, Systems, and Methods"; U.S. Provisional Application No. 62/833,430 filed Apr. 12, 2019, entitled "Prosthetic Cardiac Valve Delivery Devices, Systems, and Methods"; U.S. Provisional Application No. 62/968,909, filed Jan. 31, 2020, entitled "Prosthetic Cardiac Valve Delivery Devices, Systems, and Methods"; U.S. Provisional Application No. 62/872,016, filed Jul. 9, 2019, entitled "Prosthetic Cardiac Valve Delivery Devices, Systems, and Methods"; U.S. Provisional Application No. 62/879,979, filed Jul. 29, 2019, entitled "Prosthetic Cardiac Valve Devices, Systems, and Methods"; U.S. Provisional Application No. 62/984,602, filed Mar. 3, 2020, titled "Prosthetic Cardiac Valve Devices, Systems, and Methods"; the entireties of which are incorporated by reference in their entireties.

This application may also be to U.S. patent application Ser. No. 16/546,901, filed Aug. 21, 2019, entitled "Prosthetic Cardiac Valve Devices, Systems, and Methods; U.S. patent application Ser. No. 16/594,946, filed Oct. 7, 2019, entitled "Prosthetic Cardiac Valve Devices, Systems, and Methods"; International Patent Application No. PCT/US2019/057082, filed Oct. 18, 2019, entitled "Adjustable Medical Device"; U.S. patent application Ser. No. 16/723,537, filed Dec. 20, 2019, entitled "Prosthetic Cardiac Valve Devices, Systems, and Methods"; the entireties of which are incorporated by reference in their entireties.

BACKGROUND

Blood flow between heart chambers is regulated by native valves—the mitral valve, the aortic valve, the pulmonary valve, and the tricuspid valve. Each of these valves are passive one-way valves which open and close in response to differential pressures. Patients with valvular disease have abnormal anatomy and/or function of at least one valve. For example, a valve may suffer from insufficiency, also referred to as regurgitation, when the valve does not fully close and allows blood to flow retrograde. Valve stenosis can cause a valve to fail to open properly. Other diseases may also lead to dysfunction of the valves. While medications may be used to treat the disease, in many cases the defective valve may need to be repaired or replaced at some point during the patient's lifetime. Existing valves and surgical repair and/or replacement procedures may have increased risks, limited lifespans, and/or are highly invasive. Some less-invasive transcatheter options are available, however these generally are limited to aortic valve procedures, are limited in their patient-to-patient flexibility, and often take longer than desired to implant. It would therefore be desirable to provide a less invasive procedure for repair and replacement of heart valves, including the mitral valve, quicker surgical methods, and/or prosthetic valves that can accommodate a variety of individual patients.

Additionally, existing valve repair/replacement procedures are often complicated and time-consuming. Currently available procedures often require the placement of more than one component—for example, a prosthetic valve and a mechanism to anchor it to the native anatomy. Such procedures generally utilize multiple delivery catheters to carry the various components and delivery of each component separately to the valve, which can be time-consuming (particularly if components are delivered sequential), complicated, and/or dangerous. For example, some devices provide rotational anchoring elements to capture the native anatomy such as the chordae tendineae in order to reduce delivery time. However, such anchoring elements, often by design, capture and pull the chordae along during their rotation, which can torque or otherwise stress and damage the chordae during deployment of the anchor elements, resulting in the need for additional medical interventions for the patient. Moreover, such anchoring elements may require extrusion from a low-profile (e.g., elongated) delivery configuration to an expanded configuration at or near the native valve. In at least some instances, extrusion of the anchoring elements can be complicated and may not reliably deploy into the correct expanded configuration relative to the delivery device. Incorrect deployment may result in additional time to retract and re-deploy the anchoring element, more complicated anchoring procedures, and/or damage to the native tissue. It would therefore be desirable to provide quicker, less-complicated, less dangerous, and more reliably deployable valve assemblies for valvular replacement and repair.

SUMMARY

The present disclosure generally relates to treating a diseased native valve in a patient and more particularly relates to prosthetic heart valves.

The present disclosure relates to prosthetic cardiac devices, and in some embodiments, prosthetic heart valves such as catheter-based mitral valves.

The present disclosure generally relates to treating a diseased native valve in a patient and more particularly relates to deployment of prosthetic heart valves and extrusion of anchoring elements from delivery devices.

The present disclosure generally relates to treating a diseased native valve in a patient and more particularly relates to delivery devices, systems, and methods for delivering and deploying a valve prosthesis. The valve prosthesis can include a spiral anchor and a frame structure adjacent the diseased native valve, and the spiral anchor can be deployed around one or more structures of the heart. The anchor can be configured to anchor the frame structure to the native valve when the frame structure is expanded therein.

In general, in one embodiment, a system for treating a diseased native valve in a patient includes an anchor and a tether. The anchor includes a delivery configuration and deployed configuration. The anchor in the deployed configuration is shaped to encircle chordae or leaflets of a diseased native valve in a patient. The tether is detachably coupled to the anchor and configured to longitudinally translate the anchor within a lumen of a delivery device. The anchor is configured to be actuated from the delivery configuration to the deployed configuration when the anchor is translated out of the lumen of the delivery device.

This and other embodiments can include one or more of the following features. The anchor can be configured to be actuated from the delivery configuration to the deployed configuration adjacent a native valve in a patient. The system can further include the delivery device. The delivery device can include an anchor guide having the lumen. The anchor can be configured to be disposed within the lumen of the anchor guide in the delivery configuration. The anchor can be configured to be actuated out of lumen of the anchor guide into the deployed configuration by the tether. The anchor guide can have a curvature that matches a curvature of the anchor in the deployed configuration. The anchor can include an elongated shape in the delivery configuration. The anchor can include a curved shape in the deployed configuration. The curved shape can include a spiral shape. A distal end of the tether can include a preset curved shape. The system can further include a retention wire configured to couple a distal end of the tether to a proximal end of the anchor. The anchor can be configured to wrap at least partially around a frame structure in the deployed configuration. The anchor can include a super-elastic material. The anchor can include nitinol. The system can further include a frame structure having an unexpanded configuration and an expanded configuration. The expanded configuration can be a generally tubular shape. The frame structure can include an expanded outer periphery in the expanded configuration and a compressed outer periphery when subject to an external radial force in the unexpanded configuration. The compressed outer periphery can be smaller in diameter than the expanded outer periphery. The system of can further include the delivery device which can include an inner shaft. The anchor can be configured to be disposed in a lumen of the inner shaft and maintained in the delivery configuration by radial constriction from the inner shaft. Advancement of the anchor out of the lumen of the inner shaft by translation of the tether can actuate the anchor into the deployed configuration. The tether can be configured to extend from the anchor to a proximal end of the delivery device. The delivery device can further include an outer sheath. The inner shaft can be disposed within the lumen of the outer sheath. The outer sheath can be steerable. The tether can be configured to advance towards an opening of the lumen of the inner shaft to advance the anchor out of the lumen of the inner shaft and actuate the anchor into the deployed configuration. The anchor can be configured to wrap at least partially around the inner shaft in the deployed configuration. A central axis of the anchor can be co-axial with a longitudinal axis of the inner shaft when the anchor is in the deployed configuration. A distal end of the inner shaft can include an anchor guide. The anchor guide can be configured to correctly orient the anchor relative the longitudinal axis of the inner shaft in order to facilitate concentric wrapping of the anchor around the inner shaft as the anchor is deployed from the delivery configuration to the deployed configuration. A distal end of the tether can have a shape corresponding to a shape of the anchor guide. A distal end of the anchor guide can include a preset curved portion. The tether can include a wire disposed in a housing. The housing can be flexible. A free end of the anchor can extend radially outward from the curved shape. The system can further include a frame structure configured for expanding within the native valve of the patient. The system can further include a frame structure. The anchor can be configured to be fully advanced from an atrial side of the native valve into a ventricle of the heart and anchor the frame structure to the native valve when the frame structure is in an expanded configuration adjacent the native valve. An unexpanded configuration of the frame structure can be sized and dimensioned for percutaneous insertion and the expanded configuration is sized and dimensioned for implantation in the native valve of the patient. The frame structure can include a first and second opposite ends. The first end can be configured to extend above a native valve, and the second end can be configured to extend below the native valve when the frame structure is anchored to the native valve. The frame structure can be configured to sit below the native valve when the frame structure is anchored to the native valve. The system of can further include a frame structure, and a valve segment within the frame structure can include a biocompatible one-way valve. At least a portion of the valve segment can be positioned within at least a portion of the frame structure. The valve segment can include at least one leaflet having an inner layer and an outer layer. The frame structure can be attached to the outer layer at one or more ends of the frame structure. The valve segment can include a plurality of leaflets.

In general, in one embodiment, a method for treating a diseased native valve in a patient includes: (1) Advancing a distal end of a delivery device from a first side of a native valve to a second side of the native valve. The delivery device includes an inner shaft which includes an anchor guide, and an anchor is disposed within a lumen of the inner shaft. The anchor includes a delivery configuration and a deployed configuration; (2) Holding the anchor with within the lumen of the inner shaft with a longitudinally-translatable tether. The anchor is detachably coupled to the tether; (3) Actuating the anchor from the delivery configuration to the deployed configuration adjacent the native valve by translating the tether distally within the lumen of the inner shaft to translate the anchor out of an opening in the delivery device; and (4) Rotating a free end of the deployed anchor around one or more structures on the second side of the native valve.

This and other embodiments can include one or more of the following features. Rotating the free end of the deployed anchor can include rotating the anchor with the anchor guide. The method can further include retracting the anchor guide while holding the anchor with the tether. A distal end of the tether can be coupled to a proximal end of the anchor with a retention wire, and the method can further include releasing the anchor from the tether by de-coupling the retention wire from the anchor. The method can further include steering the distal end of the delivery device such that the distal end of the delivery device points towards the first side of the native valve. The anchor can be configured to wrap at least partially around the delivery device in the deployed configuration. The anchor can be configured to wrap at least partially around a frame structure in the deployed configuration. A central axis of the anchor can be co-axial with a longitudinal axis of the inner shaft when the anchor is in the deployed configuration. A distal end of the inner shaft can include the anchor guide. The anchor guide can be configured to correctly orient the anchor relative the longitudinal axis of the inner shaft in order to facilitate concentric wrapping of the anchor around the inner shaft as the anchor is actuated from the delivery configuration to the deployed configuration. Actuating the anchor can include actuating the anchor from the delivery configuration to the deployed configuration on the first side of the native valve and can further include advancing the anchor in the deployed configuration through the native valve to the second side of the native valve. Advancing the anchor can further include pushing the anchor through the native valve. Advancing the anchor can further include rotating the anchor through the native valve. Actuating the anchor can include positioning the anchor such that it is located only on the second side of the native valve. The distal end of the delivery device can be detachably coupled to a frame structure, and the method can further include expanding the frame structure within the native valve from an unexpanded configuration to an expanded configuration. Expanding the frame structure can occur while holding the anchor with the tether. The frame structure can include a first and second opposite ends, and expanding the frame structure can include expanding the frame structure such that the first end extends above the first side of the native valve and the second end extends below second side of the native valve. Expanding the frame structure can include expanding at least a portion the frame structure within at least a portion of the deployed anchor to anchor the frame structure to the native valve. The method can further include releasing the frame structure from the distal end of the delivery device. Expanding the frame structure and releasing the frame structure can occur simultaneously. The method can further include retracting the delivery device from the patient. The method can further include de-coupling the anchor from the tether. The method can further include retracting the tether from the patient. The one or more structures can include one or more valve leaflets of the native valve. The one or more structures can include one or more chordae of the left ventricle. The native valve ca be in a heart of a patient. The method can further include transseptally inserting the distal end of the delivery device into a left atrium of the heart. The native valve can include a mitral valve. The first side of the native valve can include a left atrium. The second side of the native valve can include a left ventricle.

In general, in one embodiment, a delivery system for delivering a prosthesis to a diseased valve includes an outer sheath, an inner shaft, and an anchor guide. The outer sheath has a central axis. The inner shaft is within the outer sheath and is translatable and rotatable relative to the outer sheath. The anchor guide is attached to a distal end of the inner shaft. The anchor guide includes a proximal section that is on-axis with the central axis and a distal section that curves about the central axis in a tapered spiral.

This and other embodiments can include one or more of the following features. The delivery system can further include a tether configured to extend through the inner shaft and anchor guide to attach to an anchor of the prosthesis. The tether can be further configured to deploy the anchor from the anchor guide. The outer sheath can be steerable. The anchor guide can be configured to correctly orient an anchor of the prosthesis relative to a longitudinal axis of the inner shaft in order to facilitate concentric wrapping of the anchor around the inner shaft as the anchor is deployed from the anchor guide. The distal section can transition continuously from a high pitch, low radius curve at a proximal end to a low pitch, high radius curve at a distal end. A distal-most plane of the distal section can be orthogonal to the central axis. A curvature of the distal section can be configured to match a curvature of an anchor of the prosthesis. The inner shaft and the anchor guide can be of unitary construction.

In general, in one embodiment, a delivery system for delivering a prosthesis to a diseased valve includes an outer sheath, an inner shaft, and an anchor guide. The outer sheath has a central axis. The inner shaft is positioned within the outer sheath and is translatable and rotatable relative to the outer sheath. The anchor guide is attached to a distal end of the inner shaft. The anchor guide includes a proximal section that is on-axis with the central axis and a distal section that curves about the central axis. The inner shaft and anchor guide are configured to rotate relative to the outer sheath.

This and other embodiments can include one or more of the following features. The delivery system can further include a tether configured to extend through the inner shaft and anchor guide to attach to an anchor of the prosthesis. The tether can be further configured to deploy the anchor from the anchor guide. The outer sheath can be steerable. The anchor guide can be configured to correctly orient an anchor of the prosthesis relative to a longitudinal axis of the inner shaft in order to facilitate concentric wrapping of the anchor around the inner shaft as the anchor is deployed from the anchor guide. The distal section can transition continuously from a high pitch low radius curve at a proximal end to a low pitch, high radius curve at a distal end. A distal-most plane of the distal section can be orthogonal to the central axis. A curvature of the distal section can be configured to match a curvature of an anchor of the prosthesis. The inner shaft and the anchor guide can be of unitary construction.

In general, in one embodiment, a delivery system for delivering a prosthesis to a diseased valve includes an outer sheath, an inner shaft, and an anchor guide. The outer sheath has a central axis. The inner shaft is positioned within the outer sheath and is translatable and rotatable relative to the outer sheath. The anchor guide is attached to a distal end of the inner shaft. The anchor guide includes a proximal section that is on-axis with the central axis and a distal section that curves about the central axis. A distal end of the anchor guide points in a direction that is orthogonal to the axis of the inner shaft.

This and other embodiments can include one or more of the following features. The delivery system can further include a tether configured to extend through the inner shaft and anchor guide to attach to an anchor of the prosthesis. The tether can be further configured to deploy the anchor from the anchor guide. The outer sheath can be steerable. The anchor guide can be configured to correctly orient an anchor of the prosthesis relative to a longitudinal axis of the inner shaft in order to facilitate concentric wrapping of the anchor around the inner shaft as the anchor is deployed from the anchor guide. The distal section can transition continuously from a high pitch, low radius curve at a proximal end to a low pitch, high radius curve at a distal end. A distal-most plane of the distal section can be orthogonal to the central axis. A curvature of the distal section can be configured to match a curvature of an anchor of the prosthesis. The inner shaft and the anchor guide can be of unitary construction.

In general, in one embodiment, a method for treating a diseased native valve in a patient includes: (1) Advancing a distal end of a delivery device into a first chamber of a heart. The delivery devices includes an outer sheath and an inner shaft including an anchor guide; (2) Extending the anchor guide out of the outer sheath into the first chamber; (3) Rotating the inner shaft within the outer sheath until the anchor guide is in a desired orientation in the first chamber; (4) Extending an anchor out of a distal end of the anchor guide such that the anchor deploys within the first chamber; (5) moving the delivery device and the deployed anchor into a second chamber of the heart through a native valve annulus; and (6) Rotating the inner shaft within the outer sheath so as to rotate the anchor guide within the second chamber and so as to rotate the deployed anchor about one or more native valve structures.

This and other embodiments can include one or more of the following features. The method can further include retracting the anchor guide while holding the anchor with a tether of the delivery system. A distal end of the tether can be coupled to a proximal end of the anchor with a retention wire, and the method can further include releasing the anchor from the tether by de-coupling the retention wire from the anchor. The method can further include steering the outer sheath such that the distal end of the delivery device points towards the first chamber. The method can further include steering the outer sheath while moving the delivery device and the deployed anchor into the second chamber of the heart. The anchor can be configured to wrap at least partially around the delivery device when the anchor is deployed. A central axis of the anchor can be co-axial with a longitudinal axis of the inner shaft when the anchor is in the deployed configuration. The anchor guide can be configured to correctly orient the anchor relative the longitudinal axis of the inner shaft in order to facilitate concentric wrapping of the anchor around the inner shaft as the anchor is actuated from the delivery configuration to the deployed configuration. The method can further include expanding a frame structure within the native valve from an unexpanded configuration to an expanded configuration. Expanding the frame structure can occur while holding the anchor with the tether. The frame structure can include a first and second opposite ends. Expanding the frame structure can include expanding the frame structure such that the first end extends into the first chamber and the second end extends into the second chamber. Expanding the frame structure can include expanding at least a portion the frame structure within at least a portion of the deployed anchor to anchor the frame structure to the native valve. The one or more structures can include one or more valve leaflets of the native valve. The one or more structures can include one or more chordae of the left ventricle. The method can further include transseptally inserting the distal end of the delivery device into the first chamber. The method can further include counter-rotating the anchor guide to reposition the anchor prior to rotating the anchor guide within the outer sheath so as to rotate the deployed anchor about one or more native valve structures.

In general, in one embodiment, a system for treating a diseased native valve in a patient includes a valve prosthesis and a delivery device. The valve prosthesis includes an anchor and a frame. The delivery device includes an outer sheath, an inner shaft, an anchor guide, and a tether. The anchor has a delivery configuration and deployed configuration. The anchor in the deployed configuration is shaped to encircle chordae or leaflets of a diseased native valve in a patient. The frame is configured to sit within the anchor. The inner shaft is positioned within the outer sheath and is translatable and rotatable relative to the outer sheath. The anchor guide is attached to a distal end of the inner shaft and has a curved distal section. The tether is configured to detachably couple to the anchor and to longitudinally translate the anchor within the inner shaft and anchor guide. The anchor is configured to be actuated from the delivery configuration to the deployed configuration when the anchor is translated out of the anchor guide.

In a another aspect, a system for treating a diseased native valve in a patient is provided. The system comprises an anchor comprising a delivery configuration and deployed configuration and a tether detachably coupled to the anchor and configured to longitudinally translate the anchor within a lumen of a delivery device. The anchor in the deployed configuration is shaped to encircle chordae or leaflets of a diseased native valve in a patient. The anchor is configured to be actuated from the delivery configuration to the deployed configuration when the anchor is translated out of the lumen of the delivery device.

In some embodiments, the anchor may be configured to be actuated from the delivery configuration to the deployed configuration adjacent a native valve in a patient.

In some embodiments, the delivery device may comprise an anchor guide having the lumen, the anchor may be configured to be disposed within the lumen of the anchor guide in the delivery configuration, and the anchor may be configured to be actuated out of lumen of the anchor guide into the deployed configuration by the tether. The tether may be configured to extend out of the anchor guide when the anchor is in the deployed configuration.

In some embodiments, the system may further comprise a core wire disposed within a lumen of the anchor and longitudinally translatable therein. The core wire may comprise a proximal curved portion when unconstrained and a distal tip. The core wire may comprise one or more deflection features disposed adjacent the distal tip and configured to be advanced out of the lumen of the anchor.

In some embodiments, the anchor may comprise an elongated shape in the delivery configuration.

In some embodiments, the anchor may comprise a curved shape in the deployed configuration. In some embodiments, the curved shape may comprise a helical shape. In some embodiments, the curved shape may comprise a spiral shape.

In some embodiments, a distal end of the tether may comprise a curved shape that is discontinuous with the curved shape of the anchor.

In some embodiments, the system may further comprise an engagement wire configured to couple a distal end of the tether to a proximal end of the anchor.

In some embodiments, the anchor may be configured to wrap at least partially around a frame structure in the deployed configuration.

In some embodiments, the anchor may comprise a superelastic material. For example, the anchor may comprise nitinol.

In some embodiments, the system may further comprise a frame structure having an unexpanded configuration and an expanded configuration. The frame structure may comprise an expandable stent. In some embodiments, the expanded configuration may be a generally tubular expanded shape. In some embodiments, the frame structure may comprise an expanded outer periphery in the expanded configuration and a compressed outer periphery when subject to an external radial force in the unexpanded configuration, the compressed outer periphery may be smaller in diameter than the expanded outer periphery. In some embodiments, the frame structure may be balloon-expandable. In some embodiments, the frame structure may be self-expanding.

In some embodiments, the system may further comprise a delivery device. The delivery device may comprise an inner sheath and the anchor may be disposed in a lumen of the inner sheath and maintained in the delivery configuration by radial constriction from the inner sheath. Advancement of the anchor out of the lumen of the inner sheath by translation of the tether may actuate the anchor into the deployed configuration.

In some embodiments, the tether may extend from the anchor to a proximal end of the delivery device.

In some embodiments, the delivery device may further comprise an outer shaft and the inner shaft may be disposed within the lumen of the outer sheath. The outer sheath may be steerable.

In some embodiments, advancement of the tether towards an opening of the lumen of the inner shaft may advance the anchor out of the lumen of the inner shaft and actuate the anchor into the deployed configuration.

In some embodiments, the anchor may be configured to wrap at least partially around the inner shaft in the deployed configuration. Alternatively, or in combination, a central axis of the anchor is co-axial with a longitudinal axis of the inner shaft when the anchor is in the deployed configuration.

In some embodiments, the tether may be configured to extend out of the lumen of the inner shaft when the anchor is in the deployed configuration.

In some embodiments, a distal end of the inner shaft may comprise an anchor guide. In some embodiments, the tether may be configured to extend out of a lumen of the anchor guide when the anchor is in the deployed configuration. In some embodiments, the anchor guide may be configured to correctly orient the anchor relative the longitudinal axis of the inner shaft in order to facilitate concentric wrapping of the anchor around the inner shaft as the anchor is deployed from the delivery configuration to the deployed configuration. In some embodiments, a distal end of the tether may have a shape corresponding to a shape of the anchor guide. Alternatively, or in combination, a distal end of the anchor guide may comprise one or more deflection features. The one or more deflection features may be configured to interact with an opening of an outer shaft of the delivery device and cause deflection of the distal portion of the anchor guide when the inner shaft is advanced out of a lumen of the outer shaft, thereby facilitating positioning of the anchor relative to the outer shaft during actuation from the delivery configuration to the deployed configuration.

In some embodiments, the system may further comprise a frame structure. Expansion of the frame structure to an expanded configuration may detach the frame structure from the delivery device.

In some embodiments, a free end of the anchor may comprise an atraumatic tip.

In some embodiments, a free end of the anchor may comprise a ball tip.

In some embodiments, a free end of the anchor may comprise a loop.

In some embodiments, a free end of the anchor may be configured for piercing tissue.

In some embodiments, the anchor may comprise a spiral wire.

In some embodiments, the tether may comprise a wire disposed in a housing. The housing may be flexible.

In some embodiments, a free end of the anchor may extend radially outward from the curved shape.

In some embodiments, the system may further comprise a frame structure configured for expanding within the native valve of the patient.

In some embodiments, the system may further comprise a frame structure. The anchor may be configured to be fully advanced from an atrial side of the native valve into a ventricle of the heart and anchor the frame structure to the native valve when the frame structure is in an expanded configuration adjacent the native valve. In some embodiments, an unexpanded configuration of the frame structure may be sized and dimensioned for percutaneous insertion and the expanded configuration is sized and dimensioned for implantation in the native valve of the patient. In some embodiments, the frame structure may comprise a first and second opposite ends, the first end extending above a native valve and the second end extending below the native valve when the frame structure is anchored to the native valve. In some embodiments, the frame structure may sit below the native valve when the frame structure is anchored to the native valve.

In some embodiments, the system may further comprise a frame structure and a valve segment within the frame structure comprising a biocompatible one-way valve. In some embodiments, at least a portion of the valve segment may be positioned within at least a portion of the frame structure. In some embodiments, the valve segment may comprise at least one leaflet having an inner layer and an outer layer, and the frame structure may be attached to the outer layer at one or more ends of the frame structure. In some embodiments, the valve segment may comprise a plurality of leaflets.

In another aspect, a method for treating a diseased native valve in a patient is provided. The method comprises a) advancing a distal end of a delivery device from a first side of a native valve to a second side of the native valve, wherein the delivery device comprises an inner shaft comprising an anchor guide, wherein an anchor comprising a delivery configuration and a deployed configuration is disposed within a lumen of the inner shaft; b) holding the anchor with within the lumen of the inner shaft with a longitudinally-translatable tether, wherein the anchor is detachably coupled to the tether; c) actuating the anchor from the delivery configuration to the deployed configuration adjacent the native valve by translating the tether distally within the lumen of the inner shaft to translate the anchor out of an opening in the delivery device; and d) rotating a free end of the deployed anchor around one or more structures on the second side of the native valve.

In some embodiments, rotating the free end of the deployed anchor may comprise rotating the anchor with the anchor guide. Optionally, a proximal end of the anchor may coupled to the anchor guide and rotating the anchor may comprise rotating the anchor guide.

In some embodiments, the method may further comprise retracting the anchor guide while holding the anchor with the tether.

In some embodiments, a distal end of the tether may have a curve shape that is discontinuous with a curved shape of the anchor.

In some embodiments, a distal end of the tether may be coupled to a proximal end of the anchor with an engagement wire. The method may further comprise releasing the anchor from the tether by de-coupling the engagement wire from the anchor.

In some embodiments, the method may further comprise steering the distal end of the delivery device such that the distal end of the delivery device points towards the first side of the native valve.

In some embodiments, the anchor may be configured to wrap at least partially around the delivery device in the deployed configuration.

In some embodiments, the anchor may be configured to wrap at least partially around a frame structure in the deployed configuration.

In some embodiments, a central axis of the anchor may be co-axial with a longitudinal axis of the inner shaft when the anchor is in the deployed configuration.

In some embodiments, a distal end of the inner shaft may comprise the anchor guide.

In some embodiments, the anchor guide may be configured to correctly orient the anchor relative the longitudinal axis of the inner shaft in order to facilitate concentric wrapping of the anchor around the inner shaft as the anchor is actuated from the delivery configuration to the deployed configuration.

In some embodiments, a distal end of the tether may have a shape corresponding to a shape of the anchor guide.

In some embodiments, a distal portion of the anchor guide may comprise one or more deflection features. The one or more deflection features may be configured to interact with an opening of an outer shaft of the delivery device and cause deflection of the distal portion of the anchor guide when the inner shaft is advanced out of a lumen of the outer shaft, thereby facilitating positioning of the anchor relative to the outer shaft during actuation from the delivery configuration to the deployed configuration.

In some embodiments, the tether may comprise a wire disposed in a flexible housing.

In some embodiments, actuating the anchor may comprise actuating the anchor from the delivery configuration to the deployed configuration on the first side of the native valve and advancing the anchor in the deployed configuration through the native valve to the second side of the native valve. In some embodiments, advancing the anchor comprises pushing the anchor through the native valve. Advancing the anchor may further comprise rotating the anchor through the native valve.

In some embodiments, actuating the anchor may comprise positioning the anchor such that it is located only on the second side of the native valve.

In some embodiments, the distal end of the delivery device may be detachably coupled to a frame structure. The method may further comprise expanding the frame structure within the native valve from an unexpanded configuration to an expanded configuration. Expanding the frame structure occurs while holding the anchor with the tether. In some embodiments, the frame structure may comprise a first and second opposite ends and wherein the frame structure may comprise expanding the frame structure such that the first end extends above the first side of the native valve and the second end extends below second side of the native valve. Alternatively. or in combination, expanding the frame structure may comprise expanding at least a portion the frame structure within at least a portion of the deployed anchor to anchor the frame structure to the native valve. In some embodiments, the method may further comprise releasing the frame structure from the distal end of the delivery device. In some embodiments, expanding the frame structure and releasing the frame structure may occur simultaneously. In some embodiments, the frame structure may be balloon-expandable and expanding the frame structure may comprise inflating a balloon disposed within the frame structure, wherein inflation of the balloon causes expansion of the frame structure. In some embodiments, the frame structure may be self-expanding and expanding the frame structure may comprise releasing the frame structure from radial constriction by the delivery device. In some embodiments, the frame structure may comprise a valve segment therewithin comprising a biocompatible one-way valve.

In some embodiments, the method may further comprise retracting the delivery device from the patient.

In some embodiments, the method may further comprise de-coupling the anchor from the tether. In some embodiments, the method may further comprise retracting the tether from the patient.

In some embodiments, the one or more structures may comprise one or more valve leaflets of the native valve. Alternatively, or in combination, the one or more structures may comprise one or more chordae of the left ventricle.

In some embodiments, a free end of the anchor may comprise an atraumatic tip. In some embodiments, a free end of the anchor may comprise a ball tip. In some embodiments, a free end of the anchor may comprise a loop.

In some embodiments, a free end of the anchor may be configured for piercing tissue.

In some embodiments, a free end of the anchor may extend radially outward from the curved shape. In some embodiments, the curved shape may be a spiral shape.

In some embodiments, the native valve may be in a heart of a patient. The method may further comprise transseptally inserting the distal end of the delivery device into a left atrium of the heart. In some embodiments, the native valve may comprise a mitral valve, the first side of the native valve may comprise a left atrium, and the second side of the native valve may comprise a left ventricle.

Another aspect of the present disclosure provides a system for treating a diseased native valve in a patient. The system comprises a frame structure having an unexpanded configuration and an expanded configuration and an anchor comprising a coiled wire having a free end and a coiled shape. The anchor comprises a delivery configuration and a deployed configuration. The anchor is configured to be actuated from the delivery configuration to the deployed configuration adjacent a native valve in a patient, The anchor comprises one or more deflection features disposed along the coiled wire. The one or more deflection features comprise one or more kinks along the coiled wire such that at least a first portion of the coiled wire is discontinuous with the coiled shape of the coiled wire.

In some embodiments, the one or more deflection features may be configured to cause deflection of the free end when the anchor is actuated from the delivery configuration to the deployed configuration.

In some embodiments, a proximal end of the anchor may be coupled to a distal end of the frame structure.

In some embodiments, the anchor may comprise an elongated shape in the delivery configuration.

In some embodiments, the anchor may comprise a helical shape in the deployed configuration.

In some embodiments, the anchor may comprise a spiral shape in the deployed configuration.

In some embodiments, the one or more deflection features may comprise one or more pre-formed waves, bends, and/or humps in the coiled wire. For example, the one or more deflection features may comprise a plurality of waves. Alternatively. or in combination, the coiled wire may comprise a plurality of loops and the one or more deflection features may comprise a plurality of waves, each loop comprising a single wave. In some embodiments, the first portion may comprise the free end and the one or more deflection features may comprise a bend near a distal end of the coiled wire such that the free end of the coiled wire is positioned adjacent one or more loops of the coiled wire in the deployed configuration. Alternatively, or in combination, the first portion may comprise the free end and the one or more deflection features may comprise a bend near a free end of the coiled wire such that the free end of the coiled wire angles towards a proximal end of the coiled wire in the deployed configuration.

In some embodiments, the coiled wire may be configured to wrap at least partially around the frame structure in the deployed configuration.

In some embodiments, the anchor may comprise a superelastic material. For example, the anchor may comprise nitinol.

In some embodiments, the frame structure may comprise an expandable stent.

In some embodiments, the expanded configuration may be a generally tubular expanded shape.

In some embodiments, the frame structure may comprise an expanded outer periphery in the expanded configuration and a compressed outer periphery when subject to an external radial force in the unexpanded configuration. The compressed outer periphery may be smaller in diameter than the expanded outer periphery.

In some embodiments, the frame structure may be balloon-expandable.

In some embodiments, the frame structure may be self-expanding.

In some embodiments, the device may further comprise a delivery device. The delivery device may comprise an outer sheath. The anchor may be disposed in a lumen of the outer sheath and maintained in the delivery configuration by radial constriction from the outer sheath. Advancement of the anchor out of the lumen of the outer sheath may actuate the anchor into the deployed configuration. The one or more deflection features disposed along the coiled wire may deflect the free end of the coiled wire as they move past an opening of the lumen of the outer sheath during actuation of the anchor from the delivery configuration to the deployed configuration. In some embodiments, the outer sheath may be steerable.

In some embodiments, the delivery device may further comprise an inner shaft. The inner shaft may be disposed within the lumen of the outer sheath. A proximal portion of the frame structure or a proximal end of the anchor may be coupled to a distal portion of the inner shaft. Advancement of the inner shaft towards an opening of the lumen of the outer sheath may advance the anchor out of the lumen of the outer shaft and may actuate the anchor into the deployed configuration. Alternatively, or in combination, the frame structure may be maintained in the unexpanded configuration by radial constriction from the outer sheath and advancement of the inner shaft out of the lumen of the outer sheath may actuate the frame structure into the expanded configuration. In some embodiments, the coiled wire may be configured to wrap at least partially around the inner shaft in the deployed configuration. Alternatively, or in combination, a central axis of the coiled wire may be co-axial with a longitudinal axis of the inner shaft when the coiled wire is in the deployed configuration. In some embodiments, the frame structure may be detachably coupled to the delivery device in the unexpanded configuration during delivery to the native valve. Expansion of the frame structure to the expanded configuration may detach the frame structure from the delivery device.

In some embodiments, the free end may comprise an atraumatic tip. For example, the free end may comprise a ball tip.

In some embodiments, the free end may be configured for piercing tissue.

In some embodiments, the coiled wire may comprise a spiral wire.

In some embodiments, the coiled wire may comprise a helical wire. Optionally, the anchor may comprise a first portion comprising the helical wire and another portion. Alternatively, or in combination, the anchor may comprise a plurality of helical wires. For example, the anchor may comprise at least two helical wires having different diameters. Alternatively, or in combination, the anchor may comprise at least two helical wires having different winding pitches. In some embodiments, the helical wire may have a generally tubular shape. The free end of the helical wire may extend radially outward from the tubular shape. In some embodiments, the helical wire may have a generally frustoconical shape. The free end of the helical wire may extend radially outward from the frustoconical shape. In some embodiments, the helical wire may have a generally cylindrical shape. The free end of the helical wire may extend radially outward from the cylindrical shape.

In some embodiments, the frame structure may be configured for expanding within the native valve of the patient.

In some embodiments, the anchor may be configured to be fully advanced from an atrial side of the native valve into a ventricle of the heart and anchor the frame structure to the native valve when the frame structure is in the expanded configuration adjacent the native valve. The unexpanded configuration may be sized and dimensioned for percutaneous insertion and the expanded configuration may be sized and dimensioned for implantation in the native valve of the patient. The frame structure may comprise a first and second opposite ends, the first end extending above a native valve and the second end extending below the native valve when the frame structure is anchored to the native valve. Alternatively, the frame structure may sit entirely below the native valve when the frame structure is anchored to the native valve.

In some embodiments, the device may further comprise a valve segment within the frame structure comprising a biocompatible one-way valve. At least a portion of the valve segment may be positioned within at least a portion of the frame structure. In some embodiments, the valve segment may comprise at least one leaflet having an inner layer and an outer layer, and the frame structure may be attached to the outer layer at one or more ends of the frame structure. The valve segment may comprise a plurality of leaflets.

Another aspect of the present disclosure provides a system for treating a diseased native valve in a patient. The system comprises a frame structure having an unexpanded configuration and an expanded configuration, an anchor comprising a coiled wire having a free end, and an outer sheath comprising a lumen and an opening. The anchor comprises a delivery configuration when disposed within the lumen of the outer sheath and a deployed configuration when advanced out of the lumen of the outer sheath. The anchor comprises one or more deflection features disposed along the coiled wire and configured to interact with the outer sheath and cause deflection of the free end when the anchor is advanced out of the lumen of the outer sheath through the opening to actuate the anchor from the delivery configuration to the deployed configuration. The anchor is configured to be actuated from the delivery configuration to the deployed configuration adjacent a native valve in a patient.

In some embodiments, the one or more deflection features may be configured to cause deflection of the free end when the anchor is actuated from the delivery configuration to the deployed configuration.

In some embodiments, a proximal end of the anchor may be coupled to a distal end of the frame structure.

In some embodiments, the anchor may comprise an elongated shape in the delivery configuration.

In some embodiments, the anchor may comprise a helical shape in the deployed configuration.

In some embodiments, the anchor may comprise a spiral shape in the deployed configuration.

In some embodiments, the one or more deflection features may comprise one or more pre-formed waves, bends, and/or humps in the coiled wire. For example, the one or more deflection features may comprise a plurality of waves. Alternatively, or in combination, the coiled wire may comprise a plurality of loops and the one or more deflection features may comprise a plurality of waves, each loop comprising a single wave. In some embodiments, the first portion may comprise the free end and the one or more deflection features may comprise a bend near a distal end of the coiled wire such that the free end of the coiled wire is positioned adjacent one or more loops of the coiled wire in the deployed configuration. Alternatively, or in combination, the first portion may comprise the free end and the one or more deflection features may comprise a bend near a free end of the coiled wire such that the free end of the coiled wire angles towards a proximal end of the coiled wire in the deployed configuration.

In some embodiments, the coiled wire may be configured to wrap at least partially around the frame structure in the deployed configuration.

In some embodiments, the anchor may comprise a super-elastic material. For example, the anchor may comprise nitinol.

In some embodiments, the frame structure may comprise an expandable stent.

In some embodiments, the expanded configuration may be a generally tubular expanded shape.

In some embodiments, the frame structure may comprise an expanded outer periphery in the expanded configuration and a compressed outer periphery when subject to an external radial force in the unexpanded configuration. The compressed outer periphery may be smaller in diameter than the expanded outer periphery.

In some embodiments, the frame structure may be balloon-expandable.

In some embodiments, the frame structure may be self-expanding.

In some embodiments, the anchor may be disposed in a lumen of the outer sheath and maintained in the delivery configuration by radial constriction from the outer sheath. Advancement of the anchor out of the lumen of the outer sheath may actuate the anchor into the deployed configuration. The one or more deflection features disposed along the coiled wire may deflect the free end of the coiled wire as they move past an opening of the lumen of the outer sheath during actuation of the anchor from the delivery configuration to the deployed configuration. In some embodiments, the outer sheath may be steerable.

In some embodiments, the system may further comprise an inner shaft. The inner shaft may be disposed within the lumen of the outer sheath. A proximal portion of the frame structure or a proximal end of the anchor may be coupled to a distal portion of the inner shaft. Advancement of the inner shaft towards an opening of the lumen of the outer sheath may advance the anchor out of the lumen of the outer shaft and may actuate the anchor into the deployed configuration. Alternatively, or in combination, the frame structure may be maintained in the unexpanded configuration by radial constriction from the outer sheath and advancement of the inner shaft out of the lumen of the outer sheath may actuate the frame structure into the expanded configuration. In some embodiments, the coiled wire may be configured to wrap at least partially around the inner shaft in the deployed configuration. Alternatively, or in combination, a central axis of the coiled wire may be co-axial with a longitudinal axis of the inner shaft when the coiled wire is in the deployed configuration. In some embodiments, the frame structure may be detachably coupled to the delivery device in the unexpanded configuration during delivery to the native valve. Expansion of the frame structure to the expanded configuration may detach the frame structure from the delivery device.

In some embodiments, the free end may comprise an atraumatic tip. For example, the free end may comprise a ball tip.

In some embodiments, the free end may be configured for piercing tissue.

In some embodiments, the coiled wire may comprise a spiral wire.

In some embodiments, the coiled wire may comprise a helical wire. Optionally, the anchor may comprise a first portion comprising the helical wire and another portion. Alternatively, or in combination, the anchor may comprise a plurality of helical wires. For example, the anchor may comprise at least two helical wires having different diameters. Alternatively, or in combination, the anchor may comprise at least two helical wires having different winding pitches. In some embodiments, the helical wire may have a generally tubular shape. The free end of the helical wire may extend radially outward from the tubular shape. In some embodiments, the helical wire may have a generally frustoconical shape. The free end of the helical wire may extend radially outward from the frustoconical shape. In some embodiments, the helical wire may have a generally cylindrical shape. The free end of the helical wire may extend radially outward from the cylindrical shape.

In some embodiments, the frame structure may be configured for expanding within the native valve of the patient.

In some embodiments, the anchor may be configured to be fully advanced from an atrial side of the native valve into a ventricle of the heart and anchor the frame structure to the native valve when the frame structure is in the expanded configuration adjacent the native valve. The unexpanded configuration may be sized and dimensioned for percutaneous insertion and the expanded configuration may be sized and dimensioned for implantation in the native valve of the patient. The frame structure may comprise a first and second opposite ends, the first end extending above a native valve and the second end extending below the native valve when the frame structure is anchored to the native valve. Alternatively, the frame structure may sit entirely below the native valve when the frame structure is anchored to the native valve.

In some embodiments, the device may further comprise a valve segment within the frame structure comprising a biocompatible one-way valve. At least a portion of the valve segment may be positioned within at least a portion of the frame structure. In some embodiments, the valve segment may comprise at least one leaflet having an inner layer and an outer layer, and the frame structure may be attached to the outer layer at one or more ends of the frame structure. The valve segment may comprise a plurality of leaflets.

Another aspect of the present disclosure provides a method for treating a diseased native valve in a patient. The method comprises advancing a distal end of a delivery device from a first side of a native valve to a second side of the native valve, wherein the delivery device comprises an outer sheath comprising an outer sheath comprising a lumen and an opening, wherein the distal end of the delivery device is detachably coupled to an anchor and a frame structure, the anchor comprising a delivery configuration, a deployed configuration, and one or more deflection features disposed along the anchor and configured to deflect a free end of the anchor when the anchor is actuated from the delivery configuration to the deployed configuration; actuating the anchor from the delivery configuration to the deployed configuration adjacent the native valve by (i) advancing the free end of the anchor out of the lumen of the outer sheath through the opening, (ii) deflecting the free end of the anchor by moving the one or more deflection features disposed along the anchor past the opening of the lumen of the outer sheath, and (iii) advancing a remainder of the anchor out of the lumen of the outer shaft through the opening; expanding the frame structure within the native valve from an unexpanded configuration to an expanded configuration; releasing the frame structure from the distal end of the delivery device; and retracting the delivery device from the native valve.

In some embodiments, the method may further comprise steering the distal end of the delivery device such that the distal end of the delivery device points towards the first side of the native valve.

In some embodiments, the anchor may be configured to wrap at least partially around the delivery device in the deployed configuration.

In some embodiments, the anchor may be configured to wrap at least partially around the frame structure in the deployed configuration.

In some embodiments, a central axis of the coiled wire may be co-axial with a longitudinal axis of the inner shaft when the coiled wire is in the deployed configuration.

In some embodiments, actuating the anchor may comprise releasing the frame structure from radial constriction by the delivery device.

In some embodiments, actuating the anchor may comprise actuating the anchor from the delivery configuration to the deployed configuration on the second side of the native valve.

In some embodiments, actuating the anchor may comprise actuating the anchor from the delivery configuration to the deployed configuration on the first side of the native valve and advancing the anchor in the deployed configuration through the native valve to the second side of the native valve. Advancing the anchor may comprise pushing the anchor through the native valve. Alternatively, or in combination, advancing the anchor may comprise rotating the anchor through the native valve.

In some embodiments, actuating the anchor may comprise positioning the anchor such that it is located only on the second side of the native valve.

In some embodiments, the frame structure may comprise a first and second opposite ends and expanding the frame structure may comprise expanding the frame structure such that the first end extends above the first side of the native valve and the second end extends below second side of the native valve.

In some embodiments, expanding the frame structure may comprise expanding at least a portion the frame structure within at least a portion of the deployed anchor to anchor the frame structure to the native valve.

In some embodiments, expanding the frame structure and releasing the frame structure may occur simultaneously.

In some embodiments, the frame structure may be balloon-expandable and expanding the frame structure may comprise inflating a balloon disposed within the frame structure. Inflation of the balloon may cause expansion of the frame structure.

In some embodiments, the frame structure may be self-expanding and expanding the frame structure may comprise releasing the frame structure from radial constriction by the delivery device.

In some embodiments, the anchor may comprise a coiled wire having a free end and the one or more deflection features may comprise one or more pre-formed waves, bends, or humps in the coiled wire. The one or more features may comprise a plurality of waves. For example, the coiled wire may comprise a plurality of loops and the one or more deflection features may comprise a plurality of waves, each loop comprising a single wave. Alternatively, or in combination, the one or more deflection features may comprise a bend near a distal end of the coiled wire such that the free end of the coiled wire is positioned adjacent one or more loops of the coiled wire in the deployed configuration. Alternatively, or in combination, the one or more deflection features may comprise a bend near a free end of the coiled wire such that the free end of the coiled wire angles towards a proximal end of the coiled wire in the deployed configuration.

In some embodiments, the method may further comprise rotating the free end of the deployed anchor around one or more structures on the second side of the native valve. The one or more structures may comprise one or more valve leaflets of the native valve. Alternatively, or in combination, the one or more structures may comprise one or more chordae of the left ventricle.

In some e

In some embodiments, the free end may comprise an atraumatic tip. For example, the free end may comprise a ball tip.

In some embodiments, the free end may be configured for piercing tissue.

In some embodiments, the coiled wire may comprise a spiral wire.

In some embodiments, the coiled wire may comprise a helical wire. Optionally, the anchor may comprise a first portion comprising the helical wire and another portion. Alternatively, or in combination, the anchor may comprise a plurality of helical wires. For example, the anchor may comprise at least two helical wires having different diameters. Alternatively, or in combination, the anchor may comprise at least two helical wires having different winding pitches. In some embodiments, the helical wire may have a generally tubular shape. The free end of the helical wire may extend radially outward from the tubular shape. In some embodiments, the helical wire may have a generally frustoconical shape. The free end of the helical wire may extend radially outward from the frustoconical shape. In some embodiments, the helical wire may have a generally cylindrical shape. The free end of the helical wire may extend radially outward from the cylindrical shape.

In some embodiments, the frame structure may comprise a valve segment therewithin comprising a biocompatible one-way valve.

In some embodiments, the native valve may be in a heart of a patient.

In some embodiments, the method may further comprise transseptally inserting the distal end of the delivery device into a left atrium of the heart.

In some embodiments, the native valve may comprise a mitral valve, wherein the first side of the native valve comprises a left atrium, and wherein the second side of the native valve comprises a left ventricle.

In another aspect, a system for treating a diseased native valve in a patient is provided. The system includes: a delivery device comprising: an outer sheath assembly comprising an outer sheath and a distal end, wherein the outer sheath assembly comprises a lumen, an inner shaft within the lumen of the outer sheath assembly, wherein the inner shaft comprises a lumen, and an anchor delivery sheath comprising a lumen configured to maintain an anchor in a delivery configuration; and a valve prosthesis comprising a frame structure and the anchor configured to have the delivery configuration and a deployed configuration, wherein the anchor comprises a spiral band having a free end, and wherein the frame structure is maintained in the delivery configuration by radial constriction from one or more of the outer sheath or the distal end of the outer sheath assembly In some embodiments, the distal end of the outer sheath assembly can be a soft valve capsule. The soft valve capsule can comprise a cylindrical section and a tapered section. The cylindrical section and the tapered section can comprise a unitary body. The cylindrical section and the tapered section can be permanently attached to one another. The cylindrical section can comprise a flexible material disposed between a proximal ring and a distal ring, wherein the distal ring is attached to the tapered section. The flexible material can comprise a helically wound wire. The flexible material can comprise a series of rings linked by a wire. The cylindrical section and the tapered section can be configured to be separated from one another. The cylindrical section can comprise a flexible material disposed between a first ring and a second ring, wherein the first ring is attached to a proximal end of the flexible material and the second ring is attached to a distal end of the flexible material. The flexible material can further comprise a lumen disposed between a first layer of the flexible material and a second layer of the flexible material.

In some embodiments, the cylindrical section can further comprise a coil wire disposed within the lumen and coupled to the second ring, wherein the coil wire, when translated proximally, is configured to slide the distal ring relative to the proximal ring and collapse the flexible material to separate the cylindrical section from the tapered section. The lumen can comprise an inflatable lumen coupled to the distal ring or the distal end of the flexible material and configured to be deflated in order to collapse the flexible material and separate the cylindrical section from the tapered section. The cylindrical section can be releasably attached to the tapered section.

In some aspects, disclosed herein, the frame structure can be maintained in the delivery configuration by radial constriction from the distal end of the outer sheath assembly, wherein the radial constriction is removed by a separation of the outer sheath from the distal end of the outer sheath assembly. The inner shaft can be coupled to at least a portion of the distal end of the outer sheath assembly such that advancement of the inner shaft distally relative to the outer sheath causes the distal end to separate from the outer sheath. The delivery device can further comprise a guidewire disposed within a lumen of the inner shaft. The anchor can be configured to be released from the delivery configuration into an intermediate configuration and further into a deployed configuration. The anchor can be configured to be released into the intermediate configuration on an atrial side of a valve and subsequently pushed to a ventricle side of the valve. The anchor can be configured to be released into the deployed configuration from the delivery configuration on a ventricle side of a valve. The outer sheath can be configured to be steered to an edge of the valve and advanced along the guidewire into the ventricle side of the valve to position the anchor delivery sheath for delivery of the anchor.

In some embodiments, advancement of the inner shaft out of the lumen of the outer sheath can be configured to expand the frame structure into the expanded configuration. The anchor can comprise a spiral shape in the deployed configuration. The anchor can comprise an elongated shape in the delivery configuration. The anchor can comprise one or more locking mechanisms configured to maintain the anchor in the deployed configuration. The one or more locking mechanisms can comprise a frictional band, a polymer coating, or one or more key and one or more key hole features. The anchor can comprise a first loop, a second loop, and one or more locking mechanisms, and wherein the one or more locking mechanisms are configured to couple the first loop to the second loop when the anchor is in the fully deployed configuration.

In some embodiments, the spiral band can comprise one or more loops. The one or more loops can comprise at least 360 degrees of rotation. The spiral band can comprise a plurality of loops. The spiral band can comprise one or more spaces between the plurality of loops. The plurality of loops can spiral radially outward from a central point.

In some embodiments, the anchor can comprise a superelastic material. The anchor can comprise nitinol. The frame structure can comprise an expandable stent. The expanded configuration can be a generally tubular expanded shape. The frame structure can comprise an expanded outer periphery in the expanded configuration and a compressed outer periphery when subject to an external radial force in the unexpanded configuration, wherein the compressed outer periphery is smaller in diameter than the expanded outer periphery. The frame structure can be balloon-expandable. The frame structure can be self-expanding.

In some embodiments, the free end of the anchor can comprise an atraumatic tip. The free end can comprise a ball tip. The free end can be configured for piercing tissue. The free end can be bent distally. The free end can be bent proximally. The spiral band can comprise a spiral wire. The spiral band can comprise a plurality of spiral wires. The spiral band can comprise a planar spiral band. The spiral band can comprise at least one channel or lumen disposed therein. The spiral band can comprise a hollow spiral band. The at least one channel or lumen can comprise a stiffening member disposed therein. The spiral band can have a circular, tubular, hollow, square, elongated, or triangular cross-section. The spiral band can comprise a tapered spiral band. The tapered spiral band can be configured to taper in height axially.

In some embodiments, the tapered spiral band can be configured to taper from a first end of the tapered spiral band to the free end. The first end can be a proximal end and the free end is a distal end. Subsequent turns of at least a portion of the tapered spiral band nest into each other to reduce a radial footprint of the tapered spiral band. The tapered spiral band can comprise a support structure and a semi-permeable material or impermeable material disposed therein. The semi-permeable material or impermeable material can comprise a webbing material, a fabric, a polymeric material, or an elastomeric material. The free end can be disposed radially outwards from the support structure. The tapered spiral band can further comprise a lumen and a wire disposed within the lumen. The frame structure can be configured for expanding within the native valve of the patient. The unexpanded configuration can be sized and dimensioned for percutaneous insertion and the expanded configuration is sized and dimensioned for implantation in the native valve of the patient.

In some embodiments, the frame structure can comprise a first and second opposite ends, the first end extending above a native valve and the second end extending below the native valve when the frame structure is anchored to the native valve. The frame structure can sit below the native valve when the frame structure is anchored to the native valve.

In some embodiments, the system can further comprise a valve segment within the frame structure comprising a biocompatible one-way valve. At least a portion of the valve segment can be positioned within at least a portion of the frame structure. The valve segment can comprise at least one leaflet having an inner layer and an outer layer, and wherein the frame structure is attached to the outer layer at one or more ends of the frame structure. The valve segment can comprise a plurality of leaflets.

In another aspect, a method for treating a diseased native valve in a patient is provided. The method includes: advancing a distal end of a guidewire from a first side of a native valve to a second side of the native valve; advancing an outer sheath assembly over the guidewire to a native valve; separating a distal end of the outer sheath assembly from an outer sheath of the outer sheath assembly; advancing an anchor delivery sheath from within the outer sheath to deploy an anchor from the anchor delivery sheath; expanding a frame structure of a valve prosthesis within the native valve from an unexpanded configuration to an expanded configuration; securing the anchor to the native valve; and retracting the guidewire from the native valve. Deploying the anchor from the anchor delivery sheath can be followed by advancing the anchor from a first side of the native valve to a second side of the native valve. The first side of the native valve can be the left atrium and the second side of the native valve is the left ventricle.

In some embodiments, the method can further comprise, in (c), separating the distal end of the outer sheath assembly from the outer sheath to release the valve prosthesis from constraint, wherein the valve prosthesis is maintained within one or more of the outer sheath or the distal end of the outer sheath assembly by radial constriction. Separating of the distal end of the outer sheath assembly from the outer sheath can be caused by pushing an inner shaft through a lumen of the outer sheath. The anchor can be deployed from the anchor delivery sheath from a delivery configuration to an intermediate configuration and further into a deployed configuration. The anchor can be released into the intermediate configuration on the first side of the native valve and subsequently pushed to the second side of the native valve. Separating a distal end of the outer sheath assembly from the outer sheath in (c) can be caused by pushing an inner shaft through the lumen of the outer sheath. The outer sheath can be steerable. Advancing the outer sheath assembly over the guidewire to the native valve in (b) can be followed by steering the outer sheath assembly to an edge of the native valve and advancing the distal end of the outer sheath assembly from the first side of the native valve to the second side of the native valve. The outer sheath assembly can be steered to the edge of the native valve to position the anchor delivery sheath for delivery of the anchor.

In some embodiments, the method can further comprise axially separating the distal end of the outer sheath assembly from the outer sheath after the distal end of the outer sheath assembly is located in the second side of the native valve. The anchor can be deployed from the anchor delivery sheath directly into a deployed configuration such that the anchor is wrapped around the chordae tendineae of the native valve. The anchor can be a spiral band. The spiral band can comprise a free end and anchoring can comprise rotating the free end of the anchor around one or more structures of the native valve. The one or more structures can comprise one or more native chordae tendineae of native valve.

In some embodiments, a central point of the spiral band can be co-axial with a longitudinal axis of the delivery device when the spiral band is in the deployed configuration. The valve prosthesis can comprise a valve segment therewithin comprising a biocompatible one-way valve. The native valve can be in a heart of a patient. The method can further comprise transseptally inserting the distal end of the guidewire into a left atrium of the heart. The native valve can comprise a mitral valve, wherein the first side of the native valve comprises a left atrium, and wherein the second side of the native valve comprises a left ventricle. The first side of the native valve can comprise an atrium of the heart, and the second side of the native valve can comprise a ventricle of the heart.

In another aspect, a device for treating a diseased native valve in a patient is provided. The device comprises an anchor comprising an outer jacket, a first lumen disposed within the outer jacket, and a second lumen disposed within the outer jacket. The first lumen is configured to have at least one support structure fixedly disposed therewithin. The second lumen comprises an open lumen configured to allow one or more elongate members to be disposed and longitudinally translatable therein. The anchor comprises a delivery configuration and a deployed configuration. The anchor in the deployed configuration is shaped to encircle chordae or leaflets of a diseased native valve in a patient.

In some embodiments, the anchor may be configured to be actuated from the delivery configuration to the deployed configuration adjacent the native valve.

In some embodiments, the outer jacket may comprise a flexible material. The flexible material may comprise an extruded plastic or a soft textile. The flexible material may comprise polyethylene terephthalate (PET), polytetrafluoroethylene (PTFE), or pericardium.

In some embodiments, the first lumen and the second lumen may comprise a single lumen configured to remain at least partially open when the at least one support structure fixedly is disposed therewithin.

In some embodiments, the anchor may comprise an elongated shape in the delivery configuration.

In some embodiments, the anchor may comprise a curved shape in the deployed configuration. The curved shape may comprise a helical shape. The curved shape may comprise a spiral shape.

In some embodiments, the device may further comprise the at least one support structure fixedly disposed within the first lumen. The at least one support structure may comprise a wire or a hypotube.

In some embodiments, the device may further comprise the one or more elongate members disposed within the second lumen. The one or more elongate members may comprise a first wire configured to be advanced through the second lumen and out an opening in the free end into a self-assembly configuration. A distal tip of the first wire may be configured to extend radially outward, proximally, or distally of a curved shape of the anchor in the self-assembly configuration, thereby facilitating positioning of the anchor relative to a delivery device during actuation from the delivery configuration to the deployed configuration. The first wire comprises may comprise or more deflection features disposed adjacent the distal tip. The one or more deflection features may be configured to interact with the free end of the anchor and cause deflection of the distal tip when the first wire is advanced out of the second lumen of the anchor into the self-assembly configuration such that it extends radially outward, proximally, or distally of the curved shape of the anchor. In some embodiments, the one or more deflection features may comprise one or more pre-formed waves, bends, kinks, or humps adjacent the distal tip of the first wire. In some embodiments, the one or more deflection features may comprise one or more kinks along the distal tip of the first wire such that at least a portion of the distal tip is discontinuous with a curved shape of a proximal curved portion of the first wire.

In another aspect, a system for treating a diseased native valve in a patient is provided. The system comprises an anchor comprising an outer jacket and at least two lumens disposed within the outer jacket, the anchor comprising a delivery configuration and a deployed configuration, at least one support structure fixedly disposed within a first lumen of the at least two lumens, a first wire disposed within a second lumen of the at least two lumens, and a second wire disposed within the second lumen, wherein the first and second wires are configured to be longitudinally translatable independent of one another within the second lumen. The anchor in the deployed configuration is shaped to encircle chordae or leaflets of a diseased native valve in a patient.

In some embodiments, the outer jacket may comprise a flexible material. The flexible material may comprise an extruded plastic or a soft textile. The flexible material may comprise polyethylene terephthalate (PET).

In some embodiments, the first wire or the second wire may comprise a super-elastic material. The first wire or the second wire may comprise nitinol.

In some embodiments, the first wire and the second wire may be disposed within a housing. The housing may be flexible and translation of the first wire and the second wire relative to one another may change the curvature of the housing.

In some embodiments, the first wire and the second wire may be coupled to one another at a distal tip.

In some embodiments, the system may further comprise a third wire.

In some embodiments, the first and second wires may comprise pull wires.

In some embodiments, a distal tip of the first wire or the second wire may be configured to be advanced through the second lumen and out an opening in the free end when the first wire or the second wire is in a self-assembly configuration. The first wire or the second wire may be configured to be further advanced through the second lumen into an encircling configuration. The distal tip of the first wire or the second wire may be configured to extend radially outward, proximally, or distally of a curved shape of the anchor in the self-assembly configuration, thereby facilitating positioning of the anchor relative to a delivery device during actuation from the delivery configuration to the deployed configuration. In some embodiments, the distal tip may comprise an atraumatic tip, for example a ball tip. In some embodiments, the distal tip may be configured for piercing tissue.

In some embodiments, the at least one support structure may comprise a wire or a hypotube.

In some embodiments, the at least one support structure may comprise a super-elastic material such as nitinol.

In some embodiments, the anchor may be configured to wrap at least partially around a frame structure in the deployed configuration.

In some embodiments, the system may further comprise a frame structure having an unexpanded configuration and an expanded configuration. The anchor may be configured to wrap at least partially around the frame structure in the deployed configuration. A proximal end of the anchor may be coupled to a distal end of the frame structure. The frame structure may comprise an expandable stent. The frame structure expanded configuration may be a generally tubular shape. In some embodiments, the frame structure may be self-expanding. In some embodiments, the frame structure may be balloon-expandable. The anchor may be configured to be fully advanced from an atrial side of the native valve into a ventricle of the heart and to anchor the frame structure to the native valve when the frame structure is in the expanded configuration adjacent the native valve. A valve segment may be positioned within at least a portion of the frame structure. The valve segment may comprise a biocompatible one-way valve. The valve segment may comprise at least one leaflet having an inner layer and an outer layer, and the frame structure may be attached to the outer layer at one or more ends of the frame structure. In some embodiments, the valve segment may comprise a plurality of leaflets.

In some embodiments, the system may further comprise a delivery device. The delivery device may comprise an outer sheath and the anchor may be disposed in a lumen of the outer sheath and maintained in the delivery configuration by radial constriction from the outer sheath. Advancement of the anchor out of the lumen of the outer sheath may actuate the anchor into the deployed configuration. A pusher portion of the first wire or second wire may extend from a proximal portion of the anchor to a proximal end of the delivery device. The outer sheath may be steerable. In some embodiments, the system may further comprise a frame structure detachably coupled to the delivery device in an unexpanded configuration during delivery to the native valve. In some embodiments, the system may further comprise a frame structure and expansion of the frame structure to an expanded configuration may detach the frame structure from the delivery device. In some embodiments, the delivery device may further comprise an inner shaft. The inner shaft may be disposed within the lumen of the outer sheath. Advancement of the inner shaft towards an opening of the lumen of the outer sheath may advance the anchor out of the lumen of the outer shaft and actuate the anchor into the deployed configuration. In some embodiments, the system may further comprise a frame structure. The frame structure may be maintained in an unexpanded configuration by radial constriction from the outer sheath and advancement of the inner shaft out of the lumen of the outer sheath may actuate the frame structure into an expanded configuration. The anchor may be configured to wrap at least partially around the inner shaft in the deployed configuration. A central axis of the anchor may be co-axial with a longitudinal axis of the inner shaft when the anchor is in the deployed configuration.

In another aspect, a method for treating a diseased native valve in a patient is provided. The method comprises advancing a distal portion of a delivery device from a first side of a native valve to a second side of the native valve, wherein the distal portion of delivery device is detachably coupled to an anchor, the anchor comprising a delivery configuration, a deployed configuration, an outer jacket, a first lumen disposed within the outer jacket, a free end, and at least one support structure fixedly disposed within the first lumen; actuating the anchor from the delivery configuration to the deployed configuration adjacent the native valve by advancing the free end of the anchor out of the delivery device; and retracting the delivery device from the native valve.

In some embodiments, the anchor may further comprise a second lumen disposed within the outer jacket, the second lumen comprising an open lumen configured to allow one or more elongate members to be disposed and longitudinally translatable therein. The first lumen and the second lumen may comprise a single lumen configured to remain at least partially open when the at least one support structure fixedly is disposed therewithin. In some embodiments, the one or more elongate members may comprise a first wire, and the method may further comprise advancing the first wire through the second lumen and out an opening in the free end. The first wire may comprise one or more deflection features disposed adjacent a distal tip thereof, the one or more defection features may be configured to interact with the free end of the cause deflection of the distal tip when the first wire is advanced out of the second lumen of the anchor into a self-assembly configuration, and the method may further comprise deflecting the distal tip of the first wire by moving the one or more deflection features disposed along the distal tip past the opening of the second lumen into the self-assembly configuration such that it extends radially outward, proximally, or distally of the curved shape of the anchor. In some embodiments, the one or more elongate members may comprise a first wire and a second wire, and the method may further comprise advancing the first wire and the second wire through the second lumen and out an opening in the free end. The first wire and the second wire may be configured to be longitudinally translatable independent of one another. In some embodiments, the first wire and the second wire may be disposed in a housing. The housing may flexible, and the method may further comprise translating the first and second wires relative to one another, thereby changing a curvature of the housing. Alternatively. or in combination, the first wire and the second wire may be coupled to one another at a distal tip, and the method may further comprise translating the first and second wires relative to one another, thereby changing the position of the distal tip. In some embodiments, a third wire may be coupled to the first and second wires at the distal tip. In some embodiments, the method may further comprise deflecting a distal tip of the first wire or second wire into a self-assembly configuration or an encircling configuration. The distal tip of the first wire or second wire to may extend radially outward, proximally, or distally of a curved shape of the anchor in the self-assembly configuration, thereby facilitating positioning of the anchor relative to a delivery device during actuation from the delivery configuration to the deployed configuration. The distal tip may comprise an atraumatic tip, for example a ball tip. The distal tip may be configured for piercing tissue. In some embodiments, the method may further comprise rotating a distal tip of the first wire or second wire in an encircling configuration around one or more structures on the second side of the native valve.

In some embodiments, the method may further comprise rotating the free end of the deployed anchor around one or more structures on the second side of the native valve. The one or more structures may comprise one or more valve leaflets of the native valve. The one or more structures may comprise one or more chordae of the left ventricle.

In some embodiments, the at least one support structure may comprise a wire or a hypotube.

In some embodiments, the method may comprise steering the distal end of the delivery device such that the distal end of the delivery device points towards the first side of the native valve.

In some embodiments, the anchor may be configured to wrap at least partially around the delivery device in the deployed configuration.

In some embodiments, the anchor may be configured to wrap at least partially around a frame structure in the deployed configuration.

In some embodiments, a central axis of the anchor may be co-axial with a longitudinal axis of the distal portion of the delivery device when the anchor is in the deployed configuration. The method may further comprise expanding the frame structure within the native valve from an unexpanded configuration to an expanded configuration. The frame structure may comprise a first and second opposite ends and expanding the frame structure may comprise expanding the frame structure such that the first end extends above the first side of the native valve and the second end extends below second side of the native valve. Expanding the frame structure may comprise expanding at least a portion the frame structure within at least a portion of the deployed anchor to anchor the frame structure to the native valve. The method may further comprise releasing the frame structure from the distal end of the delivery device. Expanding the frame structure and releasing the frame structure may occur simultaneously.

In some embodiments, actuating the anchor may comprise releasing a frame structure detachably coupled to the distal end of the delivery device from radial constriction by the delivery device.

In some embodiments, actuating the anchor may comprise actuating the anchor from the delivery configuration to the deployed configuration on the second side of the native valve.

In some embodiments, actuating the anchor may comprise actuating the anchor from the delivery configuration to the deployed configuration on the first side of the native valve and may further comprise advancing the anchor in the deployed configuration through the native valve to the second side of the native valve. Advancing the anchor may comprise pushing the anchor through the native valve. Advancing the anchor may further comprise rotating the anchor through the native valve.

In some embodiments, the native valve may be in a heart of a patient. The method may further comprise transseptally inserting the distal end of the delivery device into a left atrium of the heart. The native valve may comprise a mitral valve, the first side of the native valve may comprise a left atrium, and the second side of the native valve may comprise a left ventricle.

In another aspect, a system for treating a diseased native valve in a patient is provided. The system comprises an inner shaft and a guidewire comprising a distal end configured to be fully advanced from an atrial side of the native valve into a ventricle of a heart. The inner shaft comprises a lumen. The inner shaft may comprise a guidewire lumen. The inner shaft lumen may comprise an anchor deployment component. The guidewire may be advanceable through the guidewire lumen. A valve prosthesis is coupled to the inner shaft. The valve prosthesis comprises an unexpanded delivery configuration and an expanded configuration. The anchor is coupled to the inner shaft and comprises a spiral band having a free end. The valve prosthesis is configured to be actuated from the unexpanded configuration to the expanded configuration adjacent a native valve in a patient. The anchor is configured to be deployed from an anchor deployment component. The anchor may be configured to be deployed from a lateral opening of the inner shaft. The lateral opening may be a side port of the inner shaft. Alternatively, the anchor deployment component may comprise an anchor drive shaft, deployment drive, and an outer shaft configured to retract along the inner shaft to form the lateral opening. The anchor is configured to secure the valve prosthesis to the native valve when the valve prosthesis is deployed into the expanded configuration adjacent the native valve.

In some embodiments, the anchor may be configured to be fully advanced from an atrial side of the native valve into a ventricle of the heart.

In some embodiments, the anchor comprises a delivery configuration and a deployed configuration. The anchor may comprise a spiral shape in the deployed configuration.

In some embodiments, the anchor is configured to be actuated from the delivery configuration to the deployed configuration adjacent the native valve. The anchor may be configured to be deployed adjacent the native valve.

In some embodiments, the delivery device comprises the inner shaft. The anchor is disposed in the inner shaft and maintained in the delivery configuration by radial constriction from the inner shaft, and wherein advancement of the anchor out of the side port of the inner shaft actuates the anchor into the deployed configuration.

In some embodiments, the valve prosthesis is maintained in the unexpanded configuration by radial constriction from the inner shaft. After the anchor is deployed, advancement of a proximal pusher within the inner shaft deploys the valve prosthesis into the expanded configuration.

In some embodiments, the valve prosthesis is detachably coupled to the proximal pusher in the unexpanded configuration during delivery to the native valve. The expansion of the valve prosthesis to the expanded configuration may detach the valve prosthesis from the proximal pusher.

In some embodiments, the inner shaft is steerable. A central point of the spiral band may be co-axial with a longitudinal axis of the inner shaft when the anchor is in the deployed configuration. In some embodiments, the spiral band comprises a one or more loops. The one or more loops may comprise at least 360 degrees of rotation. The spiral band may comprise a plurality of loops. There may be one or more spaces between the plurality of loops.

In some embodiments, the anchor comprises a super-elastic material. In some embodiments, the anchor comprises nitinol.

In some embodiments, the valve prosthesis comprises an expandable frame structure. The expanded configuration may be a generally tubular expanded shape. The valve prosthesis may comprise an expanded outer periphery in the expanded configuration and a compressed outer periphery when subject to an external radial force in the unexpanded configuration, wherein the compressed outer periphery is smaller in diameter than the expanded outer periphery.

In some embodiments, the valve prosthesis may be balloon-expandable or, alternatively, may be self-expanding.

In some embodiments, the free end of the anchor comprises an atraumatic tip, such as a ball tip. In other embodiments, the free end of the anchor is configured for piercing tissue. Alternatively, or in combination, the free end of the anchor may be bent distally. In some embodiments, the free end of the anchor may be bent proximally.

In some embodiments, the spiral band comprises a spiral wire or a plurality of spiral wires. In some embodiments, the spiral band comprises a planar spiral band. The spiral band may comprise at least one channel or lumen disposed therein. The at least one channel or lumen may comprise a stiffening member disposed therein. In some embodiments, the spiral band comprises a hollow spiral band. In some embodiments, the spiral band has a circular, tubular, hollow, square, elongated, or triangular cross-section. Alternatively, the spiral band may comprise a tapered spiral band. The tapered spiral band may be configured to taper in height axially. The tapered spiral band may be configured to taper from a first end of the tapered spiral band to the free end. In some embodiments, the first end is a proximal end and the free end is a distal end. The free end of the anchor may be disposed radially outwards from the support structure.

In some embodiments, subsequent turns of at least a portion of the tapered spiral band may nest into each other to reduce a radial footprint of the tapered spiral band. The tapered spiral band may comprise a support structure and a semi-permeable material or impermeable material disposed therein. The semi-permeable material or impermeable material may comprise a webbing material, a fabric, a polymeric material, or an elastomeric material. The tapered spiral band can further include a lumen and a wire disposed within the lumen.

In some embodiments, the valve prosthesis is configured for expanding within the native valve of the patient. The unexpanded configuration may be sized and dimensioned for percutaneous insertion and the expanded configuration is sized and dimensioned for implantation in the native valve of the patient. The valve prosthesis may comprise first and second opposite ends, the first end being configured to extend above a native valve and the second end being configured to extend below the native valve when the valve prosthesis is anchored to the native valve. The valve prosthesis may be configured to sit below the native valve when the frame structure is anchored to the native valve.

In some embodiments, a valve segment within the valve prosthesis comprises a biocompatible one-way valve. In some embodiments, at least a portion of the valve segment is positioned within at least a portion of the valve prosthesis. The valve segment may comprise at least one leaflet having an inner layer and an outer layer, and wherein the frame structure is attached to the outer layer at one or more ends of the valve prosthesis. The valve segment may comprise a plurality of leaflets.

In another aspect, a method for treating a diseased native valve in a patient is provided. The method comprises (i) advancing a distal end of a guidewire from a first side of a native valve to a second side of the native valve. (ii) advancing a distal end of an inner shaft over the guidewire to the first side of a native valve, (iii) deploying an anchor from an anchor deployment component of the inner shaft, (iv) securing the anchor to adjacent to the native valve, (v) expanding a valve prosthesis within the native valve from an unexpanded configuration to an expanded configuration, (vi) releasing the valve prosthesis from the inner shaft, (vii) retracting the inner shaft from the native valve, and (viii) retracting the guidewire from the native valve.

In some embodiments, securing the anchor comprises deploying the anchor from a delivery configuration to a deployed configuration. In some embodiments, deploying the anchor comprises actuating the anchor from the delivery configuration to the deployed configuration. Deploying the anchor may comprise actuating the anchor from the delivery configuration to the deployed configuration on the second side of the native valve.

In some embodiments, deploying the anchor comprises deploying the anchor from a side port of the inner shaft. Alternatively, deploying the anchor may comprise actuating an outer shaft, an anchor drive shaft, and a deployment drive.

In some embodiments, anchoring the anchor comprises actuating the anchor from the delivery configuration to the deployed configuration on the first side of the native valve and advancing the anchor in the deployed configuration through the native valve to the second side of the native valve. Advancing the anchor may comprise pushing the anchor through the native valve. Advancing the anchor may further comprise rotating the anchor through the native valve. Securing the anchor may comprise positioning the anchor such that it is located only on the second side of the native valve.

In some embodiments, the valve prosthesis comprises a first and second opposite ends, and wherein expanding the valve prosthesis comprises expanding the valve prosthesis such that the first end extends above the first side of the native valve and the second end extends below second side of the native valve. Expanding the valve prosthesis may comprise expanding at least a portion the valve prosthesis within at least a portion of the deployed anchor to anchor the valve prosthesis to the native valve. Expanding the valve prosthesis and releasing the valve prosthesis may occur simultaneously. The valve prosthesis may be balloon-expandable and expanding the valve prosthesis may comprise inflating a balloon disposed within the inner shaft, wherein inflation of the balloon causes expansion of the valve prosthesis. Alternatively, the valve prosthesis may be self-expanding and expanding the valve prosthesis may comprise releasing the valve prosthesis from radial constriction by the inner shaft using a proximal pusher. In some embodiments, the valve prosthesis may comprise a valve segment therewithin comprising a biocompatible one-way valve.

In some embodiments the anchor may be a spiral band. A central point of the spiral band may be co-axial with a longitudinal axis of the delivery device when the anchor is in the deployed configuration. The spiral band may comprise a free end and anchoring may comprise rotating the free end of the anchor around one or more structures on the second side of the native valve. The one or more structures may comprise one or more native chordae tendineae of the left ventricle. The free end of the spiral band may comprise an atraumatic tip, for example a ball tip. Alternatively, the free end of the spiral band is configured for piercing tissue. In some embodiments, the free end of the spiral band is bent distally. Alternatively, the free end of the spiral band may be bent proximally.

In some embodiments, the spiral band may comprise a spiral wire or a plurality of spiral wires. The spiral band may comprise a planar spiral band. The spiral band may comprise a hollow spiral band. In some embodiments, the spiral band may comprise at least one channel or lumen disposed therein. The at least one channel or lumen may comprise a stiffening member disposed therein. The spiral band may comprise a circular, tubular, hollow, square, elongated, or triangular cross-section. In some embodiments, the spiral band comprises a tapered spiral band.

In some embodiments, advancing the delivery device further comprises transseptally inserting the distal end of the guidewire into a left atrium of the heart.

In some embodiments, the native valve is in a heart of a patient. In some embodiments, the native valve comprises a mitral valve, wherein the first side of the native valve comprises a left atrium, and wherein the second side of the native valve comprises a left ventricle. In some embodiments the first side of the native valve comprises an atrium of the heart, and the second side of the native valve comprises a ventricle of the heart. The first side of the native valve may comprise a ventricle of the heart, and the second side of the native valve may comprise an atrium of the heart. Another aspect of the present disclosure comprises a device for treating a diseased native valve in a patient, the device comprising a guidewire, an inner shaft having a lumen through which the guidewire is advanceable, an anchor, and a valve prosthesis. The anchor may be deployed from the inner shaft through a port located on the side of the inner shaft. Alternatively, the anchor may be deployed by a retraction of an outer shaft followed by a series of rotations of an anchor drive shaft followed by an advancement of the outer shaft, followed by an exposure of a deployment drive. The valve prosthesis may be deployed after the anchor is deployed.

In some embodiments, the valve prosthesis is deployed by a proximal pusher located within the inner shaft. The valve prosthesis may comprise first and second opposite ends, wherein when expanded the first end extends above the first side of the native valve and the second end extends below second side of the native valve. Placement of the valve prosthesis may be facilitated by an opening and closing of the valve during a cardiac cycle.

In some embodiments, the valve prosthesis is detachably coupled to the proximal pusher. In some embodiments, when the valve prosthesis is in the expanded position it is released from the proximal pusher.

In some embodiments, the anchor is a spiral band. The spiral band may comprise a free end. The spiral band may be anchored to one or more native chordae tendinae of the left ventricle. The free end may comprise an atraumatic tip, for example a ball tip. The free end may comprise a key configured to fit into a lock located on the band of the anchor. The spiral band may comprise at least one channel or lumen disposed therein.

In another aspect, a system for treating a diseased native valve in a patient is provided. The system comprises an anchor and a core wire disposed within a lumen of the anchor. The anchor comprises a delivery configuration and deployed configuration. The anchor in the deployed configuration is shaped to encircle chordae or leaflets of a diseased native valve in a patient. The core wire is longitudinally translatable in the lumen of the anchor. The core wire comprises a proximal curved portion when unconstrained and a distal tip. The core wire comprises one or more deflection features disposed adjacent the distal tip and configured to be advanced out of the lumen of the anchor.

In some embodiments, the anchor may be configured to be actuated from the delivery configuration to the deployed configuration adjacent a native valve in a patient.

In some embodiments, a proximal end of the anchor may be coupled to a distal end of a frame structure.

In some embodiments, the anchor may comprise an elongated shape in the delivery configuration.

In some embodiments, the anchor may comprise a curved shape in the deployed configuration. For example, the curved shape may comprise a helical shape. Alternatively, or in combination, the curved shape may comprise a spiral shape. Alternatively, or in combination, the curved shape may comprise a coiled shape. In some embodiments, the proximal curved portion may have a shape which corresponds to the curved shape of the anchor.

In some embodiments, the one or more deflection features may comprise one or more pre-formed waves, bends, kinks, or humps in the distal tip portion of the core wire. The one or more deflection features may, for example, comprise one or more kinks along the distal tip of the core wire such that at least a portion of the distal tip is discontinuous with a curved shape of the proximal curved portion. Alternatively, or in combination, the one or more deflection features may comprise a plurality of waves.

In some embodiments, the core wire may comprise a self-assembly state and an encircling state. The one or more deflection features may comprise a bend near the distal tip of the core wire such that the distal tip of the core wire is positioned adjacent one or more loops of the proximal curved portion in the self-assembly state. Alternatively, or in combination, the one or more deflection features may comprise a bend near the distal tip of the core wire such that the distal tip of the core wire angles towards the proximal curved portion in the self-assembly state. In some embodiments, the one or more deflection features may comprise a bend near the distal tip of the core wire such that the distal tip of the core wire in the encircling state is continuous with a curved shape of the anchor in the deployed configuration. In some embodiments, the one or more deflection features may comprise a bend near the distal tip of the core wire such that the distal tip of the core wire angles away from the proximal curved portion in the encircling state.

In some embodiments, the one or more deflection features may be configured to interact with a free end of the anchor and cause deflection of the distal tip when the core wire is advanced out of the lumen of the anchor, thereby facilitating positioning of the anchor relative to a delivery device during actuation from the delivery configuration to the deployed configuration.

In some embodiments, the anchor may be configured to wrap at least partially around a frame structure in the deployed configuration.

In some embodiments, the core wire may comprise a super-elastic material. For example, the core wire may comprise nitinol.

In some embodiments, the system may further comprise a frame structure having an unexpanded configuration and an expanded configuration. The frame structure may comprise an expandable stent. The expanded configuration may have a generally tubular expanded shape. In some embodiments, the frame structure may comprise an expanded outer periphery in the expanded configuration and a compressed outer periphery when subject to an external radial force in the unexpanded configuration. The compressed outer periphery may be smaller in diameter than the expanded outer periphery. In some embodiments, the frame structure may be balloon-expandable. In some embodiments, the frame structure may be self-expanding.

In some embodiments, the system may further comprise a delivery device. The delivery device may comprise an outer sheath. The anchor may be disposed in a lumen of the outer sheath and maintained in the delivery configuration by radial constriction from the outer sheath. Advancement of the anchor out of the lumen of the outer sheath may actuate the anchor into the deployed configuration. In some embodiments, a pusher portion of the core wire may extend from the proximal curved portion to a proximal end of the delivery device. Optionally, the delivery device may further comprise an inner shaft disposed within the lumen of the outer sheath. A proximal portion of a frame structure or a proximal end of the anchor may be coupled to a distal portion of the inner shaft. In some embodiments, advancement of the inner shaft towards an opening of the lumen of the outer sheath may advance the anchor out of the lumen of the outer shaft and actuate the anchor into the deployed configuration. In some embodiments, the system may further comprise a frame structure and the frame structure may be maintained in an unexpanded configuration by radial constriction from the outer sheath. Advancement of the inner shaft out of the lumen of the outer sheath may actuate the frame structure into an expanded configuration. In some embodiments, the outer sheath may be steerable. In some embodiments, the anchor may be configured to wrap at least partially around the inner shaft in the deployed configuration. In some embodiments, a central axis of the anchor may be co-axial with a longitudinal axis of the inner shaft when the anchor is in the deployed configuration. In some embodiments, the system may further comprise a frame structure detachably coupled to the delivery device in an unexpanded configuration during delivery to the native valve. In some embodiments, the system may further comprise a frame structure, wherein expansion of the frame structure to an expanded configuration may detach the frame structure from the delivery device.

In some embodiments, the distal tip may comprise an atraumatic tip. For example, the distal tip may comprise a ball tip.

In some embodiments, the distal tip may be configured for piercing tissue.

In some embodiments, the proximal curved portion may comprise a spiral wire.

In some embodiments, the proximal curved portion may comprise a helical wire.

In some embodiments, the core wire may comprise a first wire and a second wire. The first wire and the second wire may be configured to be longitudinally translatable independent of one another. The first wire and the second wire may be disposed in a housing. The housing may be flexible. Translation of the first and second wires relative to one another may change the curvature of the housing.

In some embodiments, a free end of the anchor may extend radially outward from the curved shape.

In some embodiments, the system may further comprise a frame structure configured for expanding within the native valve of the patient.

In some embodiments, the system may further comprise a frame structure. The anchor may be configured to be fully advanced from an atrial side of the native valve into a ventricle of the heart and anchor the frame structure to the native valve when the frame structure is in an expanded configuration adjacent the native valve. An unexpanded configuration of the frame structure may be sized and dimensioned for percutaneous insertion and the expanded configuration may be sized and dimensioned for implantation in the native valve of the patient. In some embodiments, the frame structure may comprise a first and second opposite ends, the first end extending above a native valve and the second end extending below the native valve when the frame structure is anchored to the native valve. Alternatively, the frame structure may sit below the native valve when the frame structure is anchored to the native valve.

In some embodiments, the system may further comprise a frame structure and a valve segment within the frame structure comprising a biocompatible one-way valve. At least a portion of the valve segment may be positioned within at least a portion of the frame structure. The valve segment may comprise at least one leaflet having an inner layer and an outer layer, and the frame structure may be attached to the outer layer at one or more ends of the frame structure. Alternatively, or in combination, the valve segment may comprise a plurality of leaflets.

In another aspect, a method for treating a diseased native valve in a patient is provided. The method comprises advancing a distal end of a delivery device from a first side of a native valve to a second side of the native valve, wherein the distal end of the delivery device is detachably coupled to an anchor, the anchor comprising a delivery configuration, a deployed configuration, a lumen, an opening, a free end, and a core wire disposed within the lumen, the core wire comprising a proximal curved portion and a distal tip portion, the distal tip portion comprising a distal tip and one or more deflection features disposed therealong and configured to interact with the free end and cause deflection of the distal tip when the core wire is advanced out of the lumen of the anchor through the opening; actuating the anchor from the delivery configuration to the deployed configuration adjacent the native valve by (i) advancing the free end of the anchor out of delivery device, (ii) deflecting the distal tip of the core wire by moving the one or more deflection features disposed along the distal tip portion past the opening of the lumen of the anchor into a self-assembly state, and (iii) advancing a remainder of the anchor out of the lumen of the outer shaft through the opening; and retracting the delivery device from the native valve.

In some embodiments, the method may further comprise steering the distal end of the delivery device such that the distal end of the delivery device points towards the first side of the native valve.

In some embodiments, the anchor may be configured to wrap at least partially around the delivery device in the deployed configuration.

In some embodiments, the anchor may be configured to wrap at least partially around a frame structure in the deployed configuration.

In some embodiments, a central axis of the anchor may be co-axial with a longitudinal axis of the inner shaft when the anchor is in the deployed configuration.

In some embodiments, actuating the anchor may comprise releasing a frame structure detachably coupled to the distal end of the delivery device from radial constriction by the delivery device.

In some embodiments, actuating the anchor may comprise actuating the anchor from the delivery configuration to the deployed configuration on the second side of the native valve.

In some embodiments, actuating the anchor may comprise actuating the anchor from the delivery configuration to the deployed configuration on the first side of the native valve and may further comprise advancing the anchor in the deployed configuration through the native valve to the second side of the native valve. Advancing the anchor may comprise pushing the anchor through the native valve. Alternatively, or in combination, advancing the anchor may comprise rotating the anchor through the native valve.

In some embodiments, actuating the anchor may comprise positioning the anchor such that it is located only on the second side of the native valve.

In some embodiments, the distal end of the delivery device may be detachably coupled to a frame structure. The method may further comprise expanding the frame structure within the native valve from an unexpanded configuration to an expanded configuration. In some embodiments, the frame structure may comprise a first and second opposite ends and expanding the frame structure may comprise expanding the frame structure such that the first end extends above the first side of the native valve and the second end extends below second side of the native valve. In some embodiments, expanding the frame structure may comprise expanding at least a portion the frame structure within at least a portion of the deployed anchor to anchor the frame structure to the native valve. In some embodiments, the method may further comprise releasing the frame structure from the distal end of the delivery device. Expanding the frame structure and releasing the frame structure may occur simultaneously. In some embodiments, the frame structure may be balloon-expandable and expanding the frame structure may comprise inflating a balloon disposed within the frame structure, wherein inflation of the balloon causes expansion of the frame structure. In some embodiments, the frame structure may be self-expanding and expanding the frame structure may comprise releasing the frame structure from radial constriction by the delivery device. In some embodiments, the frame structure may comprise a valve segment therewithin comprising a biocompatible one-way valve.

In some embodiments, the one or more deflection features may comprise one or more pre-formed waves, bends, kinks, or humps in the distal tip portion of the core wire. The one or more deflection features may, for example, comprise one or more kinks along the distal tip of the core wire such that at least a portion of the distal tip is discontinuous with a curved shape of the proximal curved portion. Alternatively, or in combination, the one or more deflection features may comprise a plurality of waves.

In some embodiments, the core wire may comprise a self-assembly state and an encircling state.

In some embodiments, the one or more deflection features may comprise a bend near the distal tip of the core wire such that the distal tip of the core wire is positioned adjacent one or more loops of the proximal curved portion in the self-assembly state.

In some embodiments, the one or more deflection features may comprise a bend near the distal tip of the core wire such that the distal tip of the core wire angles towards the proximal curved portion in the self-assembly state.

In some embodiments, the one or more deflection features may comprise a bend near the distal tip of the core wire such that the distal tip of the core wire in the encircling state is continuous with a curved shape of the anchor in the deployed configuration.

In some embodiments, the one or more deflection features may comprise a bend near the distal tip of the core wire such that the distal tip of the core wire angles away from the proximal curved portion in the encircling state.

In some embodiments, the method may further comprise rotating the distal tip of the core wire around one or more structures on the second side of the native valve.

In some embodiments, the method may further comprise rotating the free end of the deployed anchor around one or more structures on the second side of the native valve. The one or more structures may comprise one or more valve leaflets of the native valve. Alternatively, or in combination, the one or more structures may comprise one or more chordae of the left ventricle.

In some embodiments, the distal tip may comprise an atraumatic tip. For example, the distal tip may comprise a ball tip.

In some embodiments, the distal tip may be configured for piercing tissue.

In some embodiments, the proximal curved portion may comprise a spiral wire.

In some embodiments, the proximal curved portion may comprise a helical wire.

In some embodiments, the core wire may comprise a first wire and a second wire. The first wire and the second wire may be configured to be longitudinally translatable independent of one another. The first wire and the second wire may be disposed in a housing. The housing may be flexible. The method may further comprise translating the first and second wires relative to one another, thereby changing a curvature of the housing.

In some embodiments, a free end of the anchor may extend radially outward from the curved shape.

In some embodiments, the native valve may be in a heart of a patient. In some embodiments, the method may further comprise transseptally inserting the distal end of the delivery device into a left atrium of the heart. In some embodiments, the native valve may comprise a mitral valve, the first side of the native valve may comprise a left atrium, and the second side of the native valve may comprise a left ventricle.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the present disclosure are utilized, and the accompanying drawings of which:

FIGS. 6A-6B show close-up views of the distal end of a delivery device during correct deployment of an anchor therefrom, in accordance with embodiments.

FIGS. 6C-6D show close-up views of the distal end of a delivery device during incorrect deployment of an anchor therefrom, in accordance with embodiments.

FIG. 15 shows a perspective view of an exemplary anchor comprising a lumen disposed therethrough, in accordance with embodiments.

FIG. 16 shows a side view of an exemplary core wire comprising a deflection feature in a distal tip section of the wire, in accordance with embodiments.

FIGS. 17A-17C show side views of various optional, non-limiting configurations of a deflection feature, in accordance with embodiments.

FIGS. 20-22 show various views of the anchor of FIG. 18 loaded on a delivery device and having a translatable core wire disposed within the its lumen, in accordance with embodiments. FIG. 20 shows a side view. FIG. 21 shows a perspective top view. FIG. 22 shows a top view.

FIG. 29 is a side view. FIG. 30 is a side cross-sectional view.

FIGS. 31-33 show sequential views of the release of the anchor of FIGS. 29-30 from the tether, in accordance with embodiments.

FIG. 34 shows a side view of an exemplary tether, in accordance with embodiments.

FIG. 35 shows a side view of an exemplary anchor, in accordance with embodiments.

FIG. 36 shows a perspective view of the tether of FIG. 34 coupled to the anchor of FIG. 35, in accordance with embodiments.

FIGS. 46-47 show various views of an anchor comprising a plurality of deflection features therealong, in accordance with embodiments. FIG. 11 shows a perspective bottom view. FIG. 12 shows an orthogonal bottom view.

FIG. 13 shows a perspective top view. FIG. 14 shows an orthogonal top view.

FIGS. 51-53 show various views of an anchor having an optional tip orientation determined by a single deflection feature near a free end thereof, in accordance with embodiments. FIG. 16 shows a perspective bottom view. FIG. 17 shows a side view. FIG. 18 shows an orthogonal bottom view.

FIGS. 54-57 show side views of optional tip orientations for a spiral anchor, in accordance with embodiments.

FIG. 58A is a side section view of a valve prosthesis secured by an anchor at a diseased native valve, in accordance with embodiments.

FIG. 58B is a topside view of a valve prosthesis secured by an anchor to a diseased native valve wherein the leaflets of the valve are visible, in accordance with embodiments.

FIGS. 68A-68C are a side views of various steps in the separation of a distal end of an outer sheath assembly comprising a distally-deploying soft valve capsule from the outer shaft, in accordance with embodiments.

FIGS. 69A-69C are side views of various steps in the separation of a distal end of an outer sheath assembly, the distal end comprising a collapsible soft valve capsule, from an outer sheath, in accordance with embodiments.

FIGS. 70A-70C are side views of various steps in the separation of a distal end of an outer sheath assembly, the distal end comprising a helical soft valve capsule from an outer sheath, in accordance with embodiments.

FIGS. 71A-71C are side views of various steps in the separation of a distal end of an outer sheath assembly, the distal end comprising a multi-ring soft valve capsule, from an outer sheath, in accordance with embodiments.

FIGS. 72A-72B are side views of various steps in the separation of a distal end of an outer sheath assembly, the distal end comprising a proximally-collapsible soft valve capsule, from an outer sheath assembly, in accordance with embodiments.

FIG. 74 shows a perspective view of an exemplary anchor comprising an outer jacket and a plurality of lumens disposed therein, in accordance with embodiments.

FIG. 75 shows a cross-sectional view of the anchor of FIG. 74, in accordance with embodiments.

FIG. 79 shows proximal deflection of a distal tip of one or more elongate members disposed within an open lumen of an exemplary anchor, in accordance with embodiments.

FIG. 80 shows distal deflection of a distal tip of one or more elongate members disposed within an open lumen of an exemplary anchor, in accordance with embodiments.

FIG. 85 shows an anchor with a grabber arm attached thereto.

FIGS. 86A-86C are side view of various configurations of grabber arms.

FIGS. 87A-87D show various view of an anchor guide.

FIG. 88A shows an inner shaft and anchor guide with the outer layer removed for clarity.

FIG. 88B is a cross-section through the anchor of FIG. 88A with the addition of the outer layer.

FIG. 88C shows a cross-section through the inner shaft of FIG. 88A with the addition of the outer layer.

FIGS. 89A-89B show a tether attached to an anchor.

FIG. 89C shows the tether and anchor of FIGS. 89A-89B inserted through an inner shaft anchor guide.

FIGS. 90A-90G show an exemplary method of deploying an anchor with an anchor guide and tether.

DETAILED DESCRIPTION

Figure 1:
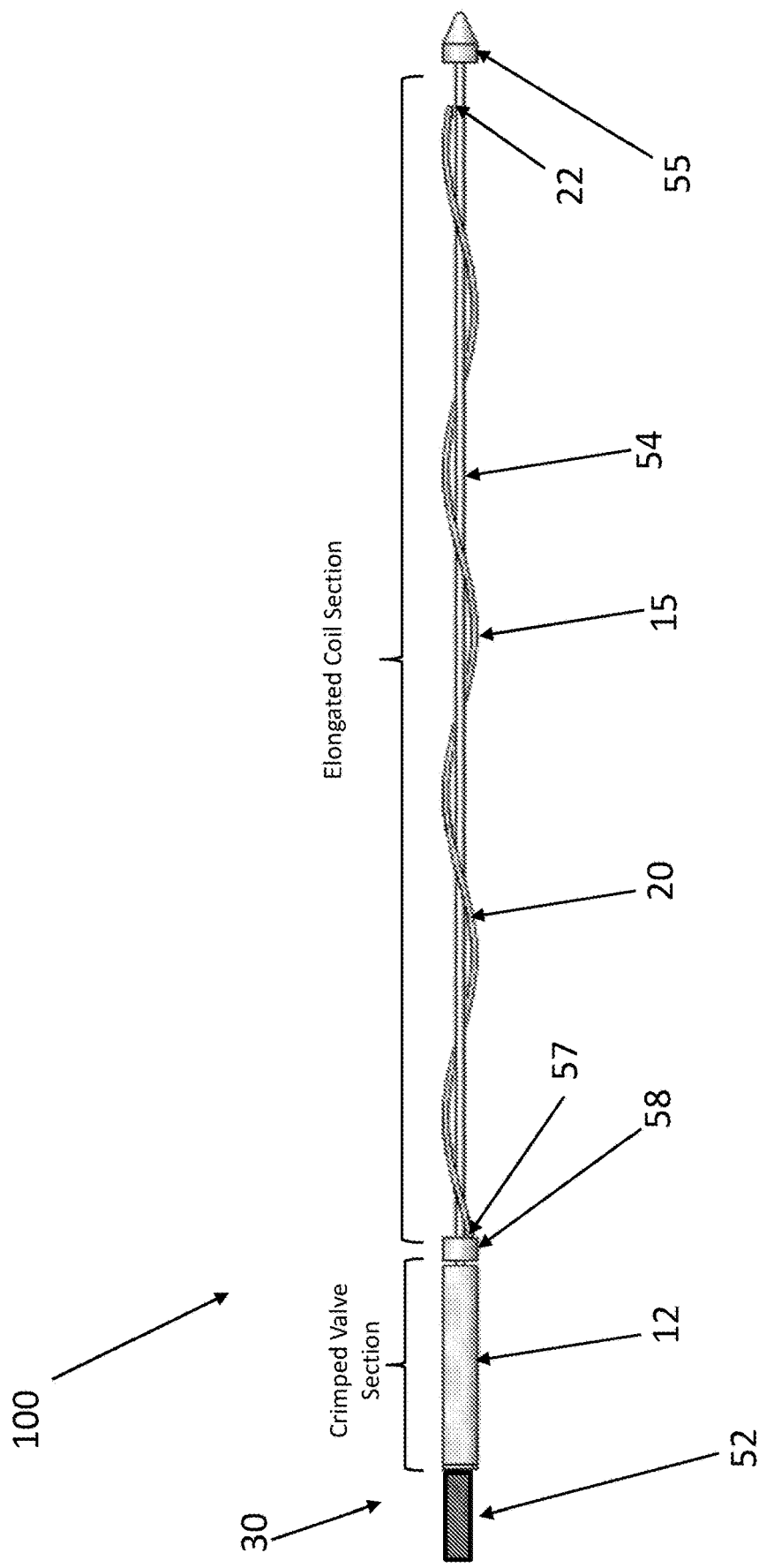
FIG. 1 shows a side view of a valve prosthesis system comprising a frame structure and an anchor loaded on a delivery device with the anchor in a delivery (e.g., elongated) configuration, in accordance with embodiments.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments, however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

The present disclosure is described in relation to deployment of systems, devices, or methods for treatment of a diseased native valve of the heart, for example a mitral valve, aortic valve, or tricuspid. However, one of skill in the art will appreciate that this is not intended to be limiting and the devices and methods disclosed herein may be used in other anatomical areas and in other surgical procedures.

For convenience in explanation and accurate definition in the appended claims, the terms "up" or "upper", "down" or "lower". "inside" and "outside" are used to describe features of the present disclosure with reference to the positions of such features as displayed in the figures.

In many respects the modifications of the various figures resemble those of preceding modifications and the same reference numerals followed by subscripts "a", "b", "c", and "d" designate corresponding parts. It will be understood by one of ordinary skill in the art that modifications of corresponding parts of the various figures are interchangeable with one another between embodiments to arrive at multiple combinations with multiple modified parts.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Figure 2:
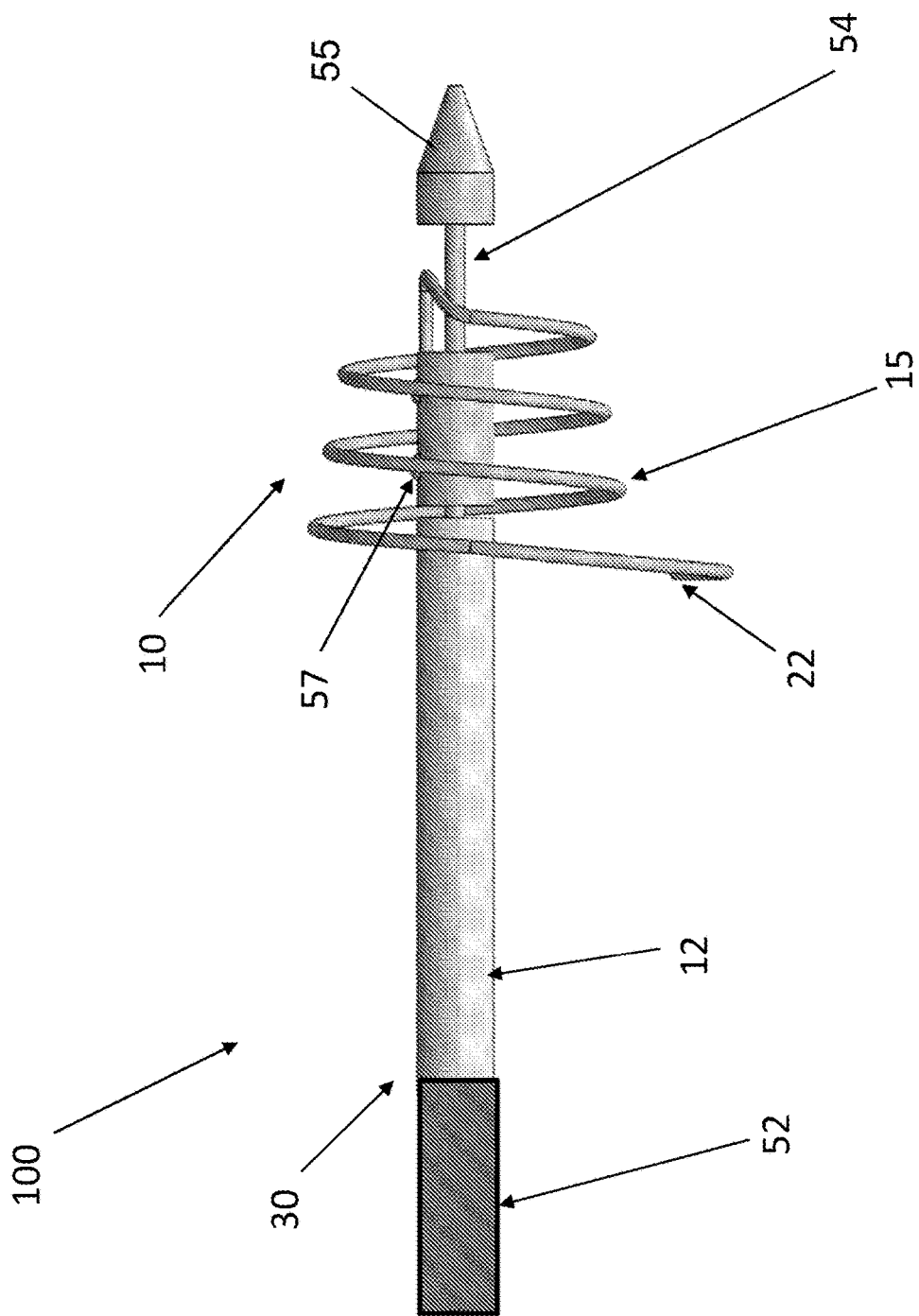
FIG. 2 shows a side view of the valve prosthesis system of FIG. 1 with the anchor in a deployed configuration, in accordance with embodiments.

FIG. 1 shows a side view of a valve prosthesis system 100 comprising a frame structure 12 and an anchor 15 loaded on a distal end of a delivery device 30 with the anchor 15 in an elongated, low-profile delivery configuration. FIG. 2 shows a side view of a valve prosthesis system 100 of FIG. 1 comprising a valve prosthesis 10 loaded on a distal end of a delivery device 30. The valve prosthesis 10 may have an unexpanded configuration (for example, a compressed configuration as described herein) and an expanded configuration. The valve prosthesis 10 in the expanded configuration may have a generally tubular expanded shape. In some embodiments, the unexpanded configuration may be sized and dimensioned for percutaneous insertion, and the expanded configuration may be sized and dimensioned for implantation in the native valve of the patient. The valve prosthesis 10 may be configured to be fully advanced from a first side of a native valve in a patient (e.g., an atrial side) to a second side of the native valve (e.g., into a ventricle of the heart) and anchor to the native valve when the valve prosthesis 10 is in the expanded configuration adjacent the native valve. It will be understood that the valve prosthesis 10 may be any valve prosthesis described herein or understood based on the teachings herein to one of ordinary skill in the art.

In various embodiments, the unexpanded configuration may be 18Fr or smaller. In various embodiments, the unexpanded configuration may be 20Fr or smaller. In various embodiments, the unexpanded configuration may be 22Fr or smaller. In various embodiments, the unexpanded configuration may be 24Fr or smaller. In various embodiments, the unexpanded configuration may be 26Fr or smaller. In various embodiments, the unexpanded configuration may be 27Fr or smaller. In various embodiments, the unexpanded configuration may be 28Fr or smaller. In various embodiments, the unexpanded configuration may be 29Fr or smaller. In various embodiments, the unexpanded configuration may be 30Fr or smaller. In various embodiments, the unexpanded configuration may be sized and dimensioned for transseptal access. In various embodiments, the unexpanded configuration may be sized and dimensioned for femoral access.

Referring to FIGS. 58A-58B, the valve prosthesis 10 can include an anchor 15, a frame structure 12, and a valve segment 14. As used herein. "prosthetic valve" may refer to all manner of prosthetic and artificial replacement valves and leaflets, including tissue (biological valves), tissue-engineered valves, polymer valves (e.g., biodegradable polymer valves), and even certain mechanical valves.

FIGS. 58A-58B show an exemplary use of the valve prosthesis 10. FIG. 58A is a section view of a diseased valve comprising a left atrium 25 and a left ventricle 26 with the valve prosthesis 10 implanted into a native valve. The anchor 15 is wrapped around the native chordae tendineae 40 of the native valve. FIG. 58B is a top view of the valve prosthesis 10 showing the valve segment 14 and the frame structure 12 within the native valve.

The valve segment 14 can be similar to existing transcatheter valves. The valve segment 14 can be similar to existing surgical tissue valves, and mechanical valves. At least a portion of the valve segment 14 may be positioned within at least a portion of the valve prosthesis 10, for example with the frame structure 12 of the valve prosthesis 10. The valve segment 14 may include leaflets formed of multi-layered materials for preferential function. The valve segment 14 may comprise at least one leaflet having an inner layer and an outer layer. The valve segment 14 may be attached directly to the valve prosthesis 10. Alternatively, the valve segment 14 may be attached to an intermediate valve structure that is in turn connected to the valve prosthesis 10. The valve segment 14 may be connected to the valve prosthesis 10 before or after the valve prosthesis 10 has been deployed adjacent a native valve. The valve prosthesis 10 may be attached to a leaflet of the valve segment 14, for example an outer layer of a leaflet, at one or more ends of the valve prosthesis 10. The valve prosthesis 10 may be attached to a leaflet of the valve segment 14, for example an outer layer of a leaflet, at one or more intermediate portions of the valve prosthesis 10. The valve segment may comprise a plurality of leaflets. The valve segment 14 may comprise a biocompatible one-way valve. Flow in one direction may cause the leaflet(s) to deflect open and flow in the opposite direction may cause the leaflet(s) to close.

The frame structure 12 may be configured like a stent. The frame structure 12 may, for example, comprise a scaffold in a diamond pattern formed from a shape memory material (e.g., NiTi). One of ordinary skill in the art will appreciate that many other structures, materials, and configurations may be employed for the frame structure 12. For example, the frame structure 12 may be formed of a polymer of sufficient elasticity. The frame structure 12 may be formed of a combination of metal and polymer, such as metal (e.g., shape memory material) covered in polymer. The frame structure 12 may include a variety of patterns besides diamond shapes. In some embodiments, frame structure 12 is a closed frame such that blood flow is forced through valve segment therein. One or more skirts and/or seals may help force blood through valve segment.

The anchor can be configured to fix the prosthesis 10 in place within the body (e.g., within a cardiac valve).

One of ordinary skill in the art will recognize based on the description herein that any of the valve prostheses described herein may comprise any of the frame structure shapes, frame structure designs, frame structure materials, anchor shapes, anchor windings, anchor materials, free end tips, leaflet(s) configurations, or any other of the variable features described herein in any combination thereof as desired.

The valve prosthesis may additionally or alternatively include any of the features of any of the valve prostheses described in PCT/US2019/047542, PCT/US2019/055049, PCT/US2019/057082, and PCT/US2019/068088, the entireties of which are incorporated by reference herein.

Referring to FIGS. 1-2, in some embodiments, the anchor 15 may comprise a wire 20 having a free end 22. The other end of the anchor 15 may be coupled to the top (proximal end) or bottom (distal end) of the frame structure 12 as described herein. Alternatively, or in combination, the other end of the anchor 15 may not be attached to the frame structure 12 as described herein. The anchor 15 may be configured to wrap at least partially around the frame structure 12 in the deployed configuration. The anchor 15 may be configured to be fully advanced from a first side of a native valve in a patient (e.g., an atrial side) to a second side of the native valve (e.g., into a ventricle of the heart) and anchor the frame structure 12 to the native valve when the frame structure 12 is in the expanded configuration adjacent the native valve.

The anchor 15 may comprise a delivery (e.g., elongated) configuration (shown in FIG. 1) and a deployed configuration (shown in FIG. 2). The frame structure 12 may be configured to remain in its unexpanded configuration while the anchor 15 is in the deployed configuration. In various embodiments, the anchor 15 may be self-expanding and may move to the deployed configuration as it is removed from the delivery sheath. In various embodiments, the anchor 15 may be configured to self-assemble when it is deployed in the heart cavity (e.g., left ventricle or atrium). The anchor 15 may be configured to be actuated from the delivery configuration to the deployed configuration adjacent the native valve using any method or mechanism understood by one of ordinary skill in the art from the description herein. For example, retraction of the guidewire 54 into a lumen of the inner shaft 52 of the delivery device 30 may actuate the anchor 15 into the deployed configuration. Alternatively, or in combination, the anchor 15 may be maintained in the delivery configuration by radial constriction from an outer sheath 50 (see, e.g., FIG. 3D) of the delivery device 30. In such an embodiment, advancement of an inner shaft 52 of the delivery device 30 out of the lumen of the outer sheath 50 may actuate the anchor 15 into the deployed configuration, as described further herein.

Although referred to as an anchor, one will appreciate that anchor 15 does not require performing an anchor function in the traditional sense. As will be described in more detail below, the anchor 15 can guide valve prosthesis 10 into a desired position within a native valve. The anchor 15 may also mitigate against undesired entanglement and disturbances to the chordae tendineae and valve leaflets of the cardiac valve, such as the mitral valve.

In some embodiments, the anchor 15 may be configured to wrap at least partially around a distal portion of the delivery device 30, for example around the inner shaft 52, in the deployed configuration.

In some embodiments, the anchor 15 may be actuated from the delivery configuration to the deployed configuration on a first side of the native valve prior to being advanced to a second side of the native valve. For example, the anchor 15 may be deployed in a left atrium of a heart prior to being advanced to a left ventricle of the heart as described herein.

Alternatively, the anchor 15 may be actuated from the delivery configuration to the deployed configuration on a second side of the native valve after being advanced to the second side from a first side of the native valve. For example, anchor 15 may be advanced from a left atrium of a heart prior to being deployed in a left ventricle of the heart.

The anchor 15 may be detachably coupled to a proximal or distal portion of the frame structure 12. Alternatively, or in combination, the anchor 15 may be detachably coupled to the delivery device 30 in the delivery configuration during delivery to the native valve. For example, the proximal end 57 of the anchor 15 may be detachably coupled to the inner shaft 52 of the delivery device 30 and/or a tether 78 (see, e.g., FIGS. 89A-89C), for example, by radial constriction from the outer sheath 50. Retraction of the outer sheath 50 away from the proximal end 57 of the anchor 15 (or, similarly, extrusion of the distal end of the anchor 15 out of an opening in the outer sheath 50) may detach the anchor 15 from the delivery device 30. Alternatively, or in combination, the proximal end 57 of the anchor 15 may be detachably coupled to the inner shaft 52 of the delivery device 30 by an attachment element 58 (see FIG. 1). Alternatively, or in combination, the proximal end 57 of the anchor 15 may be detachably coupled to the inner shaft 52 of the delivery device 30 by a weak adhesive.

The anchor 15 may be configured to rotate when the inner shaft 52 or other element of the delivery device 30 is rotated. Rotation of the anchor 15 may aid in advancement of the anchor 15 to the second side of the native valve. Alternatively. or in combination, rotation of the anchor 15 may aid in capture of one or more structures on the second side of the native valve by the free end 22 as described herein. By capturing one or more structures on the second side of the native valve, the anchor 15 may maintain its position relative to the native valve and provide an anchor point for the frame structure 12 when in the expanded configuration.

The wire 20 of anchor 15 may comprise a curved wire in the deployed configuration, for example a coiled wire or band, a helical wire or band, or a spiral wire or band as described herein. The wire 20 may be shaped to encircle chordae and/or leaflets of a diseased native valve. In various embodiments, the wire 20 may have a curved shape in the deployed configuration and an elongated—rather than curved—shape in the delivery configuration. For example, the wire 20 may be elongated into a straight shape within the delivery device 30. In various embodiments, a portion of the wire 20 may have a curved encircling shape. In various embodiments, a substantial portion of the wire or band 20 may have a curved encircling shape. In various embodiments, the wire 20 may be formed as a flat curve (in the deployed configuration) whereby the loops generally are positioned within the same plane (the plane being perpendicular to a longitudinal axis). In various embodiments, the wire may be formed as a three-dimensional curve (in the deployed configuration) whereby the loops generally are positioned out of plane with one another.

The wire 20 may comprise a helical wire in the deployed configuration. As used herein, a helix or helical shape may comprise a curve for which the tangent at any point along the curve makes a constant angle with a fixed line (e.g., a central axis). The curve may turn around an axis at a constant or continuously varying distance while moving parallel to the axis. In some embodiments, the wire 20 may comprise one or more helical portions as described herein.

In various embodiments, free end 22 extends radially outward from frame structure 12, and in particular the remainder of wire 20. As will be described below, the free end 22 is configured to encircle a larger radius than the main coils of the wire 20. When the main coils of wire 20 have a generally curved shape (e.g., spiral, helical, tubular, frustoconoical, etc.), the free end 22 may extend radially outward from the curved shape. For example, when the main coils of wire 20 have a generally spiral shape, the free end 22 may extend radially outward from the spiral shape. When the main coils of wire 20 have a generally tubular shape, the free end 22 may extend radially outward from the tubular shape. When the main coils of wire 20 have a generally helical shape, the free end 22 may extend radially outward from the helical shape. When the main coils of wire 20 have a generally frustoconical shape, the free end 22 may extend radially outward from the frustoconical shape. When the main coils of wire 20 have a generally cylindrical shape, the free end 22 may extend radially outward from the cylindrical shape. The free end 22 may be configured to encircle a larger radius than the main coils of the helical wire 20. The larger diameter facilitates capturing of the valve leaflets and/or chordae tendineae within the sweep of the free end 22 when rotated as described herein.

In various embodiments, the wire or band 20 may have a generally helical shape in the deployed configuration. In various embodiments, the wire or band 20 may be elongated-rather than helix-shaped—in the delivery configuration. For example, the wire or band 20 may be elongated into a straight shape within the delivery device. In various embodiments, a portion of the wire or band 20 may have a helical shape. In various embodiments, a substantial portion of the wire or band 20 may have a helical shape. In various embodiments, the helical wire or band 20 may be formed as a three-dimensional helix (in the deployed configuration) whereby the loops generally are positioned around the same axis (for example, a longitudinal axis of the delivery device 30).

Optionally, the anchor 15 may comprise a first portion comprising the helical wire 20 and another portion. Alternatively, or in combination, the anchor 15 may comprise a plurality of helical wires 20. For example, the anchor 15 may comprise at least two helical wires 20 having the same or different diameters. Alternatively. or in combination, the anchor 15 may comprise at least two helical wires 20 having the same or different winding pitches.

The wire 20 may comprise a spiral wire or band in the deployed configuration. As used herein, a spiral or spiral shape may comprise a curve which emanates from a point (e.g., a central point) having a continuously increasing or decreasing distance from the point. The spiral or spiral shape may be two-dimensional (e.g., planar) or three-dimensional. In some embodiments, the wire or band 20 may comprise one or more spiral portions as described herein.

In various embodiments, the anchor and/or core wire may have a spiral-shaped deployed configuration. In various embodiments, spiral refers to a shape with windings about a central axis. The spiral may be continuous. The windings may gradually widen (or tighten) along the length. The spiral may be formed in a flat plane perpendicular to the central axis. In various embodiments, the anchor and/or core wire may have a deployed configuration that is not formed in a flat plane, or in other words the deployed shape is formed in a three-dimensional and/or non-degenerate space. In various embodiments, the anchor and/or core wire may have a conical-shaped deployed configuration including, but not limited to, tubular, conical, frustoconical, and/or helical shapes.

In various embodiments, the anchor 15 may comprise a flat spiral shape. Loops of the flat spiral shaped anchor may be generally positioned within the same plane (the plane being perpendicular to a longitudinal axis of a delivery device) as described herein.

The free end 22 of the spiral band or wire 20 may extend radially outward from the frame 12, and in particular from the remainder of the spiral band or wire 20. The other end of the spiral band or wire 20 may be coupled to the top or bottom of the frame structure 12 as described herein. Alternatively, or in combination, the other end of the spiral band or wire 20 may not be attached to the frame structure 12 as described herein. The free end 22 of the spiral band or wire 20 may facilitate capturing of the valve leaflets and/or chordal tendineae within the sweep of the free end during rotation as described herein. During rotation of the spiral band or wire 20, the leaflets and/or chordae tendineae may be captured by the free end 22 and trapped between the valve frame structure 12 and an interior surface of the spiral band or wire 20.

In various embodiments, the wire or band 20 may have a generally spiral shape in the deployed configuration. In various embodiments, the wire or band 20 may be elongated—rather than spiral-shaped—in the delivery configuration. For example, the wire or band 20 may be elongated into a straight shape within the delivery device. In various embodiments, a portion of the wire or band 20 may have a spiral shape. In various embodiments, a substantial portion of the wire or band 20 may have a spiral shape. In various embodiments, the spiral wire or band 20 may be formed as a flat spiral (in the deployed configuration) whereby the loops generally are positioned within the same plane (the plane being perpendicular to a longitudinal axis).

Optionally, the anchor 15 may comprise a first portion comprising the spiral wire 20 and another portion. Alternatively, or in combination, the anchor 15 may comprise a plurality of spiral wires 20. For example, the anchor 15 may comprise at least two spiral wires 20 having the same or different diameters. Alternatively, or in combination, the anchor 15 may comprise at least two spiral wires 20 having the same or different winding pitches.

The wire 20 may comprise one or more loops. For example, the wire 20 may comprise a plurality of loops, which may increase the radial strength of the anchor by increasing friction and addition structural support. The one or more loops of the wire 20 may be substantially cylindrical around a central axis of the wire 20, for example along an axis which is coaxial with a longitudinal axis of a delivery device 30. The one or more loops of the wire 20 may be substantially helical around a central axis or helical axis of the wire 20, for example along an axis which is coaxial with a longitudinal axis of a delivery device. The one or more loops of the wire 20 may spiral radially outward from a central point or central axis of the wire 20, for example along an axis which is coaxial with a longitudinal axis of a delivery device 30 such that the wire 20 lies approximately along a plane perpendicular to the longitudinal axis of the delivery device 30.

The one or more loops (also referred to herein as coils or turns) of the wire or band 20 may comprise a curved shape that bends around back towards its origin (for example, an arc, ellipsoid, circle, or the like). In some embodiments, a loop may comprise a curved shape that bends back towards its origin but does not cross itself, making a rotation within a range of about 180 degrees to about 360 degrees. For example, a loop may comprise a curve or an arc having a central angle within a range of about 180 degrees to about 360 degrees. In at least some embodiments, the one or more loops may comprise an arc. In some embodiments, a loop may comprise a shape that bends back towards and crosses itself, making at least a 360 degree rotation. In at least some embodiments, the one or more loops may comprise a 360 degree rotation (for example, a circle). In some embodiments, the one or more loops may comprise a 360 degree to 720 degree rotation (for example, a loop crossing itself once and rotating further towards a second crossing and formation of a second 360 loop).

The one or more loops may comprise any number of loops desired, for example, one, two, three, four, five, six, seven, eight, nine, or ten loops. The one or more loops may comprise a rotation within a range of about 180 degrees to about 3600 degrees. The one or more loops may comprise a rotation within a range bounded by any of the following values: 180 degrees, 270 degrees, 360 degrees, 450 degrees, 540 degrees, 630 degrees, 720 degrees, 810 degrees, 900 degrees, 990 degrees, 1080 degrees, 1170 degrees, 1260 degrees, 1350 degrees, 1440 degrees, 1530 degrees, 1620 degrees, 1710 degrees, 1800 degrees, 1890 degrees, 1980 degrees, 2070 degrees, 2160 degrees, 2250 degrees, 2340 degrees, 2430 degrees, 2520 degrees, 2610 degrees, 2700 degrees, 2790 degrees, 2880 degrees, 2970 degrees, 3060 degrees, 3150 degrees, 3240 degrees, 3330 degrees, 3420 degrees, 3510 degrees, or 3600 degrees.

Interaction of the frame structure 12 with the one or more loops of the anchor 15 may create opposing forces therebetween that provide mechanical leverage for anchoring the frame structure 12 to the one or more anatomical structures. In some embodiments, the one or more loops may comprise at least 360 degrees of rotation when deployed such that the loops wrap around one another and provide additional mechanical leverage against the frame structure 12 in order to facilitate anchoring of the frame structure 12 as described herein. Additional loops or partial loops may provide additional mechanical strength and/or leverage.

In some embodiments, the one or more loops of the wire or band 20 may comprise one or more spaces therebetween. The spaces may facilitate movement of the captured tissue (e.g. chordae and/or leaflets) from the free end 22 to the center of the spiral structure during rotation of the anchor 15 as described herein.

The wire 20 may be configured to wrap at least partially around the frame structure 12 in the deployed configuration.

In some embodiments, the wire 20 may be configured to wrap at least partially around a distal portion of the delivery device 30, for example around the inner shaft, in the deployed configuration.

The free end 22 of the wire 20 may be sized and dimensioned for insertion through the native valve, for example through tissue at or near a commissure of the native valve or through the valve opening itself. In some embodiments, the free end 22 of the wire 20 may comprise an atraumatic tip to avoid reduce risk of injury to the native valve tissue and leaflets. For example, the free end may comprise a blunt end, a ball tip, a curved tip (e.g., J-tip or pigtail), or other atraumatic shapes. Alternatively, the free end 22 of the wire 20 may be configured for piercing tissue.

In various embodiments, the free end 22 is separate from and extends outward from the main coils of the anchor 15. In various embodiments, the main body coils of the anchor 15 circumscribe an area (in the case of a spiral coil) or a volume (in the case of a helical coil) having a diameter, and the free end 22 extends to a radius greater than the diameter of the anchor 15. In various embodiments, the free end 22 extends to a radius substantially greater than the diameter of the anchor 15. In various embodiments, the free end 22 is configured to circumscribe a larger diameter than the anchor 15. In various embodiments, the free end 22 is configured to circumscribe all of the chordae tendineae of the native valve to be treated.

In various embodiments, the free end 22 may be shaped and configured to reduce the risk of counter-rotation. For example, the tip 22 may have a curled end to cause the free end 22 to snag chordae if it is rotated in a direction opposite the anchoring rotation.

The free end 22 of the wire or band 20 may optionally rotated around one or more structures on the second side of the native valve such that the one or more structures (e.g., chordae, leaflets, or annulus) are pulled radially inwards towards the longitudinal axis of the anchor 15 and/or towards the longitudinal axis of the delivery device 30. The wire or band 20 and/or free end 22 may be configured such that minimal torque is applied to the one or more structures. Alternatively, or in combination, the wire or band 20 and/or free end 22 may be configured such that the one or more structures are not rotated, or are minimally rotated, during rotation of the wire or band 20. For example, the wire or band 20 may comprise one or more spaces between loops of the curved wire or band which facilitate radially-inward movement of the captured tissue (e.g. chordae and/or leaflets) from the free end 22 to the center of the curved structure with little or no torque and/or rotation of the structures during rotation of the wire or band 20 as described herein. Alternatively or in combination, the wire or band 20 may be configured such that, when fully deployed none of the structures reside between the loops of the curved encircling shape. Instead, the one or more structures may sit radially inward of the loops in order to facilitate capture of the one or more structures between the wire or band 20 and the expanded frame structure 12. The one or more structures may retain or nearly retain their normal anatomical position when the wire or band 20 is fully deployed.

Wire 20 may be formed of a material having sufficient rigidity to hold a predetermined shape. The wire may, for example, be formed of a shape memory material (e.g., NiTi). It may be desirable for at least an end portion (e.g., free end 22) to be relatively rigid such that it can exert a force to move chordal tendineae, while still retaining flexibility to be collapsed within a delivery device. In various embodiments, the end portion only needs sufficient rigidity to hold its shape and will deform under a load. For example, the end portion may be configured with a similar rigidity to a guidewire, or slightly stiffer.

In various embodiments, wire 20 has varying stiffness along its length. The wire 20 may have two or more segments of differing stiffness and/or the stiffness may transition over its length. In various embodiments, wire 20 is attached to frame 12 at multiple points such that free end 22 is relatively flexible and the wire 20 is more rigid along portions where it is attached to the frame structure 12.

The anchor 15 may be configured to taper in height axially. For example, the anchor 15 may be configured to taper in height from a first end of the anchor 15, which may be coupled to a delivery device and/or frame structure as described herein, to a free end 22 of the anchor 15. In some embodiments, the anchor 15 may taper in height from a proximal end to a distal end. Alternatively, the anchor 15 may taper in height from a distal end to a proximal end. The anchor 15 may be tapered such that subsequent turns of the tapered anchor 15 nest into each other so as to reduce a radial footprint of the tapered anchor 15. The anchor 15 may, for example, comprise a solid wire-like spiral band with a taper as described herein. In some embodiments, the anchor 15 may comprise a plurality of spiral support wires.

Figure 66:
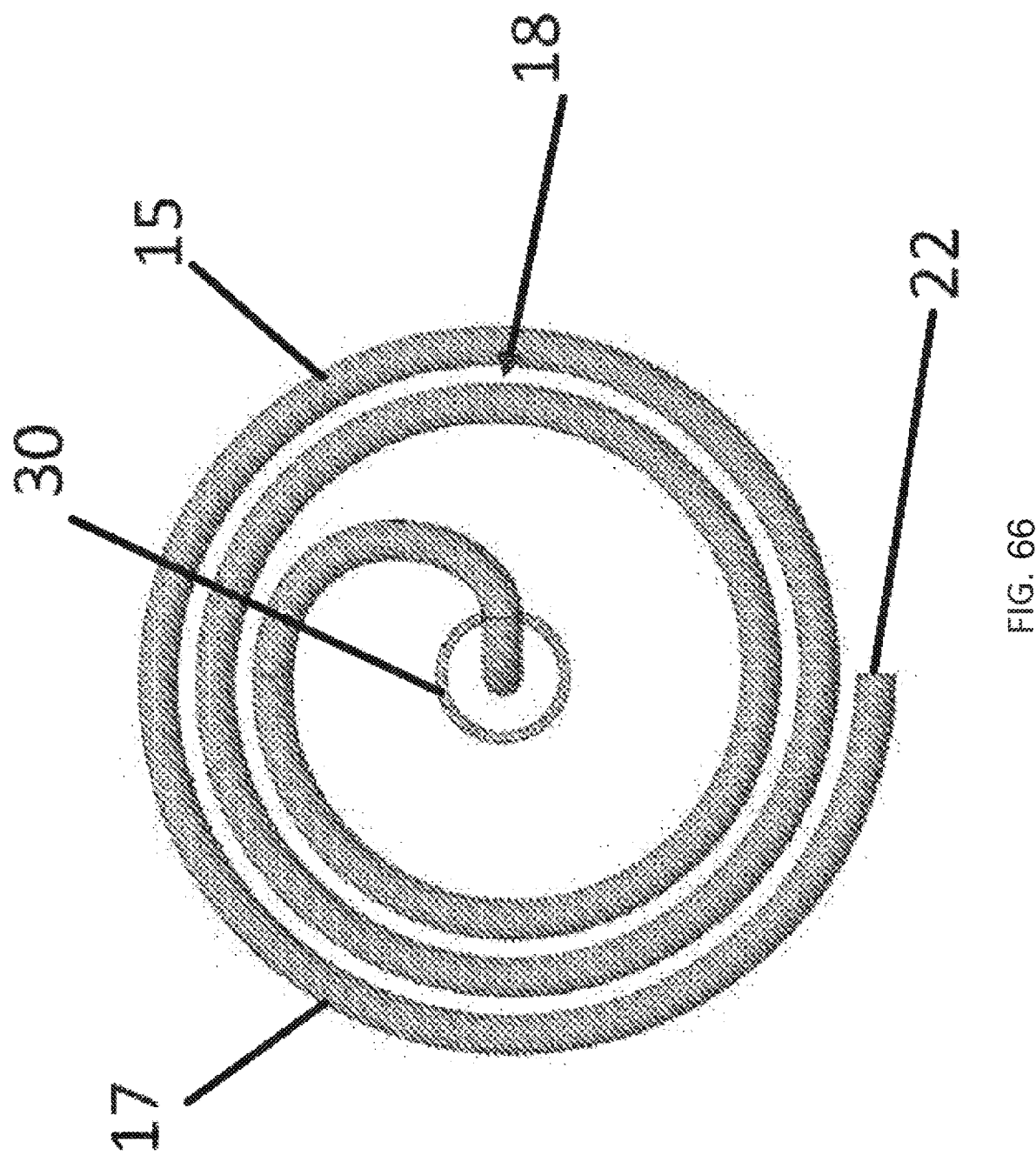
FIG. 66 is a top view of a cylindrical spiral anchor, in accordance with embodiments.
Figure 67:
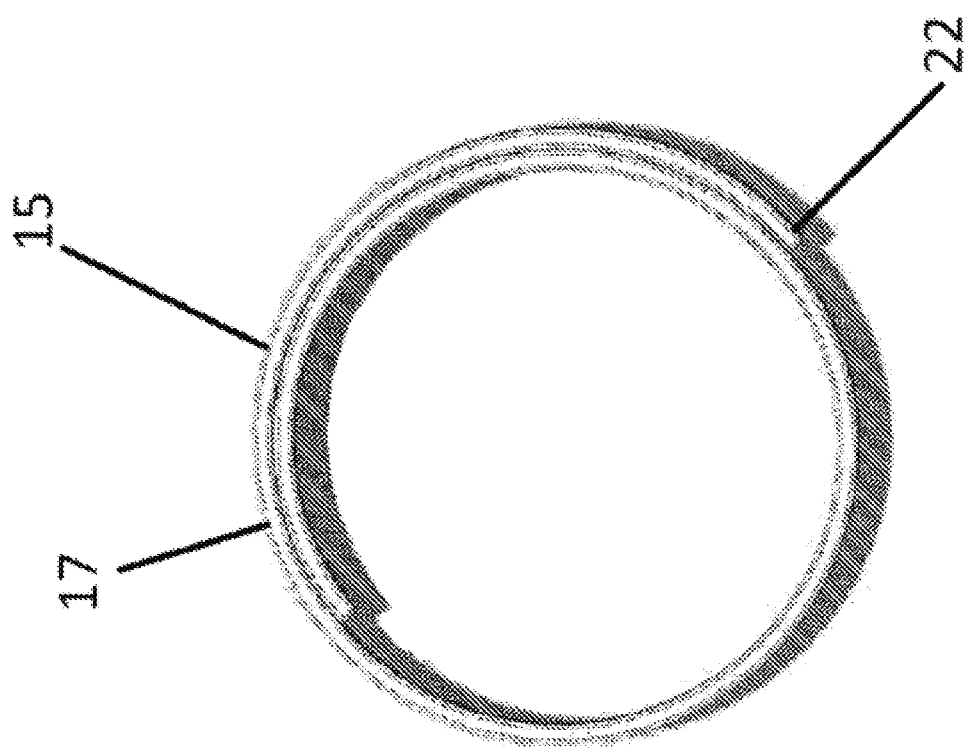
FIG. 67 is a top view of a flat spiral anchor, in accordance with embodiments.

FIGS. 66 and 67 show top views of two embodiments of an anchor 15. FIG. 66 is a top view of an anchor 15 comprising a cylindrical (i.e., a round wire or tubular) spiral band 17 and a free end 22. FIG. 67 is a top view of an anchor 15 comprising a flat (i.e., a flat ribbon) spiral band 17 and a free end 22. As used herein, a spiral or spiral shape may comprise a curve which emanates from a point (e.g., a central point) having a continuously increasing or decreasing distance from the point. The spiral or spiral shape may be two-dimensional (e.g., planar) or three-dimensional.

The spiral band 17 may be configured to anchor the frame structure 12 to the native valve when the frame structure 12 is in the expanded configuration adjacent the native valve. The frame structure 12 may be configured to be actuated from the unexpanded configuration to the expanded configuration adjacent a native valve in a patient. The spiral band 17 may be configured to be fully advanced from a first side of a native valve in a patient (e.g. an atrial side) to a second side of the native valve (e.g. into a ventricle of the heart) and anchor the frame structure 12 to the native valve when the frame structure 12 is in the expanded configuration adjacent the native valve as described herein.

During deployment and/or rotation of the spiral band 17, the leaflets and/or chordae tendineae may be captured by the free end 22 and trapped between the valve frame structure 12 and an interior surface of the spiral band 17. The free end 22 and the spiral band 17 may optionally rotated around one or more structures on the second side of the native valve such that the one or more valve structures (e.g., chordae, leaflets, or annulus) are pulled radially inwards towards the longitudinal axis of the anchor 15 and/or towards the longitudinal axis of the delivery device 30. The spiral band 17 and/or free end 22 may be configured such that minimal torque is applied to the one or more valve structures. Alternatively. or in combination, the spiral band 17 and/or free end 22 may be configured such that the one or more valve structures are not rotated, or are minimally rotated, during rotation of the spiral band 17. For example, the spiral band 17 may comprise one or more spaces 18 between loops of the spiral band 17, which facilitate movement of the captured tissue (e.g. chordae and/or leaflets) from the free end 22 to the center of the spiral band 17 with little or no torque and/or rotation of the structures during rotation of the spiral band 17. Alternatively, or in combination, the spiral band 17 may be configured such that, when fully deployed (for example, as shown in FIG. 67), none of the valve structures reside between the loops of the spiral band 17. Instead, the one or more valve structures may sit radially inward of the loops of the spiral band 17 in order to facilitate capture of the one or more valve structures between the spiral band 17 and the expanded frame structure 12. The one or more valve structures may retain or nearly retain their normal anatomical position when the spiral band 17 is fully deployed.

The spiral band 17 may comprise a delivery (e.g. an elongated) configuration and a deployed configuration. The spiral band 17 may be configured to be actuated from the delivery configuration to the deployed configuration adjacent a native valve in a patient. In various embodiments, the spiral band 17 may have a generally spiral shape in the deployed configuration. In various embodiments, the spiral band 17 may be elongated—rather than spiral-shaped—in the delivery configuration. For example, the spiral band 17 may be elongated into a straight shape within the delivery device. In various embodiments, a portion of the band 17 may have a spiral shape. In various embodiments, a substantial portion of the spiral band 17 may have a spiral shape. In various embodiments, the spiral band 17 may be formed as a flat spiral (in the deployed configuration) whereby the loops generally are positioned within the same plane (the plane being perpendicular to a longitudinal axis).

Spiral band 17 may be formed of a material having sufficient rigidity to hold a predetermined shape. The wire may, for example, be formed of a shape memory material (e.g. NiTi). It may be desirable for at least an end portion (e.g. free end 22) to be relatively rigid such that it can exert a force to move chordal tendineae, while still retaining flexibility to be collapsed within a delivery device. In various embodiments, the end portion only needs sufficient rigidity to hold its shape and will deform under a load. For example, the end portion may be configured with a similar rigidity to a guidewire, or slightly stiffer.

The one or more loops (also referred to herein as coils or turns) of the spiral band 17 may comprise a shape that bends around back towards its origin (for example, an arc, ellipsoid, circle, or the like). In some embodiments, a loop may comprise a shape that bends back towards its origin but does not cross itself, making a rotation within a range of about 180 degrees to about 360 degrees. For example, a loop may comprise an arc having a central angle within a range of about 180 degrees to about 360 degrees. In at least some embodiments, the one or more loops may comprise an arc. In some embodiments, a loop may comprise a shape that bends back towards and crosses itself, making at least a 360 degree rotation. In at least some embodiments, the one or more loops may comprise a 360 degree rotation (for example, a circle). In some embodiments, the one or more loops may comprise a 360 degree to 720 degree rotation (for example, a loop crossing itself once and rotating further towards a second crossing and formation of a second 360 loop).

The spiral band 17 may comprise a spiral wire. The spiral band 17 may comprise a plurality of spiral wires as described.

In some embodiments, the spiral band 17 may be configured to wrap at least partially around a distal portion of the delivery device 30, for example around the inner shaft, in the deployed configuration.

The spiral band 17 may comprise one or more loops. For example, the spiral band 17 may comprise a plurality of loops, which may increase the radial strength of the anchor by increasing friction and additional structural support. The one or more loops of the spiral band 17 may be spiral radially outward from a central point or central axis of the spiral, for example along an axis which is coaxial with a longitudinal axis of a delivery device 30 such that the spiral band 17 lies approximately along a plane perpendicular to the longitudinal axis of the delivery device 30.

FIG. 74 shows a perspective view of another exemplary anchor 15. The exemplary anchor 15 can include a plurality of lumens 71 disposed within an outer jacket 80. FIG. 75 shows a cross-sectional view of the anchor 15 of FIG. 74. The anchor 15 may be substantially similar to any of the anchors described herein except that, instead of a single solid band or wire 20, the anchor 15 may comprise a composite structure. For example, the anchor 15 may comprise an outer jacket 80 and one or more support structures 81 disposed within one or more lumens 71 of the outer jacket 80. The one or more support structures 81 may be fixedly disposed within the one or more lumens 71. In the exemplary embodiment shown, the anchor 15 may comprise two lumens 71 with support structures 81 disposed therein and a third open lumen 71. The third open lumen 71 may allow other device components to slide through the anchor 15 during delivery.

Figure 78:
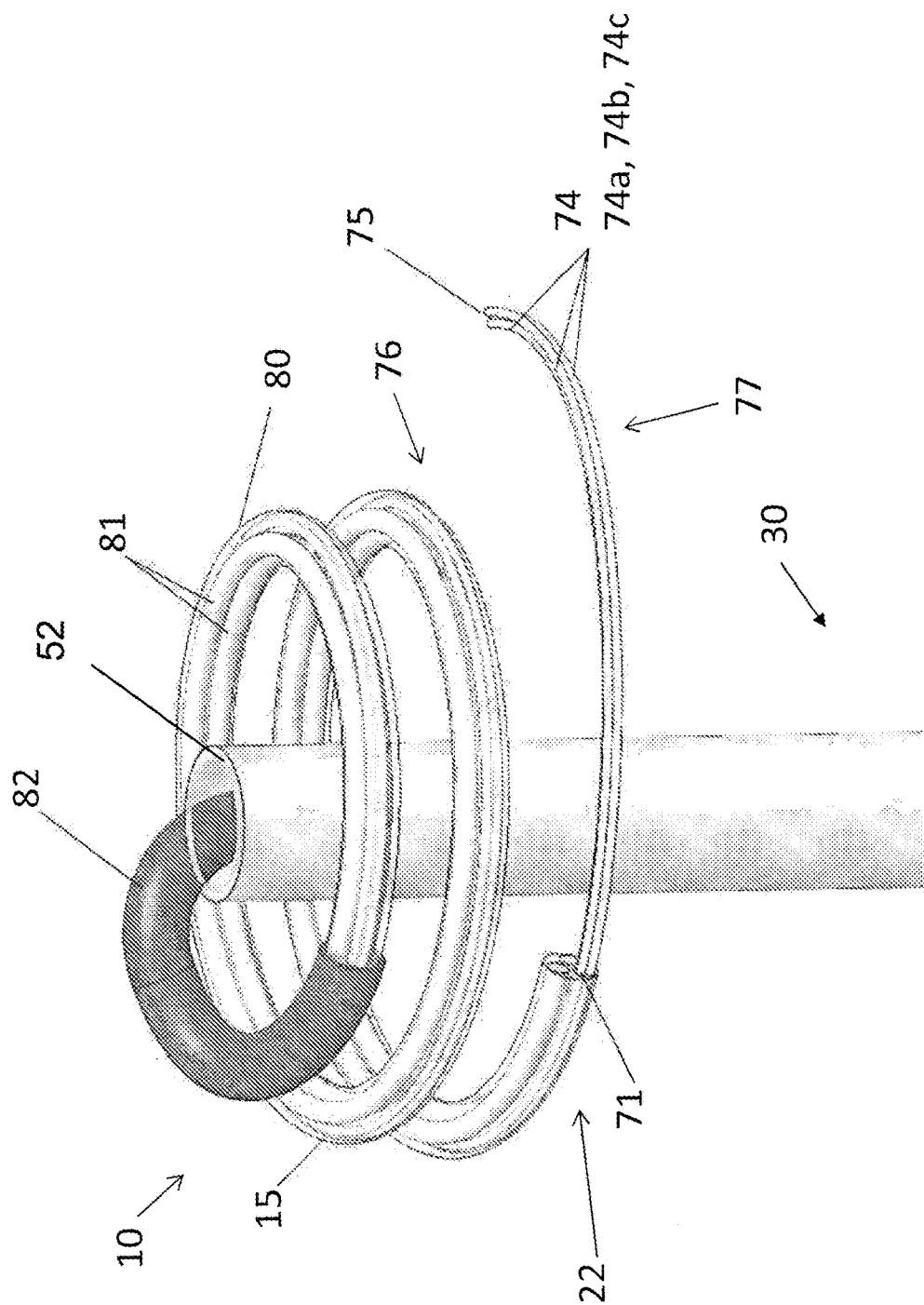
FIG. 78 shows an exemplary anchor loaded onto a delivery device, in accordance with embodiments.

The outer jacket 80 may be configured to provide circumferential constraint to the one or more support structures 81 and/or other structures (e.g., longitudinally translatable core wires 74 as shown and described with respect to FIGS. 78-80). The outer jacket 80 may comprise a soft, flexible material. For example, the outer jacket 80 may comprise an extruded plastic, a soft textile, or a biological material. For example, the outer jacket 80 may include polyethylene terephthalate (PET), polytetrafluoroethylene (PTFE), pericardium, and other materials as would be understood by one of skill based on the description herein. The outer jacket 80 may have a generally tubular shape. The outer jacket 80 may have a cross-section of any shape desired, for example a circular, tubular, hollow, square, elongated, ovoid, triangular, or any other shaped cross-section. The cross-sectional shape of the outer jacket 80 may, for example, be selected to facilitate deployment from the delivery device. Alternatively, or in combination, the shape of the outer jacket 80 may be selected to reduce pulling, torqueing, or otherwise damaging the one or more native structures as it is rotated therearound. Alternatively. or in combination, the shape of the outer jacket 80 may be selected to provide sufficient radial strength when a frame structure is expanded therein to anchor the frame structure to the one or more structures therebetween.

In some embodiments, the anchor 15 may comprise a single lumen 71 within the outer jacket 80. The single lumen 71 may comprise one or more support structures 81 disposed therein. Alternatively, or in combination, the first lumen 71 may comprise one or more translatable and/or removable core wires 74 (e.g., as shown in FIGS. 78-80) disposed therein. In one embodiment, the single lumen 71 may be configured to remain at least partially open when at least one support structure 81 is fixedly disposed therewithin in order to allow one or more translatable core wires 74 to be disposed within the open portion of the single lumen alongside the at least one support structure 81.

In some embodiments, the anchor 15 may comprise at least two lumens 71. For example, the anchor 15 may comprise a first lumen 71 and a second lumen 71. In some embodiments, the anchor 15 may further comprise a third lumen 71, for example as shown in FIGS. 74-78. In some embodiments, at least one of the plurality of lumens 71 may comprise one or more support structures 81 fixedly disposed therewithin. In some embodiments, all of the lumens 71 may comprise one or more support structures 81 fixedly disposed therewith. In some embodiments, at least one of the lumens 71 may be an open lumen 71. In some embodiments, at least a portion of at least one of the lumens 71 may remain partially open after one or more support structures are disposed therewithin. In some embodiments, all of the lumens 71 may be open (or partially open) lumens 71.

It will be understood by one of ordinary skill in the art based on the teachings herein that the anchor 15 may comprise any number of lumens 71 desired. For example, the anchor 15 may comprise 1, 2, 3, 4, 5, 6, 7, 8, 9, 10, or more lumens 71 disposed within the outer jacket 80.

In some embodiments, the one or more support structures 81 may comprise one or more stiffening members, wires, hypotubes, guidewires, or the like, or any combination thereof. The one or more support structures 81 may comprise a super-elastic material such as nitinol. The one or more support structures 81 may be shaped to correspond to the shape of the outer jacket 80 of the anchor 15.

In some embodiments, the one or more support structures 81 may comprise one or more stiffening members. The stiffening members may be configured to provide stiffness to the anchor 15. In some instances, providing one or more support structures 81 to the anchor 15 may make the anchor 15 radially stiffer than an anchor 15 that does not include a support structure 81 (e.g., that is only made up of a single band or wire 20). This may advantageously result in fewer anchor turns or loops being required to maintain sufficient engagement of the anchor 15 with the frame structure 12. It will be understood by one of ordinary skill in the art based on the teachings herein that the stiffness of the anchor 15 may be adjusted based on the material of the support structure(s) and/or number of support structure(s) disposed within the outer jacket 80.

The one or more support structures 81 may be fixedly disposed within a lumen 71 (or lumens) of the anchor 15. It will be understood by one of ordinary skill in the art based on the teachings herein that the any number of support structures 81 may be disposed within the anchor 15 as desired. For example, there may be 1, 2, 3, 4, 5, 6, 7, 8, 9, 10, or more support structures 81 disposed within one or more lumens 71 of the anchor 15 as desired.

The one or more support structures 81 may be formed of a material having sufficient rigidity to hold a predetermined shape. The one or more support structures 81 may, for example, be formed of a shape memory material (e.g., NiTi). It may be desirable for at least a distal end portion of the support structure 81 to be relatively rigid such that it can exert a force to move chordal tendineae, while still retaining flexibility to be collapsed within a delivery device 30. In various embodiments, the distal end portion of the support structure 81 has sufficient rigidity to hold its shape, but can be configured to deform under a load. For example, the end portion of the support structure 81 may be configured with a similar rigidity to a guidewire, or slightly stiffer.

The outer jacket 80 and/or support structures 81 of the anchor 15 may comprise a curved shape in the deployed configuration, for example a coiled shape, a helical shape, or a spiral shape as described herein. The outer jacket 80 and/or support structures 81 may be shaped to encircle chordae and/or leaflets of a diseased native valve. In various embodiments, the outer jacket 80 and/or support structures 81 may have a curved shape in the deployed configuration. In various embodiments, the outer jacket 80 and/or support structures 81 may be elongated-rather than curved—in the delivery configuration. For example, the outer jacket 80 and/or support structures 81 may be elongated into a straight shape within the delivery device 30. In various embodiments, a portion of the outer jacket 80 and/or support structures 81 may have a curved encircling shape. In various embodiments, a substantial portion of the outer jacket 80 and/or support structures 81 may have a curved encircling shape. In various embodiments, the outer jacket 80 and/or support structures 81 may be formed as a flat curve (in the deployed configuration) whereby the loops generally are positioned within the same plane (the plane being perpendicular to a longitudinal axis). In various embodiments, the outer jacket 80 and/or support structures 81 may be formed as a three-dimensional curve (in the deployed configuration) whereby the loops generally are positioned out of plane with one another.

The outer jacket 80 and/or support structures 81 may comprise a helical shape in the deployed configuration. In some embodiments, the outer jacket 80 and/or support structures 81 may comprise one or more helical portions as described herein.

The free end 22 of the anchor 15 may extend radially outward from the frame structure 12, and in particular from the remainder of the outer jacket 80. In some embodiments, the helical outer jacket 80 may have a generally tubular shape. The free end may extend radially outward from the tubular shape. In some embodiments, the helical outer jacket 80 may have a generally frustoconical shape. The free end 22 may extend radially outward from the frustoconical shape. In some embodiments, the helical outer jacket 80 may have a generally cylindrical shape. The free end 22 may extend radially outward from the cylindrical shape. The free end 22 may be configured to encircle a larger radius than the main coils (also referred to herein as loops or turns) of the helical outer jacket 80. The larger diameter may facilitate capturing of one or more structures, for example the valve leaflets of the chordal tendineae within the sweep of the free end 22 when rotated as described herein.

In various embodiments, the outer jacket 80 and/or support structures 81 may have a generally helical shape in the deployed configuration. In various embodiments, the outer jacket 80 and/or support structures 81 may be elongated-rather than helix-shaped—in the delivery configuration. For example, the outer jacket 80 and/or support structures 81 may be elongated into a straight shape within the delivery device. In various embodiments, a portion of the outer jacket 80 and/or support structures 81 may have a helical shape. In various embodiments, a substantial portion of the outer jacket 80 and/or support structures 81 may have a helical shape. In various embodiments, the helical outer jacket 80 and/or support structures 81 may be formed as a three-dimensional helix (in the deployed configuration) whereby the loops generally are positioned around the same axis (for example, a longitudinal axis of the delivery device 30).

The outer jacket 80 and/or support structures 81 may comprise a spiral shape in the deployed configuration. In some embodiments, the outer jacket 80 and/or support structures 81 may comprise one or more spiral portions as described herein.

In various embodiments, the outer jacket 80 and/or support structures 81 may have a spiral-shaped deployed configuration. In various embodiments, spiral refers to a shape with windings about a central axis. The spiral may be continuous. The windings may gradually widen (or tighten) along the length. The spiral may be formed in a flat plane perpendicular to the central axis. In various embodiments, the outer jacket 80 and/or support structures 81 may have a deployed configuration that is not formed in a flat plane, or in other words the deployed shape is formed in a three-dimensional and/or non-degenerate space. In various embodiments, the outer jacket 80 and/or support structures 81 may have a conical-shaped deployed configuration including, but not limited to, tubular, conical, frustoconical, and/or helical shapes.

The free end 22 of the outer jacket 80 may extend radially outward from the frame structure 12, and in particular from the remainder of the spiral outer jacket 80. The other end of the spiral outer jacket 80 may be coupled to the top or bottom of the frame structure 12 as described herein. Alternatively, or in combination, the other end of the spiral outer jacket 80 may not be attached to the frame structure 12 as described herein. The free end 22 of the spiral outer jacket 80 may facilitate capturing of the valve leaflets and/or chordal tendineae within the sweep of the free end during rotation as described herein. During rotation of the spiral outer jacket 80, the leaflets and/or chordae tendineae may be captured by the free end 22 and trapped between the valve frame structure 12 and an interior surface of the spiral outer jacket 80.

In various embodiments, the outer jacket 80 and/or support structures 81 may have a generally spiral shape in the deployed configuration. In various embodiments, the outer jacket 80 and/or support structures 81 may be elongated—rather than spiral-shaped—in the delivery configuration. For example, the outer jacket 80 and/or support structures 81 may be elongated into a straight shape within the delivery device. In various embodiments, a portion of the outer jacket 80 and/or support structures 81 may have a spiral shape. In various embodiments, a substantial portion of the outer jacket 80 and/or support structures 81 may have a spiral shape. In various embodiments, the spiral outer jacket 80 and/or support structures 81 may be formed as a flat spiral (in the deployed configuration) whereby the loops generally are positioned within the same plane (the plane being perpendicular to a longitudinal axis).

The free end 22 and/or the outer jacket 80 may be sized and dimensioned for insertion through the native valve, for example through tissue at or near a commissure of the native valve or through the valve opening itself. In some embodiments, the free end 22 may comprise an atraumatic tip to avoid reduce risk of injury to the native valve tissue and leaflets. For example, the free end may comprise a blunt end, a ball tip, a curved tip (e.g., J-tip or pigtail), or other atraumatic shapes. Alternatively, the free end 22 may be configured for piercing tissue.

The outer jacket 80 and/or free end 22 may optionally rotated around one or more structures on the second side of the native valve such that the one or more structures (e.g., chordae, leaflets, or annulus) are pulled radially inwards towards the longitudinal axis of the anchor 15 and/or towards the longitudinal axis of the delivery device 30. The outer jacket 80 and/or free end 22 may be configured such that minimal torque is applied to the one or more structures. Alternatively. or in combination, the outer jacket 80 and/or free end 22 may be configured such that the one or more structures are not rotated, or are minimally rotated, during rotation of the outer jacket 80. For example, the outer jacket 80 may comprise one or more spaces between loops to facilitate radially-inward movement of the captured tissue (e.g. chordae and/or leaflets) from the free end 22 to the center of the curved structure with little or no torque and/or rotation of the structures during rotation of the outer jacket 80 as described herein. Alternatively or in combination, the outer jacket 80 may be configured such that, when fully deployed none of the structures reside between the loops of the curved encircling shape. Instead, the one or more structures may sit radially inward of the loops in order to facilitate capture of the one or more structures between the outer jacket 80 and the expanded frame structure 12. The one or more structures may retain or nearly retain their normal anatomical position when the outer jacket 80 is fully deployed.

Figure 77:
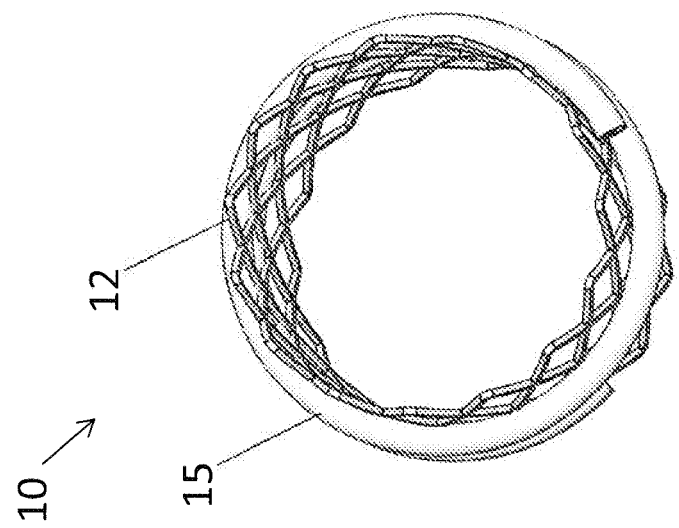
FIG. 77 shows a top perspective view of the anchor of FIG. 74 disposed around a frame structure, in accordance with embodiments.
Figure 76:
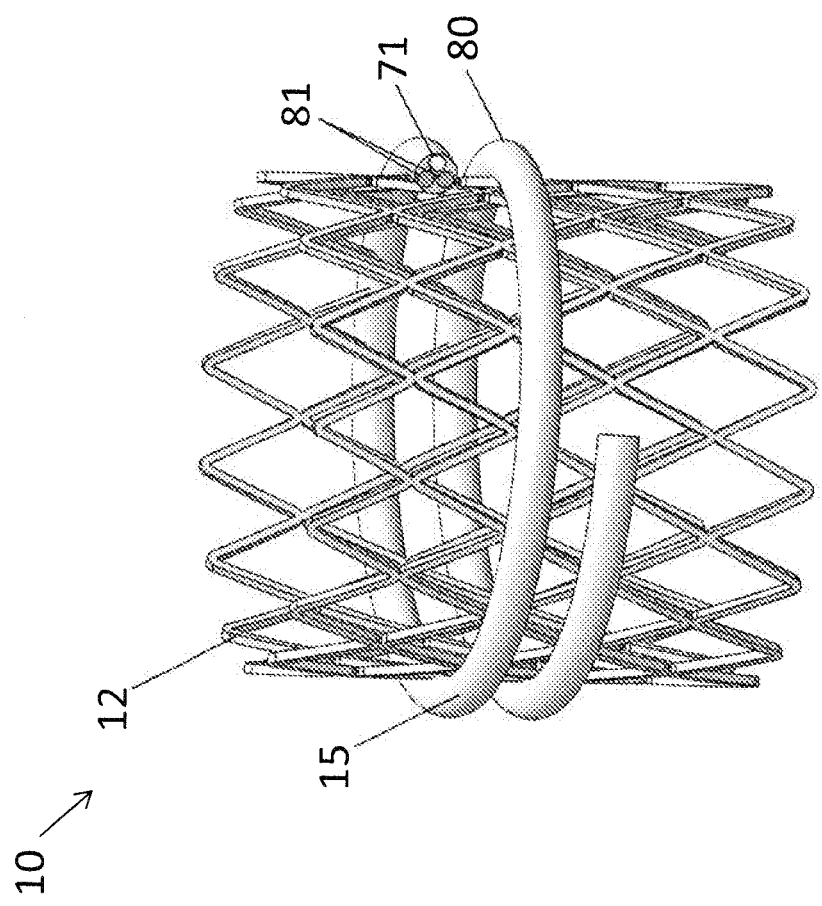
FIG. 76 shows a side view a valve prosthesis comprising the anchor of FIG. 74 disposed around a frame structure in the expanded configuration, in accordance with embodiments.

FIG. 76 shows a side view of a valve prosthesis 10 comprising the anchor 15 of FIG. 74 disposed around a frame structure 12 in the expanded configuration. FIG. 77 shows a top perspective view of the anchor 15 disposed around frame structure 12. The anchor 15 is shown in a deployed configuration. The anchor 15 may comprise a delivery (e.g., elongated) configuration (e.g., as shown in FIG. 1) and a deployed configuration (e.g., as shown in FIG. 2). In various embodiments, the anchor 15 may be self-expanding and may move to the deployed configuration as it is removed from the delivery sheath as described herein. The anchor 15 may be configured to wrap at least partially around the frame structure 12 in the deployed configuration. The frame structure 12 may have an unexpanded configuration (for example, a compressed configuration as described herein) and an expanded configuration as described herein. The frame structure 12 may be substantially similar to any of the frame structures described herein or understood by one of ordinary skill in the art from the description herein. The anchor 15 may comprise an outer jacket 80 and one or more lumens 71 as described herein. The one or more lumens 71 may comprise one or more support structures 81 and/or open lumens 71 in the deployed configuration. The anchor 15 may be configured to anchor the frame structure 12 to the native valve when the frame structure 12 is in the expanded configuration adjacent the native valve. The frame structure 12 may be configured to be actuated from the unexpanded configuration to the expanded configuration adjacent a native valve in a patient. The anchor 15 may be configured to be fully advanced from a first side of a native valve in a patient (e.g. an atrial side) to a second side of the native valve (e.g. into a ventricle of the heart) and anchor the frame structure 12 to the native valve when the frame structure 12 is in the expanded configuration adjacent the native valve as described herein. The anchor 15 may be configured to expand slightly upon expansion of the frame structure 12 therein in order to account for the increased circumferential distance.

The outer jacket 80 and/or support structures 81 may comprise one or more loops. For example, the outer jacket 80 and/or support structures 81 may comprise a plurality of loops, which may increase the radial strength of the anchor by increasing friction and addition structural support. The one or more loops of the outer jacket 80 and/or support structures 81 may be substantially cylindrical around a central axis of the outer jacket 80 and/or support structures 81, for example along an axis which is coaxial with a longitudinal axis of a delivery device 30. The one or more loops of the outer jacket 80 and/or support structures 81 may be substantially helical around a central axis or helical axis of the outer jacket 80 and/or support structures 81, for example along an axis which is coaxial with a longitudinal axis of a delivery device. The one or more loops of the outer jacket 80 and/or support structures 81 may spiral radially outward from a central point or central axis of the outer jacket 80 and/or support structures 81, for example along an axis which is coaxial with a longitudinal axis of a delivery device 30 such that the outer jacket 80 and/or support structures 81 lies approximately along a plane perpendicular to the longitudinal axis of the delivery device 30.

The one or more loops (also referred to herein as coils or turns) of the outer jacket 80 and/or support structures 81 may comprise a curved shape that bends around back towards its origin (for example, an arc, ellipsoid, circle, or the like). In some embodiments, a loop may comprise a curved shape that bends back towards its origin but does not cross itself, making a rotation within a range of about 180 degrees to about 360 degrees. For example, a loop may comprise a curve or an arc having a central angle within a range of about 180 degrees to about 360 degrees. In at least some embodiments, the one or more loops may comprise an arc. In some embodiments, a loop may comprise a shape that bends back towards and crosses itself, making at least a 360 degree rotation. In at least some embodiments, the one or more loops may comprise a 360 degree rotation (for example, a circle). In some embodiments, the one or more loops may comprise a 360 degree to 720 degree rotation (for example, a loop crossing itself once and rotating further towards a second crossing and formation of a second 360 loop).

Interaction of the frame structure 12 with the one or more loops of the outer jacket 80 and/or support structures 81 may create opposing forces therebetween that provide mechanical leverage for anchoring the frame structure 12 to the one or more anatomical structures. In some embodiments, the one or more loops may comprise at least 360 degrees of rotation when deployed such that the loops wrap around one another and provide additional mechanical leverage against the frame structure 12 in order to facilitate anchoring of the frame structure 12 as described herein. Additional loops or partial loops may provide additional mechanical strength and/or leverage.

In some embodiments, the one or more loops of the outer jacket 80 may comprise one or more spaces therebetween. The spaces may facilitate movement of the captured tissue (e.g. chordae and/or leaflets) from the free end 22 to the center of the spiral structure during rotation of the anchor 15 as described herein.

The outer jacket 80 and/or support structures 81 may be configured to wrap at least partially around the frame structure 12 in the deployed configuration.

In some embodiments, the outer jacket 80 and/or support structures 81 may be configured to wrap at least partially around a distal portion of a delivery device (e.g., delivery device 30 of FIGS. 8-10), for example around the inner shaft, in the deployed configuration.

FIG. 78 shows an exemplary anchor 15 loaded onto a delivery device 30. The anchor 15 may be substantially similar to the anchor of FIG. 74 (with outer jacket 80 and support structures 81 therein) except that that it can additionally include one or more core wires 74 translatably disposed within the open lumen of the anchor 15 (i.e., in addition to or in place of the fixed support structures 81). The anchor 15 may include a plurality of lumens 71 disposed therein (through which support structures 81 extend). One or more of the lumens 71 may comprise an open lumen configured to allow one or more core wires 74 (or other elongate member) to be slidably disposed therein. The one or more core wires 74 may, for example, comprise a first wire 74a, a second wire 74b, and a third wire 74c as shown. The outer jacket 80 may comprise one or more apertures or openings in the free end 22 to expose the lumen 71 to the surgical site. The core wires 74 can be configured to exit the anchor 15 through the one or more apertures or openings before, during, or after deployment of the anchor 15.

The one or more core wires 74 may comprise a shape memory material or super-elastic material such as nitinol. In some embodiments, the one or more core wires 74 may be made of a heat treatable material. The one or more core wires 74 may be formed of a material having sufficient rigidity to hold a predetermined shape. It may be desirable for at least the distal section 77 of the one or more core wires 74 to be relatively rigid such that it can exert a force to move chordal tendineae, while still retaining flexibility to be collapsed within the delivery device 30. In various embodiments, the distal portion 77 has sufficient rigidity to hold its shape, but is configured to deform under a load. For example, the distal section 77 may be configured with a similar rigidity to a guidewire or slightly stiffer.

The one or more core wires 74 may comprise one or more sections of wire having the same or different pre-formed shapes to facilitate deployment within the lumen(s) 71 of the anchor 15. For example, the distal section 77 can have a preformed shape (e.g., include one or more deflection features as described herein). The one or more core wires 74 may also comprise a proximal curved (or looped) section 76 proximal to the distal section 77. The curved shape of the proximal curved section 76 may be substantially similar to the curved shape of the anchor 15 in order to provide robust rotational constraint to the one or more core wires 74 so that the distal tip 75 of the one or more core wires does not rotate relative to the anchor 15 as the distal tip is translated. Alternatively, the proximal curved section 76 may be configured with a different shape or curvature that the anchor 15 in order to induce rotation in the distal tip 75 during translation as desired.

The one or more core wires 74 may comprise one or more pull-wires.

The one or more core wires 74 may be translatably disposed within an open lumen 71 (or lumens) of the anchor 15. It will be understood by one of ordinary skill in the art based on the teachings herein that the any number of core wires 74 may be disposed within the anchor as desired. For example, there may be 1, 2, 3, 4, 5, 6, 7, 8, 9, 10, or more core wires 74 disposed within one or more lumens 71 of the anchor 15 as desired.

The one or more core wires 74 may be translatable. The one or more core wires 74 may translate distally and proximally within the lumen 71 of the anchor 15. The one or more core wires 74 may be longitudinally translatable independent of one another. In some embodiments, the one or more core wires 74 may comprise a plurality of wires which may be translated relative to one another in order to change the shape of a distal section 77 and deflect the distal tip 75 of the wires 74 to facilitate wrapping of the wires 74 and/or anchor 15 around the delivery device 30 and/or one or more native structures of the valve as described herein. For example, the one or more core wires 74 may comprise a first wire 74a and a second wire 74b. The first and second wires 74a, 74b may be longitudinally translatable independent of one another within the lumen 71 of the anchor 15. In some embodiments, the one or more core wires 74 may further comprise a third wire 74c. The third wire 74 may be longitudinally translatable independent of the first and/or second wires 74a. 74b.

The anchor 15 with outer jacket 80, support structures 81, and/or core wires 74 may be detachably coupled to the delivery device 30 (see FIG. 78) and/or a frame structure 12 (see FIGS. 76-66) as described herein. The anchor 15 may be actuated from an elongated configuration to a deployed configuration adjacent a native valve of patient. Referring to FIG. 78, in some embodiments, the anchor 15 may be deployed from the inner shaft 52 of the delivery device 30 by pushing the anchor 15 out of the inner shaft 52 (if disposed within the inner shaft 52 in the elongated configuration), releasing the anchor 15 from radial constraint by retracting the outer sheath 50 (if disposed within the outer sheath 50 in the elongated configuration), or the like as described herein. When deployed from the delivery device 30, the anchor 15 may wrap at least partially around a distal portion of the delivery device 30 (e.g., around the inner shaft 52 if disposed within the inner shaft 52 or around the outer sheath 50 if disposed within the outer sheath 50). A central axis of the anchor 15 may be co-axial with a longitudinal axis of the delivery device 30 when the anchor 15 is in the deployed configuration. In some embodiments, deployment of the anchor 15 from the delivery device 30 such that the anchor 15 wraps concentrically or coaxially around a longitudinal axis 32 of the delivery device 30 may be directed, at least in part, by the positioning of the free end 22 relative to the delivery device 30. Correctly positioning the free end 22 relative to the delivery device 30 may result in efficient and/or deployment.

In some embodiments, deployment of the anchor 15 may be facilitated by longitudinal translation of the one or more core wires 74 within the lumen(s) 71 in order to advance or retract the distal tip 75 of the one or more core wires 74 away from or towards the free end 22 of the anchor 15 in order to change the shape of the distal portion of the anchor 15.

The one or more core wires 74 may be translated within the lumen(s) 71 of the anchor 15 before, during, or after deployment of the anchor 15 from the undeployed configuration to the deployed configuration. For example, the one or more core wires 74 may be translated within the anchor 15 before deployment of the anchor 15 into a self-assembly state in order to facilitate wrapping of the anchor 15 around the delivery device 30 (e.g., by extending past the free end 22 of the anchor 15). Alternatively, or in combination, the one or more core wires 74 may be translated within the lumen(s) 71 of the anchor 15 during deployment of the anchor 15 in order to actively or reactively "wiggle" or deflect the angle of the free end and/or distal tip as it deploys as described herein. Alternatively. or in combination, the one or more core wires 74 may be translated with the anchor 15 into an encircling state in order to facilitate grasping of and rotation of the anchor 15 around the one or more native valve structures as described herein.

The one or more core wires 74 may facilitate deployment of the anchor 15 from the delivery configuration to the deployed configuration. For example, the one or more core wires 74 may be configured to be advanced through the one or more lumens 71 of the outer jacket 80 and out an opening in the free end 22 of the anchor 15 into a self-assembly configuration. A distal tip 75 of one or more of the core wires 74 (e.g., a distal tip of a first wire and/or a second wire) may be configured to extend radially outward, proximally, or distally of a curved shape of the anchor 15 in the self-assembly configuration. The self-assembly configuration may facilitating positioning of the anchor relative to a delivery device during actuation from the delivery configuration to the deployed configuration.

The distal tip 75 of the one or more core wires 74 may be advanced into a self-assembly configuration prior to or during deployment of the anchor 15 from the delivery device 30 in order to facilitate wrapping of the one or more core wires 74 and anchor 15 around the delivery device 30 into the correctly deployed configuration. In the self-assembly state, the distal tip 75 may be deflected prior to or during deployment of the anchor 15 such that the distal tip 75 overlaps with one or more turns of the anchor 15 in order to ensure that the free end 22 wraps back around the delivery device 30.

In the self-assembly state, the distal tip 75 of the one or more core wires 74 may be deflected or angled proximally (e.g., towards a proximal portion of the anchor 15 and a distal end of the delivery device 30), distally (e.g., away from a proximal portion of the anchor 15 and towards a proximal portion of the delivery device 30), and/or radially (e.g., radially outwards or inwards from the main body of the anchor 15 and away from or towards the delivery device 30). In some embodiments, for example, the distal tip 75 may be positioned adjacent one or more loops of the anchor 15 when the anchor 15 is in the deployed configuration. Alternatively, or in combination, the distal tip 75 may be positioned such that it angles towards a proximal end of the anchor 15 when the anchor 15 is in the deployed configuration. Alternatively, or in combination, the distal tip 75 may be positioned such that it angles towards a distal end of the delivery device 30 when the anchor 15 is in the deployed configuration.

In at least some instances, it may be sufficient to initially advance the distal tip 75 into the self-assembly configuration during wrapping as described herein in order to form the first loop of the anchor 15 around the delivery device 30. Once the first loop as wrapped around the delivery device 30, the remaining loops may be more inclined or biased to wrap correctly around the delivery device 30 without additional deflection or manipulation. The one or more core wires 74 may remain in the self-assembly configuration for the entirety of the deployment of the anchor 15 from the delivery device 30. Alternatively, once the free end 22 has made a first loop around the delivery device 30 facilitated by the distal tip 75, the distal tip 75 may be translated proximally and retracted at least partially back into the anchor 15 for the remainder of the deployment of the anchor 15.

Alternatively, or in combination, the one or more core wires 74 may facilitate capture of and rotation of the anchor 15 around the one or more structures as described herein. For example, during and/or following core wires 74 may be configured to be advanced (or further advanced from the self-assembly configuration) into an encircling configuration. A distal tip 75 of the one or more core wires 74 (e.g., a first wire and/or a second wire) may be configured to angle away from the anchor 15 in the encircling configuration.

In the encircling configuration, the distal tip 75 of the one or more core wires 15 may be configured to deflect or angle proximally (e.g., towards a proximal portion of the anchor 15 and a distal end of the delivery device 30), distally (e.g., away from a proximal portion of the anchor 15 and towards a proximal portion of the delivery device 30), and/or radially (e.g., radially outwards or inwards from the main body of the anchor 15 and away from or towards the delivery device 30, respectively).

In at least some instances, deflection (e.g., angling proximally, distally, and/or radially outward) of the distal tip 75 away from the loops of the anchor 15 may aid in capture of the one or more structures by forming a "grabber" arm. For example, during rotation of the anchor 15, the grabber arm distal tip 75 may be rotated to capture the one or more structures of the native valve.

The distal tip 75 of the one or more core wires 74 may optionally rotated around one or more structures on the second side of the native valve such that the one or more native valve structures (e.g., chordae, leaflets, and/or annulus) are pulled radially inwards towards the longitudinal axis of the anchor 15 and/or towards the longitudinal axis of the delivery device 30. The distal tip 75, anchor 15, and/or free end 22 may be configured such that minimal torque is applied to the one or more native structures. Alternatively, or in combination, the distal tip 75, anchor 15, and/or free end 22 may be configured such that the one or more native valve structures are not rotated, or are minimally rotated, during rotation of the anchor 15.

Following deployment of the anchor 15 and/or rotation of the free end 22 (optionally facilitated by distal tip 75 as described herein) around the one or more structures of the native valve and/or expansion of the frame structure 12 within the anchor 15 adjacent the native valve, the one or more core wires 74 may be removed from the system, leaving the composite anchor 15 wrapped around the frame structure 12 at the native valve. By removing the one or more core wires 74 from the system following correct deployment of the valve prosthesis 10, potential complications related to having a discontinuously shaped distal end and/or translatable element left within the native valve may be reduced. Alternatively, the one or more core wires 74 may be fixed and left in the system following correct deployment if desired.

In various embodiments, the one or more core wires 74 may have a spiral-shaped deployed configuration. In various embodiments, spiral refers to a shape with windings about a central axis. The spiral may be continuous. The windings may gradually widen (or tighten) along the length. The spiral may be formed in a flat plane perpendicular to the central axis. In various embodiments, the one or more core wires 74 may have a deployed configuration that is not formed in a flat plane, or in other words the deployed shape is formed in a three-dimensional and/or non-degenerate space. In various embodiments, the one or more core wires 74 may have a conical-shaped deployed configuration including, but not limited to, tubular, conical, frustoconical, and/or helical shapes.

The distal tip 75 of the one or more core wires 74 may extend radially outward from the frame structure 12, and in particular from the remainder of the spiral one or more core wires 74 and/or anchor 15. The distal tip 75 of the one or more core wires 74 may facilitate capturing of the valve leaflets and/or chordal tendineae within the sweep of the free end during rotation as described herein. During rotation of the anchor 15 and one or more core wires 74 extending distally therefrom, the leaflets and/or chordae tendineae may be captured by distal tip 75 and trapped between the valve frame structure 12 and an interior surface of the anchor 15 and/or one or more core wires 74.

In various embodiments, the one or more core wires 74 may have a generally spiral shape in the deployed configuration. In various embodiments, the one or more core wires 74 may be elongated-rather than spiral-shaped—in the delivery configuration. For example, one or more core wires 74 may be elongated into a straight shape within the delivery device. In various embodiments, a portion of the one or more core wires 74 may have a spiral shape. In various embodiments, a substantial portion of the one or more core wires 74 may have a spiral shape. In various embodiments, the spiral one or more core wires 74 may be formed as a flat spiral (in the deployed configuration) whereby the loops generally are positioned within the same plane (the plane being perpendicular to a longitudinal axis).

The distal tip 75 of the one or more core wires 74 may be sized and dimensioned for insertion through the native valve, for example through tissue at or near a commissure of the native valve or through the valve opening itself. In some embodiments, the distal tip 75 of the one or more core wires 74 may comprise an atraumatic tip to avoid reduce risk of injury to the native valve tissue and leaflets. For example, the distal tip 75 may comprise a blunt end, a ball tip, a curved tip (e.g., J-tip or pigtail), or other atraumatic shapes. Alternatively, the distal tip 75 of the one or more core wires 74 may be configured for piercing tissue.

In various embodiments, the distal tip 75 may be shaped and configured to reduce the risk of counter-rotation. For example, the distal tip 75 may have a curled end to cause the distal tip 75 to snag chordae if it is rotated in a direction opposite the anchoring rotation.

The distal tip 75 of the one or more core wires 74 may optionally rotated around one or more structures on the second side of the native valve such that the one or more structures (e.g., chordae, leaflets, or annulus) are pulled radially inwards towards the longitudinal axis of the anchor 15 and/or towards the longitudinal axis of the delivery device 30. The distal tip 75 of the one or more core wires 74 may be configured such that minimal torque is applied to the one or more structures. Alternatively, or in combination, the distal tip 75 of the one or more core wires 74 may be configured such that the one or more structures are not rotated, or are minimally rotated, during rotation of the anchor 15.

In some embodiments (e.g., instead of or in addition to having multiple core wires 74), one or more of the core wires 74 and/or distal end of the anchor 15 may comprise one or more deflecting features such that, when advanced distally past the free end 22 of the anchor 15, a distal tip of the one or more core wires 74 may be caused to "wiggle" or deflect away from the curvature of the anchor body 15 and change the deployment angle of the distal tip out of the anchor body 15 in order to facilitate wrapping of the anchor 15 around the delivery device 30 as described herein (e.g., radially outward, proximally, or distally of the curved shape of the anchor). The deflecting features may, for example, comprise one or more pre-formed waves, bends, kinks, or humps adjacent the distal tip 75 of the one or more core wires 74. For example, the one or more deflection features may comprise one or more kinks along the distal tip 75 of one or more of the core wires 74 such that at least a portion of the distal tip 75 is discontinuous with a curved shape of a proximal curved portion of the one or more core wires 74. The movable core wires 74 may be translated within the anchor 15 before, during, or after deployment of the anchor 15 from the undeployed configuration to the deployed configuration. For example, the one or more core wires 74 may be translated within the lumen(s) 71 of the anchor 15 before deployment of the anchor into a self-assembly state in order to facilitate wrapping of the anchor 15 around the delivery device (e.g., by extending past the free end 22 of the anchor 15 and acting similarly to the free end 22 comprising the deflecting features described herein). Alternatively, or in combination, one or more core wires 74 may be translated within the lumen(s) 71 of the anchor 15 during deployment of the anchor 15 in order to actively or reactively "wiggle" or deflect the angle of the distal tip as it deploys. Alternatively, or in combination, the one or more core wires 74 may be translated with the lumen(s) 71 of the anchor 15 into an encircling state in order to facilitate grasping of and rotation of the anchor 15 around the one or more native structures as described herein. By utilizing movable core wires 74 comprising one or more deflecting features, the anchor 15 may comprise a relatively simpler shape compared to an anchor having one or more deflecting features itself, which may facilitate design and fabrication of the anchor. For example, the anchor 15 may have a shape with a substantially continuous curvilinear shape and/or the reduction of complex bends. Alternatively, or in combination, the behavior of the free end 22 of the anchor 15 and/or the free end 75 of the core element 74 may be optimized to facilitate various deployment and/or implantation steps of the anchor. The lumen 71 of the anchor 15 may be sized and dimensioned to match or be slightly larger than the diameter of the one or more core wires 74 in order to enable translation therein. In some embodiments, the one or more core wires 74 may be made of a shape memory material such as nitinol in order to allow shaping of the one or more core wires 74. In some embodiments, the one or more core wires 74 may be made of a heat treatable material in order to allow shaping thereof. The anchor 15 may be relatively stiffer than the core wire 74. The anchor 15 may be sufficiently stiffer than the one or more core wires 74 such that the core wire 74 anchor 15 experiences little or no deflection itself when the one or more core wires 74 are disposed therein. The anchor 15 may be relatively stiffer than the one or more core wires 74 in order to prevent or reduce deflection of the anchor body when the movable core element is disposed in a lumen thereof. In some embodiments, the one or more core wires 74 may comprise a relatively more complex shape compared to the anchor in order to guide and the free end 22 of the relatively stiffer anchor 15.

FIG. 79 shows proximal deflection of a distal tip 75 of one or more core wires 74 disposed within an open lumen of an exemplary anchor 15. FIG. 80 shows distal deflection of a distal tip 75 of one or more core wires 74 disposed within an open lumen of an exemplary anchor 15. The anchor 15 may comprise multiple translatable core wires 74 disposed therein. The anchor 15 may be substantially similar to any of the anchors described herein, for example a helix-shaped anchor having a three lumens or channels 71 in the deployed configuration as shown. The anchor 15 may be detachably coupled to a delivery device 30 as described herein. The anchor 15 may be directly coupled to a frame structure 12, for example at a proximal or distal end thereof, as described herein. Alternatively, or in combination, the anchor 15 may be detachably coupled to the delivery device 30 prior to deployment at the native valve. Alternatively. or in combination, the anchor 15 may be operably coupled to the frame structure 12 and/or delivery device 30 by a proximal pusher section 73 of the one or more core wires 74 as described herein. The delivery device 30 may be substantially similar to any of the delivery devices described herein. For example, a proximal end of the anchor 15 may be detachably coupled to the inner shaft 52 during delivery to the native valve. Alternatively, or in combination, a proximal end of the anchor 15 may be coupled to a distal end of the frame structure or a proximal end of the frame structure. Alternatively, or in combination, a proximal end of the anchor 15 may be coupled to a proximal pusher section 73 of the one or more core wires 74, thereby operably coupling the anchor 15 to the delivery device 30. Alternatively, or in combination, the delivery device 30 may comprise an actuation arm 82 which may be detachably coupled to a proximal end of the anchor 15 and configured to push the anchor 15 out of the delivery device 30 from the delivery configuration to the deployed configuration. For example, longitudinal translation and/or rotational motion of the actuation arm 82 may be translated to the anchor 15 to facilitate deployment as described herein. The anchor 15 is shown in a deployed configuration. The anchor 15 may comprise a delivery (e.g., elongated) configuration (e.g., as shown in FIG. 1) and a deployed configuration (e.g., as shown in FIG. 2). In various embodiments, the anchor may be self-expanding and may move to the deployed configuration as it is removed from the delivery sheath as described herein. The anchor 15 may be configured to wrap at least partially around the frame structure 12 in the deployed configuration. The anchor 15 may be configured to wrap at least partially around a distal end of the delivery device 30 in the deployed configuration.

The one or more core wires 74 may comprise a plurality of wires which may be translated relative to one another in order to change the shape of a distal tip portion 77 and deflect the distal tip 75 of the wires 74 to facilitate wrapping of the wires 74 and/or anchor 15 around the delivery device 30 and/or one or more native structures as described herein. For example, the one or more core wires 74 may comprise a first wire 74a and a second wire 74b. The first and second wires 74a, 74b may be longitudinally translatable independent of one another within the lumen 71 of the anchor 15. In some embodiments, the one or more core wires 74 may further comprise a third wire 74c. The third wire 74 may be longitudinally translatable independent of the first and/or second wires 74a. 74b. Translation of the first, second, and/or third wires 74a, 74b, 74c may facilitate deployment of the anchor 15 and/or capture of the chordae as described herein.

In some embodiments, the one or more core wires 74 (e.g., wires 74a, 74b, 74c) may comprise a proximal pusher section 73 proximal to the proximal curved section 76 which extends from the proximal curved section 76 to a proximal end of the delivery device 30. The proximal pusher section 73 may act as an actuation mechanism and facilitate longitudinal translation of the one or more core wires 74 within the lumen 71 of the anchor 15. For example, the proximal end of the proximal pusher section 73 may be coupled to an actuation mechanism in/on the delivery device 30 in order to translate the one or more core wires 74. Alternatively, the proximal end of the proximal pusher section 73 may be manually manipulated by at or near a proximal end of the delivery device in order to translate the one or more core wires 74. The proximal pusher section 73 of the first and second wires 74a, 74b74b (and the third wire 74c, a fourth wire, etc.) may or may not be disposed within the housing. For example, the proximal pusher portion 73 be disposed within the housing between the proximal end of the anchor and the distal end of the frame structure 12.

The core wires 74a, 74b, 74c may extend through and towards a proximal end of the delivery device 30. The wires 74a, 74b. 74c may be coupled to one or more actuation mechanisms in/on the delivery device in order to translate the wires 74a. 74b, 74c relative to one another and/or the anchor 15. Alternatively, the wires 74a, 74b, 74c may be manually manipulated by at or near a proximal end of the delivery device in order to translate the core wires 74a. 74b, 74c. The wires 74a, 74b, 74c may be independently translated in order to generate additive curvatures. The wires 74a, 74b, 74c may be pulled/pushed distally or proximally relative to one another to cause the distal tip portion 77 to deflect in any number and manner of shapes or curvatures desired.

In some embodiments, the first wire 74a and the second wire 74b (and the third wire 74c, a fourth wire, etc.) may be coupled to one another at the distal tip 75. Translation of the first and second wires 74a. 74b relative to one another may change the curvature of the distal section 77, thereby deflecting the distal tip 75 of the core wires 74 in order to facilitate anchor deployment and/or wrapping of the anchor 15 around one or more structures of the native valve as described herein. By providing two or more wires 74a, 74b coupled to one another at a distal tip 75, the distal tip 75 of the core wire 74 may be deflected into more complex and/or varying shapes than may be possible with a deflection feature disposed on or along the one or more core wires 74 or a single wire as described herein. The two wires 74a. 74b may be independently translated in order to generate additive curvatures. The wires 74a, 74b may be pulled/pushed distally or proximally relative to one another to cause the entire "grabber arm" of the distal section 77 to deflect in any number and manner of shapes or curvatures desired. In this way, the wires 74a. 74b may act as pull wires for the grabber arm of the distal section 77 and alter the shape thereof.

For example, the distal tip 75 may be deflected proximally or distally as shown in FIGS. 79 and 80, respectively, by relative translation of the wires 74a, 74b. 74c, which may be coupled to one another at the distal tip 75 or along the distal section 77 as described herein. In some embodiments, one or more of the wires 74 may remain untranslated. It will be understood by one of ordinary skill in the art that the number, complexity, and manner of the shapes or curvatures of the distal tip portion 77 may be adjusted by changing the location(s) at which the wires 74 are coupled to one another, changing the number of wires 74, and/or changing the shape of the wires 74 (e.g., by adding deflecting features, curvatures, etc. as described herein).

In some embodiments, the first wire 74a and the second wire 74b (and the third wire 74c, a fourth wire, etc.) may be disposed within a housing. The housing may comprise a flexible material. Translation of the first and second wires 74a, 74b relative to one another may change the curvature of the housing, thereby deflecting the distal tip 75 of the core wires 74 in order to facilitate anchor deployment and/or wrapping of the anchor 15 around one or more structures of the native valve as described herein. By providing two or more wires 74a, 74b within a housing, the distal tip 75 of the core wire 74 may be deflected into more complex and/or varying shapes than may be possible with a deflection features disposed on or along the one or more core wires 74 described herein. The two wires 74a, 74b may be independently translated in order to generate additive curvatures. The wires 74a, 74b may be pulled/pushed distally or proximally relative to one another to cause the housing of the distal tip portion 77 to deflect in any number and manner of shapes or curvatures desired. In some embodiments, the entire "grabber arm" of the distal tip portion 77 may be made up of wires.

Alternatively, or in combination, at least a portion of the anchor 15 may include a support covering and/or band material disposed on or around the anchor 15. The anchor 15 material may comprise a permeable, semi-permeable, or impermeable material while the support covering or band material may be flexible, semi-flexible, or rigid. In some embodiments, the anchor 15 material may be relatively soft so as to reduce the risk of injury to the one or more structures during rotation of the anchor 15. The anchor 15 material may, for example, comprise a webbing material, a fabric, a polymeric material, an elastomeric material, or the like. The anchor 15 material may fully span the support covering so as to reduce leakage therethrough. Alternatively, or in combination, the anchor 15 material may be configured to improve alignment of the support covering. It will be understood by one of ordinary skill in the art from the description herein that any of the anchors 15 described herein may comprise a support covering and/or a material disposed therein or thereon.

In some embodiments, the support covering may comprise one or more channels or lumens disposed therein. The support covering may comprise a hollow, tubular cross-section.

In some embodiments, the support covering may, for example, comprise a hypotube. The lumen of the support covering may be configured to pass another component (e.g. a wire, guidewire, etc.) therethrough. The support covering may, for example, comprise an upper (proximal) wire and a lower (distal) wire. The upper and lower wires may be coupled to one another at a proximal attachment point and/or a distal attachment point. The wires may be round wires or have other cross-sectional shapes. In various embodiments, the support covering may comprise a scaffold such as a laser-etched Nitinol scaffold or a mesh. The anchor 15 may be tapered such that subsequent turns of the anchor 15 and support covering nest into each other so as to reduce a radial footprint of the anchor 15. The upper and lower wires of the support covering may be configured to nest with one another when the in the deployed configuration.

In some embodiments, the upper wire and lower wires of the support covering may be bundled together during deployment from an undeployed configuration to an intermediate deployed configuration. The intermediate configuration may be configured to reduce the size the size of the lumen and/or aperture in or through which, respectively, the anchor 15 may travel (for example, a lumen or aperture of the delivery device) during deployment. The anchor 15 may be maintained in the intermediate configuration during rotation around the one or more native valve structures as described herein. In at least some instances, coupling the upper and lower wires of the support covering together into an intermediate configuration may facilitate alignment of the wires of the support covering. After delivery from the delivery device 30 and/or rotation around one or more native valve structures, the anchor 15 may be fully deployed into the deployed configuration by releasing the bundle and allowing the upper and lower wires to "spring out" into the deployed configuration. In some embodiments the anchor and/or upper and lower wires "spring out" or expand into the deployed configuration. In some embodiments, the anchor 15 is pushed out of the delivery device into the deployed configuration. The support covering may have a band material disposed therein or thereon as described herein. The band material may span the distance between upper and lower wires in order to couple the wires to one another. The band material may span the structural support so as to reduce leakage therethrough as described herein. Alternatively, or in combination, the band material may be configured to improve alignment of the support covering upper and lower wires such that they maintain a desired relative position to one another.

In some embodiments, the support covering may comprise one or more channels or lumens disposed therein. For example, one or more of the wires may comprise one or more channels or lumens. One or more of the wires may comprise a hollow, tubular cross-section. The support covering or anchor 15 may, for example, comprise a hypotube. The lumen of the spiral band may be configured to pass another component (e.g. a wire, guidewire, etc.) therethrough. The channels or lumens may for example be left as open lumens. Alternatively, or in combination, the channels or lumens may be filled, for example with one or more stiffening members.

Any of the free ends 22 of the anchors 15 described herein can include a "grabber" arm extending therefrom. The grabber arm can be configured to extend radially outwards from the rest of the anchor 15 to help capture one or more native valve structures as the anchor 15 is rotated. For example, FIG. 85 shows an exemplary anchor 15 with a grabber arm 91 extending from the free end 22. The grabber arm 91 can be continuous with the anchor 15 and can spiral in the same direction (e.g., clockwise or counterclockwise). However, as shown in FIGS. 85A-85B, the grabber arm 91 can extend in a wider arc or angle that the loops of the anchor 15, thereby providing a larger space with which to grab the structures of the native valve. In some embodiments, the distal tip of the grabber arm 91 can hook or bend radially inwards to further aid in grabbing of native valve structure. Once implanted, the grabber arm 91 may not engage or anchor against native valve structures.

Referring to FIG. 86A, the grabber arm 91 can, in some embodiments, be configured to lie in the same plane 93 as the anchor 15. When the anchor 15 is implanted, the plane 93 can be positioned mid-leaflet relative to the native valve or aligned with the leaflet free edge of the native valve. Referring to FIG. 86B, the grabber arm 91 can, in some embodiments, be configured such that the grabber arm 91 inclines from the plane 93 towards a more proximal plane 94. When the anchor 15 is implanted, the proximal plane 94 can be substantially parallel with the subannular plane. Referring to FIG. 86C, the grabber arm 91 can, in some embodiments, be configured such that the grabber arm 91 inclines towards and plateaus along the plane 94. In some embodiments, having the grabber 91 extend proximally towards the plane 94 (e.g., the subannular plane) can help move the anchor 15 towards the annulus and prevent paravalvular leakage upon implantation.

In some embodiments, the anchor 15 may comprise one or more locking mechanisms configured to maintain the anchor 15 in the deployed configuration. The one or more locking mechanisms may be any of the locking mechanisms described herein or understood by one of ordinary skill in the art from the description herein. In various embodiments, one or more loops may be nested with each other when the anchor is in the deployed configuration.

Figure 3C:
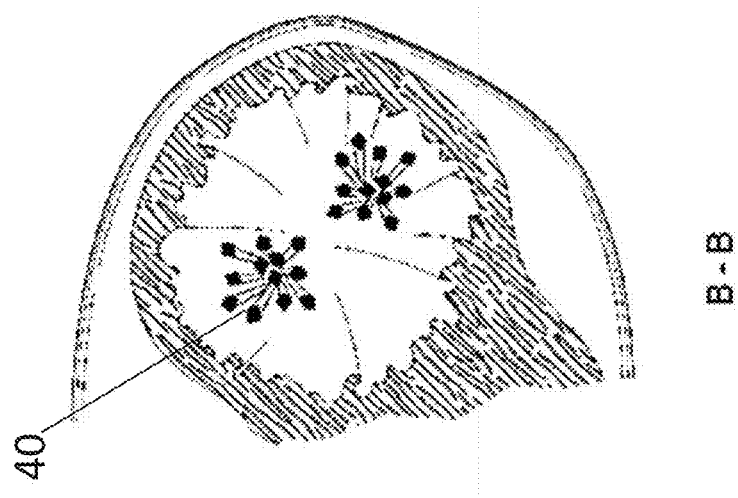
FIGS. 3A-3AC show sequential views of a method of implanting a valve prosthesis using a delivery device, in accordance with embodiments.
Figure 3B:
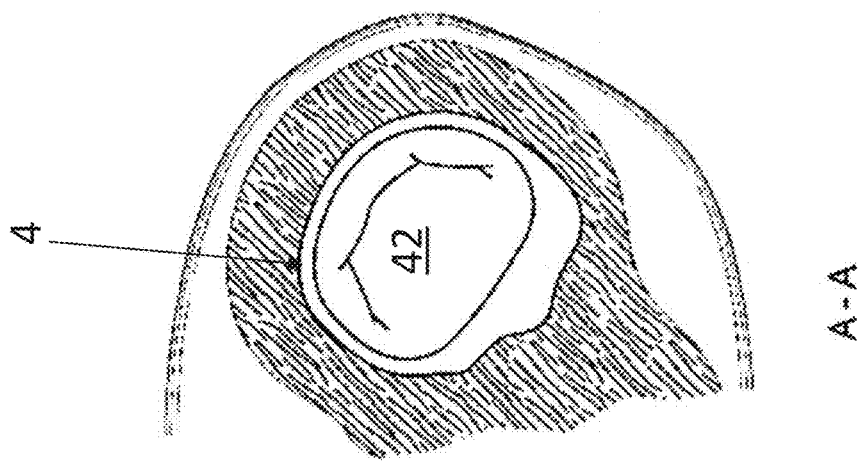
Figure 3A:
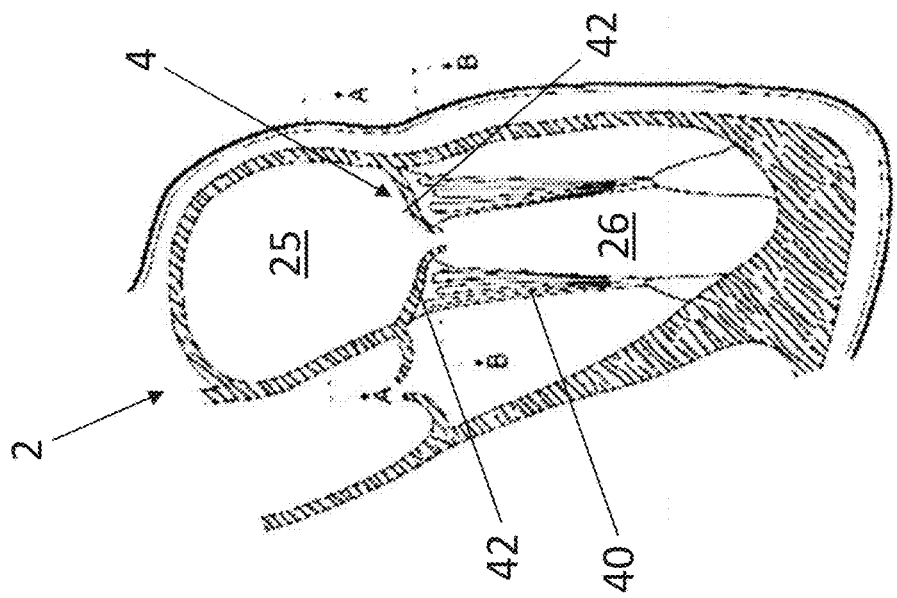
Figure 3F:
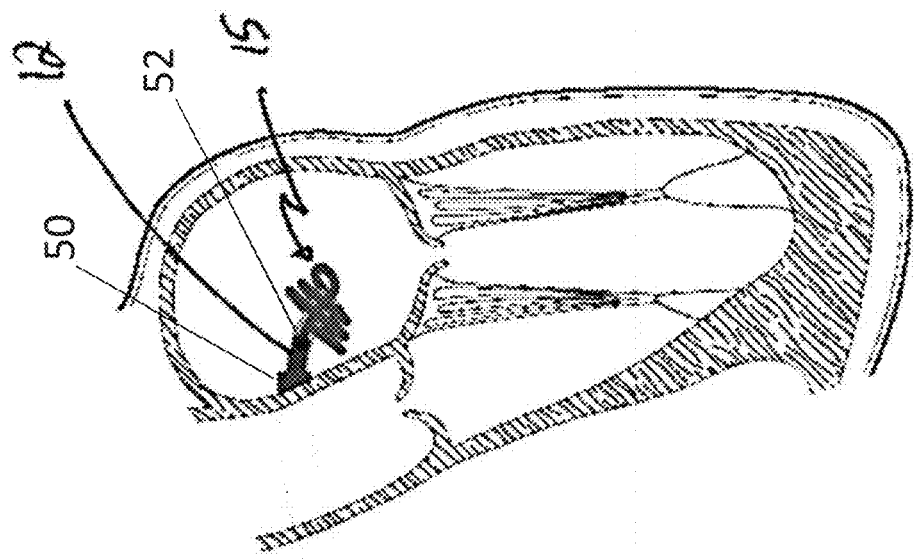
Figure 3E:
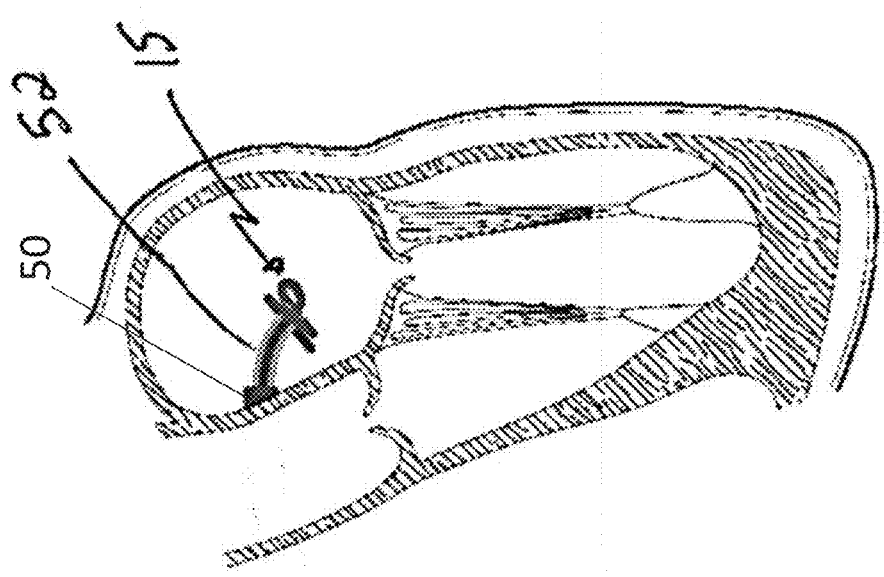

Referring to FIGS. 3A-3AC, at least a portion of the valve prosthesis 10 may be expanded within the native valve. For example, the valve prosthesis 10 may be deployed such that it captures one or more structures therein, for example one or more chordae tendineae and/or one or more valve leaflets. Expansion of the valve prosthesis 10, or a portion thereof, may compress the captured structures therein to anchor the valve prosthesis 10 in place.

The valve prosthesis 10 may comprise first and second opposite ends, the first end extending above a native valve and the second end extending below the native valve when the valve prosthesis 10 is anchored to the native valve. Alternatively, the valve prosthesis 10 may be configured to sit entirely below the native valve when the valve prosthesis 10 is anchored to the native valve.

In some embodiments, the valve prosthesis 10 may comprise an expanded outer periphery in the expanded configuration and a compressed outer periphery when subject to an external radial force in the unexpanded configuration. The compressed outer periphery may be smaller in diameter than the expanded outer periphery.

In some embodiments, at least a portion of the valve prosthesis 10 may be actuated from the unexpanded configuration to the expanded configuration on a first side of the native valve prior to being advanced to a second side of the native valve. For example, the valve prosthesis 10 may be expanded in a left atrium of a heart prior to being advanced to a left ventricle of the heart as described herein.

Alternatively, or in combination, at least a portion of the valve prosthesis 10 may be actuated from the unexpanded configuration to the expanded configuration on a second side of the native valve after being advanced to the second side from a first side of the native valve. For example, valve prosthesis 10 may be advanced from a left atrium of a heart prior to being expanded in a left ventricle of the heart.

Delivery device 30 may refer to various components in certain embodiments. For example, delivery device 30 may refer to a steerable catheter for transseptal delivery. Delivery device 30 may refer to a catheter for delivery of the replacement valve, frame structure, and/or anchor. In some embodiments, delivery device 30 may refer to a first delivery device component detachably coupled to the anchor and a second delivery device component detachably coupled to the frame structure. In some embodiments, one or more valve prosthesis components may be different delivery devices or different components of a delivery device system.

Referring to FIGS. 3A-3AC, the delivery device 30 may include an outer sheath (e.g., an outer catheter), an inner shaft 52 (e.g., a delivery tube) disposed within a lumen of the outer sheath 50, and an optional guidewire 54 disposed within a lumen of the inner shaft 52. As described further below, a tether 78 (see, e.g., FIGS. 89A-89C) may also be used. The guidewire 54 may optionally comprise a nosecone 55 to facilitate guidance of the guidewire 54 to the native valve. The proximal end 57 of the anchor 15 may be detachably coupled to the inner shaft 52 (or tether 78) during delivery to the native valve as described herein. The outer sheath 50 may be steerable.

The valve prosthesis 10 may be operably coupled to the delivery device 30 as described herein. In some embodiments, at least a portion of the valve prosthesis 10 may be directly coupled to the inner shaft 52 (or tether 78). Alternatively, or in combination, at least a portion of the valve prosthesis 10 may be indirectly coupled to the inner shaft 52 (or tether 78). For example, at least a portion of the valve prosthesis 10 may be coupled to a torque hub or other connector, which may be coupled to the inner shaft 52.

The valve prosthesis 10 may be detachably coupled to the delivery device 30 in the unexpanded configuration during delivery to the native valve. Expansion of the valve prosthesis 10 to the expanded configuration may detach (i.e. release) the valve prosthesis 10 from the delivery device 30.

The valve prosthesis 10 may be balloon-expandable, self-expanding, or otherwise expansible as will be understood to one of ordinary skill in the art from the description herein.

Figure 3D:
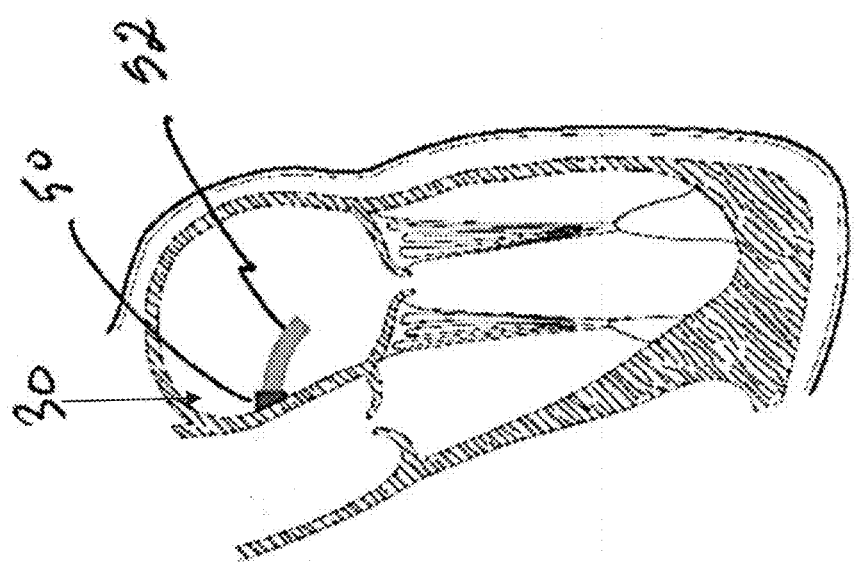
Figure 3I:
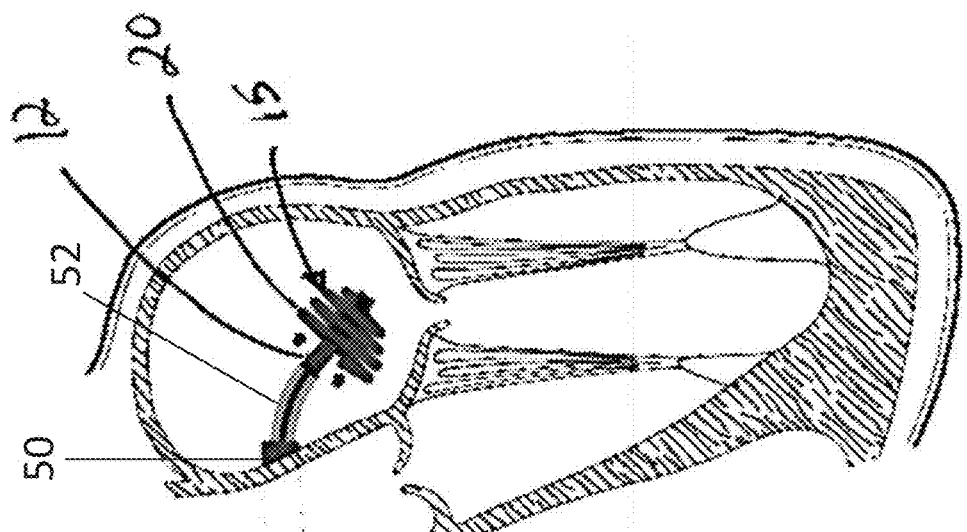
Figure 3H:
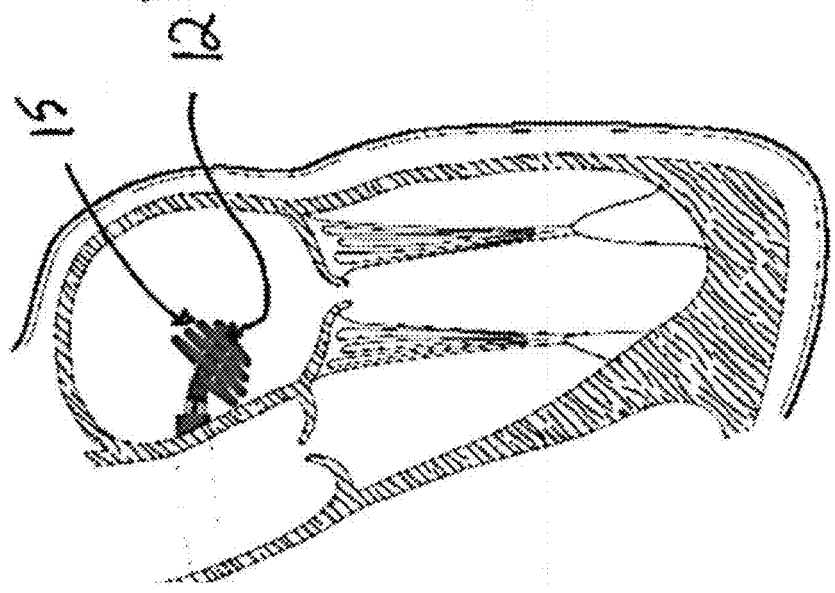
Figure 3G:
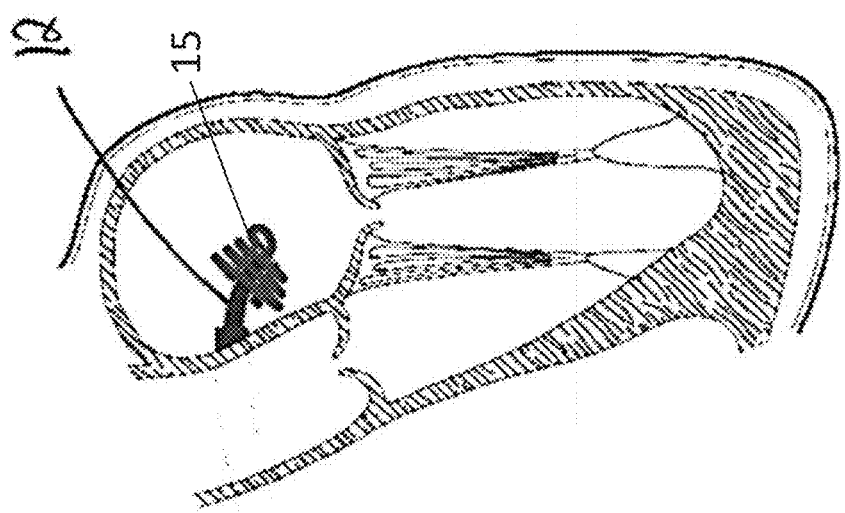
Figure 3K:
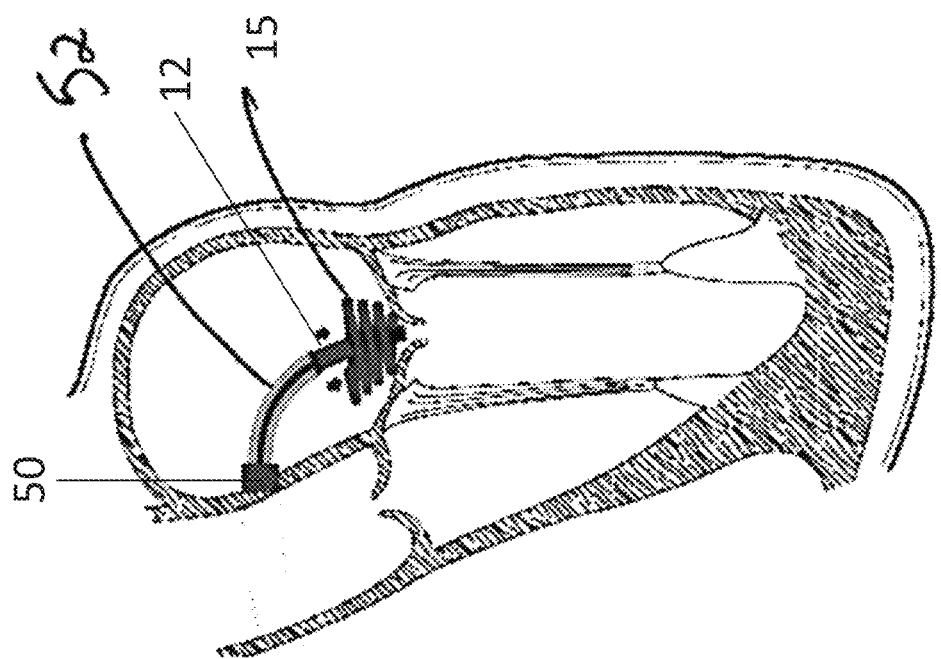
Figure 3J:
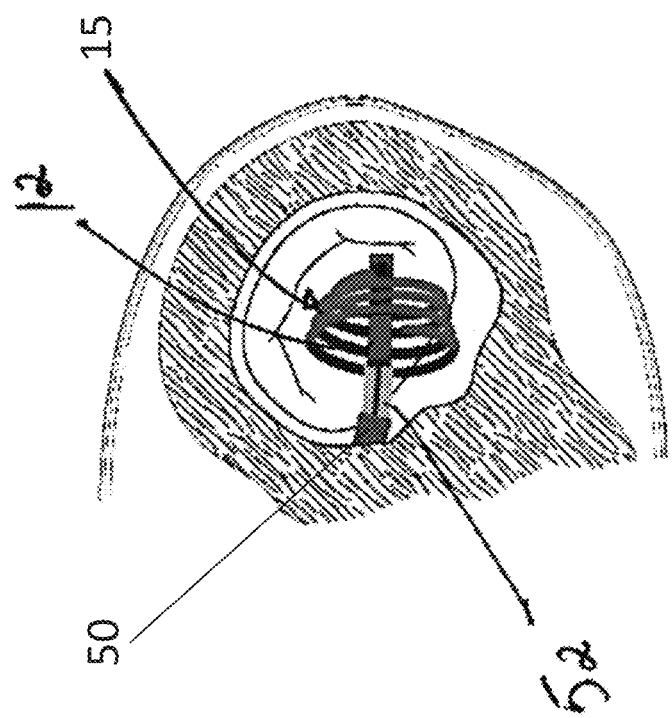
Figure 3N:
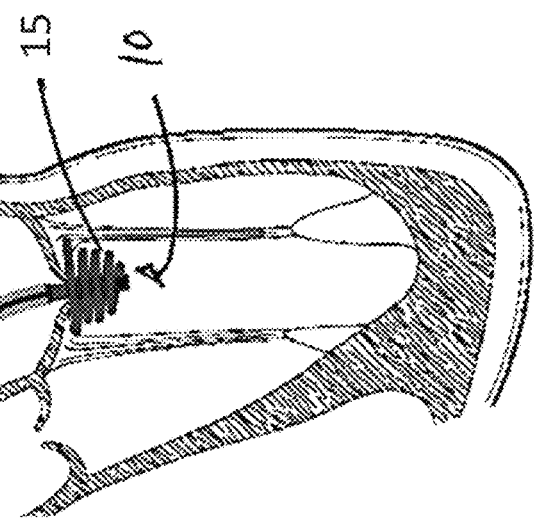
Figure 3M:
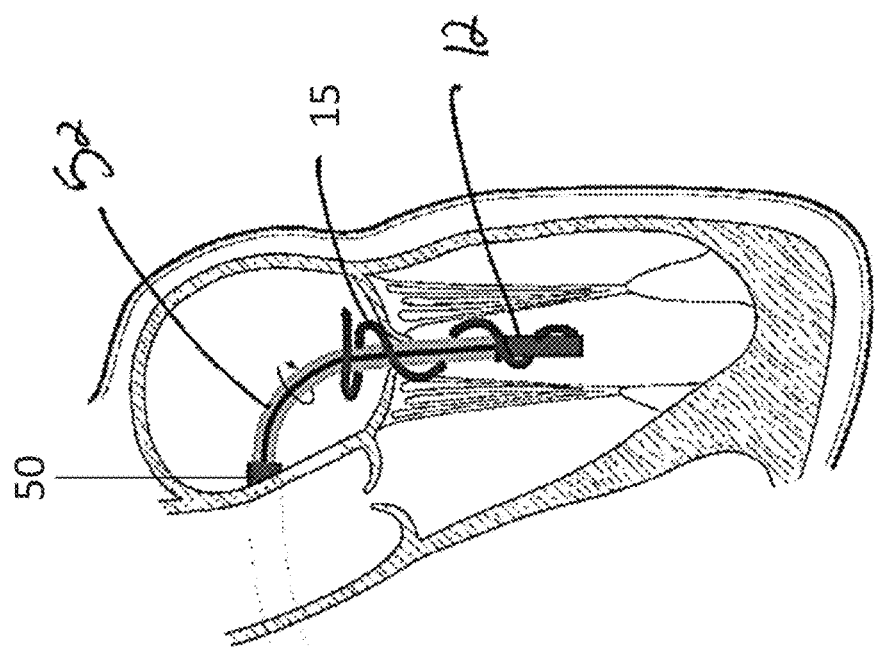
Figure 3L:
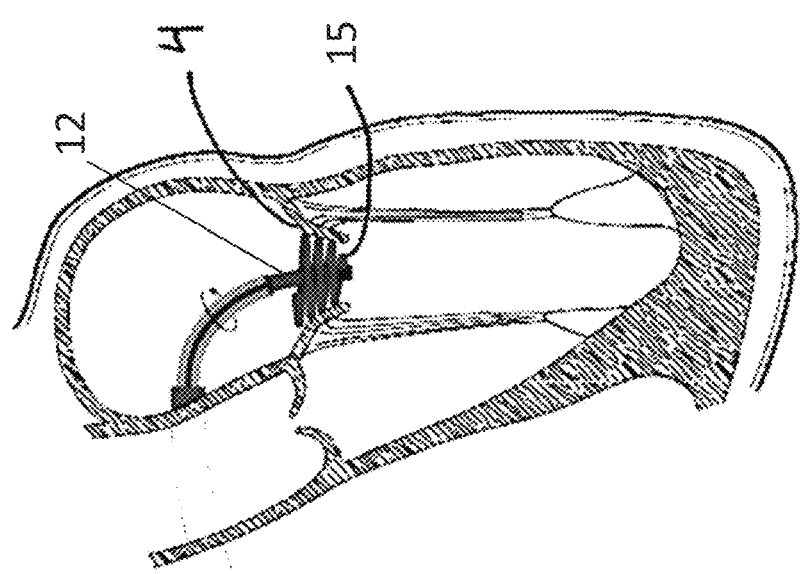
Figure 3Q:
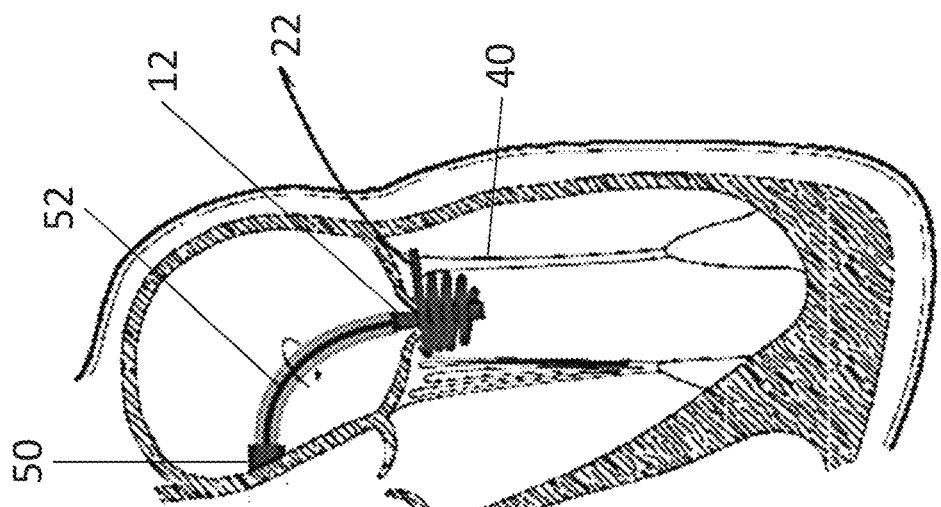
Figure 3P:
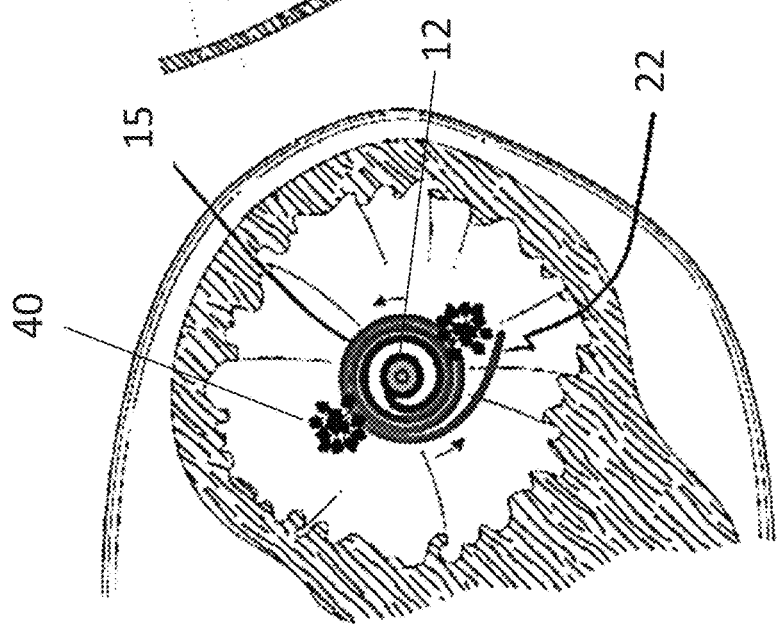
Figure 3O:
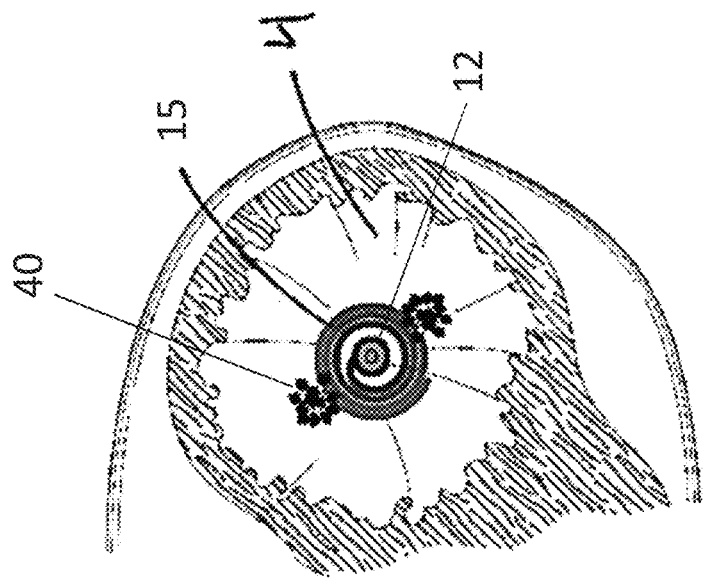
Figure 3S:
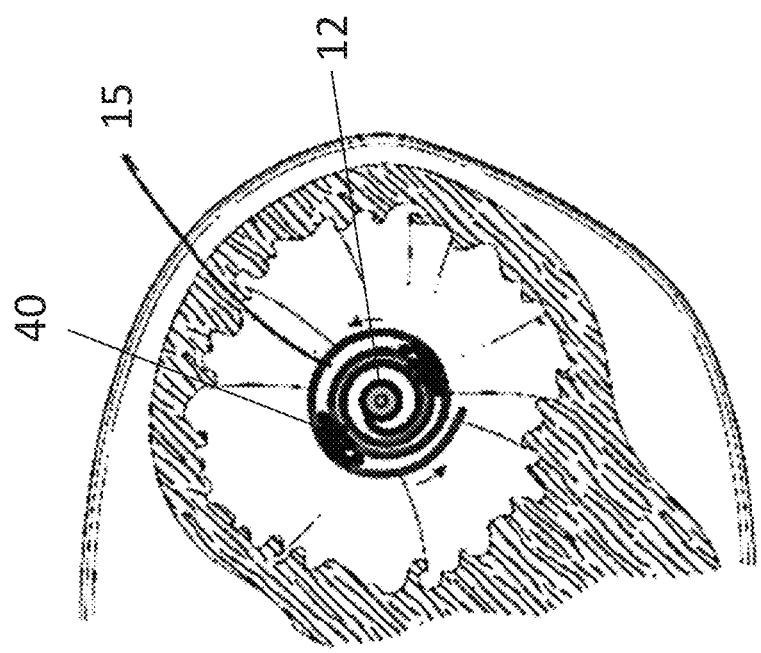
Figure 3R:
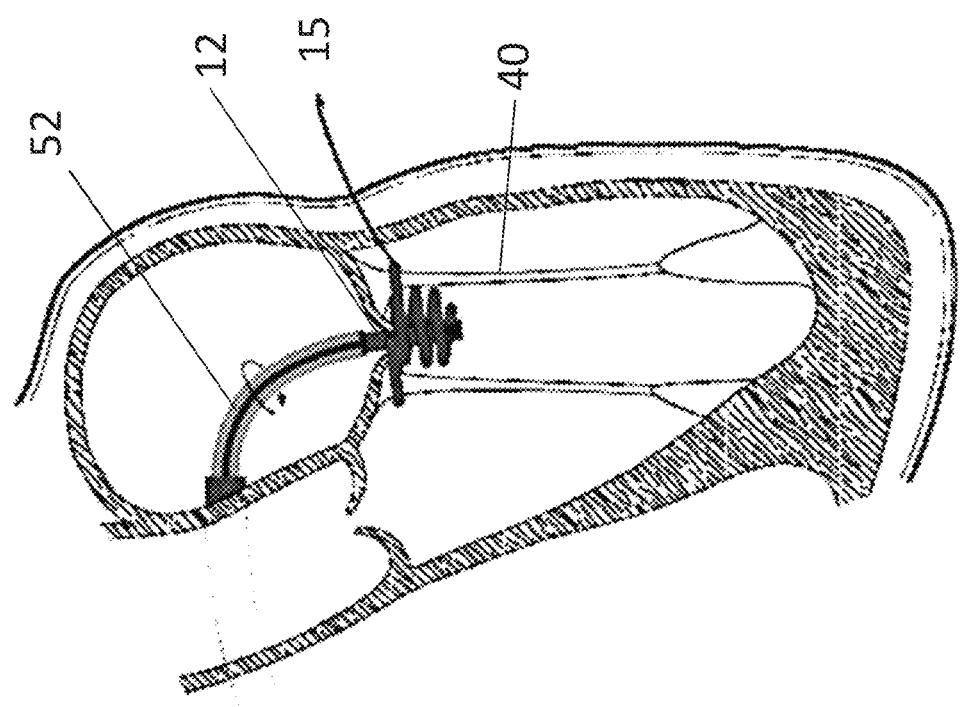
Figure 3U:
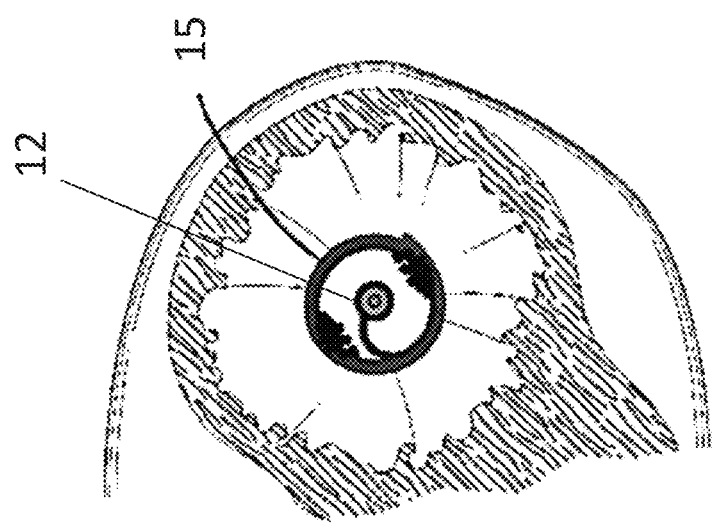
Figure 3T:
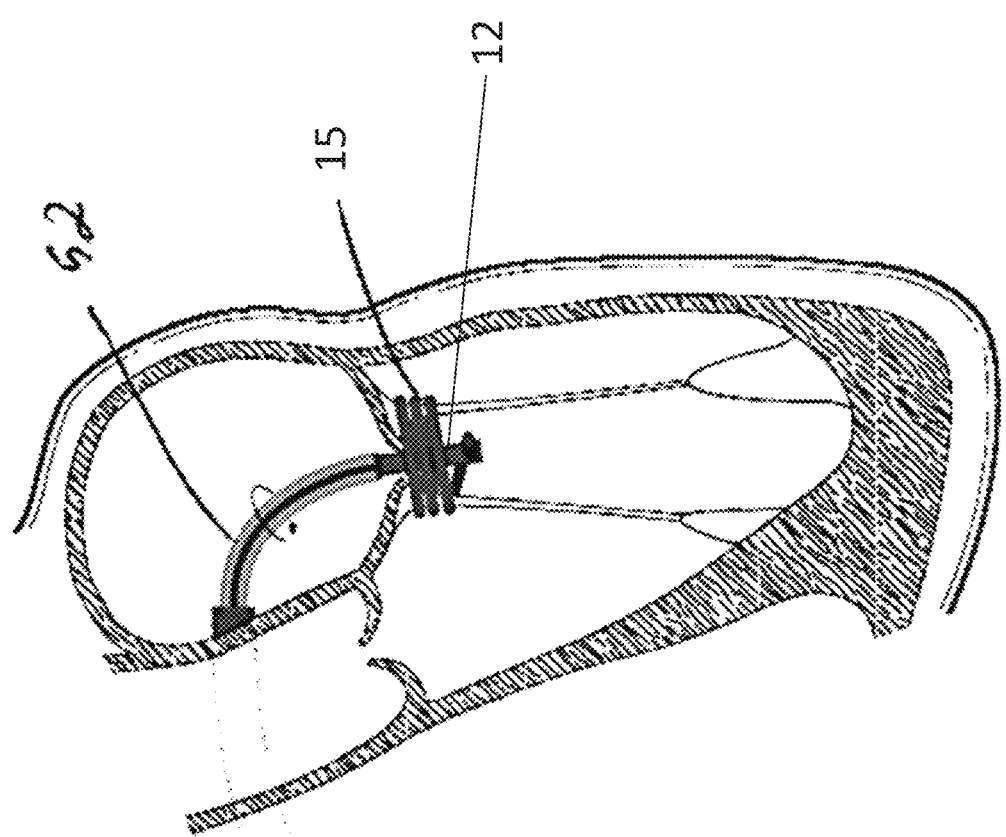
Figure 3W:
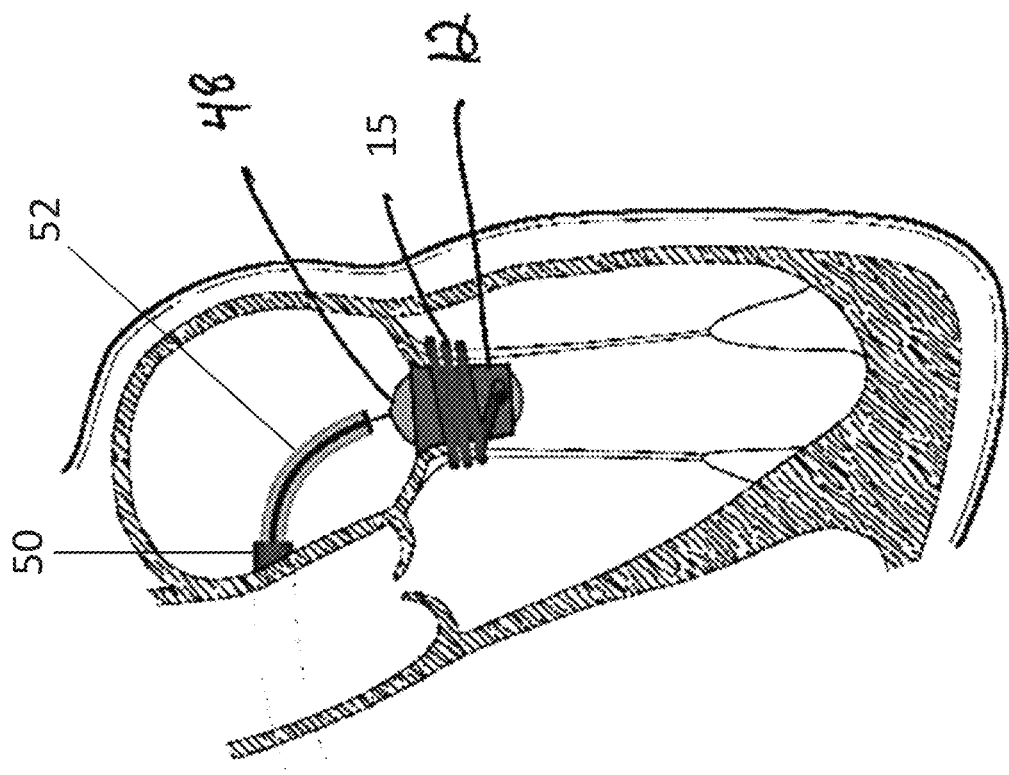
Figure 3V:
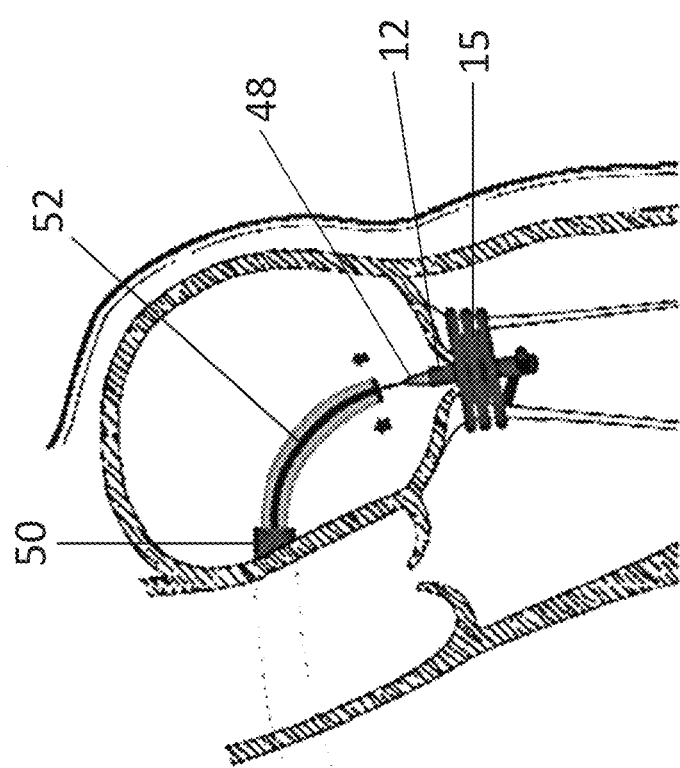

For example, the delivery system 30 may comprise an inflatable balloon (for example, as shown in FIGS. 3V-3AA) disposed within the valve prosthesis 10. Inflation of the balloon may cause expansion of the valve prosthesis 10.

Alternatively, or in combination, the valve prosthesis 10 may be self-expandable. The valve prosthesis 10 may be maintained in the unexpanded configuration by radial constriction from the outer sheath of the delivery device 30 when disposed in a lumen of the outer sheath. Advancement of the inner shaft 52 out of the lumen of the outer sheath may actuate the valve prosthesis 10 into the expanded configuration. Stated another way, retraction of the outer sheath away from the valve prosthesis 10 may actuate the valve prosthesis 10 into the expanded configuration.

The anchor 15 of the prosthesis 10 may be directly coupled to the frame structure 12 (or tether 78), for example at a proximal or distal end thereof. Alternatively, or in combination, the anchor 15 may be detachably coupled to the delivery device 30 prior to deployment at the native valve. For example, a proximal end 57 (see FIG. 2) of the anchor 15 may be detachably coupled to the inner shaft 52 during delivery to the native valve. The proximal end 57 may be configured to remain engaged with the inner shaft 52 after being actuated from the elongated configuration to the deployed configuration adjacent the native valve. Alternatively, or in combination, a proximal end 57 of the anchor 15 may be coupled to a distal end of the frame structure 12 or a proximal end of the frame structure 12. The anchor 15 is shown in a deployed configuration.

The frame structure 12 may have an unexpanded configuration (for example, as shown in FIGS. 1, 2 and 3F-3V) when the valve prosthesis 10 is in its unexpanded configuration and an expanded configuration (for example, as shown in FIGS. 3W-3AC & 58A-B) when the valve prosthesis 10 is in its expanded configuration. As shown in FIG. 2, the frame structure 12 in the expanded configuration may have a generally tubular expanded shape. The frame structure 12 may be configured for expanding within the native valve of the patient. In some embodiments, the unexpanded configuration may be sized and dimensioned for percutaneous insertion and the expanded configuration may be sized and dimensioned for implantation in the native valve of the patient. The frame structure 12 may be configured to remain in its unexpanded configuration while the anchor 15 is in the deployed configuration.

The frame structure 12 may comprise a first and second opposite ends, the first end extending above a native valve and the second end extending below the native valve when the frame structure 12 is anchored to the native valve. Alternatively, the frame structure 12 may be configured to sit entirely below the native valve when the frame structure 12 is anchored to the native valve.

In some embodiments, the frame structure 12 may comprise an expanded outer periphery in the expanded configuration and a compressed outer periphery when subject to an external radial force in the unexpanded configuration. The compressed outer periphery may be smaller in diameter than the expanded outer periphery.

The frame structure 12 may be balloon-expandable, self-expanding, or otherwise expansible as will be understood by one of ordinary skill in the art. The frame structure 12 may, for example, comprise an expandable stent.

The delivery system 30 may comprise an inflatable balloon (for example as shown in FIGS. 3V-3AA) disposed within the frame structure 12 and inflation of the balloon may cause expansion of the frame structure 12 as described herein.

In some embodiments, the delivery device 30 may be configured to carry the anchor 15 in an undeployed configuration and deploy the anchor 15 into a deployed configuration as the desired location as described herein.

The delivery device 30 may additionally or alternatively include any of the features of the delivery devices described in PCT/US2019/047542, PCT/US2019/055049. PCT/US2019/057082, and PCT/US2019/068088, the entireties of which are incorporated by reference herein.

In use, a valve prosthesis 10 may be loaded onto the delivery device 30. The valve system may optionally be primed before or after loading onto the delivery device 30. The delivery device 30 may be inserted through an introducer into a vessel. The delivery device 30 can be guided over a guidewire to a target location using the Seldinger technique.

The distal end of the delivery device 30 may be configured to be advanced from a first side of a native valve to a second side of the native valve. For example, the distal end of the delivery device 30 may be advanced from a left atrial side of a mitral valve to a left ventricular side of a mitral valve. In some instances, the distal end of the delivery device 30 may be transseptally inserted into the left atrium of the heart prior to advancement into the left ventricle. Alternatively. or in combination, the distal end of the delivery device 30 may be steerable such that it is positionable to point towards the first side of the native valve before being advanced to the second side of the native valve.

After advancing to the second side of the native valve, the anchor 15 may be fully deployed on the second side of the native valve. Fully deploying the anchor 15 may comprise actuating the anchor 15 from an elongated delivery configuration as shown in FIG. 1 to a deployed configuration as shown in FIG. 2.

In some embodiments, fully deploying the anchor 15 may comprise actuating the anchor 15 from an elongated delivery configuration to a deployed configuration on the first side of the native valve and advancing the anchor 15 in the deployed configuration through the native valve to the second side of the native valve. Advancing the anchor 15 may comprise pushing the anchor through the native valve. Advancing the anchor 15 may further comprise rotating the anchor 15 through the native valve.

In some embodiments, fully deploying the anchor 15 may comprise positioning the anchor 15 such that it is located only on the second side of the native valve.

In some embodiments, the anchor 15 may be actuated from the delivery configuration to the deployed configuration on a first side of the native valve prior to being advanced to a second side of the native valve. For example, the anchor 15 may be deployed in a left atrium of a heart prior to being advanced to a left ventricle of the heart as described herein.

Alternatively, the anchor 15 may be actuated from the delivery configuration to the deployed configuration on a second side of the native valve after being advanced to the second side from a first side of the native valve. For example, anchor 15 may be advanced from a left atrium of a heart prior to being deployed in a left ventricle of the heart.

The free end 22 of the deployed anchor 15 may optionally be rotated around one or more structures on the second side of the native valve. The one or more structures may comprise one or more valve leaflets of the native valve. Alternatively, or in combination, the one or more structures may comprise one or more chordae of the left ventricle.

The free end 22 of the deployed anchor 15 may optionally rotated around one or more structures on the second side of the native valve such that the one or more structures (e.g., chordae, leaflets, or annulus) are pulled radially inwards towards the longitudinal axis of the anchor 15 and/or towards the longitudinal axis of the delivery device 30. The anchor 15 and/or free end 22 may be configured such that minimal torque is applied to the one or more structures. Alternatively, or in combination, the anchor 15 and/or free end 22 may be configured such that the one or more structures are not rotated, or are minimally rotated, during rotation of the anchor 15.

In some embodiments, the valve prosthesis 10, for example anchor 15, may be counter-rotated in order to reposition the anchor 15 with respect to the one or more structures of the native valve before continuing the rotation in the first direction. For example, counter-rotation may be applied if the one or more structures are caught by the free end of the anchor 15 (or another part of the valve prosthesis 10 or delivery device 30) during the initial rotation. In such instances, counter-rotation may enable to the clinician to disengage some or all of the one or more structures to reduce the stress or torque on the one or more structures (e.g., by adjusting the position of the valve prosthesis 10) before resuming rotation. Rotation and counter-rotation may be applied as many times as desired by the clinician in order to properly position the anchor 15 around the one or more structures of the native valve.

The anchor 15 may then be released from the distal end of the delivery device 30. The anchor 15 may be released from the distal end of the delivery device 30 on the second side of the native valve.

The frame structure 12 may be expanded within the native valve from an unexpanded configuration to an expanded configuration. The valve prosthesis 10 is finally anchored when the frame structure 12 is expanded within the native valve 4. The frame structure 12 dilates the valve leaflets 14 and the compressive force fixes the valve prosthesis 10 into position. Thereafter tissue ingrowth ensures the valve prosthesis 10 remains seated and does not migrate.

The frame structure 12 may be released from the distal end of the delivery device 30. In some embodiments, at least a portion the frame structure may be expanded within at least a portion of the deployed anchor to anchor the frame structure to the native valve.

In some embodiments, expanding the frame structure and releasing the frame structure may occur simultaneously.

Finally, the delivery device 30 may be retracted from the native valve.

The valve devices described herein in accordance with the present disclosure provides several advantages over conventional valve systems. Embodiments described herein provide an easy-to-use, repositionable device. Unlike conventional valve systems, the valve prosthesis described herein reduces the risk of injuring or tearing chordac. Typical mitral valve replacement systems involve implanting a prosthetic annulus or ring around the valve. The ring increases the circumference of the valve and risks occluding the entry to the aortic valve. The valve device described herein overcomes these and other problems.

FIGS. 3A-3AC and 58A-58B show sequential views of a method of implanting a valve prosthesis 10 using a delivery device 30. The valve prosthesis 10 may be similar to any of the valve prostheses described herein or understood by one of ordinary skill in the art from the description herein. Similarly, the delivery device 30 may be substantially similar to any of the delivery devices described herein or understood by one of ordinary skill in the art from the description herein. Not all prosthesis 10 or delivery device 30 elements are labeled in each of FIGS. 3A-3AC and 58A-B in order to make the illustrations less cluttered and easier to see.

While the method shown in FIGS. 3A-3AC and 58A-B is described in relation to a mitral valve replacement procedure, it will be understood by one of ordinary skill in the art that the methods described herein may be applied to a variety of procedures or anatomical areas, for example other atrioventricular valves of the heart or the like. For example, the methods described herein may be applied to replacement of a diseased aortic valve or tricuspid valve.

FIGS. 3A-3C shows various cross-sectional views of a heart 2 having a diseased mitral valve 4 which may be treated using the devices, systems, and methods described herein. The mitral valve 4 sits between the left atrium 25 and the left ventricle 26 and, when functioning properly, allows blood to flow from the left atrium 25 to the left ventricle 26 while preventing backflow or regurgitation in the reverse direction. As shown in FIG. 3A, the native valve leaflets 42 of the diseased mitral valve 4 do not fully prolapse and the patient experiences regurgitation. FIG. 3B shows a cross-sectional view of the heart 2 taken along line A-A, shown in FIG. 3A, which shows the native valve leaflets 42 of the mitral valve 4 from the viewpoint of the left atrium 25. FIG. 3C shows a cross-sectional view of the heart 2 taken along line B-B, shown in FIG. 3A, which shows the chordae tendineae 40 of the left ventricle 26.

As shown in FIG. 3D, a distal end of the delivery device 30 may be inserted into the left atrium 25 of the heart 2 via a transseptal puncture as described herein. For example, the distal ends of inner shaft 52 and/or outer sheath 50 may be advanced into the left atrium 25 of the heart 2. The inner shaft 52 may optionally be advanced distally into the left atrium 25 away from the distal end of the outer sheath 50. In some embodiments, advancing the inner shaft 52 relative to the outer sheath 50 may aid in deployment and/or placement of the valve prosthesis 10 as described herein. Alternatively, both the inner shaft 52 and the outer sheath 50 may be advanced distally into the left atrium 25 through the transseptal puncture.

FIGS. 3E-3H show deployment of the anchor 15 from the distal end of the delivery device 30. As described herein, at least a portion of the valve prosthesis 10 may be deployed from an undeployed (for example, compressed or unexpanded) configuration to an expanded configuration within the left atrium 25. At least a portion of the anchor 15 may be deployed from a delivery and/or elongated configuration to a deployed configuration within the heart. For example anchor 15 may be actuated from an elongated configuration (e.g., from a straightened shaped) to a deployed configuration (e.g., a pre-formed shape for implantation, such as a spiral, helical, or conical shape) within the left atrium 25 as described herein. In some embodiments, the anchor 15 may be deployed from the inner shaft 52 by pushing the anchor 15 out of the inner shaft 52, releasing the anchor 15 from radial constraint by retracting the outer sheath 50, or the like as described herein. In some embodiments, the anchor 15 may be pushed out of the inner shaft 52 using a pusher on a proximal handle (not shown) located outside the body). After the anchor 15 has been deployed from the delivery device 30, the frame structure 12 may be at least partially deployed from the delivery device 30 as shown in FIG. 3H so as to place the frame structure 12 within the anchor 15. The frame structure 12 may be deployed from the delivery device 30 in either the unexpanded configuration or the expanded configuration, depending on the location of deployment, as will be understood by one of ordinary skill in the art based on the teachings herein.

FIGS. 3I-3K show advancement of the valve prosthesis 10, with anchor 15 deployed around the unexpanded frame structure 12, towards the native valve 4 requiring treatment. The distal end of the delivery device 30 (for example, the distal end of the inner shaft 52 and/or the outer sheath 50) may be steered such that the distal end of the delivery device 30 points toward the atrial side of the native valve 4. Such steering may occur prior to, during, or after deployment of at least a portion (for example deployment of an anchor 15) of the valve prosthesis 10. In some embodiments, the distal end of the outer sheath 50 may be steerable. Alternatively, or in combination, the inner shaft 52 may comprise a joint configured to change an angle of the distal portion of the inner shaft 52 relative to a proximal portion of the inner shaft 52. The inner shaft 52 may be steered by changing the angle of the distal portion of the inner shaft 52 relative to the proximal portion of the inner shaft 52. The angle of the joint may be changed passively or actively. In various embodiments, the angle may be selectively controlled by a proximal handle. For example, pull wires or other mechanisms may connect to the joint to controls on the handle.

FIGS. 3L-30 show the valve prosthesis 10 being advanced through the native valve 4 by the delivery device 30 from the left atrium 25 to the left ventricle 26. Advancement of the valve prosthesis 10 and optionally delivery device 30 through the mitral valve 4 may be facilitated by the natural opening and closing of the valve 4 during the cardiac cycle. The distal end of the delivery device 30 and/or valve prosthesis 10 may be configured to be advanced from a first side of a native valve to a second side of the native valve. For example, the distal end of the delivery device 30 and/or valve prosthesis 10 may be advanced from a left atrial side of a mitral valve 4 to a left ventricular side of a mitral valve 4. Advancing the anchor 15 may comprise pushing the anchor 15 through the native valve 4. Alternatively, or in combination, advancing the anchor 15 may comprise rotating the anchor 15 through the native valve 4. In some instance, the combination of rotational motion and pushing may facilitate advancement of the device from the first side of the native valve 4 to the second side of the native valve 4. Rotation of the valve prosthesis 10, for example rotation of the anchor 15 and/or frame structure 12, may be facilitated by the inner shaft 52 described herein. For example, the inner shaft 52 may transmit rotational motion to the valve prosthesis 10 in order to rotate the valve prosthesis 10 during advancement through the native valve 4.

In some instances, advancing the anchor 15 through the native valve 4 may cause the anchor 15 to be stretched or elongated as shown in FIG. 3M. Rotation of the anchor 15 during advancement may assist with the stretching process by aiding in unwinding the anchor 15. Additionally, the rotational motion may reduce the risk of the free end 22 of the anchor 15 undesirably engaging other anatomy during insertion through the native valve leaflets 42. The anchor 15 may be sufficiently elastic so as to enable relatively easy insertion through the native valve 4 and/or reduce the risk of injury to the native leaflets 43. At the same time, the anchor 15 may be sufficiently rigid to for guiding through and anchoring to the structures in the heart. After the anchor 15 has stretched through the native valve 4 it may return to the deployed configuration as shown in FIG. 3N. FIG. 3O shows the position of the valve prosthesis 10 within the ventricle 26 and, in particular, the position of the anchor 15 relative to the native chordae tendineae 40 and native valve annulus.

In some embodiments, the anchor 15 may be advanced into the ventricle after being fully deployed from the delivery (e.g., elongated) configuration to the deployed configuration.

In some embodiments, the anchor 15 may be advanced into the ventricle before being deployed from the delivery (e.g., elongated) configuration to the deployed configuration.

FIGS. 3P-3S show rotation of the valve prosthesis 10 around one or more native valve structures on the ventricular side of the mitral valve 4. The one or more structures may comprise one or more valve leaflets 43 and/or one or more chordae tendineae 40. After the anchor 15 has been at least partially deployed within the left ventricle 26 adjacent one or more chordae tendineae 40, the valve prosthesis 10 may be rotated to capture and anchor the native chordae 40 and/or native leaflets 42. The free end 22 of the anchor 15 may extend radially outward from the rest of the anchor 15 to facilitate capture of the native structures. The free end 22 of the anchor 15 may be rotated around one or more of the chordae tendineae 40 as shown in FIGS. 3P-3Q. Additional rotation of the valve anchor 15 may gradually capture additional chordae tendineae 40 as shown in FIGS. 3R-3S.

Rotation of the valve prosthesis 10, for example rotation of the anchor 15 and/or frame structure 12, may be facilitated by the delivery device 30 described herein. For example, the inner shaft 52 may be rotated and rotational motion may be transmitted from the inner shaft 52 to the valve prosthesis 10 in order to rotate the valve prosthesis 10 around one or more of the structures on the ventricle side of the mitral valve 4 as described herein.

In some embodiments, the valve prosthesis 10, for example anchor 15, may be counter-rotated in order to reposition the anchor 15 with respect to the chordae tendineae 40 before continuing the rotation in the first direction. For example, counter-rotation may be applied if the chordae tendineae 40 are caught by the free end of the anchor 15 (or another part of the valve prosthesis 10 or delivery device 30) during the initial rotation. In such instances, counter-rotation may enable to the clinician to disengage some or all of the chordae tendineae 40 to reduce the stress or torque on the chordae tendineae 40 (e.g., by adjusting the position of the valve prosthesis 10) before resuming rotation. As another example, the anchor 15 may encounter friction or other resistance to rotation. In this case the clinician may counter-rotate the anchor 15 to return to the original position and then begin rotating the anchor 15 to re-start and/or continue encircling chordae tendineae 40. Rotation and counter-rotation may be applied as many times as desired by the clinician in order to properly position the anchor 15 around the valve structures.

FIGS. 3T-3U show the valve prosthesis 10 wrapped around the captured chordae tendineae 40. The valve prosthesis 10 may be rotated around the chordae tendineae 40 such that the chordae tendineae 40 are pulled inwardly into bunches. As shown in FIG. 3T, the native valve leaflets 42 may also be in communication with the valve prosthesis 10. The valve prosthesis 10 may be rotated to capture enough chordae tendineae 40 and/or valve leaflets 42 to rigidly anchor the anchor 15 adjacent the native valve annulus. The valve prosthesis 10 may be anchored by wrapping around only a portion of the chordae 40. Although it may be possible to capture all or substantially all the chordae 40, this may not be necessary to provide sufficient anchoring of the valve prosthesis 10. As described further herein, the prosthesis may be further anchored by expansion of the frame structure 12 within the native valve 4 and against the anchor 15. Alternatively. or in combination, the anchor may be sufficiently anchored after winding around some or only a portion of the chordae. It is believed that only a portion of the chordae are necessary for anchoring.

In some embodiments, the anchor 15 may be deployed such that at least a portion of the anchor 15 resides within a subvalvular plane. For example, at least 50%, 60%, 70%, 80%, 90%, 100% of the anchor 15 may reside within the subvalvular plane after being deployed. The subvalvular plane may be located at the posterior valve annulus, below the valve annulus and around the native valve leaflets 42, and/or parallel to a plane within at least three points of the plane in which the valve annulus resides. In some instances, the anchor 15 may be rotated in the subvalvular plane around the chordae tendineae 40. In some instances, the anchor 15 may be rotated in a plane below to the subvalvular plane in order to encircle the chordae tendineae 40 before the anchor 15 is moved into the subvalvular plane (e.g., by pulling the anchor 15 into the sub-annular space).

Once the anchor 15 has been anchored adjacent to the native valve 4, the frame structure 12 and prosthetic valve segment 14 may be expanded at least partially within the anchor 15 as described herein. The frame structure 12 and the valve segment 14 may be deployed (e.g., expanded) simultaneously. Alternatively, or in combination, the frame structure 12 and the valve segment 14 may be deployed sequentially, for example by first expanding the frame structure 12 and then receiving the prosthetic valve segment 14 therein.

Figure 3Y:
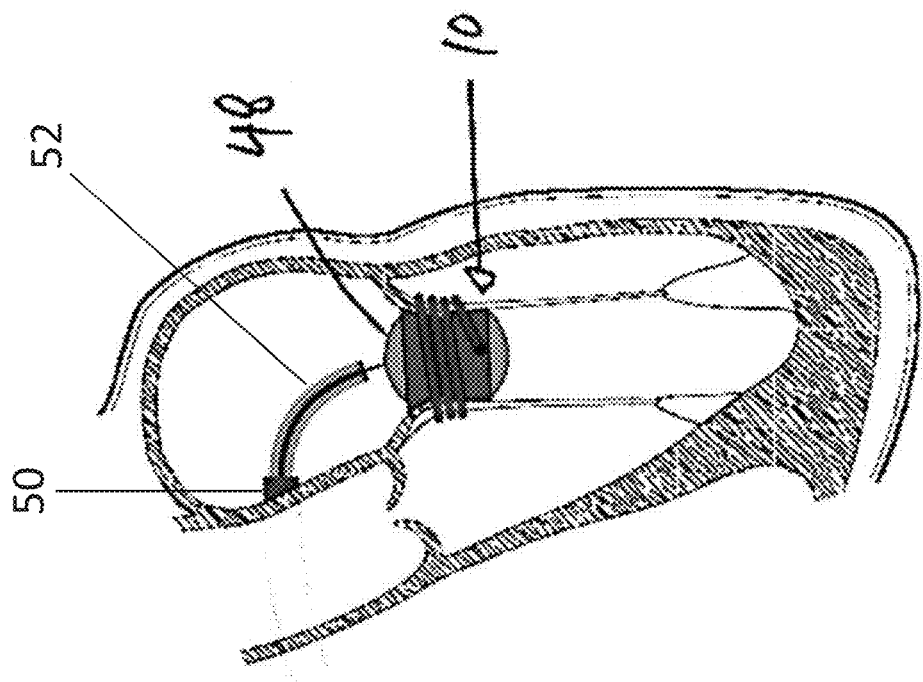
Figure 3X:
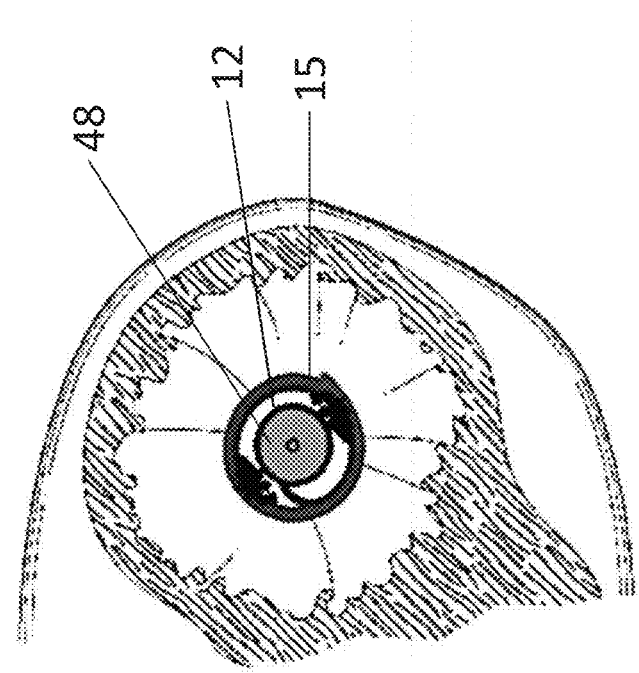
Figure 3A:
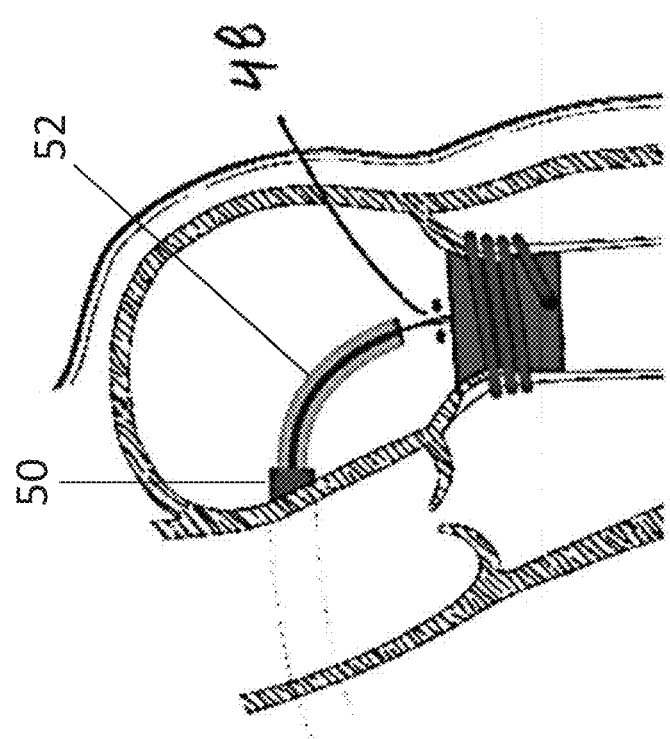
Figure 3Z:
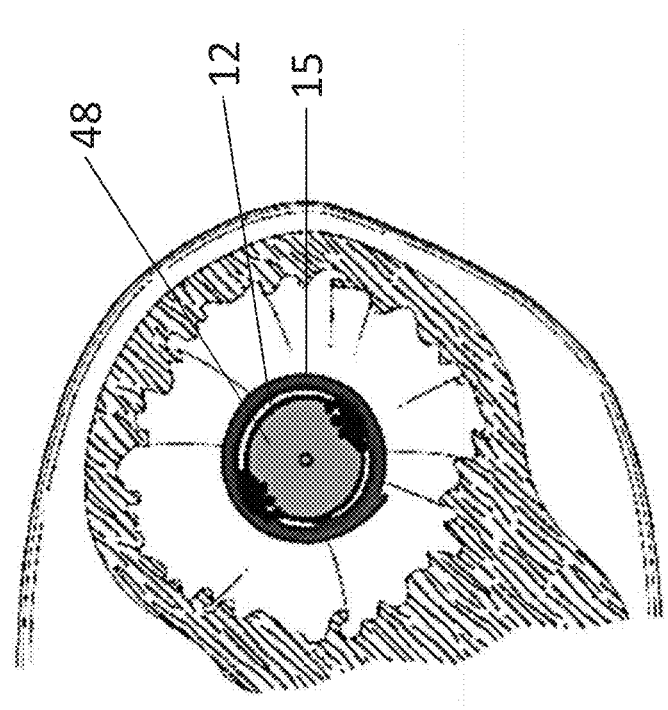
Figure 3A:
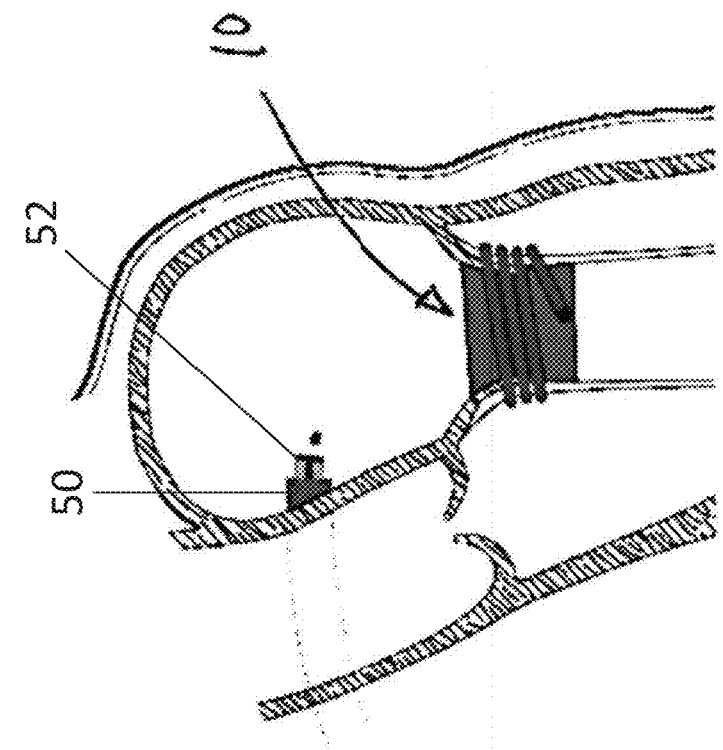
Figure 3A:
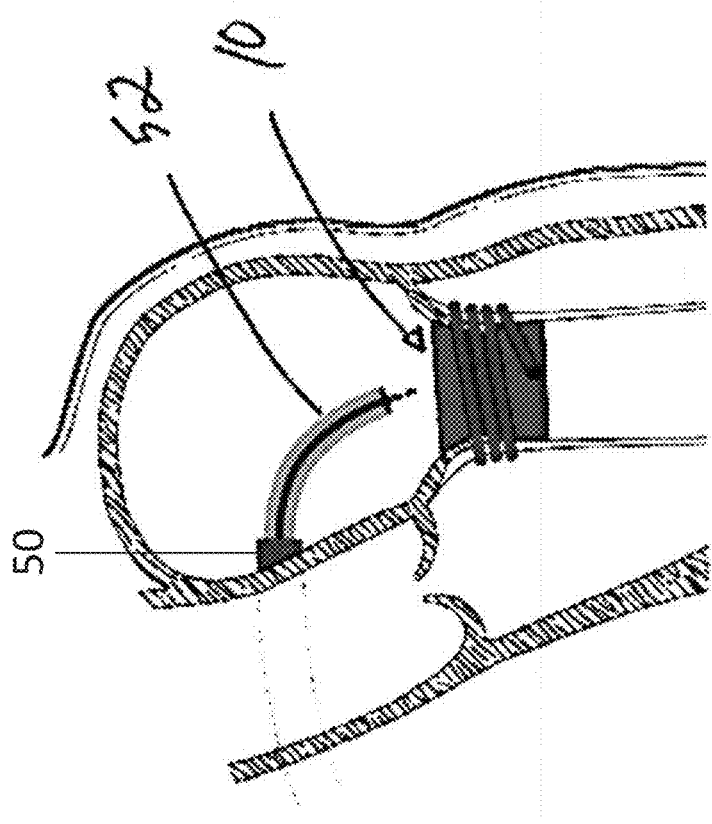

FIGS. 3V-3Z show expansion of the frame structure 12 within the native valve 4. The frame structure 12 may be expanded within the native valve 4 from an unexpanded configuration to an expanded configuration. In some embodiments, at least a portion the frame structure 12 may be expanded within at least a portion of the deployed anchor 15 to anchor the frame structure 12 to the native valve 4. In some embodiments, the frame structure 12 may comprise an expandable stent. In some embodiments, the frame structure 12 of valve prosthesis 10 may be self-expandable. In some embodiments, the frame structure 12 of valve prosthesis 10 may be balloon-expandable. The delivery device 30 may comprise a balloon 48 which may be disposed within the valve prosthesis 10 in order to expand the valve prosthesis 10. The balloon 48 may be positioned within at least a portion of the valve prosthesis 10, for example within at least a portion of frame structure 12 in an uninflated configuration, as shown in FIG. 3V, prior to being inflated. The inflatable balloon 48 may, for example, be disposed within the inner shaft 52 or outer sheath 50 while the anchor 15 is being positioned adjacent the native valve 4 and then advanced therefrom (or the inner shaft 52 or outer sheath 50 is retracted therefrom) to be positioned within the frame structure 12. Alternatively, the inflatable balloon 48 may be disposed within the frame structure 12 during placement of the valve prosthesis 10. FIGS. 3W-3X show the frame structure 12 partially expanded by partially-inflated balloon 48. As shown in FIG. 3X, the frame structure 12 may be partially expanded towards the anchor 15 in order to capture the chordae tendineae 40 therebetween. As the frame structure 12 continues to be expanded to a fully expanded state, as shown in FIGS. 3Y-3Z, the chordae tendineae 40 may be sandwiched between the anchor 15 and the frame structure 12. The frame structure 12 and anchor 15 may thus be anchored to the chordae tendineae 40.

The valve prosthesis 10 may then be released from the delivery device 30. In some embodiments, releasing the valve prosthesis 10 may comprise releasing the anchor 15 and/or the frame structure 12. Releasing the valve prosthesis 10 from the delivery device 30 may comprise expanding the valve prosthesis 10 from the unexpanded configuration to the expanded configuration. For example, expanding the frame structure 12 and releasing the frame structure 12 may occur simultaneously as described herein. Alternatively, the frame structure 12 may be released prior to or after being expanded.

FIGS. 3AA-3AC show deflation of the balloon 48 (FIG. 3AA), retraction of the balloon 48 into inner shaft 52 (FIG. 3AB), and removal of the delivery device 30 from the heart 2 (FIG. 3AC). After the frame structure 12 has been expanded and anchored to the native valve 4 as described herein, the inflatable balloon 48 may be deflated. The balloon 48 may optionally be retracted back into the delivery device 30, for example into inner shaft 52. The delivery device 30 may then be removed from the heart 2.

FIGS. 58A-58B show the valve prosthesis 10 fully expanded with the native valve leaflets 42 and chordae tendineae 40 captured between the frame structure 12 and the anchor 15. As described herein, the valve prosthesis 10 may comprise one or more valve segments 14 disposed therein to replace the native valve leaflets 42.

Although the steps above show a method of deploying a valve prosthesis 10 within a native valve 4 in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as necessary to assemble at least a part of an article.

For example, in some embodiments, deploying the valve prosthesis 10 may occur in multiple steps such that a portion of the valve prosthesis 10 (e.g., anchor 15) may be deployed before another portion the valve prosthesis 10 (e.g., frame structure 12). Alternatively, or in combination, in some embodiments, deploying the anchor 15 may occur in multiple steps such that a portion of the anchor 15 may be deployed before being advanced through the native valve 4 and another portion of the anchor 15 may be deployed after being advanced through the native valve 4. Alternatively, or in combination, the delivery device 30 may be advanced from the left atrium 25 to the left ventricle 26 with the valve prosthesis 10 undeployed. In many embodiments, the frame structure 12 may be self-expanding and the balloon 48 may not be necessary for expansion of the frame structure 12. Alternatively, or in combination, the anchor 15 may be released after the frame structure 12 has been expanded within it.

Although shown and described with respect to a mitral valve, one of ordinary skill in the art will understand that the principles described herein may be applied equally to other atrioventricular valves. Aspects of the procedure, delivery tool and implanted valve prosthesis are similar to those described in U.S. Pat. Nos. 9,034,032; 9,005,273; 8,323,336; 8,075,615; 7,621,948; and 7,175,656 and U.S. Pub. No. 2011/0288637, which are incorporated herein for all purposes in their entirety.

In some embodiments, any of the valve prostheses 10 described herein may be deployed to replace a diseased mitral valve. The first side of the native valve may comprise a left atrium and the second side of the native valve may comprise a left ventricle.

In some embodiments, any of the valve prostheses 10 described herein may be deployed to replace a diseased tricuspid valve. The first side of the native valve may comprise a right atrium and the second side of the native valve may comprise a right ventricle.

In some embodiments, any of the valve prostheses 10 described herein may be deployed to replace a diseased aortic valve. The first side of the native valve may comprise a left ventricle and the second side of the native valve may comprise an aorta.

The valve prosthesis device and implant method described herein in accordance with the present disclosure may provide many advantages as will be understood by one of ordinary skill in the art. The overall device and method may provide a simpler way to approach the native valve compared to existing devices. The system may enable a transcatheter approach through the septal wall compared to more invasive transapical approaches. The device may provide a consistent and relatively easy mechanism for anchoring to the native valve. Clinicians need only use the common technique of inserting the device through the valve and then rotating the anchor. The coil may provide preliminary anchoring in the native valve. If desired, the clinician can readjust the anchor and/or retrieve the anchor (e.g. by counterrotation). The device is then easily set by expanding within the native valve leaflets. The device and methods in accordance with the present disclosure may also address unmet clinical needs with atrioventricular repair and replacement. Existing devices face challenges with the complex anatomy of the mitral and tricuspid valves, for example. The present disclosures address these complications by reshaping the native valve annulus to a conventional round shape and providing a robust, yet simple, anchoring mechanism.

FIGS. 4A-4H show sequential views of an exemplary deployment of an anchor 15 from the distal end of a delivery device 30. The anchor 15 and delivery device 30 may be substantially similar to any of the anchors and delivery devices described herein, respectively. The anchor 15 may be detachably coupled to the delivery device 30 and/or a frame structure 12 (not shown in FIGS. 4A-4H) as described herein. As described herein, the anchor 15 may be actuated from an elongated configuration to a deployed configuration adjacent a native valve of patient. In some embodiments, the anchor 15 may be deployed from the inner shaft 52 by pushing the anchor 15 out of the inner shaft 52 (if disposed within the inner shaft 52 in the elongated configuration), releasing the anchor 15 from radial constraint by retracting the outer sheath 50 (if disposed within the outer sheath 50 in the elongated configuration), or the like as described herein. When correctly deployed from the delivery device 30, the anchor 15 may wrap at least partially around a distal portion of the delivery device 30 (e.g., around the inner shaft 52 if disposed within the inner shaft 52 or around the outer sheath 50 if disposed within the outer sheath 50). A central axis of the curved anchor 15 may be co-axial with a longitudinal axis of the delivery device 30 when the curved anchor 15 is in the deployed configuration.

Figures 4A, 4B:
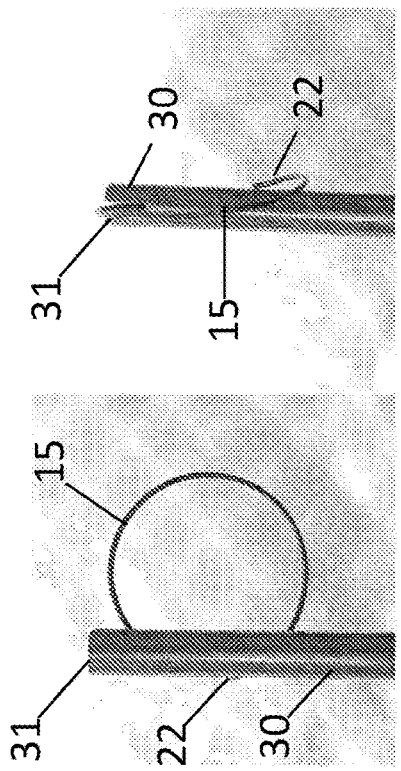
FIGS. 4A-4H show sequential views of correct deployment of an anchor from the distal end of a delivery device, in accordance with embodiments.

FIG. 4A shows the free end 22 of the anchor 15 being advanced out of a lumen of the delivery device 30 via aperture 31 (also referred to herein as an opening or hole). FIG. 4B shows a 90° rotated view of FIG. 4A. The aperture 31 may be disposed at a distal end of the delivery device as shown. Alternatively, the aperture 31 may be disposed at a location proximal to the distal end of the delivery device 30.

Figures 4C, 4D:
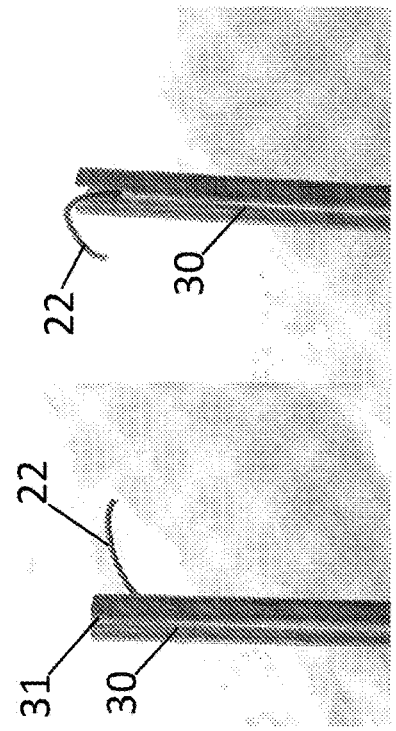

FIG. 4C shows the free end 22 of the anchor 15 being further advanced through the opening 31 such that it begins to wrap around the distal end of the delivery device 30. FIG. 4D shows a 90° rotated view of FIG. 4C. As the first loop of the anchor 15 is deployed, the free end 22 may be positioned to the right side of the delivery device 30. It will be understood by one of skill in the art that the position of the free end 22 with respect to the delivery device 30 at this stage (i.e. positioned along the right side or the left side) needed for correct deployment of the anchor 15 may be dependent on the handedness of the loops (also referred to herein as coils or turns) of the anchor 15.

Figures 4E, 4F:
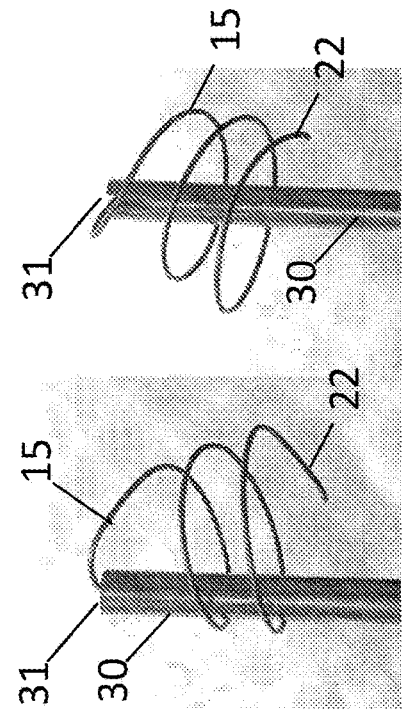

FIG. 4E shows the free end 22 of the anchor 15 being further advanced through the opening 31 such that a second turn of the anchor 15 wraps around the delivery device 30. FIG. 4F shows a 90° rotated view of FIG. 4E. The free end 22 may again be positioned to the right side of the delivery device 30 as the anchor 15 continues to loop around the delivery device 30.

Figures 4G, 4H:
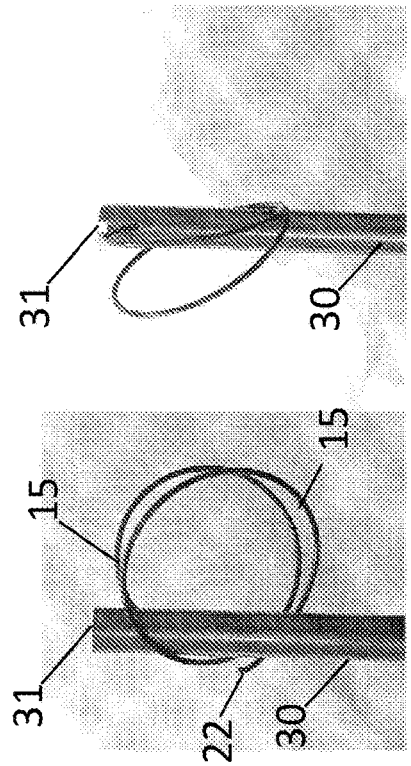

FIG. 4G shows the anchor 15 in the final deployed configuration. FIG. 4H shows a 90° rotated view of FIG. 4G. The remainder of the anchor 15 may be advanced out of the opening 31 in order to deploy the anchor 15 as described herein. While three loops of the anchor 15 have been shown wrapped around the distal end of the delivery device 30, one of ordinary skill in the art will understand that the anchor 15 may comprise any number of loops desired, for example, one, two, three, four, five, or six loops, and may be configured such that at least a portion of the anchor is wrapped around the delivery device 30 when deployed. A central axis of the anchor 15 may be co-axial or concentric with a longitudinal axis of the delivery device 30 when the anchor 15 is in the deployed configuration.

After the anchor 15 has been deployed from the delivery device 30, the frame structure 12 may be at least partially deployed from the delivery device 30 (for example as shown in FIG. 3H) so as to place the frame structure 12 within the anchor 15. The anchor 15 may then be used to capture one or more structures as described herein.

FIGS. 5A-5H show sequential views of a different and possibly less preferable deployment of an anchor 15 from the distal end of a delivery device 30 in accordance with embodiments. The anchor 15 and delivery device 30 may be substantially similar to any of the anchors 15 and delivery devices 30 described herein, respectively. When deployed from the delivery device 30, the anchor 15 one or more loops of the anchor 15 may not wrap around a distal portion of the delivery device 30 (e.g., around the inner shaft 52 if disposed within the inner shaft 52 or around the outer sheath 50 if disposed within the outer sheath 50). A central axis of the curved anchor 15 may not be co-axial with a longitudinal axis of the delivery device 30 when the curved anchor 15 is in this deployed configuration. In this configuration, the anchor 15 may not sit coplanar with the valve annulus and/or may not wrap around native valve structures, such as the chordae tendinae.

Figure 5A:
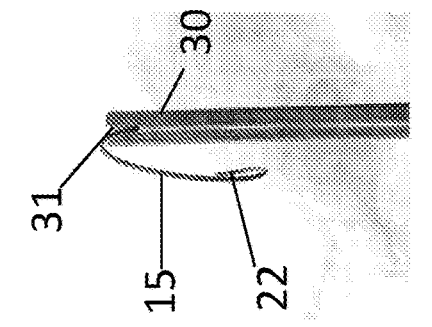
FIGS. 5A-5H show sequential views of incorrect deployment of an anchor from the distal end of a delivery device, in accordance with embodiments.
Figure 5B:
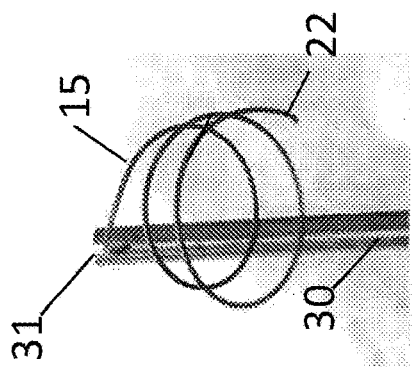

FIG. 5A shows the free end 22 of the anchor 15 being advanced out of a lumen of the delivery device 30 via aperture 31. FIG. 5B shows a 900 rotated view of FIG. 5A.

Figure 5C:
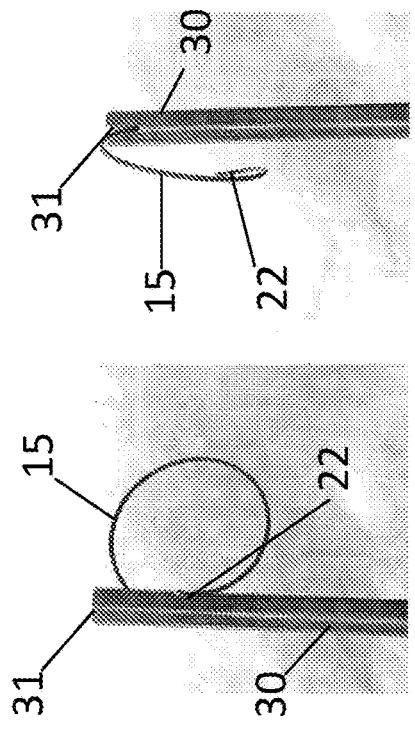
Figure 5D:
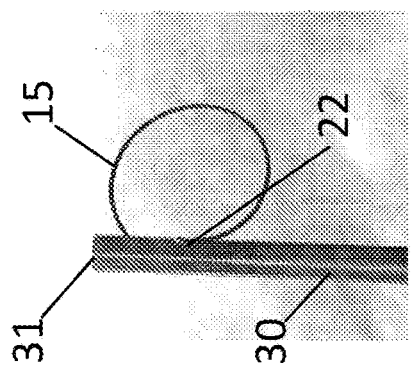

FIG. 5C shows the free end 22 of the anchor 15 being further advanced through the opening 31 such that it begins to form a loop adjacent the distal end of the delivery device 30. FIG. 5D shows a 90° rotated view of FIG. 5C. As the first loop of the anchor 15 is deployed, the free end 22 may be positioned to the left side of the delivery device 30.

Figure 5E:
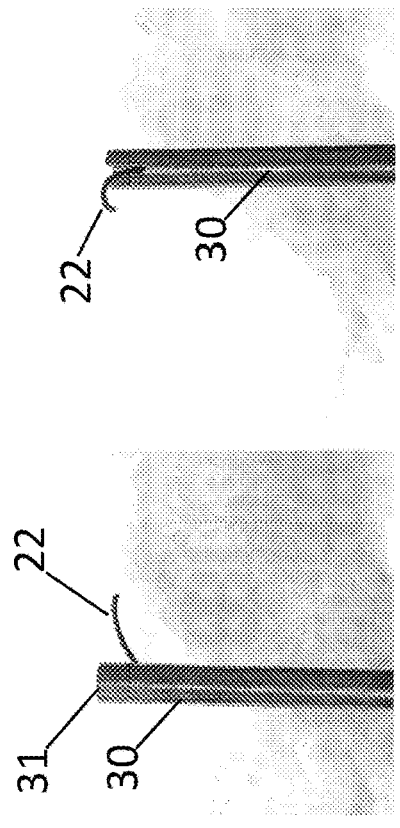
Figure 5F:
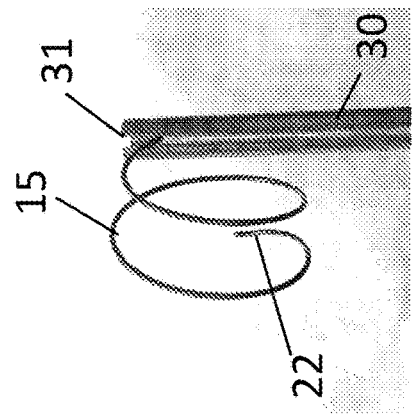

FIG. 5E shows the free end 22 of the anchor 15 being further advanced through the opening 31 such that a second turn of the anchor 14 deploys adjacent the delivery device 30. FIG. 5F shows a 90° rotated view of FIG. 5E. The free end 22 may again be positioned to the left side of the delivery device 30 as the anchor 15 continues form loops next to, but not around, the delivery device 30.

Figure 5G:
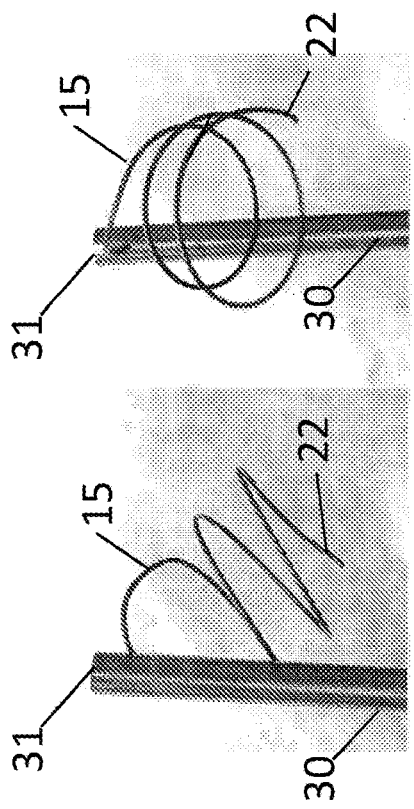
Figure 5H:
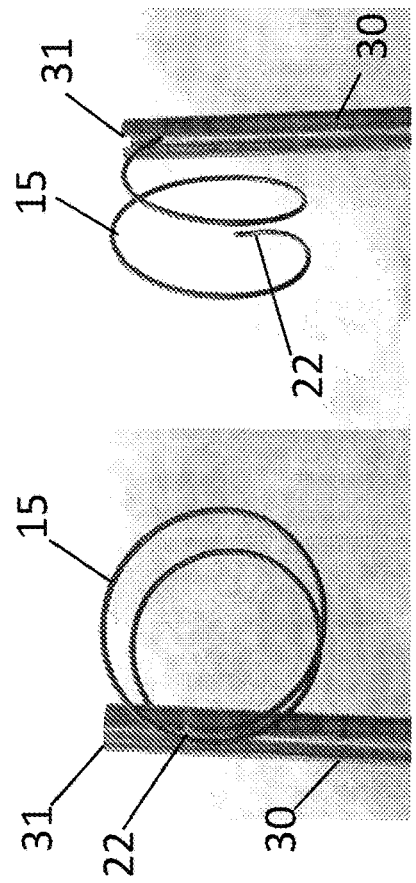

FIG. 5G shows the anchor 15 in the final deployed configuration. FIG. 5H shows a 90° rotated view of FIG. 5G. The remainder of the anchor 15 may be advanced out of the opening 31 in order to deploy the anchor 15. When deployed in this manner, the anchor 15 may not be wrapped around the delivery device 30. The anchor 15 may instead sit to the side of the delivery device 30. A central axis of the anchor 15 may not be co-axial or concentric with a longitudinal axis of the delivery device 30 when the anchor 15 is in the deployed configuration. Instead, the central axis (e.g., helical axis) of the anchor 15 may be at an angle relative to the longitudinal axis of the delivery device 30.

After the anchor 15 has been deployed from the delivery device 30 in the configuration shown in FIGS. 5A-5H, the frame structure 12 may, in some embodiments, be unable to be deployed from the delivery device 30 to sit within the anchor 15, which may subsequently make capturing of the one or more structures and/or anchoring of the frame structure 12 to the anchor 12 more difficult or impossible.

FIGS. 6A-6B show close-up views of the distal end of a delivery device 30 during another (possibly more preferable) deployment of an anchor 15 therefrom. FIGS. 6C-6D show close-up views of the distal end of a delivery device 30 during deployment of the anchor 15 therefrom. In this deployment method, the anchor 15 wraps concentrically or coaxially around a longitudinal axis 32 of the delivery device 30. Such wrapping may be directed, at least in part, by the positioning of the free end 22 relative to the delivery device 30. Correctly positioning the free end 22 relative to the delivery device 30 may result is proper deployment. If the free end 22 is positioned on the right side of the delivery device 30 as it loops towards the delivery device 30, the free end 22 may be able to wrap around the delivery device 30 and encircle it as indicated by the arrows in FIGS. 6A-6B. If the free end 22 is instead positioned on the left side of the delivery device 30, the free end 22 may be unable to wrap around the delivery device 30 and will continue to loop towards the left as indicated by the arrows in FIGS. 6C-6D. It would therefore be desirable to provide an anchor 15 which may be reliably deflected towards the correct side of the delivery device 30 to ensure wrapping and deployment of the anchor 15.

In some embodiments, the delivery system 30 can include an anchor guide 153 and/or a tether 78. For example, an anchor guide 153 is shown in FIGS. 10-11, 20-22, 26, 27, 46-47, 50, and 51-53. Similarly, a tether 78 is shown in FIGS. 28-34, 36, 83.

Figure 26:
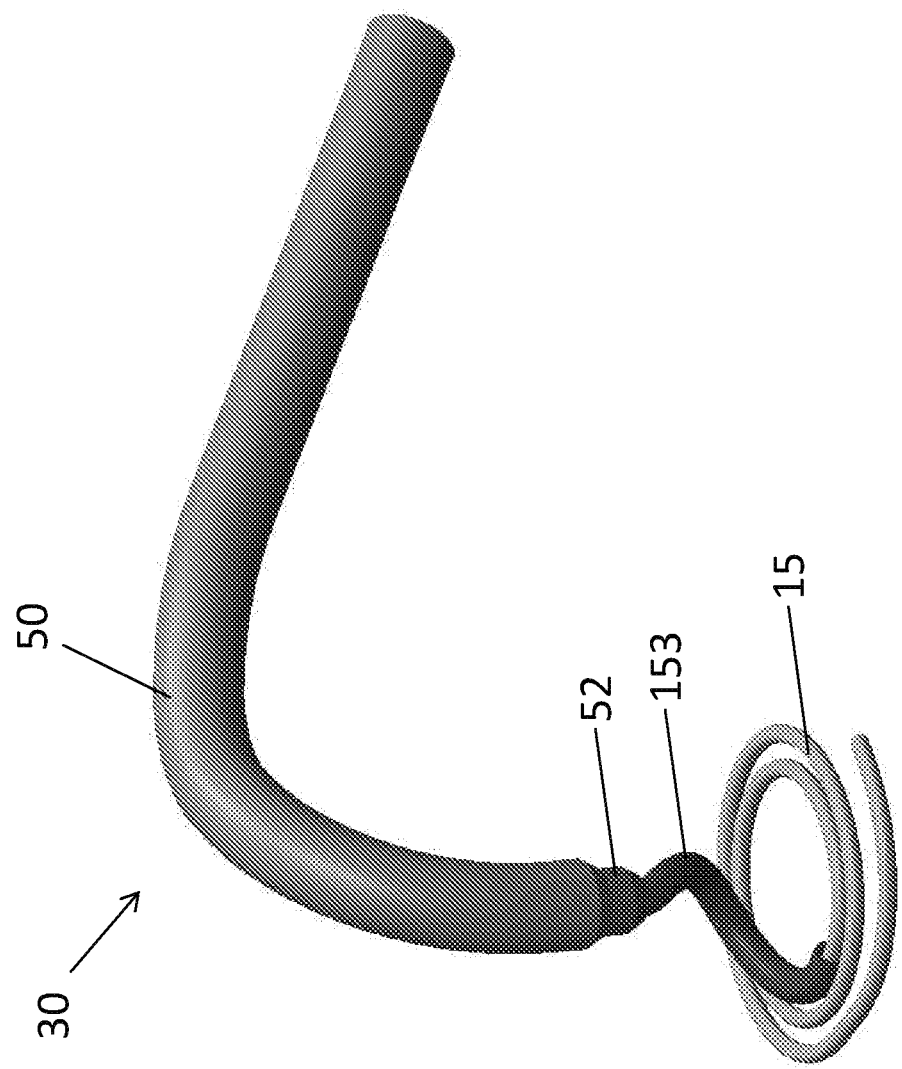
FIG. 26 shows a perspective view of an exemplary anchor delivery system, in accordance with embodiments.

FIG. 26 shows a perspective view of an exemplary anchor delivery system 30 coupled to an anchor 15. The delivery device 30 may comprise an inner shaft 52 as described herein, an outer sheath 50, and an anchor guide 153. In some embodiments, the outer sheath 50 may be delivered through an introducer or itself act as an introducer. In some embodiments, the inner shaft 52 and the outer sheath 50 may be separate sub-assemblies of the delivery device 30 and may be translatable relative to one another. The anchor 15 may be detachably coupled to the delivery device 30 and/or a frame structure 12 as described herein. The anchor 15 may be detachably coupled to a retention wire or tether 78 (see FIG. 28) that may be translatable within the delivery device 30 (e.g., within the inner shaft 52) relative to the other components of the delivery device 30. As described herein, the anchor 15 may be actuated from an elongated configuration to a deployed configuration adjacent a native valve of patient. In some embodiments, the anchor 15 may be deployed from the inner shaft 52 by pushing the anchor 15 out of the inner shaft 52 (e.g., with a tether 78). When correctly deployed from the delivery device 30, the anchor 15 may wrap at least partially around a distal portion of the delivery device 30 and/or a central axis of the anchor 15 may be co-axial with a longitudinal axis of the distal end of the delivery device 30 when the anchor 15 is in the deployed configuration.

Figure 27:
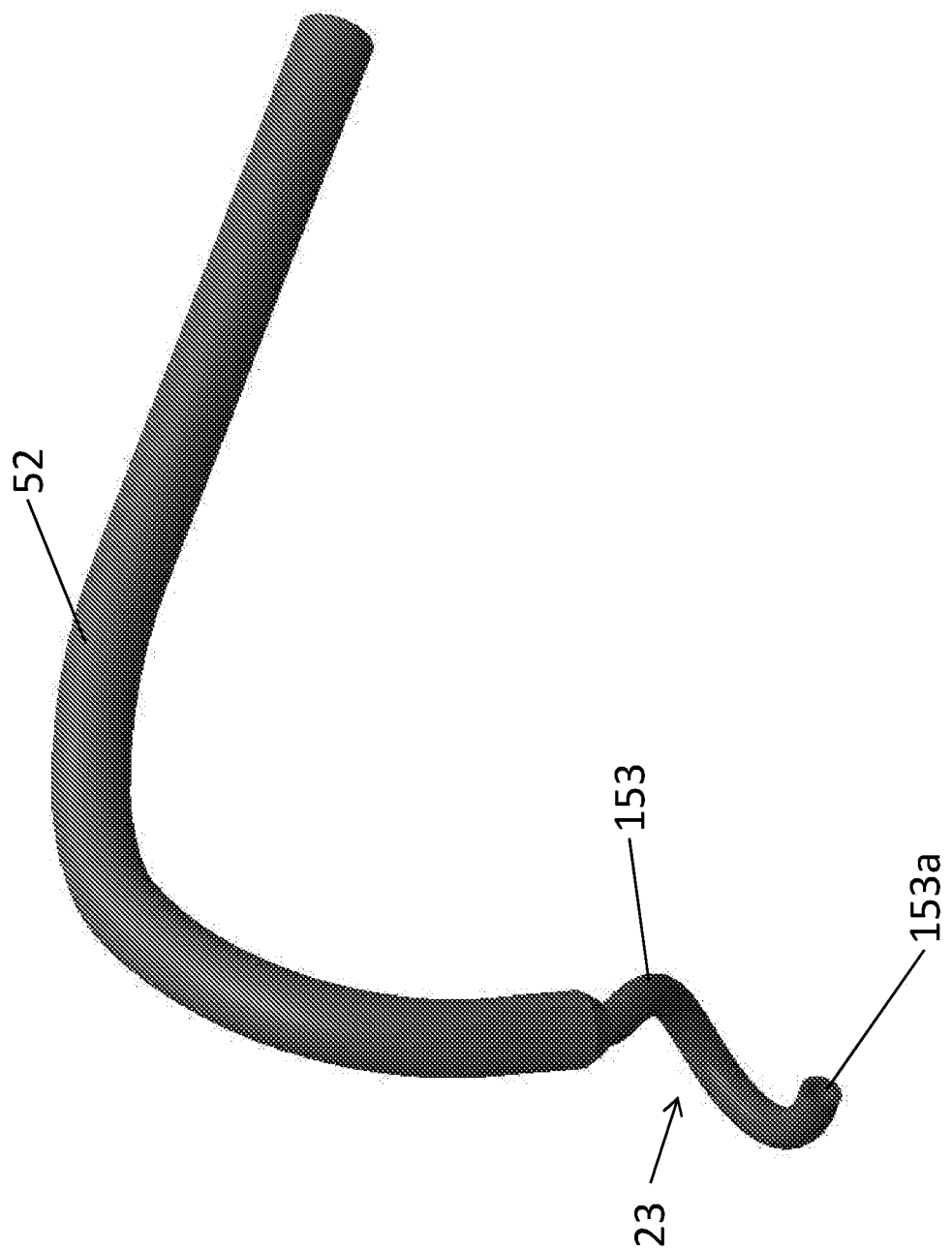
FIG. 27 shows a perspective view of an inner shaft of the delivery device of FIG. 26, in accordance with embodiments.

FIG. 27 shows a perspective view of an inner shaft 52 of the delivery device 30 of FIG. 26. The inner shaft 52 may be substantially similar to any of the inner shafts described herein. The anchor 15 may be configured to rotate with the inner shaft 52 when the inner shaft 52 is rotated. A distal end of the inner shaft 52 may comprise a curved anchor delivery sheath or anchor guide 153 (also referred to herein as a "throwdown arm") at the distal end thereof. The anchor guide 153 may be configured to deliver the anchor 15 to the native valve as described herein.

Referring to FIGS. 87A-87C, the anchor guide 153 can include a proximal section 161 and a distal section 162. The proximal section 161 can be substantially straight and/or axially aligned with the inner shaft 52. The distal section 162, in contrast, can be curved, bent, or looped, such that it forms a tapered spiral (or tapered corkscrew) about the same axis as the proximal section 161 and/or the inner shaft 52. The tapered spiral can transition continuously from a high-pitch, low-radius curve at the proximal end to a low-pitch, high-radius curve at the distal end. The distal-most plane of the tapered spiral of the distal section 162 can be orthogonal to the central axis of the proximal section 161 and/or inner shaft 52. Having the distal-most plane of the distal section 162 be orthogonal to the central axis of the proximal section 161 and/or inner shaft 52 can advantageously ensure that the anchor 15 is stable (e.g., does not wobble) during deployment. Further, the distal-most portion of the tapered spiral of the distal section 162 can have a curvature that substantially matches the curvature of the spiral of the anchor 15. Having matching curvatures can advantageously ensure that the anchor 15 rotates on-axis with the proximal section 161 of the guide 153 and the inner shaft 52 as the inner shaft 52 is rotated and/or as the anchor 15 is released.

In some embodiments (as best shown in FIG. 87C), the curved distal section 162 can form a spiral or tapered spiral that extends approximately 360°. In other embodiments, the curved section can extend less than 180° (e.g., 90°-120°) 180°-360°, or greater than 360°. In one specific embodiment, the height h of the distal section 162 can be 10-20 mm, such as approximately 15 mm. In one specific embodiment, the radius r of the distal portion of the tapered spiral can be 7-12 mm, such as approximately 9 mm.

The distal section 162 of the anchor guide 153 may direct the anchor 15 out of the guide 153 in an initial direction that is transverse to the longitudinal axis of the inner shaft 52 and/or proximal section 161. As the anchor 15 is rotated, however, the spiral can form about the longitudinal axis of the inner shaft 52 and/or proximal section 161. The anchor guide 153 may thus be shaped to act as a throwdown arm and may be configured to correctly orient the anchor 15 relative to the chordae tendineae and/or prevent twisting of the anchor 15 during deployment and/or rotation, as well as ensure that the anchor 15 will self-assemble around the inner shaft 52 and/or frame structure 12, after the outer sheath 50 is advanced through the native valve. During anchor deployment, translation and/or rotation of the inner shaft 52 and anchor guide 153 may provide control over the direction and orientation of anchor self-assembly. During encircling of the chordae tendineae, the axial position of the inner shaft 52 and anchor guide 153 may control the height of the anchor relative to the valve annulus, and rotation of the inner shaft 52 and anchor guide 153 may be translated to the anchor 15 to provide encircling motion thereto as described herein.

In some embodiments, the anchor guide 153 may be held in a relatively straight collapsed configuration when positioned within the lumen of the outer sheath 50 (e.g., by radial constriction from the sheath 50). The anchor guide 153 may be shape-set such that distal translation of the anchor guide 153 relative to the distal tip of the outer sheath 50, and release of radial constriction therefrom, allows the anchor guide 153 to bend at the distal section 162. In some embodiments, the anchor guide 153 can be retracted into the outer sheath 50 (i.e., return to the collapsed configuration) after deployment of the anchor 15. The anchor guide 153 can thus be an extendable and retractable anchor guide 153.

In some embodiments, the anchor guide 153 may comprise one or more deflection features, similar to as described herein for other elements, in order to facilitate delivery of the anchor 15 to the native valve. The one or more deflection features may help provide the anchor guide 153 with a shape configured to correctly orient the anchor 15 relative the longitudinal axis of the inner shaft 52 in order to facilitate concentric wrapping of the anchor 15 around the inner shaft 52 as the anchor 15 is deployed from the delivery configuration to the deployed configuration.

Referring to FIG. 87D, in some embodiments, the anchor guide 153 can be shape-set. The anchor guide 153 can include a portion with a laser cut pattern configured to provide the spiraled or tapered spiral formation. The laser cut pattern can advantageously create a rigid, fixed shape when deployed, but allow for straightening of the anchor 15 during delivery and/or retraction. The anchor guide 153 can further be designed to have the maximum curvature possible (e.g., to reduce deployment forces) while maintaining a minimum footprint. The stiffness of the anchor 15 can also be designed so as to maintain stability as the anchor 15 is deployed and/or as the anchor guide 153 is translated and/or rotated within and/or about native valve structures.

In some embodiments, the anchor guide 153 can be designed such that the distal end thereof overlaps with a proximal end of the anchor 15 even when the anchor 15 is fully deployed, thereby increasing torsional and bending stiffness of the anchor. Further, in some embodiments, the distal end of the anchor guide 153 can be tapered to minimize the step size between the anchor guide 153 and the anchor 15, thereby reducing the chances of the anchor guide 153 getting stuck on native valve structures during deployment.

The anchor guide 153 can advantageously ensure deployment of the anchor 15 in a concentric direction with the delivery device 30, avoiding tangling of the anchor 15 with the delivery device 30. Additionally, the anchor guide 153 can advantageously provide a stable support for the anchor 15 after the anchor 15 has been advanced and as the anchor 15 is rotated about the native valve structures.

In some embodiments, the inner shaft 52 and anchor guide 153 may be translated (or "wiggled") within the outer sheath 50 prior to, during, or after deployment of the anchor 15 in order to actively or reactively move the distal tip 156 of the anchor guide 153. Translating the inner shaft 52 and anchor guide 153 back-and-forth during deployment of the anchor 15 may correspondingly adjust the angle of the anchor 15 and/or free end 22 of the anchor 15 as it deploys. This may facilitate deployment of the anchor 15 in tight spaces and/or facilitate encircling of the chordae tendineae (e.g., by adjusting the orientation and/or location of the free end 22). In some embodiments, the anchor guide 153 can be moved with respect to the sheath 50 to change the shape or length of the anchor guide 153 during deployment of the anchor 15.

In some embodiments, the anchor guide 153 is a unitary construct with the distal end of the inner shaft 52. Referring to FIG. 88A, in other embodiments, the anchor guide 153 can be a separate component from the distal end of the inner shaft 52 and can be bonded at bond region 163 or otherwise coupled to distal end of the inner shaft 52.

Referring to FIGS. 88A-88B, in some embodiments, the anchor guide 153 may be formed from a shape memory (e.g., NiTi) layer 171. In some embodiments, the guide 153 can further include an inner layer 172 (e.g., PTFE liner) to reduce friction as the anchor 15 is moved through the guide 153. In some embodiments, the anchor guide 153 can include an outer jacket layer 173 (e.g., Pebax® (i.e., a polyether block amide) or urethane). The outer jacket layer 173 can advantageously help reduce friction with the outer sheath 50 (which may be steerable) and can advantageously remain flexible as the shape memory layer 171 takes shape. Further, the outer jacket layer 173 can advantageously help maintain the integrity of the inner layer 172.

Referring to FIGS. 88A and 88C, in some embodiments, the shaft 52 can include a braided layer, such as a stainless steel braid. The inner layer 175 can be similar to the inner layer 172 of the anchor guide 153. Likewise, the outer layer 176 can be similar to the outer layer 173 of the anchor guide 153. In some embodiments, the inner layers 172/175 can be continuous with one another. Similarly, the outer layers 173/176 can be continuous with one another.

Figure 28:
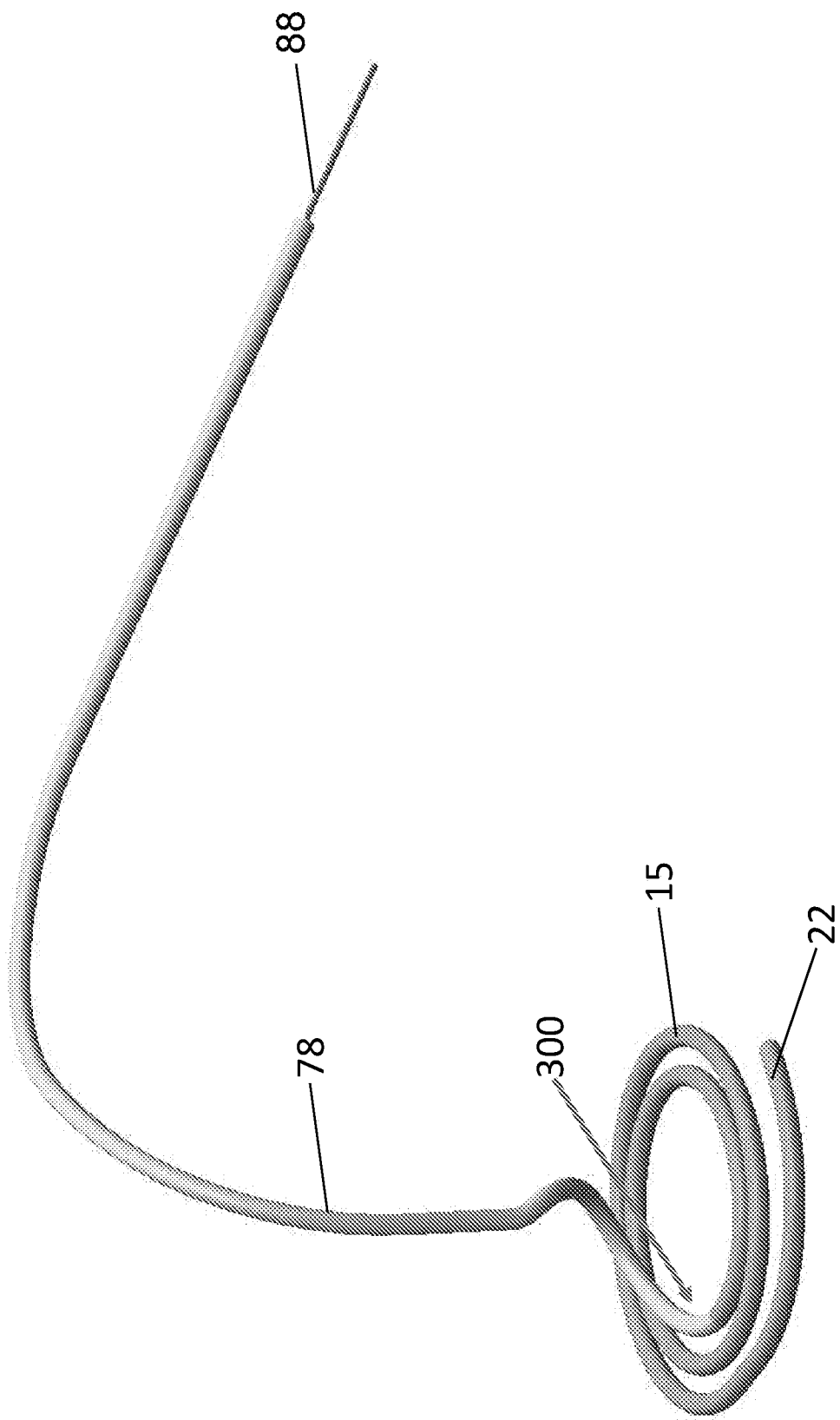
FIG. 28 shows a perspective view of an exemplary anchor of the system of FIG. 26, in accordance with embodiments.

FIG. 28 shows a perspective view of an exemplary anchor 15 of the system of FIG. 26. The anchor 15 may be substantially similar to any of the anchors described herein. The proximal end 57 of the anchor 15 may be detachably coupled to a tether 78, which may be disposed within the lumen of the inner shaft 52 (and anchor guide 153) and extend towards a proximal end of the delivery device 30. The anchor 15 may comprise a body having a coiled shape (e.g., a spiral shape) as described herein. The body of the anchor 15 may comprise a plurality of turns or loops as described herein. The body of the anchor 15 may, for example, comprise a spiral shape having one or more loops as described herein. In various embodiments, the anchor 15 may comprise a flat spiral shape. Loops of the flat spiral shaped anchor may be generally positioned within the same plane (the plane being perpendicular to a longitudinal axis of a delivery device) as described herein. The anchor 15 may comprise a free end 22 configured to act as a "grabber" arm as described herein. The free end 22 may be disposed proximally, distally, and/or radially outward from the rest of the anchor body. In some embodiments, the free end 22 may be "L"-shaped relative to the body of the anchor 15. In some embodiments, the free end 22 may be unitary construct with the body of the anchor 15. In some embodiments, the free end 22 may be formed as a separate component from the coiled body of the anchor 15 and bonded or otherwise coupled to the anchor body prior to deployment.

The anchor 15 may comprise a delivery (e.g., elongated, radially collapsed, or unexpanded) configuration and a deployed configuration. In various embodiments, the anchor 15 may be self-expanding and may move to the deployed configuration as it is deployed (e.g., pushed out from the anchor guide 153 by the tether 78). In various embodiments, the anchor 15 may be configured to self-assemble when it is deployed in the heart cavity (e.g., left ventricle or left atrium). The anchor 15 may be actuated from the delivery configuration to the deployed configuration adjacent the native valve using any method or mechanism understood by one of ordinary skill in the art from the description herein. Advancement of the inner shaft 52 and guide 153 out of the lumen of the outer sheath 50 may actuate the anchor 15 into the deployed configuration as described herein.

Referring to FIGS. 89A-89C, the tether 78 can be detachably coupled to the anchor 15, such as via connection mechanism 300. Further, as shown in FIGS. 89A-89B, the tether 78 can, in some embodiments, include a distal portion 89 and a proximal portion 87. The distal portion 89 can be more flexible than the proximal portion 87 so as to fit, and easily flex and/or translate, within the anchor guide 153. The proximal portion 88, in contrast, may be stiffer and ensure that push/pull force is transmitted to the anchor 15 to deploy and/or retract the anchor from/into the inner shaft 52 and anchor 153. The proximal portion 87 may be substantially similar to the proximal pushers described herein.

In some embodiments, and as shown in FIG. 89B, the distal portion 89 of the tether 78 may be shaped to correspond to the shape of the anchor guide 153. The anchor 15 may self-assemble around the inner shaft 52 and/or outer sheath 50 as it is pushed from the lumen of the anchor guide 153 by the tether 78 as described herein.

A proximal end of the anchor 15 may be detachably coupled to the tether 78. The tether 78 may be disposed within a lumen of the delivery device 30 (e.g., within a lumen of the inner shaft 52 and anchor guide 153) and may operably couple the anchor 15 to the delivery device 30. The tether 78 may act as an actuation mechanism and facilitate longitudinal translation of the anchor 15 through the delivery device 30 during deployment. For example, a proximal end of the tether 78 may be coupled to an actuation mechanism in/on the delivery device 30 in order to translate the anchor 15. Alternatively, the proximal end of tether 78 may be manually manipulated by, at, or near a proximal end of the delivery device 30 in order to translate the anchor 15.

The tether 78 may comprise a flexible advancement member housed and translatable within the inner shaft 52. The tether 78 may comprise a flexible shaft or stylet, for example, in the form of a wire or a metal wire, and/or flexible hypotube with a lumen to accommodate a guidewire. The tether 78 may be sufficiently flexible to allow for easy rotation within the deflectable delivery device 30.

The tether 78 may be comprise a release actuation mechanism (e.g., retention wire 88).

In various embodiments, the anchor 15 may be self-expanding and may move to the deployed configuration as it is deployed (e.g., pushed out) from the anchor guide 153 by the tether 78. The anchor 15 may be rotated by the rotating the inner shaft 52 (and anchor guide 153) and/or the tether 78. In some embodiments, the tether 78 may be rotated, and rotational motion may be translated from the tether 78 to the anchor 15. Rotation of the anchor 15 via the anchor guide 153 and/or tether 78 can enable the anchor 15 to wrap around the one or more native valve structures on the ventricle side of the mitral valve as described herein.

The anchor 15 may be disposed in the inner shaft 52 (and anchor guide 153) and maintained in the delivery configuration by radial constriction from the inner shaft 52 and anchor guide 153. Advancement of the anchor 15 out of the inner shaft 52 may actuate the anchor 15 into the deployed configuration. The proximal end 57 of the anchor 15 may be detachably coupled to the tether 78 within the lumen of the inner shaft 52 as described herein. Although the anchor 15 is described as being pushed out of the inner shaft 52 in some embodiments, one will appreciate from the description herein that different mechanisms may be employed to deploy the anchor depending on the anchor 15 and/or inner shaft 52 design. In some respects, pushing is used somewhat interchangeably with rotation in reference to deployment of the anchor 15. For example, the anchor 15 can be rotated out of a lateral opening with a rotational action.

Figure 29:
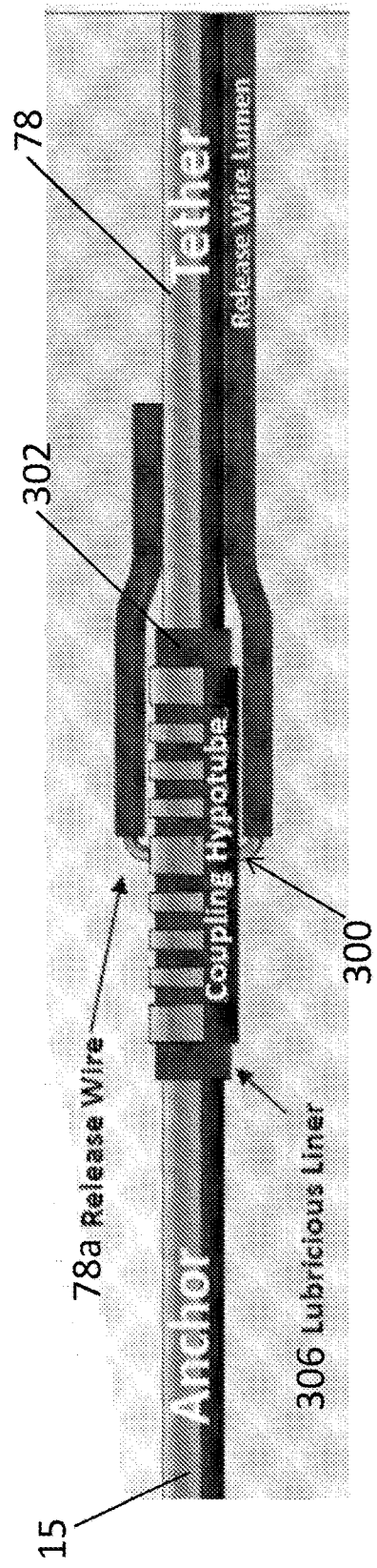
FIGS. 29-30 show various views of an anchor coupled to a proximal tether, in accordance with embodiments.
Figure 30:
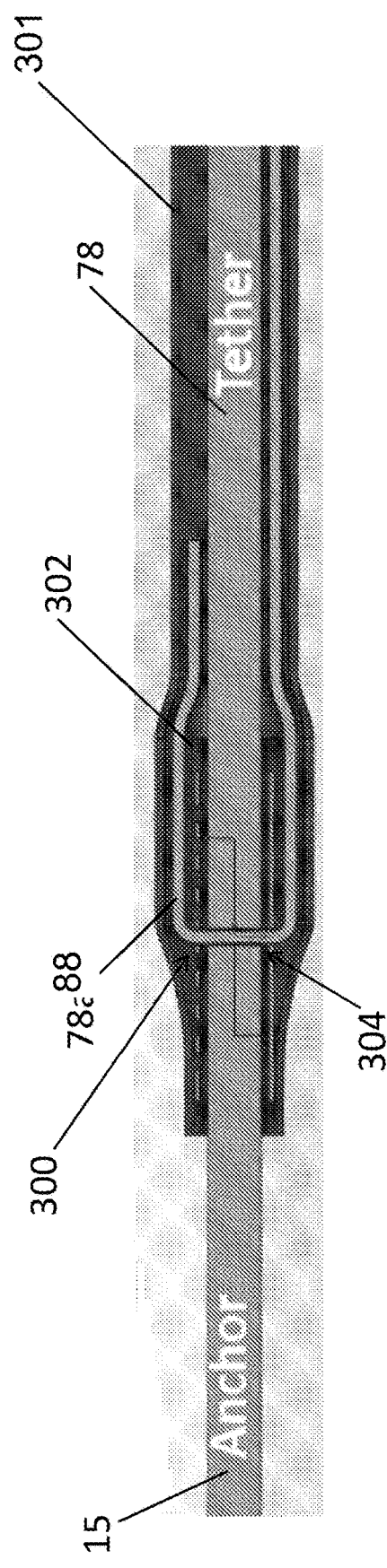

FIGS. 29-30 show various views of an anchor 15 coupled to a tether 78 at with connection mechanism 300. FIG. 29 is a side view. FIG. 30 is a side cross-sectional view. The tether 78 may comprise a round wire housed in a tubular housing 301. The housing 301 may, for example, comprise a mesh. The mesh may comprise a wire or polymer mesh. A distal end of the tether 78 may comprise a hypotube 302 bonded to the housing 301 (e.g., mesh). The hypotube end 302 of the housing 301 may provide support to the connection point 300 between the anchor 15 and the tether 78. The coupling hypotube 302 may comprise a lubricous liner 306 therein to facilitate de-coupling of the anchor 15 and the pusher arm 78. The wire (or wires) of the tether 78 may be substantially similar in cross-section and structure to the anchor 15 in order to facilitate overlap of the layers and provide support.

The tether 78 may be coupled to the anchor 15 by a retention wire 88. The retention wire 88 may run the length of the tether 78 from the connection point 300 to the proximal end. A distal end of the retention wire 88 may be threaded through a hole 304 spanning at least a portion of both the anchor 15 and the tether wire 78 when aligned in the delivery configuration. When threaded as such, the retention wire 88 may act as an engagement pin to keep the anchor 15 and tether wire 78 together during deployment of the anchor 15. Once the anchor 15 is deployed, the proximal end of the retention wire 88 may be translated proximally in order to disengage the retention wire 88 from the anchor 15 and release the anchor 15 from the tether 78. The proximal end of the retention wire 88 may be coupled to an actuation mechanism in/on the delivery device in order to translate the retention wire 88. Alternatively, the proximal end of the retention wire 88 may be manually manipulated by, at, or near a proximal end of the delivery device in order to translate the retention wire 88. Once disengaged, the tether 78 may be retracted from the body, leaving the deployed anchor 15 adjacent the native valve as described herein.

Figure 43:
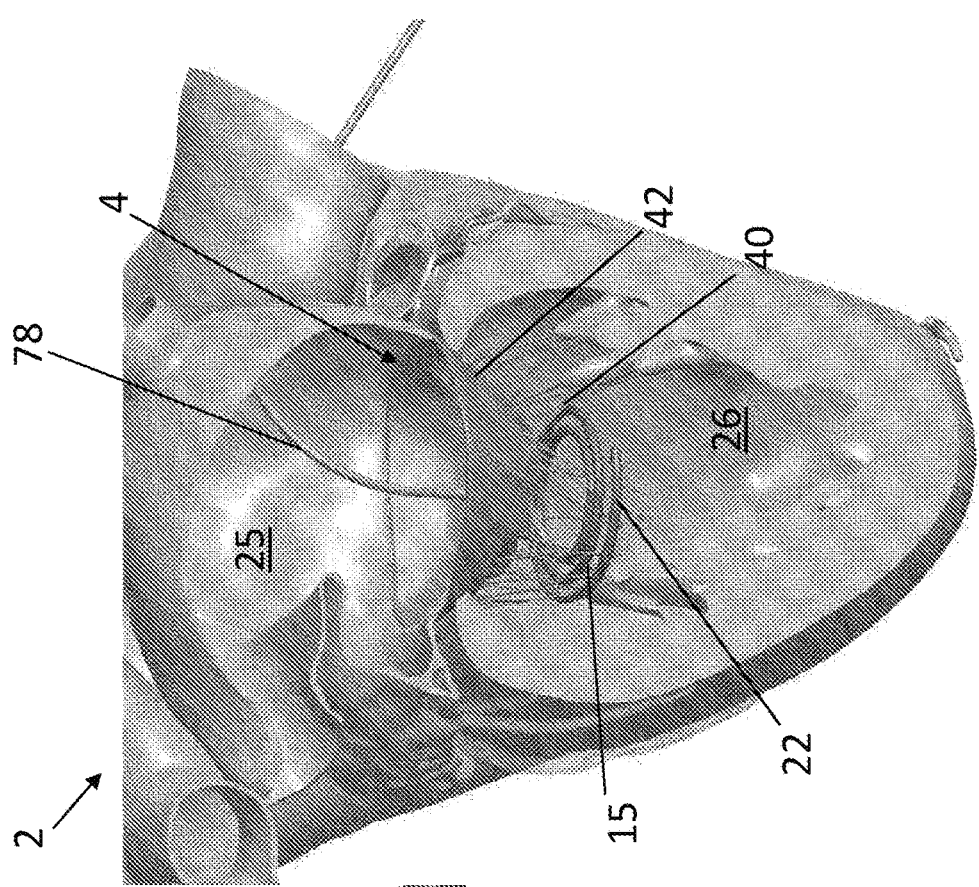

FIGS. 31-33 show sequential views of the release of the anchor 15 from the tether 78. FIG. 31 shows the anchor 15 coupled to the tether 78 (e.g., during deployment of the anchor 15 to the heart). After the anchor 15 has encircled the one or more structures of the native valve, the inner shaft 52 has been retracted (e.g., as shown in FIG. 43), the frame structure 12 has been deployed, valve positioning has been confirmed, and/or hemodynamics have been assessed, the anchor 15 may be decoupled from the proximal pusher 78. As shown in FIG. 32, actuation of the release mechanism (e.g., proximal translation of the retention wire 88) may disengage the retention wire 88 from the hole 304. As shown in FIG. 33, the tether 78 may then be retracted into the delivery device 30 and de-coupled from the anchor 15.

FIG. 34 shows a side view of an exemplary tether 78. FIG. 35 shows a side view of an exemplary anchor 15. FIG. 36 shows a perspective view of the tether 78 coupled to the anchor 15 with an inset showing a magnified view of the connection mechanism 300 between the two elements. The anchor 15 and the tether 78 may be substantially similar to any of the anchor and tethers, respectively, described herein. In some embodiments, the free end 22 of the anchor may comprise a loop. The loop may comprise the same or a different material as the body of the anchor 15. The loop may be configured to provide a different stiffness to the free end 22 compared to the body of the anchor 15 (e.g., by varying the shape, thickness, size, etc.). In some embodiments, the loop may be secured to the distal portion of the free end 22 with a collar or other retaining mechanism. In some embodiments, the loop may comprise a wire loop. In some embodiments, the loop may be flat wire or a round wire. The loop may have a diameter within a range of about 2 mm to about 10 mm. A flat, for example rectangular, wire loop may have a cross-section of about 0.1 mm to about 0.5 mm wide and about 0.2 mm to about 1.5 mm tall. A round, for example circular, wire loop may have a diameter of about 0.25 mm to about 1 mm. In some embodiments, the tip (e.g., loop) of the anchor 15 may be unitary construct with the free end 22. In some embodiments, the tip (e.g., loop) may be formed as a separate component from the free end 22 and bonded or otherwise coupled to the free end 22 prior to deployment.

FIGS. 90A-90G show sequential views of a method of implanting a valve prosthesis 10 using the delivery system 30 of FIGS. 26-28 and 87A-89C. At FIG. 90A, a transseptal puncture is made. The guidewire 54 is then routed through the puncture site and left either in the left atrium 25 or across the mitral valve into the left ventricle 26. At FIG. 90B, the outer sheath 50 (optionally with an inner dilator 51) is tracked over the guidewire 54 until the distal end of the outer sheath 50 protrudes into the left atrium 25. The guidewire 54 and inner dilator 51 are then removed from the outer sheath 50. At FIG. 90C, the inner sheath and anchor guide 153 are inserted through the outer sheath 50 until the distal tip of the anchor guide 153 extends into the left atrium 25. The anchor guide 153 can be positioned and/or oriented as desired by steering the distal end of the sheath 50 and/or rotating the inner shaft and anchor guide 153 within the sheath 50. At FIG. 90D, once the anchor guide 153 is in the correct orientation, the anchor 15 can be pushed out through distal tip of the anchor guide 153. At FIG. 90E, the curvature of the anchor guide 153 can cause torsion on the anchor 15, causing the anchor 15 to deploy concentrically with the outer sheath 50 into the atrium 25. At FIG. 90F, the entire delivery system 30 can be pushed and steered (for example, via steering mechanisms in the outer sheath 50) towards an apex of the ventricle 26, crossing through the mitral valve. In some embodiments, counter-rotation of the anchor 15 (via counter-rotation of the inner shaft and guide 153) may aid in getting the anchor across the mitral valve without tangling.

Once the anchor 15 is at the correct depth within the ventricle 26, forward rotation of the anchor 15 (via forward rotation of the inner shaft and guide 153) will allow the anchor 15 to encircle the mitral leaflets and chordae. In some embodiments, the anchor 15 can be deployed towards the apex to avoid interference with mitral leaflet motion. At FIG. 90G, the outer sheath 40, inner sheath, and anchor guide 153 are removed, leaving the tether 78 in place (and still attached to the anchor 15). The frame structure 12 can then be delivered over the tether 78 and into place within the mitral valve.

Figure 37:
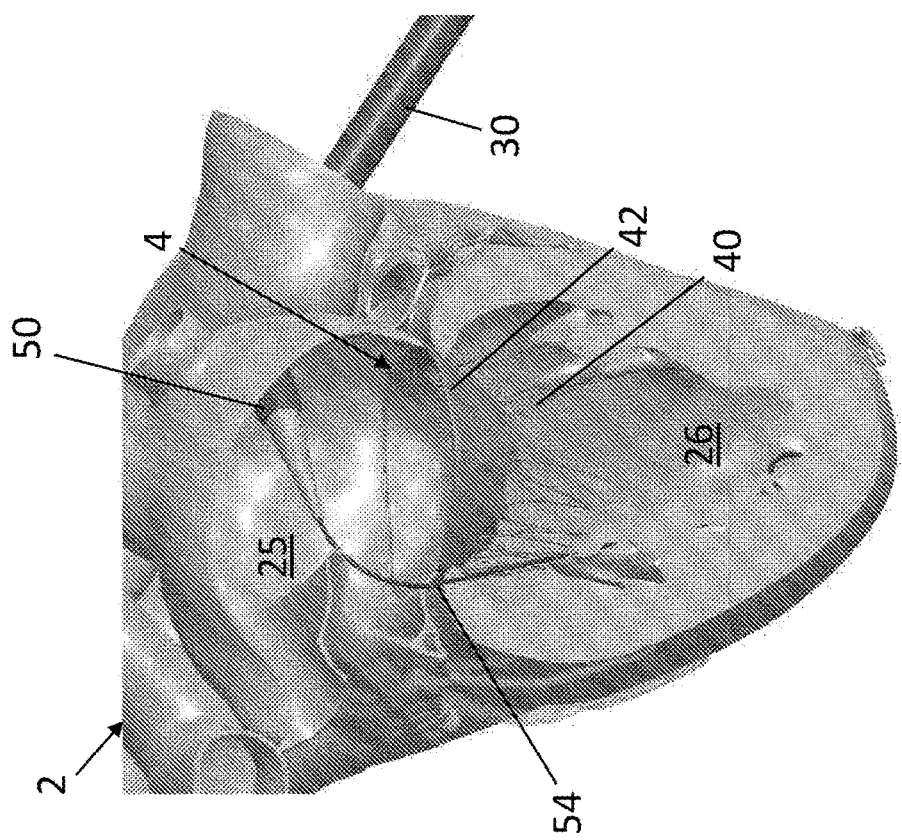

FIGS. 37-44 also show sequential views of a method of implanting a valve prosthesis 10 using the delivery system 30 of FIG. 26. Thus, FIG. 37 shows advancement of the delivery device 30 over a guidewire 54. The guidewire 54 may be advanced into the heart of a patient, for example, through a transseptal puncture. The guidewire 54 may be routed through the puncture side and left either in the left atrial appendage or positioned across the mitral valve in the left ventricle as desired. The delivery device 30 may comprise an outer sheath 50, an inner shaft 52, an anchor guide 153, and a proximal pusher 78 as described herein. The delivery device 30 may be configured to deliver a valve prosthesis 10 comprising an anchor 15 and a frame structure 12 as described herein.

Figure 38:
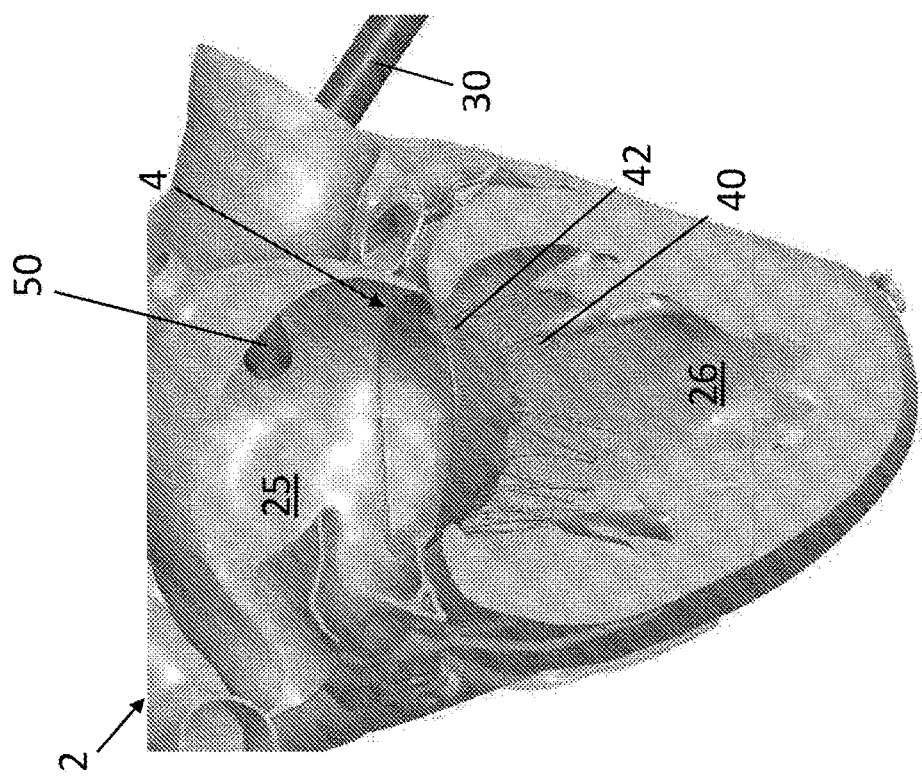
FIGS. 37-44 show sequential views of a method of implanting a valve prosthesis using the delivery system of FIG. 26, in accordance with embodiments.

FIG. 38 shows removal of the guidewire 54 (and optional introducer) from the heart.

Figure 39:
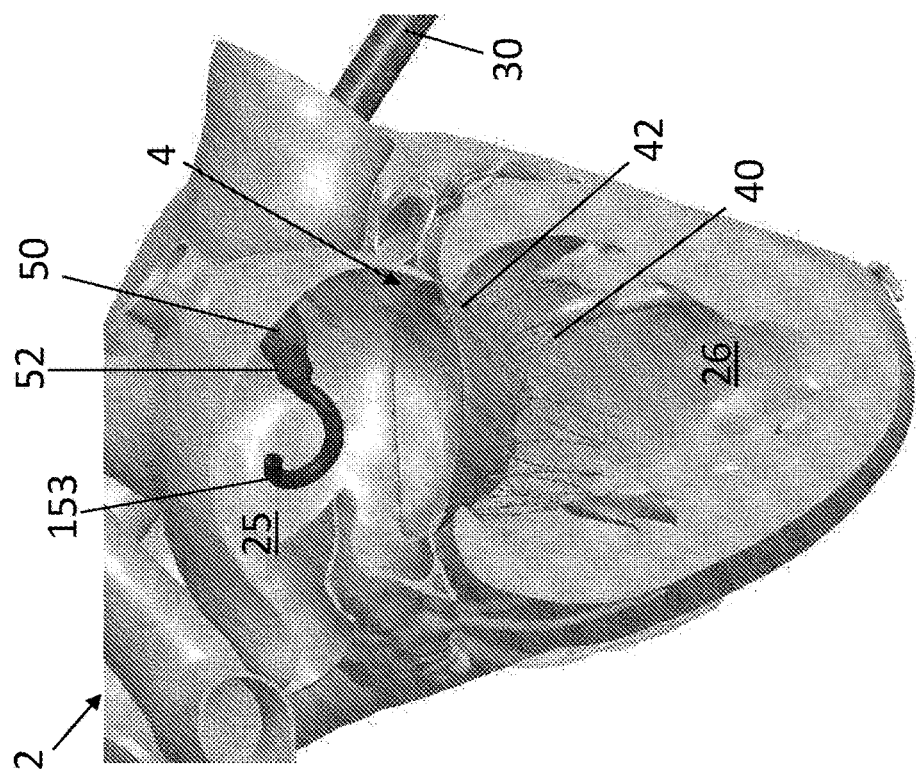

FIG. 39 shows advancement of the inner shaft 52 distally into the left atrium 25 away from the distal end of the outer sheath 50. In some embodiments, advancing the inner shaft 52 relative to the outer sheath 50 may aid in deployment and/or placement of the valve prosthesis 10 as described herein. For example, advancement of the inner shaft 52 may expose the anchor guide 153 from the distal end of the outer sheath 50, freeing it from radial constriction and allowing the anchor guide 153 to take on its pre-set shape.

Figure 40:
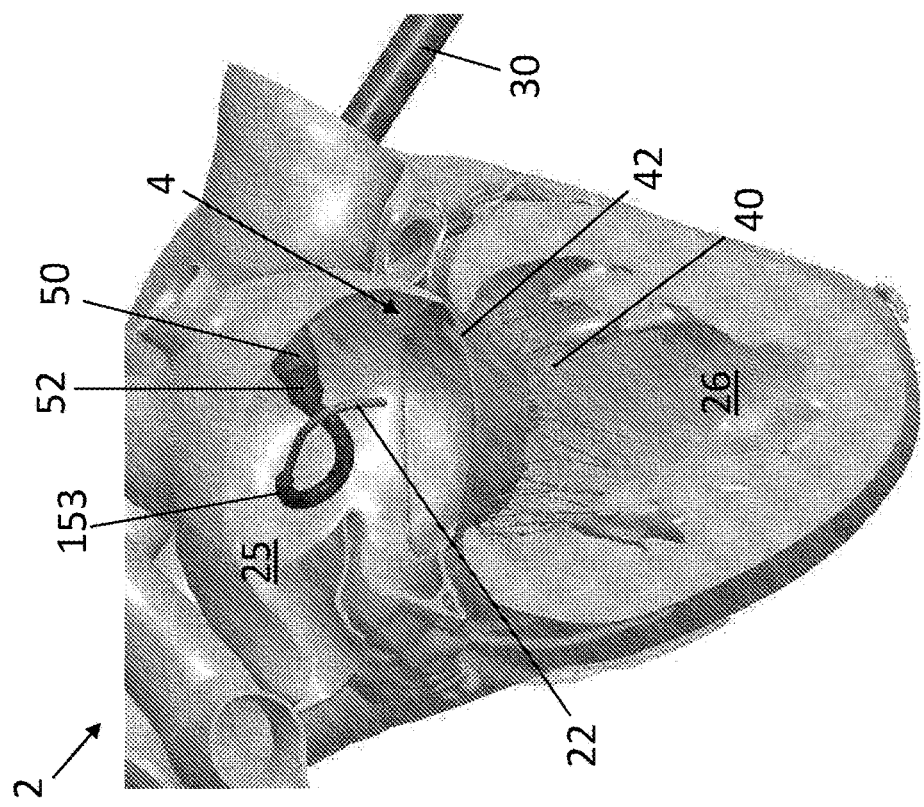
Figure 41:
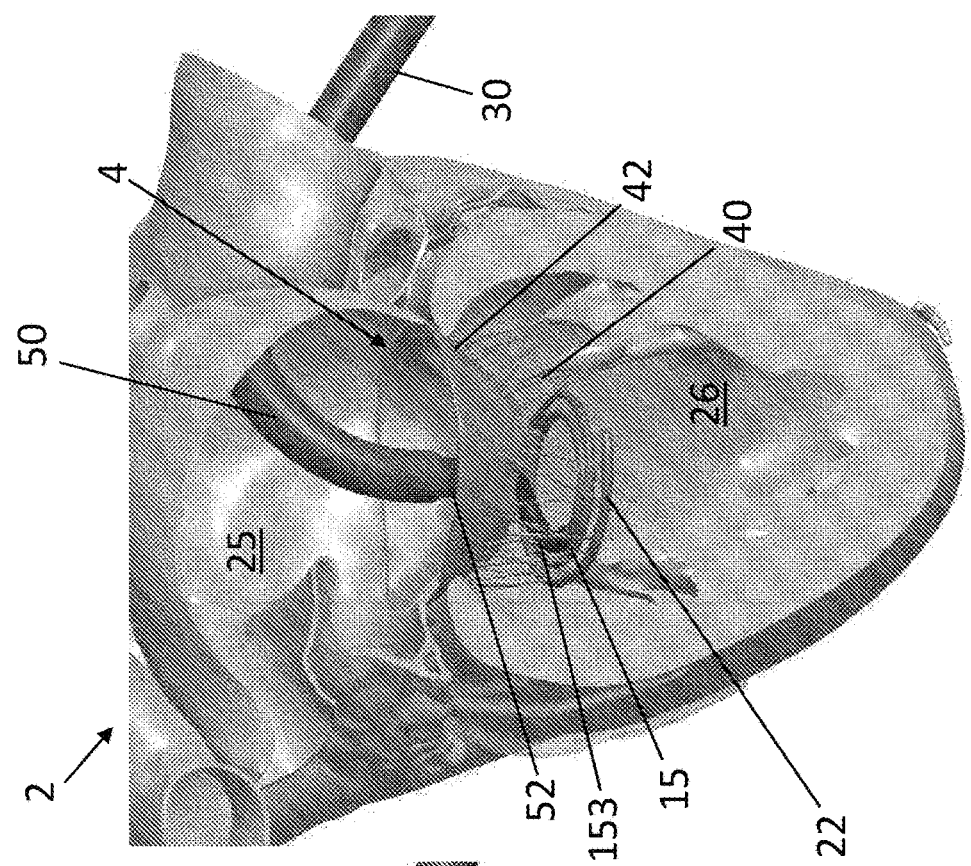

FIGS. 40-41 show deployment of the anchor 15 out of the anchor guide 153. The anchor guide 153 may be shaped and configured to facilitate deployment of the anchor 15 in the correct orientation relative to the delivery device 30 as described herein. For example, the curvature of the anchor guide 153 may cause torsion on the anchor 15, which may cause the anchor 15 to be deployed concentrically with the longitudinal axis of the distal end of the inner shaft. The anchor 15 may be deployed from an elongated delivery configuration to a spiral deployed configuration. The anchor 15 may be fully deployed in the left atrium 25. In some embodiments, the anchor 15 may be deployed relatively aligned to the apex of the ventricle 26 in order to maximize the amount of space in which the anchor 15 deploys within the left atrium 25.

Figure 42:
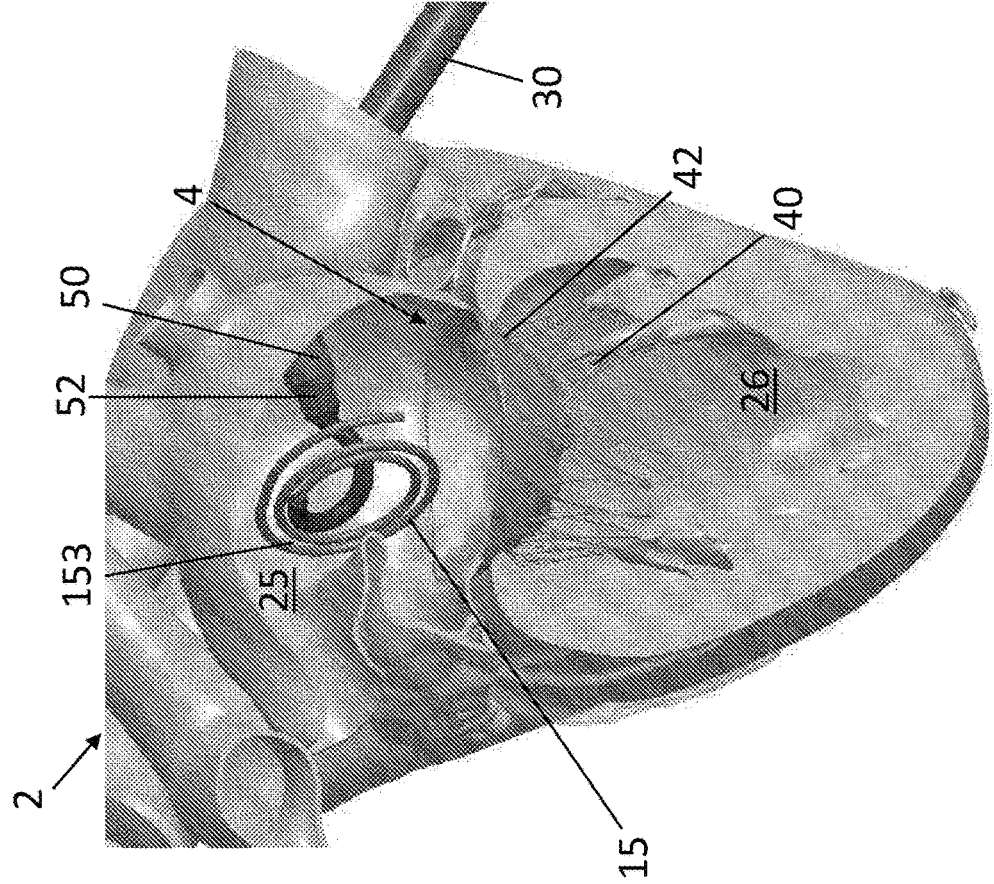

FIG. 42 shows advancement of the delivery device 30 and anchor 15 from the left atrial side 25 of the mitral valve 4 to the left ventricle side 26 of the mitral valve 4. The distal end of the delivery device 30 may be steerable such that it is positionable to point towards the first side of the native valve before being advanced to the second side of the native valve as described herein. The delivery system 30 may be advanced distally and deflected towards the apex of the ventricle 26 (so that the anchor 15 is relatively perpendicular to the apex) before crossing the mitral valve 4.

Advancing the anchor 15 may comprise pushing the anchor 15 through the native valve 4. Advancing the anchor 15 may further comprise rotating the anchor 15 through the native valve 4.

The free end 22 of the deployed anchor 15 may optionally be rotated around one or more structures on the second side of the native valve 4. The one or more structures may comprise one or more valve leaflets 42 of the native valve 4. Alternatively, or in combination, the one or more structures may comprise one or more chordae tendineae 40 of the left ventricle 23.

The free end 22 of the deployed anchor 15 may optionally rotated around one or more structures on the second side of the native valve such that the one or more structures (e.g., chordae, leaflets, or annulus) are pulled radially inwards towards the longitudinal axis of the anchor 15 and/or towards the longitudinal axis of the delivery device 30. The anchor 15 and/or free end 22 may be configured such that minimal torque is applied to the one or more structures. Alternatively, or in combination, the anchor 15 and/or free end 22 may be configured such that the one or more structures are not rotated, or are minimally rotated, during rotation of the anchor 15.

In some embodiments, the anchor 15 may be counter-rotated in order to reposition the anchor 15 with respect to the one or more structures of the native valve before continuing the rotation in the first direction. For example, counter-rotation may be applied if the one or more structures are caught by the free end of the anchor 15 (or another part of the valve prosthesis 10 or delivery device 30) during the initial rotation. In such instances, counter-rotation may enable to the clinician to disengage some or all of the one or more structures to reduce the stress or torque on the one or more structures (e.g., by adjusting the position of the valve prosthesis 10) before resuming rotation. Rotation and counter-rotation may be applied as many times as desired by the clinician in order to properly position the anchor 15 around the one or more structures of the native valve.

In some embodiments, the anchor 15 may be deployed towards the apex of the ventricle 26 in order to avoid interference with motion of the native leaflets 42 during positioning. In some embodiments, the anchor 15 may then be pulled upwards to seat the anchor 15 adjacent the native leaflets 42.

FIG. 43 shows retraction of the anchor guide 153 into the outer sheath 50 following positioning of the anchor 15 around the one or more structures of the native valve 4.

Figure 44:
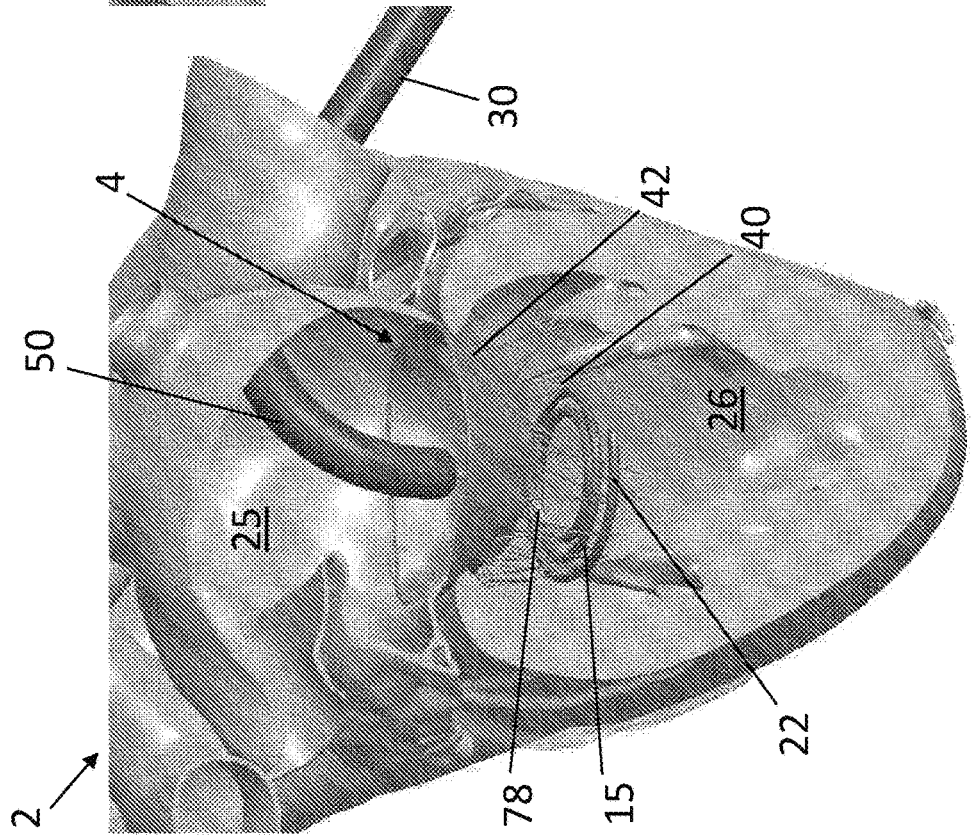

FIG. 44 shows retraction of the outer sheath 50 from the heart, leaving the anchor retention wire 78 and anchor 15 in place. An engagement wire (e.g., engagement wire 88 shown in FIGS. 29-33) may then be actuated to de-couple the proximal pusher 78 from the anchor 15 as shown in FIGS. 31-33. The anchor retention wire 78 may be disengaged from the anchor 15 and pulled back into the delivery device 30.

The frame structure 12 may deployed before, during, or after retraction of the anchor guide 153 and/or outer sheath 50.

Referring to FIGS. 59-62B, in some embodiments, the delivery device 30 may comprise an outer sheath assembly 155, an inner shaft 52 disposed within a lumen of the outer sheath 50, and an optional guidewire 54 disposed within a lumen of the inner shaft 52. The outer sheath assembly 155 can include an outer sheath 50 and a valve capsule 154.

The valve capsule 154 may comprise a flexible material or a rigid material. The valve capsule 154 may be relatively rigid such that it can exert a compression force on a frame structure 12 delivered within the valve capsule 154 while still retaining flexibility to deform under an external force. The valve capsule 154 may comprise a soft or flexible material.

As described herein, the inner shaft 52 may be disposed within a lumen of the outer sheath assembly 155, and a guidewire 54 may be disposed adjacent to the inner shaft 52 within a lumen of the outer sheath assembly 155. Alternatively, the guidewire 54 may be disposed in a lumen of inner shaft 54. The guidewire 54 may optionally comprise a nosecone to facilitate guidance of the guidewire 54 to the native valve. A proximal end of the valve prosthesis 10 may be operably coupled to the inner shaft 52 (or tether 78, such as described with respect to FIGS. 89A-89C) during delivery to the native valve as described herein. The outer sheath 50 may be steerable. The outer sheath 50 may be guided by a guidewire 54. The outer sheath 50 may be guided by a guidewire 54 in conjunction with an anchor guide 153. The outer sheath 50 may likewise be guided by the anchor guide 153.

FIGS. 59-62B show various steps of an exemplary method of delivering a valve prosthesis 10 to a native valve of a patient using the delivery device 30.

Figure 59:
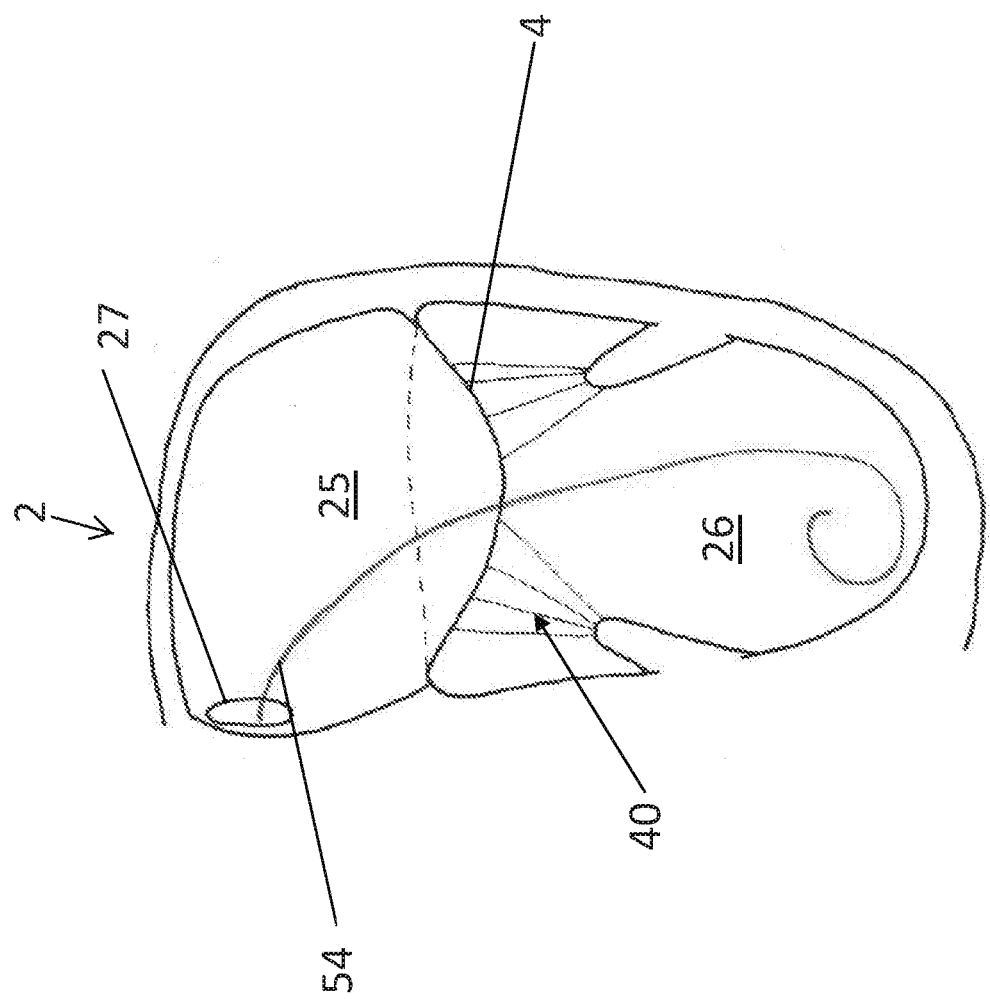
FIG. 59 is a side section view of a diseased valve wherein a guidewire of a delivery device has been guided to the left atrium and left ventricle through a transseptal puncture, in accordance with embodiments.

FIG. 59 is a section view of a heart 2 with a diseased valve 4. A guidewire 54 of a delivery device 30 may be guided to the left atrium 25 and left ventricle 26 through a transseptal puncture 27.

Figure 60C:
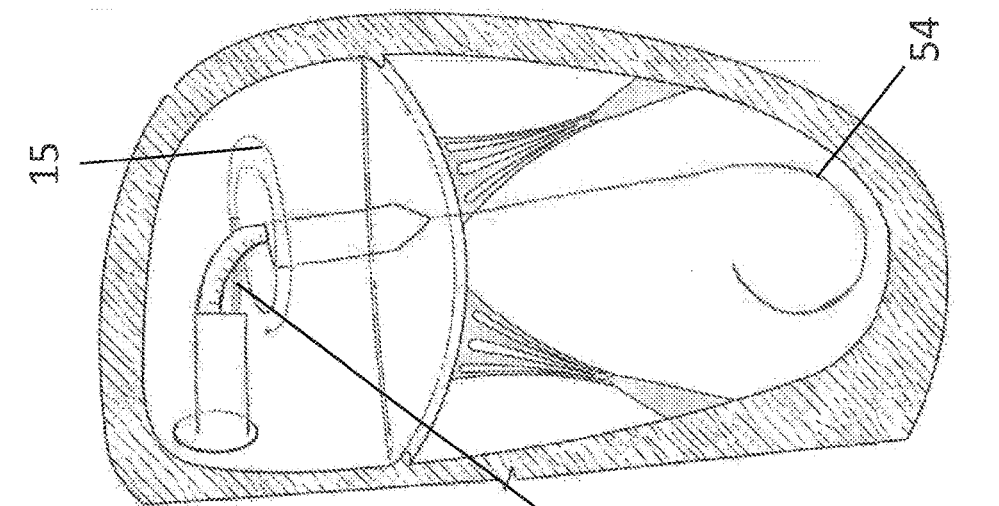
FIG. 60C is a section view of the delivery device wherein an anchor sheath has been pushed through the lumen of the outer sheath into the left atrium and the anchor has been released around the inner shaft, in accordance with embodiments.
Figure 60B:
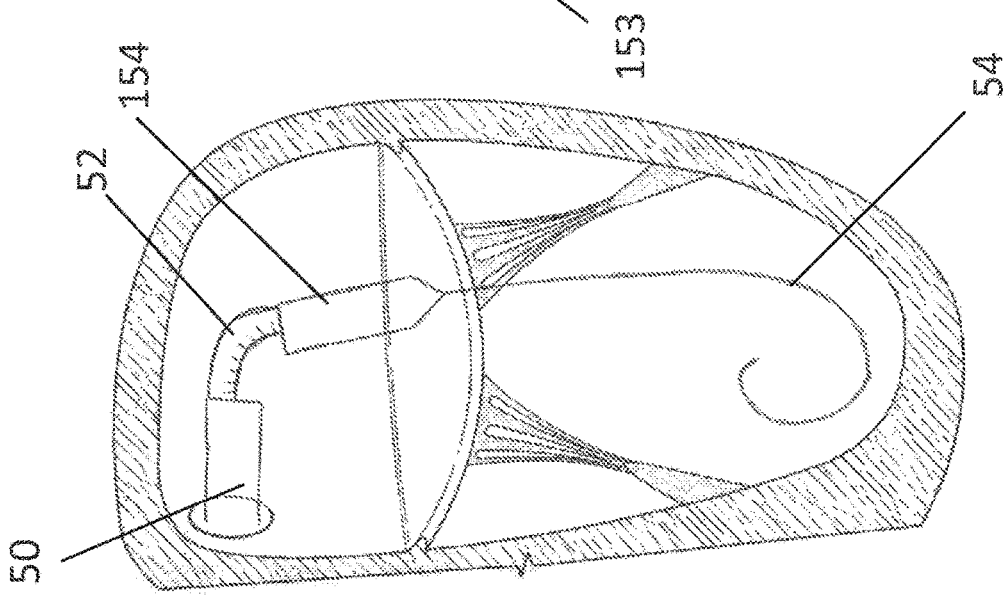
FIG. 60B is a section view of a delivery device comprising an outer sheath assembly and an inner shaft which have been guided over the guidewire into the left atrium, in accordance with embodiments.
Figure 60A:
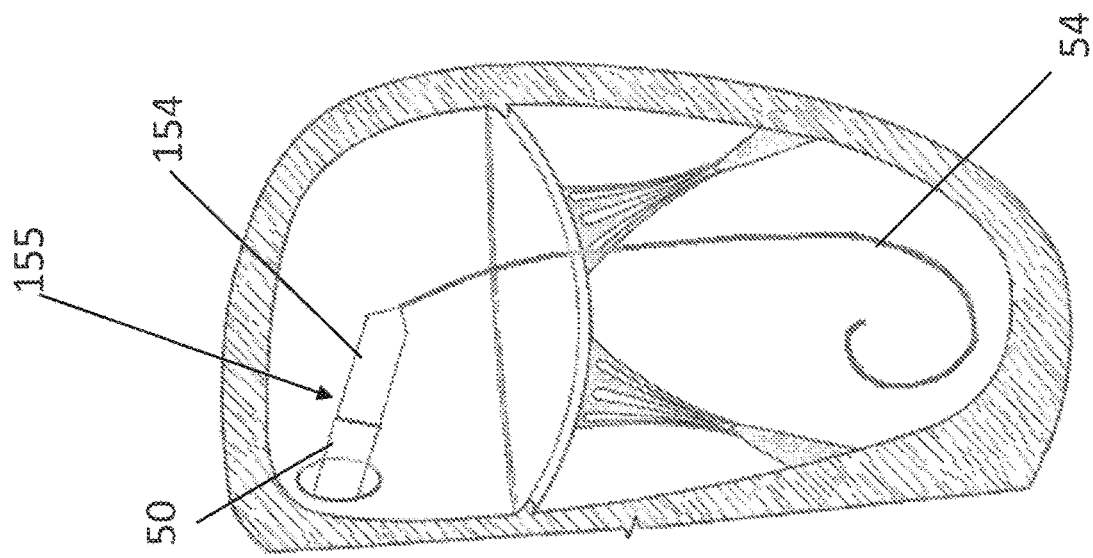
FIG. 60A is a section view of a delivery device comprising an outer sheath assembly guided over the guidewire into the left atrium, in accordance with embodiments.

FIG. 60A is a section view of the delivery device 30 being guided into over the guidewire 54 into the left atrium 25 of the heart 2. The guidewire 54 may be located in a lumen of the outer sheath assembly 155. The delivery device 30 can be steered by movement of the guidewire 54. The outer sheath 50 can be steered by an advancement of the anchor guide 153 through the lumen of the outer sheath 50 as described herein.

FIG. 60B is a section view of the delivery device 30 comprising the outer sheath assembly 155. As the delivery device 30 is advanced further into the left atrium, the valve capsule 154 of the outer sheath assembly 155 may be separated from the outer sheath 50 to expose an inner shaft 52 disposed within a lumen of the outer sheath assembly 155. The inner shaft 52 may comprise a tight bend configured align the inner shaft 52 and/or distal tip 154 with the mitral valve. Correct alignment of the distal tip 154 with the mitral valve may facilitate deployment of the anchor 15 around the inner shaft 52 and/or frame structure 12 as described herein. The outer sheath 50 and the valve capsule 154 may be translated relative to one another; for example, the valve capsule 154 may be advanced relative to the outer sheath 50 to separate the two components, forming an opening between the two components and exposing the lumens of the outer sheath 50 and the valve capsule 154 to the exterior.

In some embodiments, the valve capsule 154 of the outer sheath assembly 155 may be steerable. The valve capsule 154 of the outer sheath assembly 155 may be steered prior to or after separation of the valve capsule 154 from the outer sheath 50 such that the valve capsule 154 points towards the native valve.

The valve prosthesis 10 may be operably coupled to the delivery device 30 as described herein. In some embodiments, at least a portion of the valve prosthesis 10 may be directly coupled to the inner shaft 52 (or tether 78). Alternatively, or in combination, at least a portion of the valve prosthesis 10 may be indirectly coupled to the inner shaft 52. For example, at least a portion of the valve prosthesis 10 may be coupled to a torque hub or other connector, which may be coupled to the inner shaft 52.

FIG. 60C is a section view of the delivery device 30 after the anchor guide 153 has been pushed through a lumen of the outer sheath 50 into the left atrium 25. The anchor guide 153 may be configured to deliver an anchor 15 of the valve prosthesis 10 to the native valve 4. The inner shaft 52 can form a tight bend (e.g., a 90 degree angle), thereby centering the valve capsule 154 of the delivery device to the center of the mitral valve. The anchor guide 153 can then push the anchor 15 through the outer sheath 50 and around the bent inner shaft 52. The anchor guide 153 (also referred to herein as a throwdown arm or anchor guide sheath) may be configured to correctly orient the anchor 15 relative to the bent inner shaft 52 in order to facilitate wrapping of the anchor 15 around the inner shaft 52 as the anchor 15 is deployed from the delivery configuration to the deployed configuration.

In some embodiments, the anchor 15 may be partially deployed to an intermediate deployed configuration in the left atrium before being advanced through the native valve into the left ventricle. In the intermediate deployed configuration, the anchor 15 may be wrapped at least partially around the inner shaft 52.

In some embodiments, the anchor 15 may be fully deployed from the anchor guide 153 into a deployed configuration within the left atrium prior to being advanced into the left ventricle.

The anchor 15 may comprise a delivery (e.g., elongated, radially collapsed, or unexpanded) configuration and a deployed configuration. A frame structure of the valve prosthesis (e.g., frame structure 12 shown in FIGS. 62A-62B) may remain in its unexpanded configuration while the anchor 15 is in the deployed configuration. In various embodiments, the anchor 15 may be self-expanding and may move to the deployed configuration as it is deployed (e.g., pushed out) from the anchor guide 153 by a proximal pusher arm or a tether. In various embodiments, the anchor 15 may be configured to self-assemble when it is deployed in the heart cavity (e.g., left ventricle or left atrium). The anchor 15 may be actuated from the delivery configuration to the deployed configuration adjacent the native valve using any method or mechanism understood by one of ordinary skill in the art from the description herein. For example, retraction of the guidewire 54 into the lumen of the inner shaft 52 may actuate the anchor 15 into the deployed configuration. Alternatively, or in combination, the anchor 15 may be maintained in the delivery configuration by radial constriction from one or more of the outer sheath 50 or the valve capsule 154 of the outer sheath assembly 155. Advancement of the inner shaft 52 out of the lumen of the outer sheath 50 may actuate the anchor 15 into the deployed configuration as described herein.

In some embodiments, the anchor 15 may be actuated from the delivery configuration to the deployed configuration (or intermediate configuration) on a first side of the native valve prior to being advanced to a second side of the native valve. For example, the anchor 15 may be deployed in a left atrium of a heart prior to being advanced to a left ventricle of the heart as described herein (e.g. as shown in FIGS. 60A-62B). The anchor 15 may be fully advanced from a first side of a native valve in a patient (e.g., an atrial side) to a second side of the native valve (e.g., into a ventricle of the heart) and anchor a frame structure (e.g., frame structure 12 shown in FIGS. 62A-62B) to the native valve when the frame structure is in the expanded configuration adjacent the native valve.

Figure 61B:
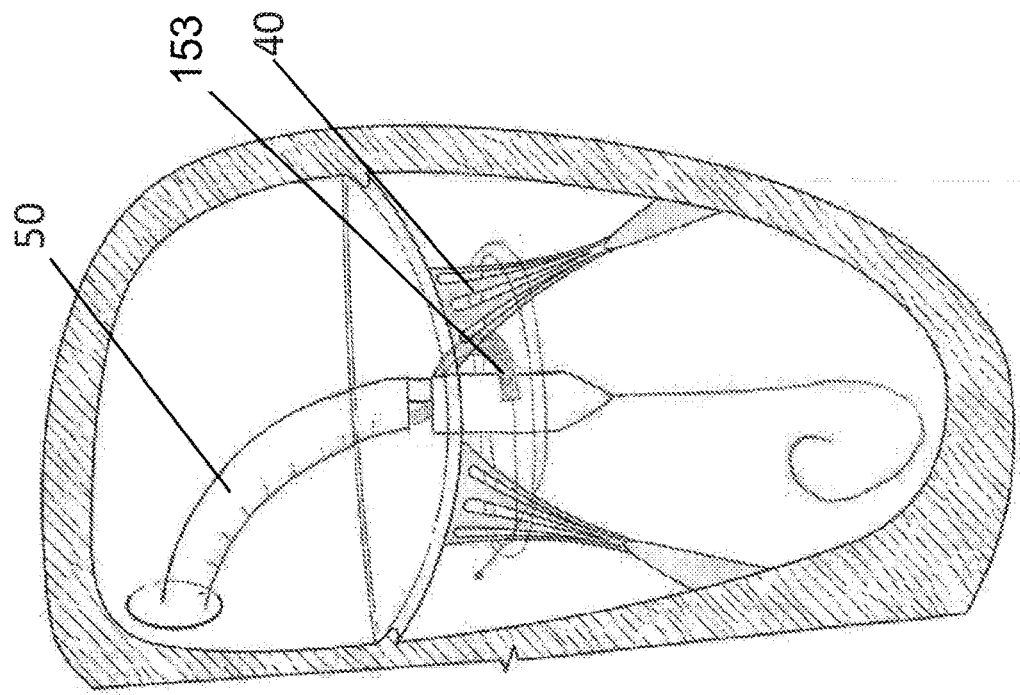
FIG. 61B is a section view of the anchor being secured around the native chordae tendineae of the native valve by rotating the anchor, in accordance with embodiments.
Figure 61A:
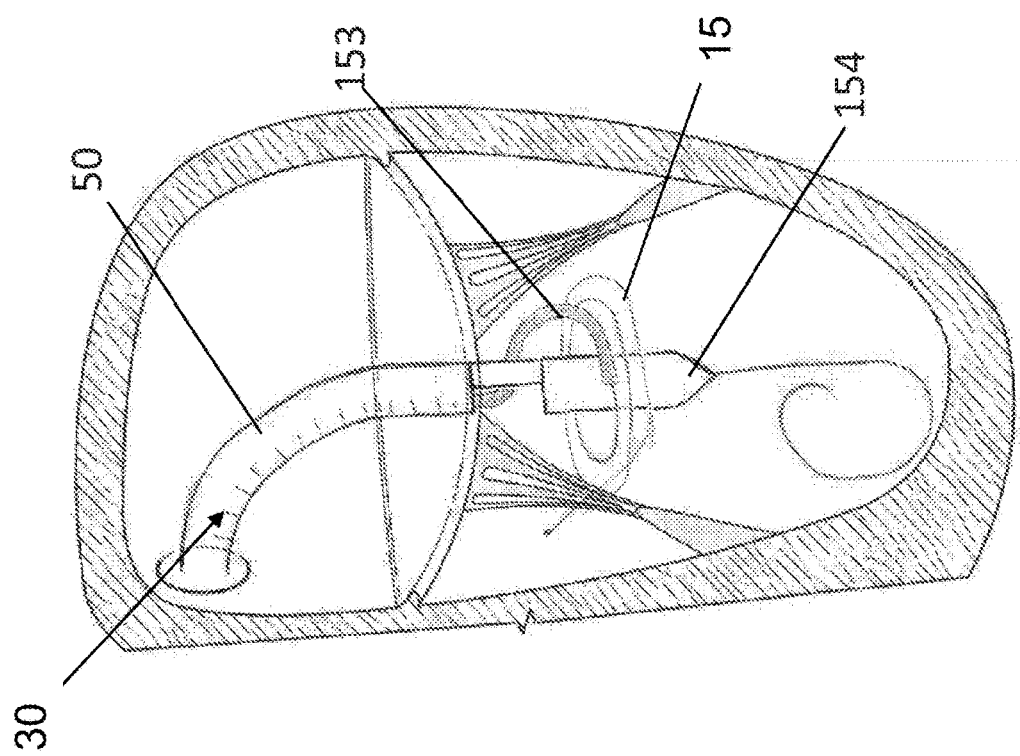
FIG. 61A is a section view of the positioning of the released anchor after the anchor has been pushed through the native valve into the left ventricle, in accordance with embodiments.

FIG. 61A shows a section view of the delivery device 30 after the anchor 15 in the intermediate deployed configuration has been pushed through the diseased valve into the left ventricle 26, adjacent to the native chordae tendineae 40. As the anchor guide 153 is pushed through the outer sheath 50, the tight bend of the inner shaft 52 may be pulled straighter (e.g., towards 180 degrees) by the guidewire 54. The outer sheath 50 may then be further directed to a (e.g., by the rigid shape of a proximal pusher arm within the) anchor guide 153 as it is advanced through a lumen of the outer sheath 50.

Advancement of the anchor guide 153 as the outer sheath 50 is brought into alignment with the mitral valve and/or advanced through the mitral valve may expose a bend in the anchor guide 153. The bend in the anchor guide 153 can act as a throwdown arm and may be configured to correctly orient the anchor 15 relative to the chordae tendineae 40 and/or prevent twisting of the anchor 15 during deployment and/or rotation, as well as ensure that the anchor 15 will self-assemble around the inner shaft 52 and/or frame structure 12, after the outer sheath 50 is straightened.

FIG. 61B shows a section view of the delivery device 30 with the anchor 15 being wrapped around the native chordae tendineae 40. The anchor 15 may, for example, be wrapped around the chordae tendineae 40 by further advancing the anchor 15 through the anchor guide 153. The anchor 15 may be wrapped around the native chordae tendineae 40 by being urged out of the anchor guide 153 positioned radially offset from the longitudinal axis of the outer sheath 50. Alternatively, or in combination, the anchor 15 may be wrapped around the native chordae tendineae 40 by rotating the inner shaft 52, outer sheath 50, and/or anchor guide 153, thereby rotating the anchor 15 around the chordae tendineae 40. In some embodiments, advancement of the anchor guide 153 may facilitate wrapping of the anchor 15 around the chordae tendineae. The anchor guide 153 may direct the anchor to a direction transverse to the longitudinal axis of the outer sheath 50 while centered about the longitudinal axis of the outer sheath 50.

Figure 62B:
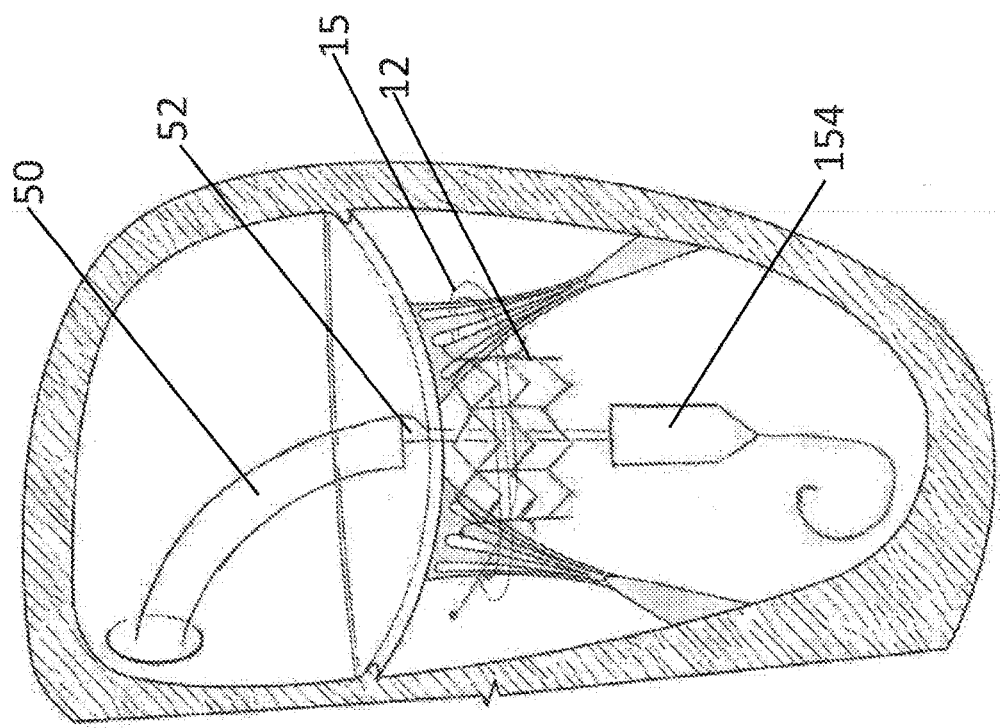
FIG. 62B is a section view of the final position of the valve prosthesis prior to retraction of the anchor sheath, the anchor being wrapped around the native chordae tendineae, thereby locking the valve prosthesis in place, in accordance with embodiments.
Figure 62A:
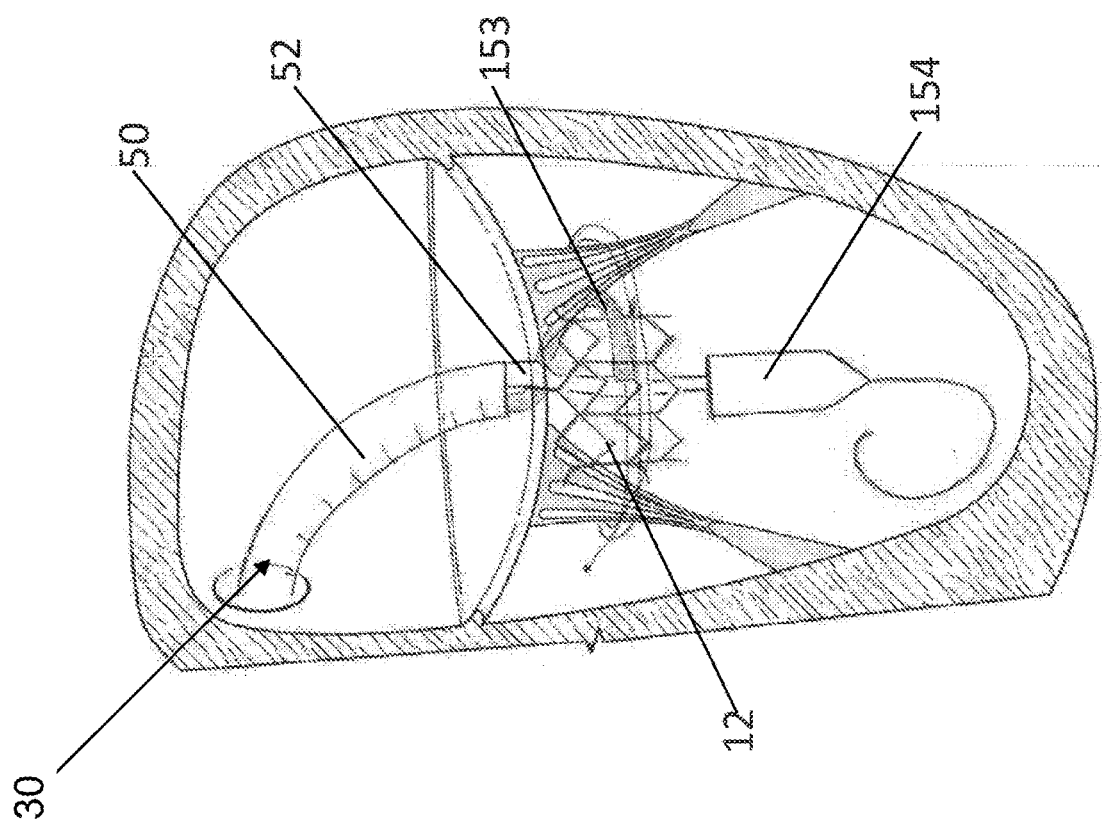
FIG. 62A is a section view of expansion of the frame structure from an opening created by the separation of the distal end of the outer sheath assembly from the inner shaft, in accordance with embodiments.

FIG. 62A is a section view showing expansion of a frame structure 12 of the valve prosthesis 10 from an opening created by separation of the valve capsule 154 of the outer sheath assembly 155 from the outer sheath 50. The valve capsule 154 may be advanced distally into the left ventricle in order to unsheathe and expose the frame structure 12 by expanding the opening of the outer sheath assembly 155. The valve capsule 154 may be collapsible upon removal of the frame structure 12. The valve capsule 154 may comprise a pliable material configured not to cause damage to anatomical structures. The guidewire 54 may comprise an element at a fixed position on the guidewire 54 to prevent movement of the valve capsule 154 past a certain point. The element may be. For example, a bend or a fixed structure with a diameter greater than that of the lumen of the valve capsule 154.

In some embodiments, the valve capsule 154 of the outer sheath assembly 155 may comprise a soft valve capsule as described herein.

Figure 65:
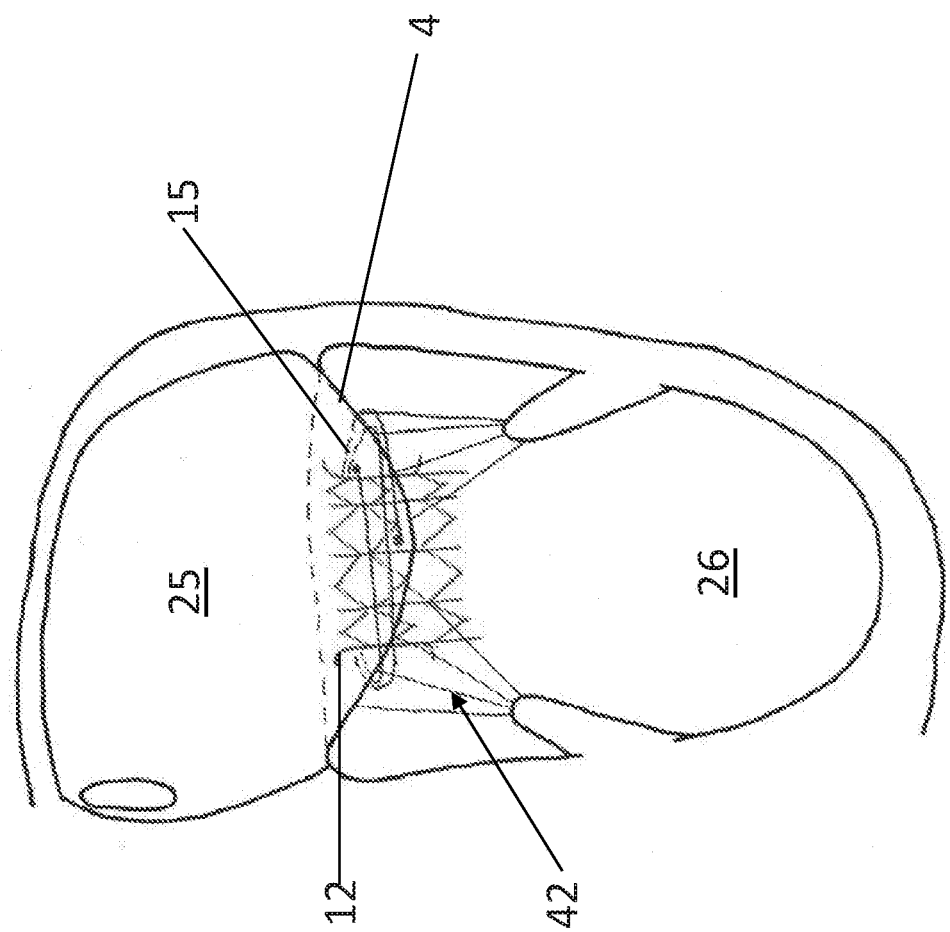
FIG. 65 is a section view of a valve prosthesis secured by an anchor at a diseased native valve, in accordance with embodiments.

FIG. 62B is a section view showing the final position of the valve prosthesis 10 following retraction of the anchor guide 153. The anchor 15 may be wrapped around the native chordae tendineae 40 in order to lock the valve prosthesis 10 in place as described herein. The frame structure 10 may be released from the delivery device 30 as described herein. The delivery device 30 may then be retracted to leave the valve prosthesis 10 in place (e.g., as shown in FIG. 65).

The separation of the valve capsule 154 of the outer sheath assembly 155 from the outer sheath 50 may be facilitated by advancement of an inner shaft 52 through the lumen of the outer sheath 50. In some embodiments, the frame structure 12 may be housed within the valve capsule 154 of the outer sheath assembly 155 and can be maintained in the delivery configuration by radial constriction from one or more of the valve capsule 154 or by the outer sheath 50.

Figures 64A, 64B, 64C:
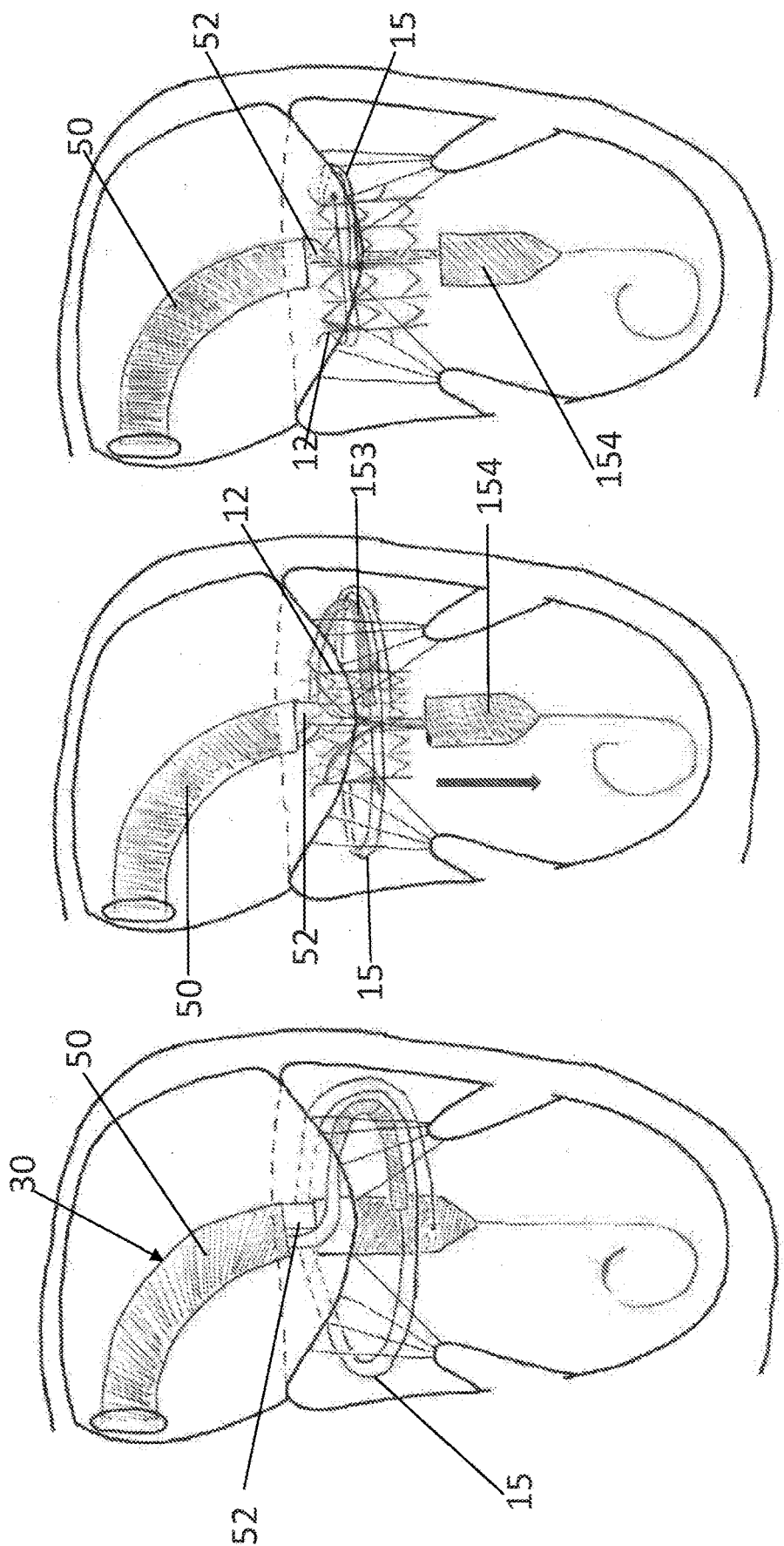
FIG. 64A is a section view of the repositioning of the delivery device to the center of the diseased valve, in accordance with embodiments.
FIG. 64B is a section view of the deployment of the frame structure from an opening created by the separation of the distal end of the outer sheath assembly from the outer sheath, in accordance with embodiments.
FIG. 64C is a section view of the final position of the valve prosthesis prior to retraction of the anchor delivery sheath wherein the anchor is wrapped around the native chordae tendineae, locking the valve prosthesis in place, in accordance with embodiments.

FIGS. 6A3-64C sequentially describe a method of deploying a valve prosthesis within the native valve, in accordance with many embodiments.

Figures 63A, 63B, 63C:
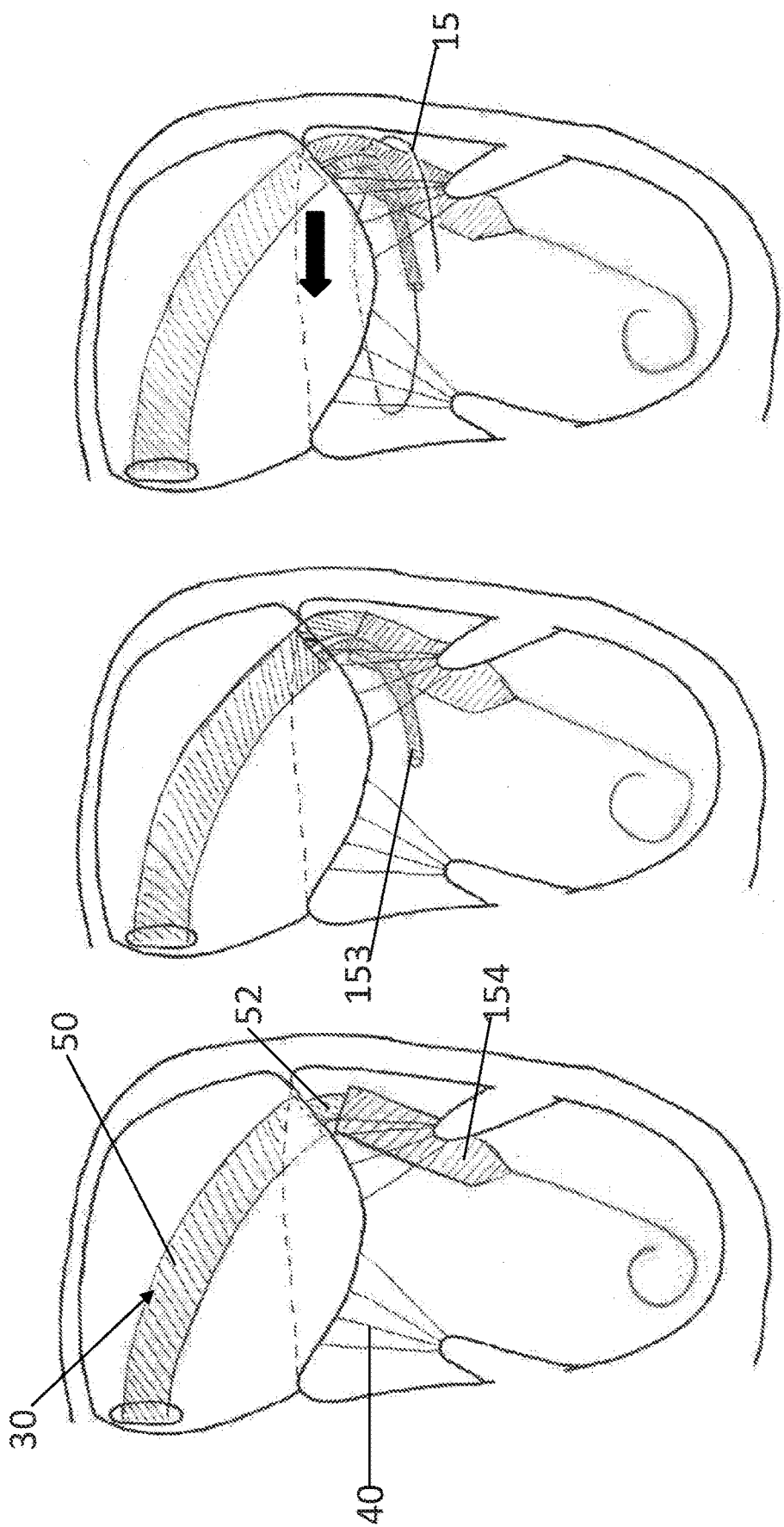
FIG. 63A is a section view of a delivery device wherein an outer sheath assembly and inner shaft have been guided over a guidewire through the left atrium and into the left ventricle, and the delivery device has been steered to a wall of the diseased native valve, in accordance with embodiments.
FIG. 63B is a section view of the delivery device after an anchor delivery sheath has been pushed through the inner shaft, in accordance with embodiments.
FIG. 63C is a section view of the delivery device and an anchor partially pushed through the anchor delivery sheath and wrapped around the native chordae tendineae, in accordance with embodiments.

FIGS. 63A-63C sequentially describe a method of delivering a valve prosthesis 10 directly to a left ventricle of the heart. FIG. 63A is a section view of a delivery device 30 which has been steered to an edge of the native valve prior to deployment of the anchor 12. The delivery device 30 may be configured to be delivered into the heart over a guidewire 54 through a transseptal puncture in a manner substantially similar to that described herein (e.g., as shown in FIGS. 59-60A). The delivery device 30 may comprise an outer sheath assembly 155 which may be substantially similar to any of the outer sheath assemblies described herein. For example, the outer sheath assembly 153 may comprise an outer sheath 50 and a valve capsule 154 as described herein.

The outer sheath assembly 155 may be steerable as described herein. The outer sheath assembly 155 may be steered through the native valve such that the valve capsule 154 is positioned on below the native valve and the outer sheath 50 is positioned above the native valve. Steering of the valve capsule 154 of the outer sheath assembly 155 may be accomplished by a guidewire 54 with a deflection element such as a rigid bend. The anchor guide 153 may also position the anchor 15 for attachment to the chordae tendineae 40 as described herein. A proximal pusher arm or tether within the anchor guide 153 may position the anchor 15 for attachment to the chordae tendineae 40 as described herein. Alternatively, or in combination, the distal end of the anchor 15 may comprise a deflection element to steer the anchor 15 as it is released from the radial constriction of the anchor guide 153. The outer sheath 50 and the valve capsule 154 may be separated to form an opening therebetween and expose an inner shaft 52 of the delivery device 30 as described herein. The outer sheath 50 and the valve capsule 154 may be separated from one another such that the opening spans the native valve. The outer sheath 50 and the valve capsule 154 may be separated from one another such that the opening entirely on the second side of the native valve (e.g., on a ventricular side of the native valve).

FIG. 63B is a side section view of the delivery device 30 after an anchor guide 153 has been pushed through a lumen of the outer sheath 50 into the left ventricle. The opening formed by the separation of the outer sheath 50 and the valve capsule 154 may enable the anchor guide 153 to be delivered directly into the left ventricle. The anchor guide 153 may be substantially similar to any of the anchor delivery sheaths described herein.

FIG. 63C is a side section view of the delivery device 30 after an anchor 15 has been partially pushed through the anchor guide 153, thereby partially deploying the anchor 15 from the delivery conformation directly into the deployed conformation while simultaneously wrapping the anchor 15 around the native chordae tendineae 40. The anchor 15 may be pushed through the anchor guide 153 (e.g., with a proximal pusher arm or tether 78 disposed within the lumen of the anchor guide 153. The anchor 15 may be substantially similar to any of the anchors described herein.

FIG. 64A is a section view of the repositioning of the delivery device 30 to the center of the diseased valve and the continued deployment of the anchor 15 from the anchor guide 153. The anchor 15 may be wrapped around one or more structures of the native valve (e.g., chordae tendineae), as described herein. For example, direct deployment of the anchor 15 from the anchor guide 153 in the left ventricle may facilitate wrapping as the anchor 15 transitions from the delivery configuration to the deployed configuration. Alternatively, or in combination, the anchor 15 may be rotated during or after deployment as described herein.

FIG. 64B is a section views of the deployment of the frame structure 12 of the valve prosthesis 10 from an opening created by the separation of the distal end of the valve capsule 154 from the outer sheath 50. The frame structure 12 may be substantially similar to any of the frame structures described herein. The frame structure 12 may be expanded from an unexpanded configuration to an expanded configuration as described herein. Separation of the valve capsule 154 from the outer sheath 50 may be facilitated by the advancement of an inner shaft 52 through the lumen of the outer sheath 50 such that the valve capsule 154 is pushed away from the outer sheath 50 by the inner shaft 52. The frame structure 12 can be maintained in the delivery configuration by radial constriction from one or more of the valve capsule 154 or the outer sheath 50.

The anchor 15 may be detachably coupled to a proximal or distal portion of the frame structure 12 as described herein. Alternatively, or in combination, the frame structure 12 may be detachably coupled to the delivery device 30 in the delivery configuration during delivery to the native valve. For example, the proximal end of the frame structure 12 may be detachably coupled to the inner shaft 52 of the delivery device 30 by radial constriction from the outer sheath 50 or the valve capsule 154. Retraction of the outer sheath 50 away from the proximal end of the frame structure 12 (or, similarly, extrusion of the distal end of the frame structure 12 out of an opening in the outer sheath) may detach the frame structure 12 from the delivery device 30. Alternatively, or in combination, the proximal end of the frame structure 12 may be detachably coupled to the inner shaft 52 of the delivery device 30 by an attachment element. Alternatively, or in combination, the proximal end of the frame structure 12 may be detachably coupled to the inner shaft 52 of the delivery device 30 by a weak adhesive.

FIG. 64C is a section view showing the final position of the valve prosthesis 10 following retraction of the anchor guide 153. The anchor 15 may be wrapped around the native chordae tendineae 40 in order to lock the valve prosthesis 10 in place as described herein. The frame structure 12 may be released from the delivery device 30 as described herein. The delivery device 30 may then be retracted to leave the valve prosthesis 10 in place (e.g., as shown in FIG. 65).

FIG. 65 shows a cross-section of the heart following delivery of the valve prosthesis 10 by any of the methods described herein. The valve prosthesis 10 may be positioned within the native valve as described herein. The valve prosthesis 10 may allow blood to flow from the left atrium 25 to the left ventricle 26 while preventing backflow or regurgitation in the reverse direction.

FIG. 68A shows a side view of an embodiment of a valve capsule 154 of an exemplary outer sheath assembly 155 prior to deployment of a frame structure 12. The outer sheath assembly 155 may be substantially similar to any of the outer sheath assemblies described herein and may comprise an outer sheath 50 and a valve capsule 154. The valve capsule 154 of the outer sheath assembly 155 may be configured to hold at least a portion of a valve prosthesis 10, for example at least a portion of a frame structure 12. In some embodiments, the outer sheath 50 may comprise a side port 214 through which the anchor 15 can be deployed prior to separation of the valve capsule 154 from the outer sheath 50. Alternatively, or in combination, deployment of the anchor 15 may be facilitated by separation of the valve capsule 154 and the outer sheath 50. Prior to its deployment adjacent a native valve as described herein, the frame structure 12 may be fully enclosed within the valve capsule 154. In some embodiments, the frame structure 12 may be disposed around an inner shaft 52 of the delivery device. In some embodiments, the frame structure 12 may be disposed around a distal tip of the outer sheath 50 which is covered by the valve capsule 154 of the outer sheath assembly 155 prior to separation of the valve capsule 154 and the outer sheath 50.

The valve capsule 154 may comprise a cylindrical proximal section 220 and a tapered distal section 219. In some embodiments, the valve capsule 154 may comprise a single unitary construction (i.e., the cylindrical proximal section 220 and a tapered distal section 219 can be of single unitary construction). In some embodiments, the cylindrical section 220 and the tapered distal section 219 may comprise different structural features or elements (for example, as shown in FIGS. 69A-69C). Alternatively, or in combination, the cylindrical section 220 and the tapered distal section 219 may comprise two separate pieces which may be coupled and uncoupled (for example, as shown in FIGS. 72A-73C). It will be understood by one of ordinary skill in the art that any of the cylindrical sections 220 described herein may be combined with any of the tapered tip sections 219 described herein to form the valve capsule 154, and any of the valve capsules 154 described herein may be combined with any of the outer sheaths 50 described herein to form an outer sheath assembly 155.

FIG. 68B shows a side view of the outer sheath assembly 155 of FIG. 68A as the valve capsule 154 begins to separate from the outer sheath 50. FIG. 68C shows a side view of the outer sheath assembly 155 of FIG. 68A following the separation of the valve capsule 154 of the outer sheath assembly 155 from the outer sheath 50. The valve capsule 154 of the outer sheath assembly 155 may be distally away from the outer sheath 50 to expose the frame structure 12. In some embodiments, a distal end of the inner shaft 52 may extend through a lumen of the outer sheath 50 and the valve capsule 154 as described herein and may be connected to an internal surface of the tapered distal section 219 of the valve capsule 154 of the outer sheath assembly 155. Distal translation of the inner shaft 52 relative to the outer sheath 50 may push the valve capsule 154 away from the outer sheath 50 to expose the frame structure 12. Translation of the valve capsule 154 away from the outer sheath 50 may release the frame structure 12 from radial constriction provided by the valve capsule 154 and allow the frame structure 12 to expand (e.g., self-expand or with the aid of a balloon as described herein) as described herein.

FIG. 69A shows a side view of an embodiment of the valve capsule 154 including a cylindrical proximal section 220 and a tapered distal section 219. FIGS. 69B-69C show side views of the separation of the valve capsule 154 from the outer sheath 50, exposing the frame structure 12 wherein the cylindrical section 220 comprises a collapsing mechanism by which the cylindrical proximal section 220 may collapse during separation to expose the frame structure 12. The mechanism can comprise a pull wire to actuate the collapse of the cylindrical proximal section 220 of the valve capsule 154 or a coil spring in a compressed state wherein separation from the frame structure 12 releases tension on the coil spring, thereby allowing the cylindrical section 220 of the valve capsule 154 to collapse.

FIG. 70A shows a side view of an embodiment of the valve capsule 154 including a cylindrical proximal section 220 and a tapered distal section 219, wherein the cylindrical proximal section 220 includes a helically wound wire 226 and a ring 227. FIGS. 70B-70C show side views of the separation of the valve capsule 154 from the outer sheath 50, exposing the frame structure 12 wherein the helically wound wire 226 of the cylindrical proximal section 220 comprises a releasing mechanism by which the ring 227 of the cylindrical proximal section 220 is released from the outer sheath 50. The mechanism can comprise a pull wire to actuate the collapse of the helically wound wire 226. Advancement of the inner shaft 52 relative to the outer sheath 50 may transmit force to the ring 227 in order slide the ring 227 off of the outer sheath 50. Release of the ring 227 from the outer sheath can enable the helically wound wire 226 to release to an actuated height. In some embodiments, the helically wound wire 226 can have has a delivery height greater than an actuated height. In some embodiments, the helically wound wire 226 can have an actuated height less than a delivery height. The helically wound wire 226 can be a round wire, a flat wire, a square wire, an oval wire, a triangular wire, etc. Further, the valve capsule 154 can comprise nitinol.

FIG. 71A shows a side view of an embodiment of the valve capsule 154 including a cylindrical proximal section 220 and a tapered distal section 219, wherein the cylindrical proximal section 220 includes a plurality of rings 227 connected by a wire 228. FIGS. 71B-71C show side views of the separation of the distal end of the valve capsule 154 from the outer sheath 50, exposing the frame structure 12. The cylindrical proximal section 220 includes mechanism by which the rings 227 of the cylindrical section are released from the outer sheath 50. The mechanism can include a pull wire to actuate the collapse of the series of rings 227 connected by a wire 228 of the cylindrical section. The mechanism can include a force from the advancement of an inner shaft 52 relative to the outer sheath 50 to slide the ring 227 off of the outer sheath 50. Release of the rings 227 from the outer sheath 50 can enable the series of rings 227 connected by a wire 228 to release to an actuated height. In some embodiments, the series of rings 227 connected by a wire 228 can have a delivery height greater than an actuated height. In some embodiments, the series of rings 227 connected by a wire 228 can have an actuated height less than a delivery height. Further, the valve capsule 154 may comprise nitinol.

FIG. 72A shows a side view of an embodiment of the valve capsule 154 wherein the valve capsule 154 includes a cylindrical proximal section 220 and a tapered lowered section 219 wherein the cylindrical proximal section 220 and the tapered distal section 219 are releasably attached. FIG. 72B shows a side view of the separation of tapered distal section 219 of the valve capsule 154 from the cylindrical proximal section 220 of the outer sheath assembly 155, attached to the outer sheath 50, exposing the frame structure 12. FIG. 72B shows an embodiment wherein the cylindrical section 220 comprises a mechanism by which it collapses to during separation to expose the frame structure 12, while the tapered distal section 219, attached to an inner shaft 52, remains stationary relative to the frame structure 12. The mechanism can include a wire 223 within a spiral lumen 221 of the cylindrical section 220 which can be pulled to actuate the collapse of the cylindrical section 220 of the valve capsule. The mechanism can comprise a balloon within a spiral lumen 221 of the cylindrical section 220 which can be deflated (e.g., by a vacuum) to actuate the collapse of the cylindrical section 220 of the valve capsule.

Figures 73A, 73B, 73C:
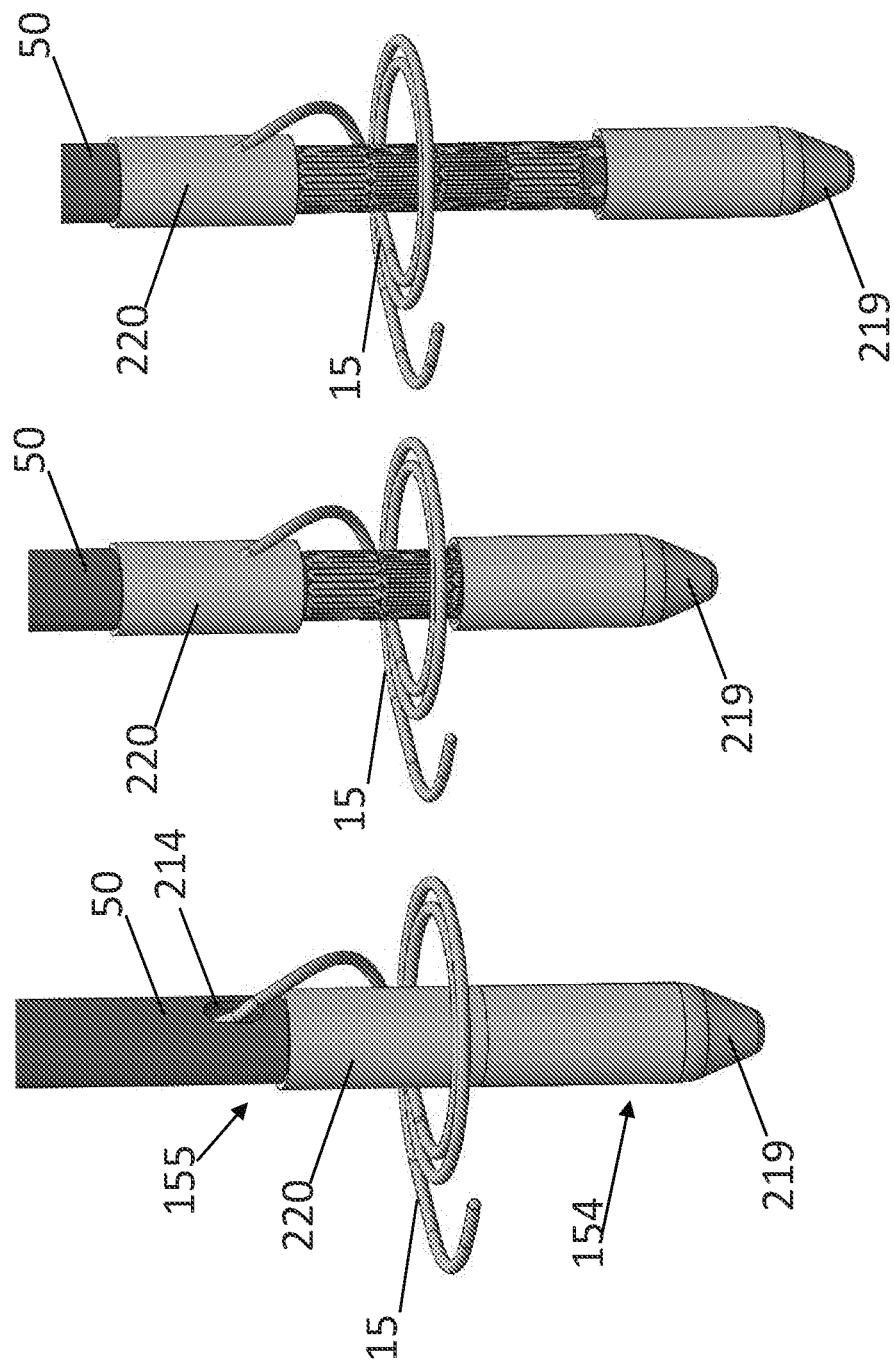
FIGS. 73A-73C are side views of various steps in the separation of a distal end of an outer sheath assembly, the distal end comprising a split-valve soft valve capsule, from an outer sheath assembly, in accordance with embodiments.

FIG. 73A shows a side view of another embodiment of the valve capsule 154 wherein the valve capsule 154 includes a cylindrical proximal section 220 and a tapered distal section 219 wherein the cylindrical proximal section 220 and the tapered distal section 219 are releasably attached. FIGS. 73B-73C show side views of the separation of tapered distal section 219 of the valve capsule 154 from the cylindrical proximal section 220 of the valve capsule 154, attached to the outer sheath 50, exposing the frame structure 12. FIG. 73B shows an embodiment wherein the cylindrical proximal section 220 and the tapered distal section 219 both move away from each other to expose the frame structure 12.

During use of any of the delivery devices 30 of FIGS. 59-73CA, a guidewire may be advanced into the heart of a patient, for example, through a transseptal puncture (e.g., as shown in FIG. 59). A distal end of the guidewire may be advanced from a first side of a native valve to a second side of the native valve. For example, the distal end of the guidewire may be advanced from a left atrial side of a mitral valve to a left ventricular side of a mitral valve.

The delivery device 30 may be advanced into the heart over the guidewire 54 (e.g., as shown in FIG. 60A). The distal end of the delivery device 30 may be configured to be advanced from a first side of a native valve to a second side of the native valve. For example, the distal end of the delivery device 30 may be advanced from a left atrial side of a mitral valve to a left ventricular side of a mitral valve. The distal end of the delivery device 30 (e.g., the sheath 50) may be steerable such that it is positionable to point towards the first side of the native valve before being advanced to the second side of the native valve.

The valve capsule 154 may be separated from the outer sheath 50 adjacent the native valve to form the opening and expose the inner shaft 52 and anchor guide 153. The opening may be formed prior to, during, or after advancing the distal end of the delivery device 30 from the first side of the native valve to the second side of the native valve.

In some embodiments, the distal end of delivery device 30 may be advanced from the first side of the native valve to the second side of the native valve after at least partially deploying the anchor 15 (e.g., as shown in FIG. 61A). In some embodiments, the distal end of the delivery device 30 may be advanced from the first side of the native valve to the second side of the native valve prior to deploying the anchor 15 (e.g., as shown in FIG. 63A).

Figure 7B:
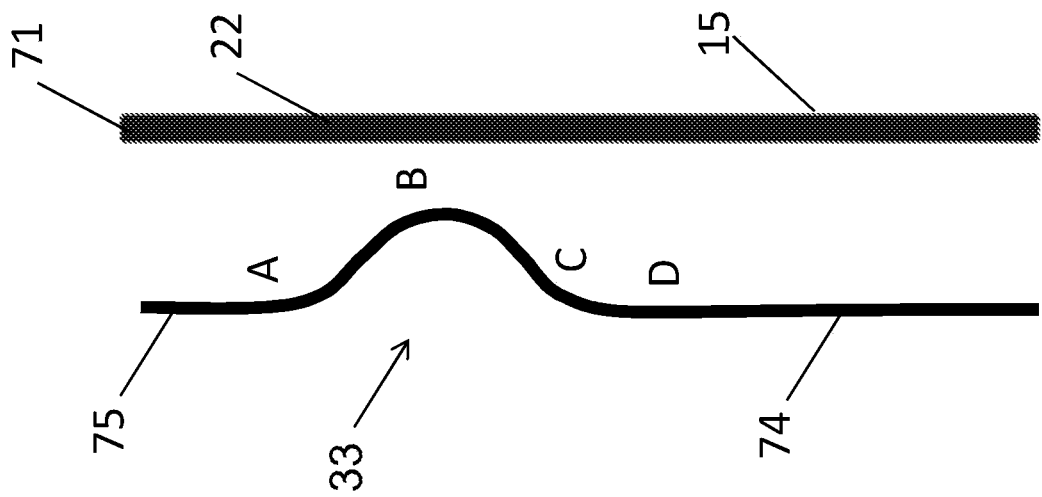
FIG. 7B shows a core wire comprising a deflecting feature, in accordance with embodiments.
Figure 7A:
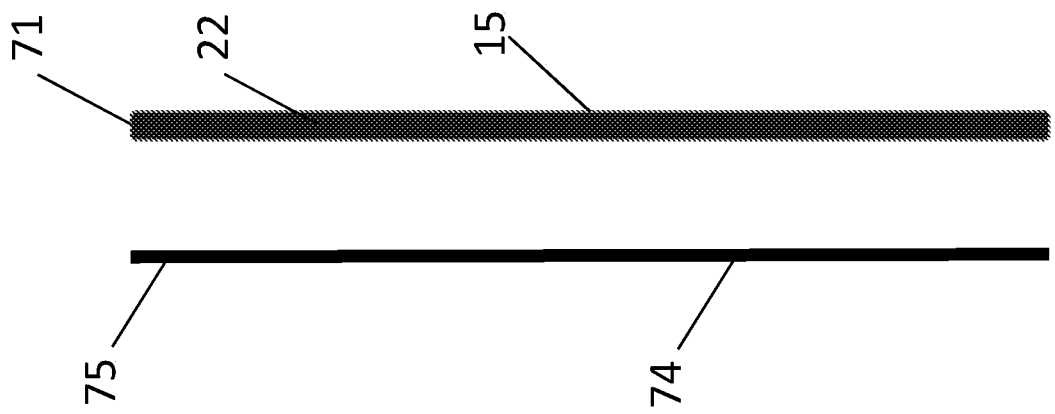
FIG. 7A shows an exemplary straight anchor and a core wire, in accordance with embodiments

After advancing to the second side of the native valve, the anchor 15 may be fully deployed from the anchor guide 153 on the second side of the native valve (e.g., as shown in FIGS. 61B and 7A). Fully deploying the anchor 15 may comprise actuating the anchor 15 from an elongated delivery configuration.

In some embodiments, fully deploying the anchor 15 from the anchor guide 153 may comprise actuating the anchor 15 from an elongated delivery configuration to a deployed configuration on the first side of the native valve (e.g., as shown in FIG. 60C) and advancing the anchor 15 in the deployed configuration through the native valve to the second side of the native valve (e.g., as shown in FIG. 61A). Advancing the anchor 15 may comprise pushing the anchor 15 through the native valve. Advancing the anchor 15 may further comprise rotating the anchor 15 through the native valve.

In some embodiments, fully deploying the anchor 15 from the anchor guide 153 may comprise positioning the anchor 15 such that it is located only on the second side of the native valve as can be seen in FIGS. 61B and 64A.

In some embodiments, the anchor 15 may be actuated from the delivery configuration to the deployed configuration on a first side of the native valve prior to being advanced to a second side of the native valve (e.g., as shown in FIG. 60C). For example, the anchor 15 may be deployed in a left atrium of a heart prior to being advanced to a left ventricle of the heart as described herein.

Alternatively, the anchor 15 may be actuated from the delivery configuration to the deployed configuration on a second side of the native valve after being advanced to the second side from a first side of the native valve (e.g., as shown in FIG. 63C). For example, anchor 15 may be advanced from a left atrium of a heart prior to being deployed in a left ventricle of the heart.

The free end of the deployed anchor 15 may optionally be rotated around one or more native valve structures on the second side of the native valve. The one or more native valve structures may comprise one or more valve leaflets of the native valve. Alternatively. or in combination, the one or more native valve structures may comprise one or more chordae of the left ventricle.

The free end of the deployed anchor 15 may optionally rotated around one or more native valve structures on the second side of the native valve such that the one or more native valve structures (e.g., chordae, leaflets, or annulus) are pulled radially inwards towards the longitudinal axis of the anchor and/or towards the longitudinal axis of the delivery device. The anchor and/or free end may be configured such that minimal torque is applied to the one or more native valve structures. Alternatively, or in combination, the anchor 15 and/or free end may be configured such that the one or more native valve structures are not rotated, or are minimally rotated, during rotation of the anchor.

In some embodiments, rotation of the free end may occur simultaneously with deployment of the anchor 15 from the anchor delivery sheath.

The anchor 15 may then be released from the anchor guide 153. The anchor 15 may be released from the anchor guide 153 on the second side of the native valve.

The frame structure 12 may be expanded within the native valve from an unexpanded configuration to an expanded configuration (e.g., as shown in FIGS. 62A and 64B).

The frame structure 12 may be released from the distal end of the delivery device.

The frame structure 12 may be held within the valve capsule 154. In some embodiments, the cylindrical proximal section 220 and the tapered distal section 219 of the valve capsule 154 may be permanently attached to one another (e.g., as shown in FIGS. 68A-68C, 69A-69C, 70A-70C, and 71A-71C). Release of the frame structure 12 may comprise distal translation of the valve capsule 154 away from the outer sheath 50 and frame structure 12 held thereon (e.g., as shown in FIGS. 68A-68C). Release of the frame structure 12 may comprise collapse of the valve capsule 154 into an actuated position (e.g., as shown in FIGS. 69A-69C. 70A-70C, 71A-71C). In some embodiments, the cylindrical section 220 and the tapered section 219 may be releasably attached to one another (e.g., as shown in FIGS. 72A-72B, 73A-73C). Release of the frame structure 12 may comprise proximal translation of the cylindrical proximal section 220 of the valve capsule away from the tapered distal section 219 (e.g., as shown in FIG. 72B). Release of the frame structure 12 may comprise translation of both the cylindrical proximal section 220 (e.g., proximal translation) and the tapered distal section 219 (e.g., distal translation) to separate the cylindrical proximal section 220 from the tapered distal section 219 (e.g., as shown in FIG. 73B-73C).

In some embodiments, at least a portion the frame structure 12 may be expanded within at least a portion of the deployed anchor 15 to anchor the frame structure 12 to the native valve.

In some embodiments, expanding the frame structure 12 and releasing the frame structure 12 may occur simultaneously.

In some embodiments, the frame structure 12 may be self-expanding and may be maintained in the unexpanded configuration by radial constriction from one or more of the outer sheath 50 of the delivery device 30 or by the valve capsule 154 of the outer sheath assembly 155. Advancement of the inner shaft 52 out of the lumen of the outer sheath 50 may actuate the frame structure 12 into the expanded configuration. Advancement of the inner shaft 52 out of the lumen of the outer sheath assembly 155 may actuate the frame structure 12 into the expanded configuration by the separation of the valve capsule 154 of the outer sheath assembly 155 from the outer sheath 50.

Finally, the delivery device 30 may be retracted from the native valve as shown in FIG. 65.

While FIGS. 3E-3H and 4A-8D show deployment of the anchor 15 from an opening in the distal tip of the delivery device 30 (e.g., a distal tip of the inner shaft 52 or a distal tip of the outer sheath 50), it will be understood by one of ordinary skill in the art that the anchor 15 may be deployed from an opening in a distal end of the delivery device 30 that is proximal to the distal tip, for example from an opening in a side wall of the delivery device 30 (e.g., a side opening in the inner shaft 52 or a side opening in the outer sheath 50).

Figure 81A:
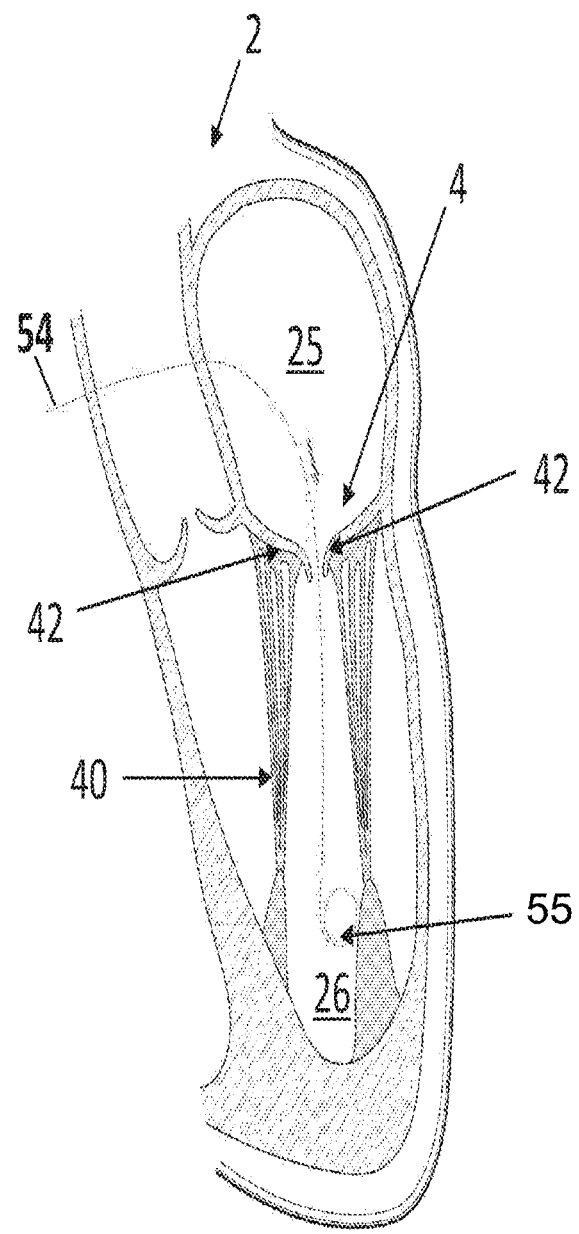
FIG. 81A shows a cross-sectional view of a heart having a diseased mitral valve 4 which may be treated using the devices, systems, and methods described herein, in accordance with many embodiments.

FIGS. 81A-81I and 82A-G show sequential views of a method of implanting a valve prosthesis 10 using a delivery device 30 with a lateral or side opening 215. FIG. 83 shows a magnified side view of the delivery device 30 highlighting the start of deployment of the anchor 15 from the side opening 215 in the delivery device 30. FIG. 81A shows a cross section view of a heart having a diseased mitral valve 4 which may be treated using the devices, systems, and methods described herein. The mitral valve 4 sits between the left atrium 25 and the left ventricle 26 and, when functioning properly, allows blood to flow from the left atrium 25 to the left ventricle 26 while preventing backflow or regurgitation in the reverse direction. As shown in FIG. 81A, the native valve leaflets 42 of the diseased mitral valve 4 do not fully prolapse and the patient experiences regurgitation. The native chordae tendineae 40 of the heart 2 are shown. A guide wire 54 may be inserted into the left atrium 25 of the heart 2 via a transseptal puncture as described herein. The distal end or nosecone 55 of the guidewire 54 may be placed in the left ventricle 26.

The delivery device 30 may comprise an optional outer sheath 50 (e.g., an outer catheter) and an inner shaft 52 (e.g., a delivery tube) disposed within a lumen of the outer sheath 5-. A proximal end of the valve prosthesis 10 may be operably coupled to the inner shaft 52 during delivery to the native valve as described herein. The outer sheath 50 may be steerable. The inner shaft 52 may be steerable and may include the side opening 215.

Figures 81B, 81C, 81D, 81E:
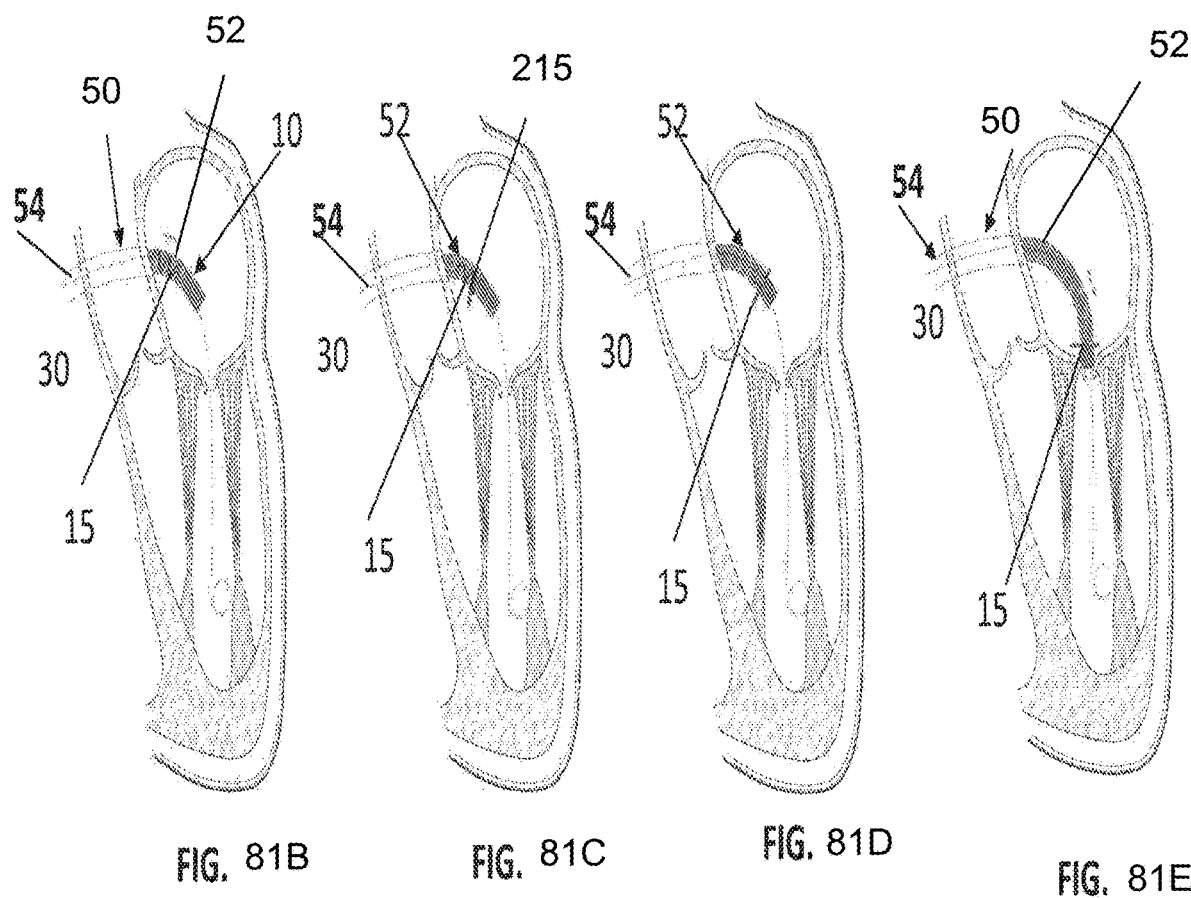
FIGS. 81B-81E show cross-sectional views of the deployment of the anchor from the side of the delivery device, in accordance with many embodiments.
Figures 81F, 81G, 81H, 81I:
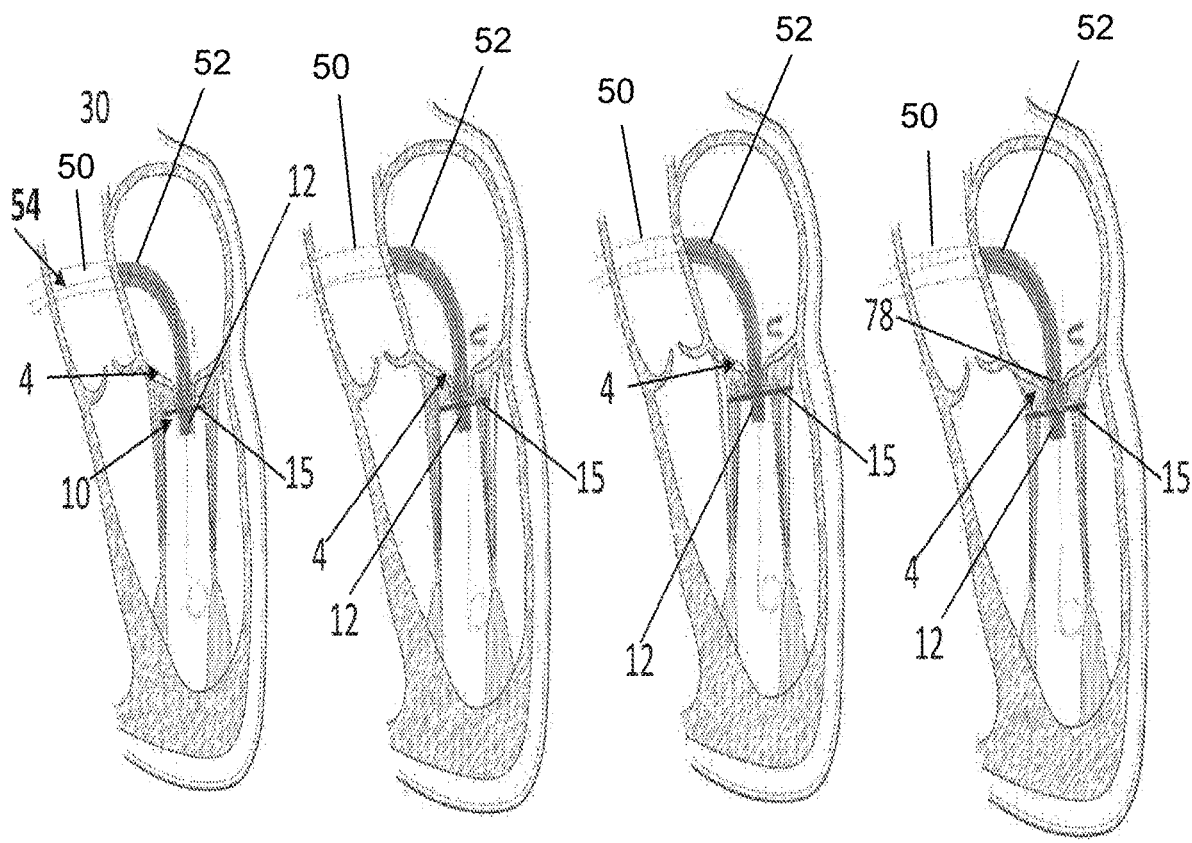
FIGS. 81F-81I show cross-sectional views of the valve prosthesis being advanced through the native valve by the delivery device from the left atrium to the left ventricle, in accordance with many embodiments.
Figures 82A, 82B, 82C, 82D:
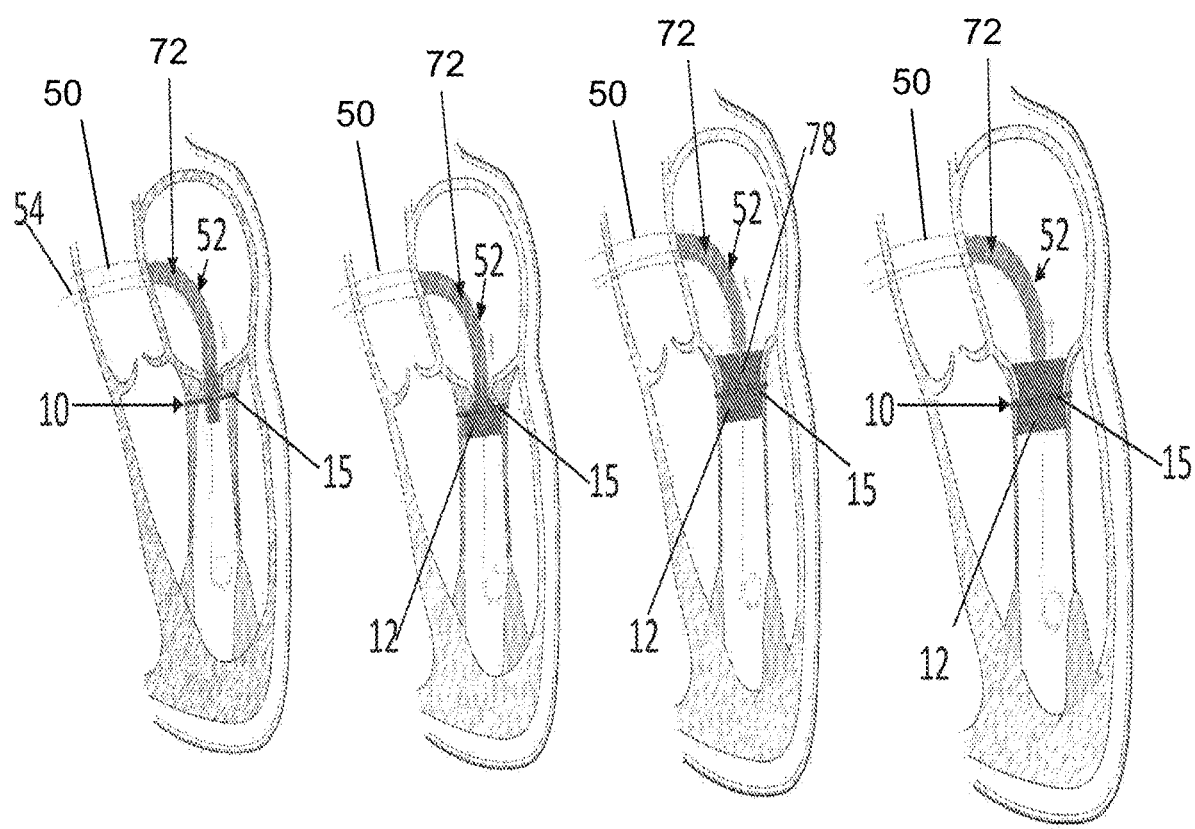
FIGS. 82A-82D show cross-sectional views of the release of a valve prosthesis from the inner shaft, in accordance with many embodiments.
Figure 84:
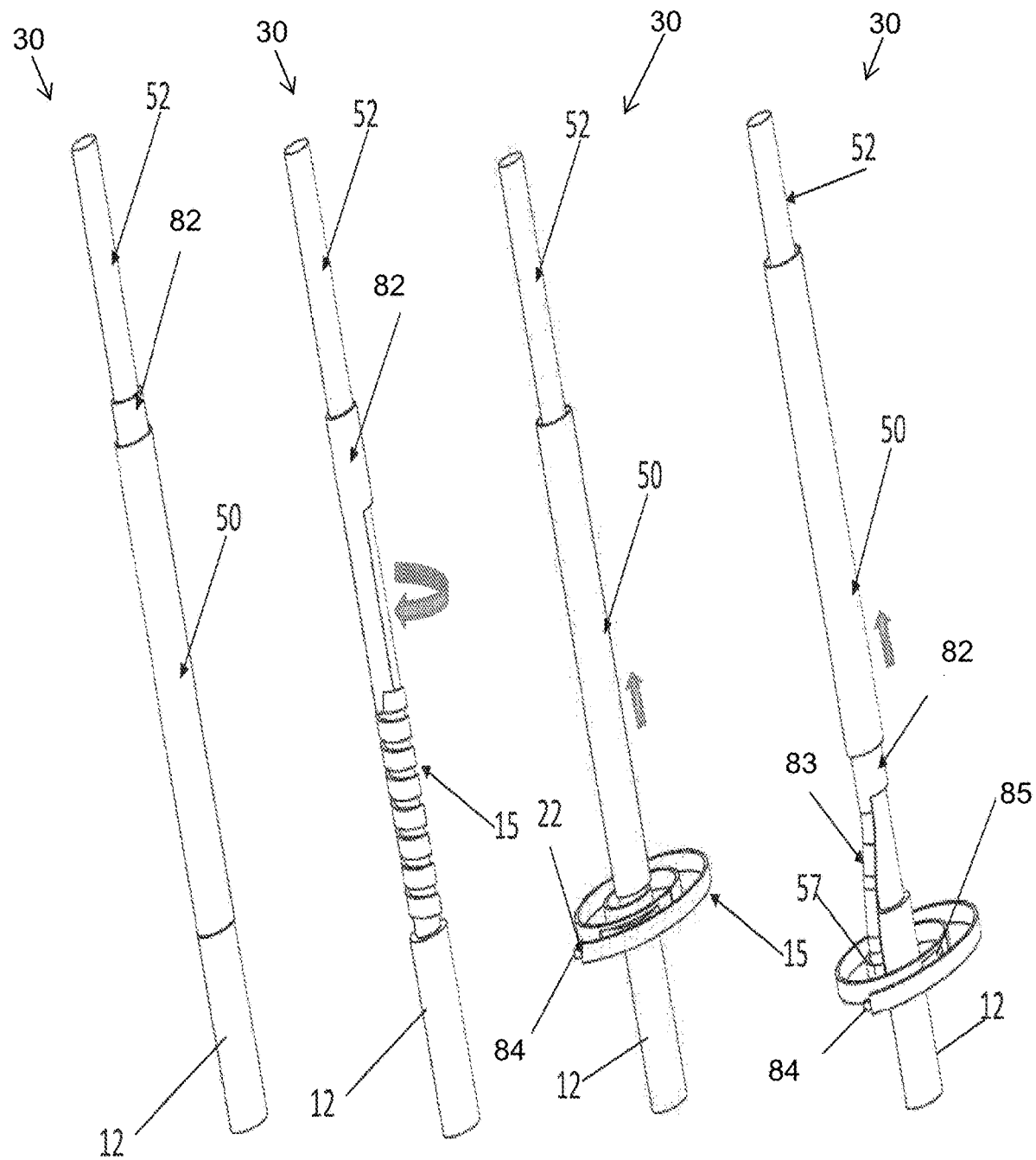
FIGS. 84A-84D show perspective views deployment of the anchor from a flat screw embodiment of the delivery device, in accordance with many embodiments.
Figure 90B:
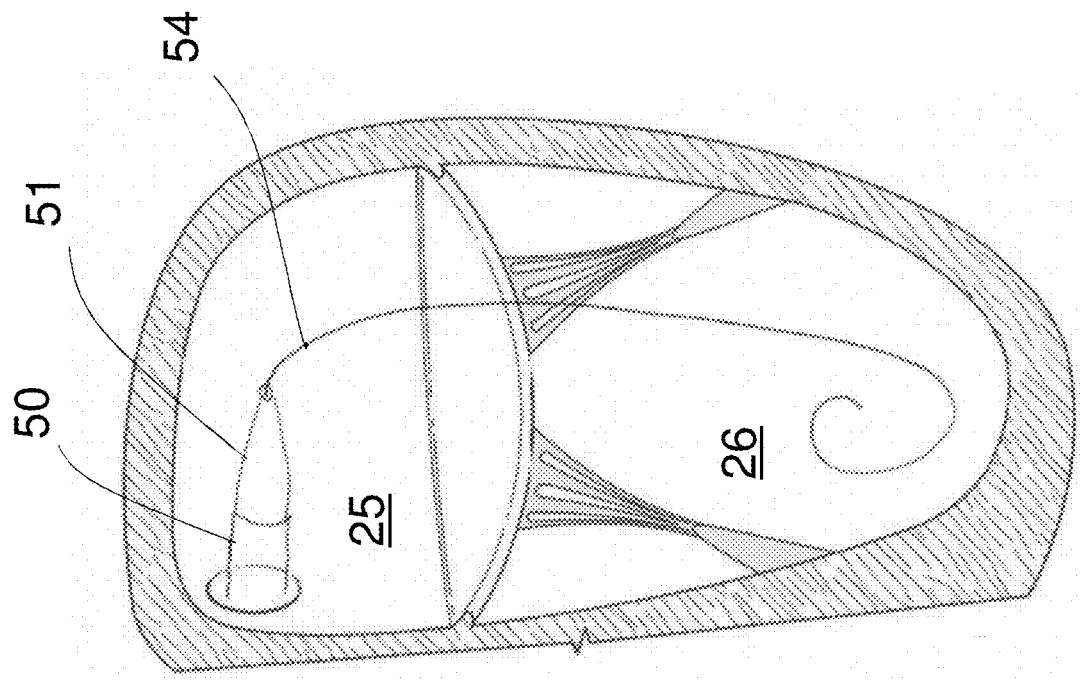
Figure 90A:
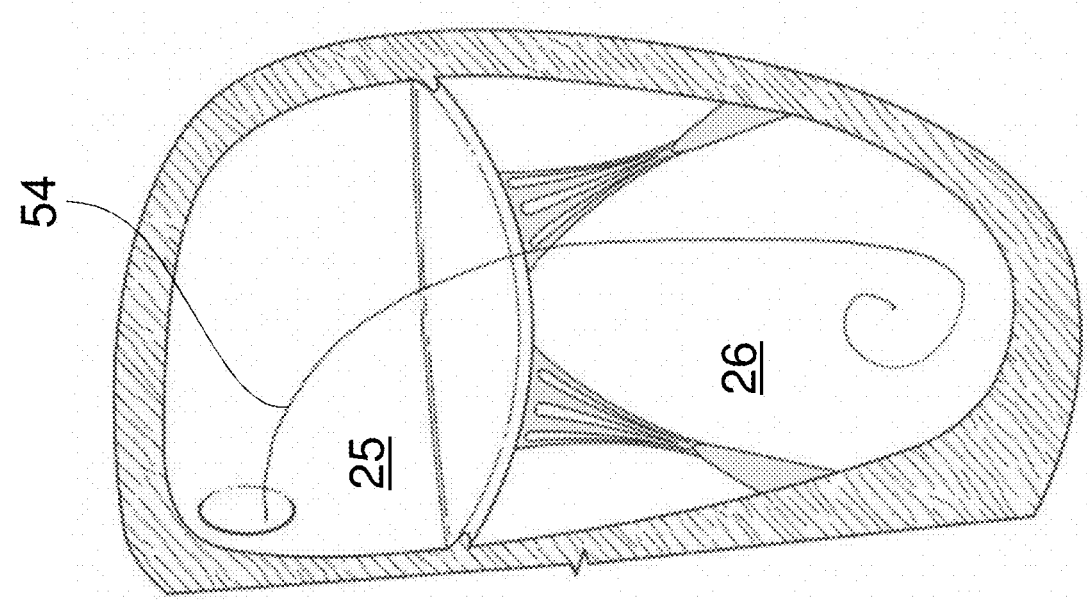
Figure 90E:
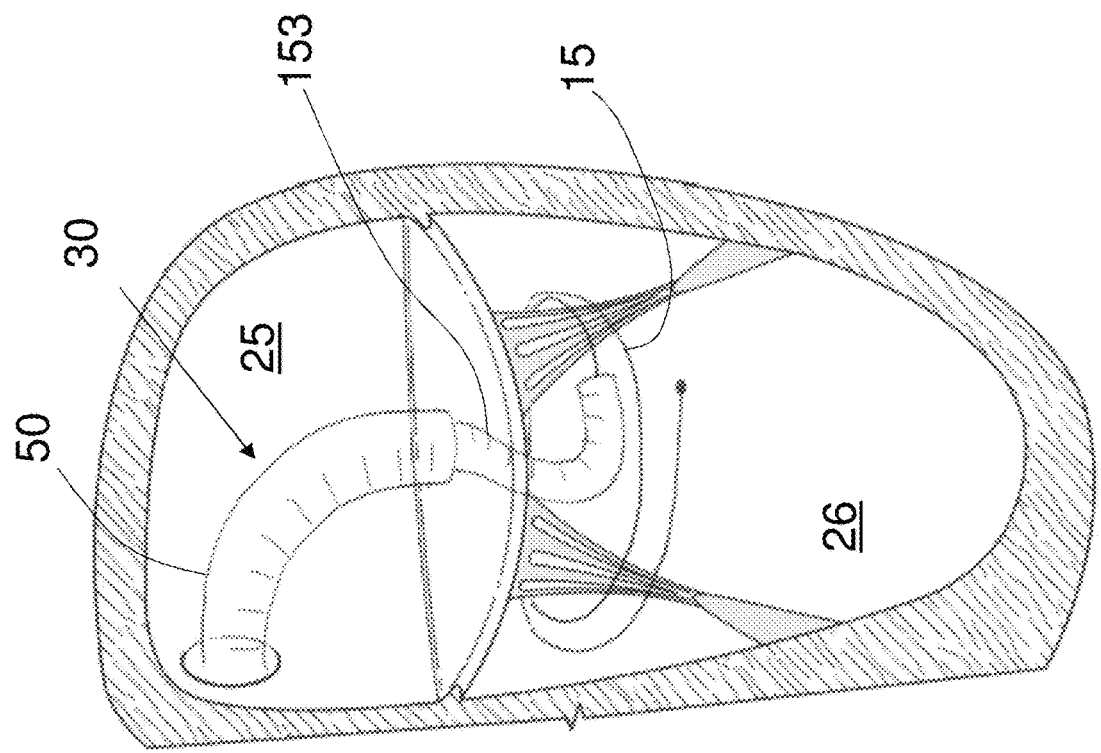
Figure 90F:
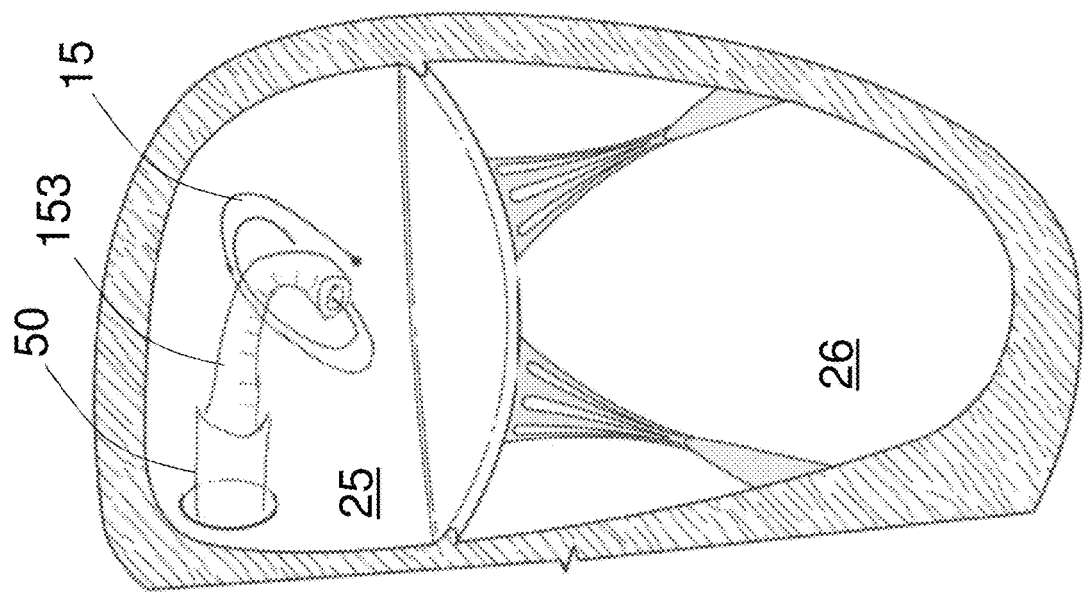

The valve prosthesis 10 may be similar to any of the valve prostheses described herein. For example, the valve prosthesis may include a frame structure 12 and an anchor 15. The anchor 15 may be directly coupled to the frame structure 12, for example at a proximal or distal end thereof. Alternatively, or in combination, the anchor 15 may be detachably coupled to the delivery device 30 prior to deployment at the native valve. The anchor 15 may comprise a deployed configuration (for example, as shown in FIGS. 81I and 84D). The frame structure 12 may have an unexpanded configuration (for example, as shown in FIGS. 81B-81I and 82A), for example when the valve prosthesis 10 is in its unexpanded configuration, and an expanded configuration (for example, as shown in FIGS. 82B-82G), for example when the valve prosthesis 10 is in its expanded configuration. The frame structure 12 is shown in the unexpanded configuration. The expanded configuration may have a generally tubular expanded shape. The frame structure 12 may be configured for expanding within the native valve of the patient. In some embodiments, the unexpanded configuration may be sized and dimensioned for percutaneous insertion and the expanded configuration may be sized and dimensioned for implantation in the native valve of the patient.

The frame structure 12 may comprise a first and second opposite ends, the first end extending above a native valve and the second end extending below the native valve when the frame structure 12*m* is anchored to the native valve. Alternatively, the frame structure 12 may be configured to sit entirely below the native valve when the frame structure 12 is anchored to the native valve.

The frame structure 12 may be self-expanding and may be maintained in the unexpanded configuration by radial constriction from the outer shaft 54 or inner shaft 52 of the delivery device 30. In some embodiments, advancement of the inner shaft 52 out of the lumen of the outer shaft may actuate the frame structure 12 into the expanded configuration. In some embodiments, advancement of the frame structure 12 out of the lumen of the inner shaft 52, for example with the aid of a proximal pusher 78 (see FIG. 83) and/or balloon as described herein, may actuate the frame structure 12 into the expanded configuration. In some embodiments, the frame structure 12 may be detachably coupled to and/or disposed within the delivery device 30 at a location proximal to the anchor 15. In some embodiments, the frame structure 12 may be detachably coupled to and/or disposed within the delivery device 30 at a location distal to the anchor 15. In some embodiments, at least a portion of the frame structure 12 may be detachably coupled to and/or disposed within the delivery device 30 at a location adjacent (e.g., within) the anchor 15.

In some embodiments, the anchor 15 may be detachably coupled to and/or disposed within the delivery device 30 at a location proximal to the frame structure 12. In some embodiments, the anchor 15 may be detachably coupled to and/or disposed within the delivery device 30 at a location distal to the frame structure 12. In some embodiments, at least a portion of the anchor 15 may be detachably coupled to and/or disposed within the delivery device 30 at a location adjacent (e.g., around) the frame structure 12. In some embodiments, the anchor 15 may be disposed in a lumen of the inner shaft 52. The anchor 15 may or may not be coupled to the inner shaft 52. The anchor 15 may be maintained in the delivery configuration by radial constriction from the inner shaft 52. Advancement of the anchor 15 out of the inner shaft 52, for example out of the side port 215 of the inner shaft 52, may actuate the anchor 15 into the deployed configuration. The proximal end 57 of the anchor 15 may be detachably coupled to an actuation arm (e.g., proximal pusher 78 shown in FIG. 83) which may be disposed within the lumen of the inner shaft 52 and extend towards a proximal end of the delivery device 30.

The anchor 15 may comprise a curved wire in the deployed configuration, for example a coiled wire or band, a helical wire or band, or a spiral wire or band as described herein. In various embodiments, the anchor 15 may have a curved shape in the deployed configuration. In various embodiments, the anchor may be elongated-rather than curved—in the delivery configuration. For example, the anchor 15 may be elongated into a straight shape within the delivery device 30. In various embodiments, a portion of the anchor 15 may have a curved shape. In various embodiments, a substantial portion of the anchor 15 may have a curved shape. In various embodiments, the anchor 15 may be formed as a flat curve (in the deployed configuration) whereby the loops generally are positioned within the same plane (the plane being perpendicular to a longitudinal axis). In various embodiments, the anchor 15 may be formed as a three-dimensional curve (in the deployed configuration) whereby the loops generally are positioned out of plane with one another.

The anchor 15 may comprise a spiral wire or band in the deployed configuration. As used herein, a spiral or spiral shape may comprise a curve which emanates from a point (e.g., a central point) having a continuously increasing or decreasing distance from the point. The spiral or spiral shape may be two-dimensional (e.g., planar) or three-dimensional. In some embodiments, the anchor 15 may comprise one or more spiral portions as described herein. In various embodiments, the anchor 15 may have a spiral-shaped deployed configuration. In various embodiments, spiral refers to a shape with windings about a central axis. The spiral may be continuous. The windings may gradually widen (or tighten) along the length. The spiral may be formed in a flat plane perpendicular to the central axis. In various embodiments, the anchor 15 may have a deployed configuration that is not formed in a flat plane, or in other words the deployed shape is formed in a three-dimensional and/or non-degenerate space. In various embodiments, the anchor 15 may have a conical-shaped deployed configuration including, but not limited to, tubular, conical, frustoconical and/or helical shapes.

The anchor 15 may comprise one or more loops. For example, the anchor 15 may comprise a plurality of loops, which may increase the radial strength of the anchor by increasing friction and addition structural support. The one or more loops of the anchor 15 may be spiral radially outward from a central point or central axis of the spiral, for example along an axis which is coaxial with a longitudinal axis of a delivery device 30 such that the anchor 15 lies approximately along a plane perpendicular to the longitudinal axis of a delivery device. In some embodiments, the one or more loops of the anchor 15 may comprise one or more spaces therebetween. The spaces may facilitate movement of the captured tissue (e.g. chordae and/or leaflets) from the free end 22 to the center of the anchor 15 during rotation of the anchor 15 as described herein.

The free end 22 of the anchor 15 may extend radially outward from the frame 12, and in particular from the remainder of the spiral band or wire 20. The other end of the anchor 15 may be coupled to the top or bottom of the frame structure 12 as described herein. Alternatively, or in combination, the other end of the anchor 15 may not be attached to the frame structure 12 as described herein. The free end 22 of the anchor 15 may facilitate capturing of the valve leaflets and/or chordal tendineae within the sweep of the free end during rotation as described herein. During rotation of the anchor 15, the leaflets and/or chordae tendineae may be captured by the free end 22 and trapped between the valve frame structure 12 and an interior surface of the anchor 15.

The anchor 15 (e.g., including a tapered spiral band) may comprise a delivery (e.g., elongated) configuration and a deployed configuration (and optional intermediate configurations) as described herein. The anchor 15 may be configured to be actuated from the elongated configuration to the deployed configuration adjacent a native valve in a patient. The anchor 15 may be delivered to the native valve by a delivery device in the elongated configuration as described herein. The anchor 15 may be coupled to the delivery device and/or a frame structure of a valve prosthesis as described herein, for example at a proximal portion (e.g. adjacent proximal attachment point on an interior of the spiral) or distal portion (e.g. adjacent distal attachment point on an exterior of the spiral) thereof. The anchor 15 may be deployed adjacent the native valve substantially similarly to other anchor embodiments as described herein.

After extending out of the side opening 215, the free end 22 of the anchor 15 may optionally rotated around one or more native valve structures on the second side of the native valve such that the one or more native valve structures (e.g., chordae, leaflets, or annulus) are pulled radially inwards towards the longitudinal axis of the anchor 15 and/or towards the longitudinal axis of the delivery device 30. The anchor 15 may be configured such that minimal torque is applied to the one or more structures. Alternatively, or in combination, the anchor 15 may be configured such that the one or more native valve structures are not rotated, or are minimally rotated, during rotation of the anchor 15. For example, the anchor 15 may comprise one or more spaces between loops of the anchor 15 which facilitate movement of the captured tissue (e.g. chordae and/or leaflets) from the free end 22 to the center of the spiral structure with little or no torque and/or rotation of the native valve structures during rotation of the tapered spiral band as described herein. Alternatively or in combination, the anchor 15 may be configured such that, when fully deployed, none of the native valve structures reside between the loops of the spiral. Instead, the one or more native valve structures may sit radially inward of the loops in order to facilitate capture of the one or more structures between anchor 15 and the expanded frame structure 12 as described herein. The one or more native valve structures may retain or nearly retain their normal anatomical position when the spiral band is fully deployed. The free end 22 may be disposed radially outwards from the remainder of the anchor 15. Disposing the free end 22 radially outward from the remainder of the anchor 15 may, for example, aid in deployment of the anchor 15 from the delivery device and/or capture of the one or more native valve structures as described herein. The free end 22 may be angled proximally (e.g., towards a proximal portion of the anchor 15 and a distal end of the delivery device 30) or distally (e.g., away from a proximal portion of the anchor 15 and towards a proximal portion of the delivery device 30) from the rest of the anchor 15. Angling the free end 22 proximally or distally towards or away from the delivery device 30 may, for example, aid in deployment of the anchor 15 from the side opening 215 delivery device and/or capture of the one or more native valve structures as described herein.

The distal end of the delivery device 30 may be configured to be advanced from a first side of a native valve to a second side of the native valve. For example, the distal end of the delivery device 30 may be advanced from a left atrial side of a mitral valve to a left ventricular side of a mitral valve. In some instances, the distal end of the delivery device 30 may be transseptally inserted into the left atrium of the heart prior to advancement into the left ventricle. Alternatively, or in combination, the distal end of the delivery device 30 may be steerable such that it is positionable to point towards the first side of the native valve before being advanced to the second side of the native valve.

After advancing to the second side of the native valve, the anchor 15 may be fully deployed on the second side of the native valve. In some embodiments, fully deploying the anchor 15 may comprise positioning the anchor 15 such that it is located only on the second side of the native valve. One will appreciate from the description here, that alternatively the anchor may be deployed on the first side of the valve (e.g., in one of the atria) and then pushed through the respective valve and subsequently rotated to anchor to the chordae and/or native valve.

Advancing the anchor 15 may comprise pushing the anchor through the native valve. Advancing the anchor 15 may further comprise rotating the anchor 15 through the native valve.

In some embodiments, the anchor 15 may be actuated from the delivery configuration to the deployed configuration on a first side of the native valve prior to being advanced to a second side of the native valve. For example, the anchor 15 may be deployed in a left atrium of a heart prior to being advanced to a left ventricle of the heart as described herein.

Alternatively, the anchor 15 may be actuated from the delivery configuration to the deployed configuration on a second side of the native valve after being advanced to the second side from a first side of the native valve. For example, anchor 15 may be advanced from a left atrium of a heart prior to being deployed in a left ventricle of the heart by the retreat of an outer sheath 50 or advancement out of an inner shaft 52.

The free end 22 of the deployed anchor 15 may optionally be rotated around one or more structures on the second side of the native valve. The one or more structures may comprise one or more valve leaflets of the native valve. Alternatively, or in combination, the one or more structures may comprise one or more chordae of the left ventricle.

The free end 22 of the deployed anchor 15 may optionally rotated around one or more structures on the second side of the native valve such that the one or more structures (e.g., chordae, leaflets, or annulus) are pulled radially inwards towards the longitudinal axis of the anchor 15*m* and/or towards the longitudinal axis of the delivery device 30. The anchor 15 and/or free end 22 may be configured such that minimal torque is applied to the one or more structures. Alternatively, or in combination, the anchor 15 and/or free end 22 may be configured such that the one or more structures are not rotated, or are minimally rotated, during rotation of the anchor 15.

The anchor 15 may then be released from the distal end of the delivery device 30. The anchor 15 may be released from the distal end of the delivery device 30 on the second side of the native valve.

The frame structure 12 may be expanded within the native valve from an unexpanded configuration to an expanded configuration.

The frame structure 12 may be released from the distal end of the delivery device 30. In some embodiments, at least a portion the frame structure 12 may be expanded within at least a portion of the deployed anchor 15 to anchor the frame structure 12 to the native valve.

In some embodiments, expanding the frame structure 12 and releasing the frame structure 12 may occur simultaneously.

Finally, the delivery device 30 may be retracted from the native valve.

As noted, FIGS. 81A-81I, 82A-82G show sequential views of a specific exemplary method of implanting a valve prosthesis 10 using a delivery device 30 with a side opening 215. FIG. 83 shows a magnified side view of the delivery device 30 highlighting the start of deployment of the anchor 15 from the side opening 215 in the delivery device 30. The valve prosthesis 10 may be similar to any of the valve prostheses described herein or understood by one of ordinary skill in the art from the description herein. For example, valve prosthesis 10 may be substantially similar to any of the valve prostheses 10 may comprise a frame structure 12 and anchor 15 as described herein. The delivery device 30 may comprise an inner shaft 52 as described herein. The delivery device 30 may optionally comprise an outer sheath 50, a guidewire 54, a proximal pusher 72 and/or a tether 78, in any combination thereof as desired by one of ordinary skill in the art. The proximal pusher 72 may comprise a flexible advancement member housed and advancable within the inner shaft 52. The proximal pusher 72 may comprise a flexible shaft or stylet, for example, in the form of a wire or a metal wire, and/or flexible hypotube with a lumen to accommodate the guidewire 54. Not all elements are labeled in each of FIGS. 81A-81I. 82A-82G in order to make the illustrations less cluttered and easier to see.

While the method shown in FIGS. 81A-84 is described in relation to a mitral valve replacement procedure, it will be understood by one of ordinary skill in the art that the methods described herein may be applied to a variety of procedures or anatomical areas, for example other atrioventricular valves of the heart or the like.

Returning to FIG. 81A, a distal end of the delivery device 30 may be inserted into the left atrium 25 of the heart 2 via a transseptal puncture as described herein. For example, the nosecone 55 of guidewire 54 may be advanced into the left atrium 25 of the heart 2. As shown in FIG. 81B, the inner shaft 52 may be advanced distally into the left atrium 25 following the distal end of the guidewire 54. In some embodiments, advancing the inner shaft 52 relative to the guidewire 54 may aid in deployment and/or placement of the valve prosthesis 10 as described herein. Both the guidewire 54 and the inner shaft 52 may be advanced distally into the left atrium 25 through the transseptal puncture.

FIGS. 81B-81E show advancement of the valve prosthesis 10, with anchor 15 deployed around the compressed or unexpanded frame structure 12, towards the native valve 4 requiring treatment. The distal end of the delivery device 30 (for example, the distal end of the outer sheath 50, the inner shaft 52, and/or the guidewire 54) may be steered such that the distal end of the delivery device 30 points toward the atrial side of the native valve 4. Such steering may occur prior to, during, or after deployment of at least a portion (for example deployment of an anchor 15) of the valve prosthesis 10. In some embodiments, the distal end of the guidewire 54 may be steerable. Alternatively, or in combination, the inner shaft 52 may comprise a joint configured to change an angle of the distal portion of the inner shaft 52 relative to a proximal portion of the inner shaft 52. The inner shaft 52 may be steered by changing the angle of the distal portion of the inner shaft 52 relative to the proximal portion of the inner shaft 52. The angle of the joint may be changed passively or actively. In various embodiments, the angle may be selectively controlled by a proximal handle. For example, pull wires or other mechanisms may connect to the joint to controls on the handle.

FIGS. 81C-81E (as well as FIG. 83) also show deployment of the anchor 15 from the lateral or side opening 215 of the inner shaft 52 of the delivery device 30. The side opening 215 may, for example, comprise a side port. Alternatively, or in combination, the side opening 215 may comprise an opening which exposes the distal end of the anchor 15 resultant of a retraction of the outer sheath. As described herein, at least a portion of the valve prosthesis 10 may be deployed from an undeployed (for example, compressed or unexpanded) configuration to an expanded configuration within the left atrium 25. At least a portion of the anchor 15 may be deployed from a delivery and/or elongated configuration to a deployed configuration within the heart. For example anchor 15, may be actuated from an elongated configuration to a deployed configuration within the left atrium 25 as described herein. In some embodiments, the anchor 15 may be deployed from the inner shaft 52 by pushing the anchor 15 out of the side port 215 of the inner shaft 52 (e.g., with a the proximal pusher 72 or the tether 78 as described herein), releasing the anchor 15 from radial constraint by retracting the outer sheath 50, or the like as described herein. After the anchor 15 has been deployed from the delivery device 30, the valve prosthesis 10 comprising frame structure 12 may be at least partially deployed from the delivery device 30 (e.g., as shown in FIG. 82B) so as to place the frame structure 12 within the anchor 15. The valve prosthesis 10 comprising frame structure 12 may be deployed from the inner shaft 52 of the delivery device 30 in either the unexpanded configuration or the expanded configuration, depending on the location of deployment, as will be understood by one of ordinary skill in the art.

FIGS. 81E-81F show the partially deployed anchor 15 being advanced through the native valve 4 by the delivery device 30 from the left atrium 25 to the left ventricle 26. Advancement of the anchor 15 and optionally delivery device 30 through the mitral valve 4 may be facilitated by the natural opening and closing of the valve 4 during the cardiac cycle. The deployed anchor 15 may be optionally wrapped around the distal end of the inner shaft 52. After the anchor 15 has been deployed to the distal end of the inner shaft 52, the inner shaft 52 may be moved or steered further along the guidewire 54 so as to place the anchor 15 above the native leaflets 42 of the diseased mitral valve 4, as shown in FIG. 81E. FIGS. 81G-81I show the securing of the anchor 15 to the native chordae tendinae. The anchor 15 may be rotated by the rotating of the inner shaft 52, the anchor guide 153, and/or the proximal pusher 72. Advancing the anchor 15 may comprise pushing the anchor 15 through the native valve 4. Alternatively, or in combination, advancing the anchor 15 may comprise rotating the anchor 15 through the native valve 4. In some instance, the combination of rotational motion and pushing may facilitate advancement of the device from the first side of the native valve 4 to the second side of the native valve 4. Rotation of the anchor 15 may be facilitated by the inner shaft 52 as described herein. For example, the inner shaft 52 or the anchor guide 153 may transmit rotational motion to the anchor 15 in order to rotate the anchor 15 to secure the anchor 15 to the tendinae chordae as shown in FIGS. 81G-81I.

The distal end of the delivery device 30 and/or valve prosthesis 10 may be configured to be advanced from a first side of a native valve to a second side of the native valve. For example, the distal end of the delivery device 30 and/or valve prosthesis 10 may be advanced from a left atrial side of a mitral valve 4 to a left ventricular side of a mitral valve 4.

FIGS. 81G-81I show rotation of the valve prosthesis 10 around one or more native valve structures on the ventricular side of the mitral valve 4. The one or more native valve structures may comprise one or more valve leaflets 43 and/or one or more chordae tendineae 40 (e.g., as shown in FIGS. 85A-85C). After the anchor 15 has been placed within the left ventricle 26 adjacent one or more chordac tendineae 40, the valve prosthesis 10 (e.g., the anchor 15 and, optionally, the frame structure 12) may be rotated to capture and anchor the native chordae 40 and/or native leaflets 43. The free end 22 of the anchor 15 may extend radially outward from the rest of the anchor 15 to facilitate capture of the native structures. The free end 22 of the anchor 15 may be rotated around one or more of the chordae tendineae 40 as shown in FIG. 81G. Additional rotation of the valve coil 15 may gradually capture additional chordae tendineae 40 as shown in FIGS. 81H-81I.

Rotation of the valve prosthesis 10, for example, rotation of the anchor 15 and/or frame structure 12, may be facilitated by the delivery device 30 described herein. For example, the inner shaft 52 may be rotated and rotational motion may be transmitted from the inner shaft 52 or the anchor guide 153 to the valve prosthesis 10 in order to rotate the valve prosthesis 10 around one or more of the structures on the ventricle side of the mitral valve 4 as described herein. Alternatively, or in combination, a proximal portion of the anchor 15 may be detachably coupled to a tether 78 that extends through a lumen of the inner shaft 52 to a distal end thereof. The tether 78 may be rotated and rotational motion may be translated from the tether 78 to the anchor 15 in order to rotate the anchor 15 around the one or more structures on the ventricle side of the mitral valve 4 as described herein.

Figure 82E:
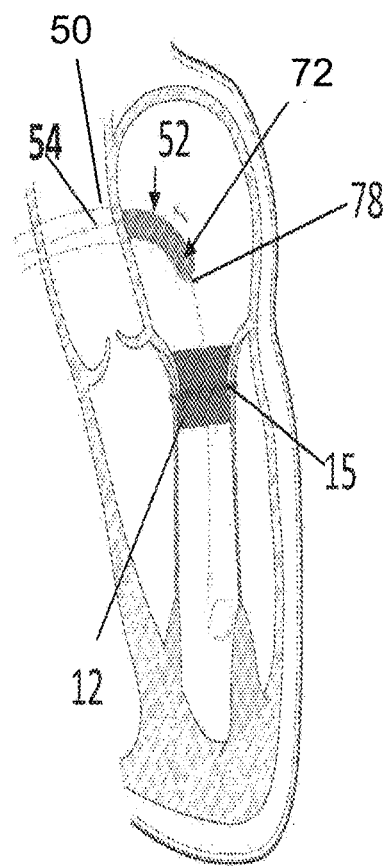
FIG. 82E shows removal of the delivery device from the heart, in accordance with many embodiments.
Figure 82F:
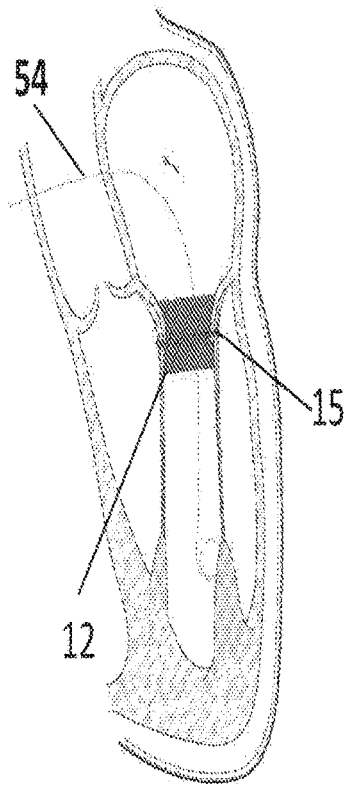
FIG. 82F shows removal of the guidewire from the heart, in accordance with many embodiments.
Figure 82G:
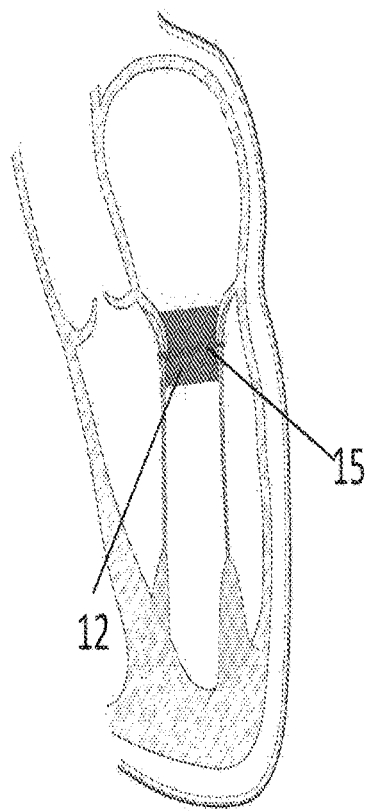
FIG. 82G shows the valve prosthesis fully expanded with the native valve leaflets and chordae tendineae captured between the frame structure and the anchor, in accordance with many embodiments.
Figure 83:
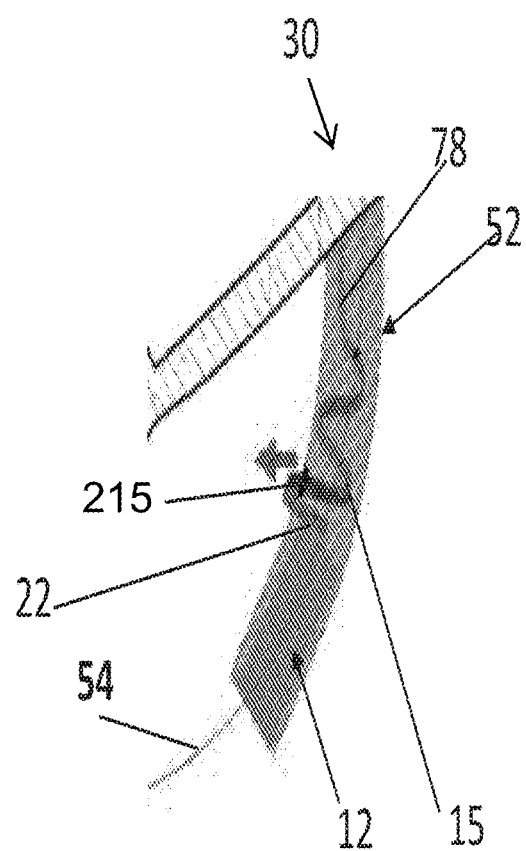
FIG. 83 shows a magnified side view of the delivery device side port on the inner shaft where an anchor is released from the inner shaft proximal to the valve prosthesis, in accordance with many embodiments.

FIGS. 82A-82G show the valve prosthesis 10 wrapped around the captured chordae tendineae 40. The valve prosthesis 10 may be rotated around the chordae tendineae 40 such that the chordae tendineae 40 are pulled inwardly into bunches. As shown in FIG. 82G, the native valve leaflets 43 may also be in communication with the valve prosthesis 10. The valve prosthesis 10 may be rotated to capture enough chordae tendineae 40 and/or valve leaflets 43 to rigidly anchor the anchor 15 adjacent the native valve annulus. The valve prosthesis 10 may be anchored by wrapping around only a portion of the chordae 40. Although it may be possible to capture all or substantially all the chordae 40, this may not be necessary to provide sufficient anchoring of the valve prosthesis 10. As described further herein, the prosthesis 10 may be further anchored by expansion of the frame structure 12 within the native valve 4 and against the anchor 15.

Once the anchor 15 has been anchored adjacent to the native valve 4, the valve prosthesis 10 comprising the frame structure 12 and prosthetic valve segment 14 may be expanded at least partially within the anchor 15 as described herein. The frame structure 12 and the valve segment 14 may be deployed (e.g., expanded) simultaneously. Alternatively, or in combination, the frame structure 12 and the valve segment 14 may be deployed sequentially, for example by first expanding the frame structure 12 and then receiving the prosthetic valve segment 14 therein.

FIGS. 82A-82D show expansion of the valve prosthesis comprising the frame structure 12 within the native valve 4. The frame structure 12 may be expanded within the native valve 4 from an unexpanded configuration to an expanded configuration. In some embodiments, at least a portion the frame structure 12 may be expanded within at least a portion of the deployed anchor 15 to anchor the frame structure 12 to the native valve 4. In some embodiments, the frame structure 12 may comprise an expandable stent. In some embodiments, the frame structure 12 of valve prosthesis 10 may be balloon-expandable. In some embodiments, the frame structure 12 of valve prosthesis 10 may be self-expandable. The delivery device 30 may comprise a proximal pusher 72 which may be disposed within the valve prosthesis 10 in order to expand the valve prosthesis 10. The proximal pusher 72 may be positioned proximal to the valve prosthesis 10 as shown in FIG. 82A-82D. The proximal pusher 72 may be configured to operably couple to a proximal portion of the frame structure 12, for example, in order to longitudinally translate the frame structure 12 within the lumen of the inner shaft 52. Alternatively, if the proximal pusher 72 is expandable (e.g., an expandable balloon-like element), the proximal pusher 72 may be positioned within at least a portion of the valve prosthesis 10, for example within at least a portion of frame structure 12 in an unexpanded configuration, prior to being expanded. The proximal pusher 72 may, for example, be disposed within a proximal portion of the inner shaft 52 or outer sheath 50 while the anchor 15 is being positioned adjacent the native valve 4 and then advanced therefrom (or the inner shaft 52 or outer sheath 50 is retracted therefrom) to be positioned proximal to or within the frame structure 12. Alternatively, the proximal pusher 72 may be disposed within the frame structure 12 during placement of the valve prosthesis 10.

FIG. 82A shows advancement of the proximal pusher 72 within the inner shaft 52 towards a proximal end of the frame structure 12. FIG. 82B shows the frame structure 12 partially expanded following engagement with the proximal pusher 72, for example self-expanded after being partially pushed by the pusher 72 out of a distal end of the inner shaft 52. The frame structure 12 may be deployed from a distal end of the delivery device 30. The frame structure 12 may be at least partially expanded towards the anchor 15 in order to capture the chordae tendineae 40 therebetween. As the frame structure 12 continues to be expanded to a fully expanded state, for example by continued advancement of the proximal pusher 72 as shown in FIG. 82C, the chordae tendineae 40 may be sandwiched between the anchor 15 and the frame structure 12. The frame structure 12 and anchor 15 may thus be anchored to the chordae tendineae 40.

In some embodiments, the frame structure 12 and the anchor 15 may be located within the same lumen of the delivery device 30 prior to deployment. In some embodiments, the frame structure 12 and the anchor 15 may be located within different lumens of the delivery device 30.

In some embodiments, the frame structure 12 and the anchor 15 may be deployed from the same opening (e.g., the side port 215) in the delivery device 30. In some embodiments, the frame structure 12 and the anchor 15 may be deployed from different openings in the delivery device 30.

The valve prosthesis 10 may then be released from the delivery device 30. Releasing the valve prosthesis 10 from the delivery device 30 may comprise expanding the valve prosthesis 10 from the unexpanded configuration to the expanded configuration. For example, expanding the frame structure 12 and releasing the frame structure 12 may occur simultaneously as described herein. Alternatively, the frame structure 12 may be released prior to or after being expanded.

After the frame structure 12 has been expanded and anchored to the native valve 4 as described herein, the proximal pusher 72 may be retracted. The delivery device 30, comprising the guidewire 54, may then be removed from the heart 2.

FIG. 82D shows retraction of the proximal pusher 72 towards the proximal end of the delivery device 30. FIG. 82E shows removal of the delivery device 30, proximal pusher 72, tether 78, and inner shaft 52 from the heart 2. FIG. 82F shows removal of the guidewire 54 from the heart 2.

FIG. 82G shows the valve prosthesis 10 fully expanded with the native valve leaflets 42 and chordae tendineae 40 captured between the frame structure 12 and the anchor 15. As described herein, the valve prosthesis 10 may comprise one or more valve segments 14 disposed therein to replace the native valve leaflets 42.

Although the steps above show a method of deploying a valve prosthesis 10 within a native valve 4 in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as necessary to assemble at least a part of an article.

For example, in some embodiments deploying the valve prosthesis 10 may occur in multiple steps such that a portion of the valve prosthesis 10 (e.g., anchor 15) may be deployed before another portion the valve prosthesis 10 (e.g., frame structure 12). Alternatively. or in combination, in some embodiments, deploying the anchor 15 may occur in multiple steps such that a portion of the anchor 15 may be deployed before being advanced through the native valve 4 and another portion of the anchor 15 may be deployed after being advanced through the native valve 4. Alternatively. or in combination, the delivery device 30 may be advanced from the left atrium 25 to the left ventricle 26 with the valve prosthesis 10 undeployed. In many embodiments, the frame structure may 12 be balloon-expandable and the delivery device may comprise a balloon instead of or in addition to the proximal pusher 72 in order to expand the frame structure 12. Alternatively, or in combination, the anchor 15 may be released after the frame structure 12 has been expanded within it.

As shown in FIG. 83, the anchor 15 may be disposed in the inner shaft 52 and maintained in the delivery configuration by radial constriction from the inner shaft 52. Advancement of the anchor 15 out of the side port 215 of the inner shaft 52 may actuate the anchor 15 into the deployed configuration. The proximal end 57 of the anchor 15 may be detachably coupled to a tether 78 within the lumen of the inner shaft 52 as described herein. Although the anchor 15 is described as being pushed out of the delivery catheter in some embodiments, one will appreciate from the description herein that different mechanisms may be employed to deploy the anchor 15 depending on the anchor 15 and/or shaft 52 design. In some respects, pushing is used somewhat interchangeably with rotation in reference to deployment of the anchor 15. For example, the anchor 15 can be rotated out of the side opening 215 with a rotational action.

FIGS. 84A-84D show an exemplary delivery device 30 including a rotatable anchor drive shaft 82. The delivery device 30 is configured to deploy the anchor 15 with a "flat screw deployment" mechanism. The anchor 15 may be substantially similar to any of the anchors described herein. In some embodiments, the anchor 15 may be coupled to the delivery device 30 and/or a frame structure 12 as described herein. The frame structure 12 may be substantially similar to any of the frame structures described herein. The delivery device 30 may comprise an inner shaft 52 and an outer sheath 50. The inner shaft 52 may be substantially similar to any of the inner shafts described herein. The outer sheath 50 may be substantially similar to any of the outer shafts described herein. The anchor 15 may be coupled to the inner shaft 52 as described herein. The frame structure 12 may be coupled to the inner shaft 52, for example around the inner shaft 52 or at a distal end of the inner shaft 52, as described herein.

The delivery device 30 may further comprise the anchor drive shaft 82. The anchor 15 may be disposed on or around the anchor drive shaft 82 in a screw-like undeployed configuration. FIG. 84B shows an exemplary anchor 15 disposed around anchor drive shaft 82 in a screw-like undeployed configuration with the outer sheath 50 removed in order to show the internal components of the delivery device 30 in relation to the undeployed valve prosthesis 10. At least a portion of the anchor drive shaft 82, for example a distal end (e.g., deployment drive 83), may be operably coupled to the anchor 15. The anchor drive shaft 82 may be rotatable relative to the outer shaft 15. The anchor drive shaft 82 may be configured to transmit rotational motion and/or torque to the anchor 15 in order to rotate the anchor out of the delivery device 30 and/or around the one or more native valve structures.

Deployment of the anchor 15 from the delivery device 30 may be facilitated by combined retraction of at least a portion of the outer sheath 50 relative to the inner shaft 52 to form or expose a lateral opening in the delivery device 30 and rotation of an anchor drive shaft 82 relative to the outer sheath 50 and/or inner shaft 52. The anchor 15 may be actuated from a delivery configuration (shown in FIG. 84B) to a deployed configuration (shown in FIG. 84C). The delivery configuration may be substantially similar to any of the delivery configurations described herein. For example, the anchor 15 may comprise a compact screw-like spiral shape when disposed around the inner shaft 52 in the delivery configuration. The deployed configuration may be substantially similar to any of the deployed configurations described herein. For example, the anchor 15 may comprise a flat spiral shape in the deployed configuration and at least a portion of the anchor 15 may be disposed about or proximal to a distal end of the inner shaft in the deployed configuration. The outer sheath 50 may be retracted such that a lateral opening is formed and the distal end 22 of the anchor 15 is exposed. Continued rotation of the anchor drive shaft 82 may actuate the anchor 15 out of the opening into the deployed configuration through its coupling with deployment drive 83.

In some embodiments, the outer sheath 50 may be moved back and forth over the anchor drive shaft 82 prior to, during, or after rotation of the anchor drive shaft 82 in order to "ratchet" incremental portions of the anchor 15 out of the delivery device 30 and away from the inner shaft 52. For example, the anchor 15 may be deployed by a retraction of the inner shaft 52 followed by a series of rotations of the anchor drive shaft 82 followed by an advancement of the anchor drive shaft 82, which may be repeated as needed to deploy the full anchor 15.

The anchor 15 may be releasably coupled to the deployment drive 83. Once the anchor 15 is in the deployed configuration, the deployment drive 83 may remain connected until the anchor 15 is fully secured around the diseased valve and fully deployed implant valve. The deployment drive 83 may be used to translate the anchor 15 distally such that it sits at least partially around the frame structure 12 (as shown in FIG. 84D). The anchor 15 may then be advanced through the native valve and rotated around one or more native structures as described herein. Alternatively, the deployment drive 83 may be disconnected from the anchor 15 prior to the anchor 15 being secured to the one or more native structures of the diseased valve.

The anchor 15 may be deployed from the delivery device 30 in the left atrium of the heart and advanced into the left ventricle through the diseased mitral valve as described herein. Alternatively, the anchor 15 may be deployed from the delivery device 30 in the left ventricle of the heart as described herein. Alternatively, the anchor 15 may be partially deployed in the left atrium, advanced into the left ventricle, and then fully deployed in the left ventricle as described herein.

In some embodiments, deployment of the anchor 15 and capture of the one or more structure of the native valve may occur in a stepwise fashion. For example, the anchor 15 may be deployed before being rotated to capture the one or more structures.

In some embodiments, deployment of the anchor 15 and capture of the one or more structure of the native valve may occur simultaneously. For example, rotation of the anchor drive shaft 82 may rotate the anchor 15 out of the delivery device 30. If deployed in the left ventricle, the free end 22 of anchor 15 may be rotated around the one or more native valve structures as the anchor 15 is rotated out of the delivery device.

The distal free end 22 of the anchor may comprise a key 84 configured to slide into a complementary lock 85 located on the band of the anchor 15. When the anchor 15 is fully deployed and wrapped around the frame structure 12 and the diseased valve, the key 84 may slide over the band of the anchor 15 until it falls into place within the lock 85. Once engaged, the key 84 and lock 85 may hold the anchor 15 in place against the one or more structures of the native valve. The respective locations of key 84 and lock 85 may be configured to lock the anchor 15 into the fully deployed configuration, the fully undeployed configuration, or any intermediate configuration therebetween. Any number of key 84 and lock 85 elements may be placed on the anchor 15 in order to allow for one or more locked configurations as desired. The key 84 and lock 85 may be replaced with or combined with other locking mechanisms. For example, a frictional band may replace or be added to the key 84 and lock 85 locking mechanism.

Referring to FIGS. 45-54, any of the anchors 15 described herein may include one or more deflecting features 23 disposed on or along the anchor body in order to cause the free end 22 of the anchor 15 to "wiggle" or deflect away from the longitudinal axis of the delivery device 30 as it is exits the delivery device, thereby causing a change in the deployment angle of the free end 22. The deflecting feature 23 may be positioned at a location along the anchor 15 such that deflection of the free end 22 is "timed" to occur with the free end 22 wrapping back towards the delivery device 30 (for example as shown in FIG. 6A) such that the free end 22 deflects towards the preferred side of the delivery device 30 as described herein. The free end 22 may, for example, be deflected each time it wraps back towards the delivery device 30.

Figure 45:
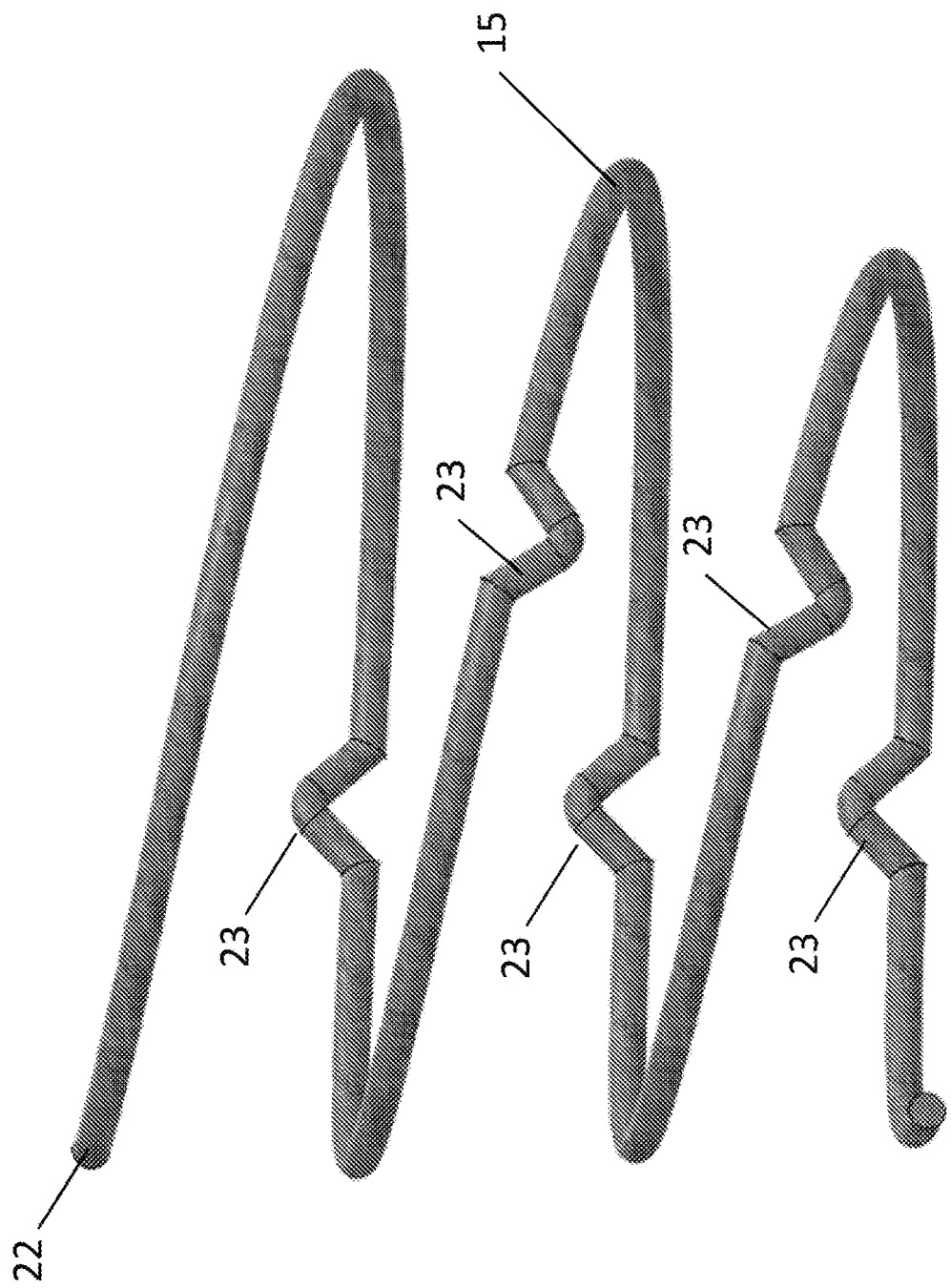
FIG. 45 shows an anchor comprising a plurality of deflection features disposed therealong, in accordance with embodiments.

FIG. 45 shows an anchor 15 comprising a plurality of deflection features 23 disposed therealong. The anchor 15 may be substantially similar to any of the anchors described herein. For example, the anchor 15 can be a helical or spiral wire anchor in the deployed configuration as shown. The plurality of deflection features 23 may be disposed at a plurality of locations along the length of the anchor 15. In some embodiments, the plurality of deflection features 23 may be positioned along the length of the anchor 15 at locations along the anchor 15 such that deflection of the free end 22 is "timed" to occur with the free end 22 wrapping back towards the delivery device as described herein. The free end 22 may, for example, be deflected each time it wraps back towards the delivery device as described herein. The plurality of deflection features 23 may, for example comprise a plurality of wave-like features (e.g., similar to FIGS. 9A-9D). Alternatively, or in combination, one or more of the plurality of deflection features 23 may comprise a bend, a hump, or the like. In some embodiments, the plurality of deflection features 23 may have the same shape. In some embodiments, at least one of the plurality of deflection features 23 may have a different shape from one or more of the other deflection features 23. The anchor 15 may comprise a plurality of loops as described herein. In some embodiments, one or more of the plurality of loops may comprise a deflection feature 23. In some embodiments, one or more of the plurality of loops may comprise a plurality deflection features 23. Alternatively, or in combination, one or more of the loops may not comprise a deflection feature 23. In some embodiments, a plurality of deflection features 23 may be disposed along the plurality of loops such that each loop comprise a single deflection feature 23.

In some embodiments, the anchor 15 may comprise a helical or spiral shape in the deployed configuration as described herein. The deflection feature 23 may be comprise one or more bends or kinks along the helical anchor which are discontinuous with the helical shape. In some embodiments, the deflection features 23 may be attached (fixedly or detachably) to the helical or spiral shape, for example in the form of a tab or a wing or the like. Alternatively or in combination, the deflection features 23 may comprise discontinuities in the helical or spiral shape, for example in the form of bends, kinks, waves, humps, bumps, or the like in the helical wire itself. In some embodiments, the deflection features 23 may position a portion of the wire inside, outside, above, below, or at an angle to the otherwise relatively continuous helical or spiral shape of the anchor 15.

FIGS. 46-47 show various views of an anchor 15 comprising a plurality of deflection features 23. The anchor 15 may be substantially similar to any of the anchors described herein, for example a spiral wire anchor as shown. The plurality of deflection features 23 may be disposed at a plurality of locations along the length of the anchor 15 as described herein. The anchor 15 may be deployed from an aperture 31 at or proximate to the distal end of a delivery device 30 as described herein. Interaction of the plurality of deflection feature 23 with the aperture 31 may cause free end 22 to deflect during deployment from the elongated configuration to the deployed configuration in order to facilitate wrapping of the anchor 15 around the delivery device 30 as described herein.

The one or more deflection features 23 may be configured so as to resist straightening of the bends when the anchor 15 is in the elongated configuration. The one or more deflection features 23 may be configured interact with the frame structure 12 to facilitate anchoring. The one or more deflection features 23 may be configured not to interact with the frame structure 12 in order to facilitate anchoring. The one or more deflection features may be introduced to the anchor 15 without adding substantial circumferential compliance into the coil.

Figure 49:
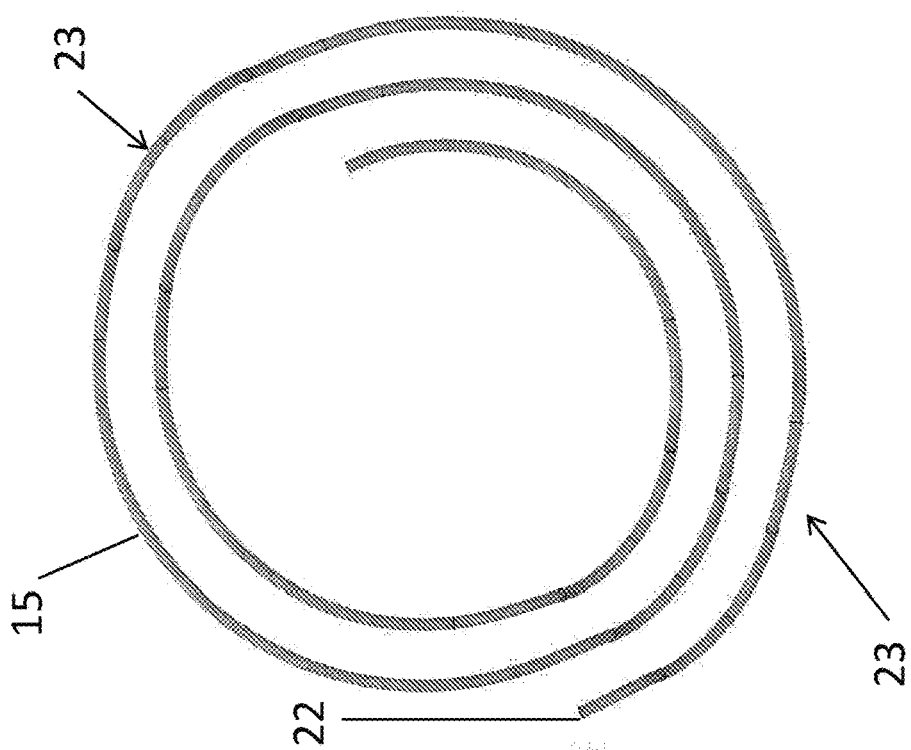
FIGS. 48-49 show various views of an anchor comprising a plurality of deflection features therealong, in accordance with embodiments.
Figure 48:
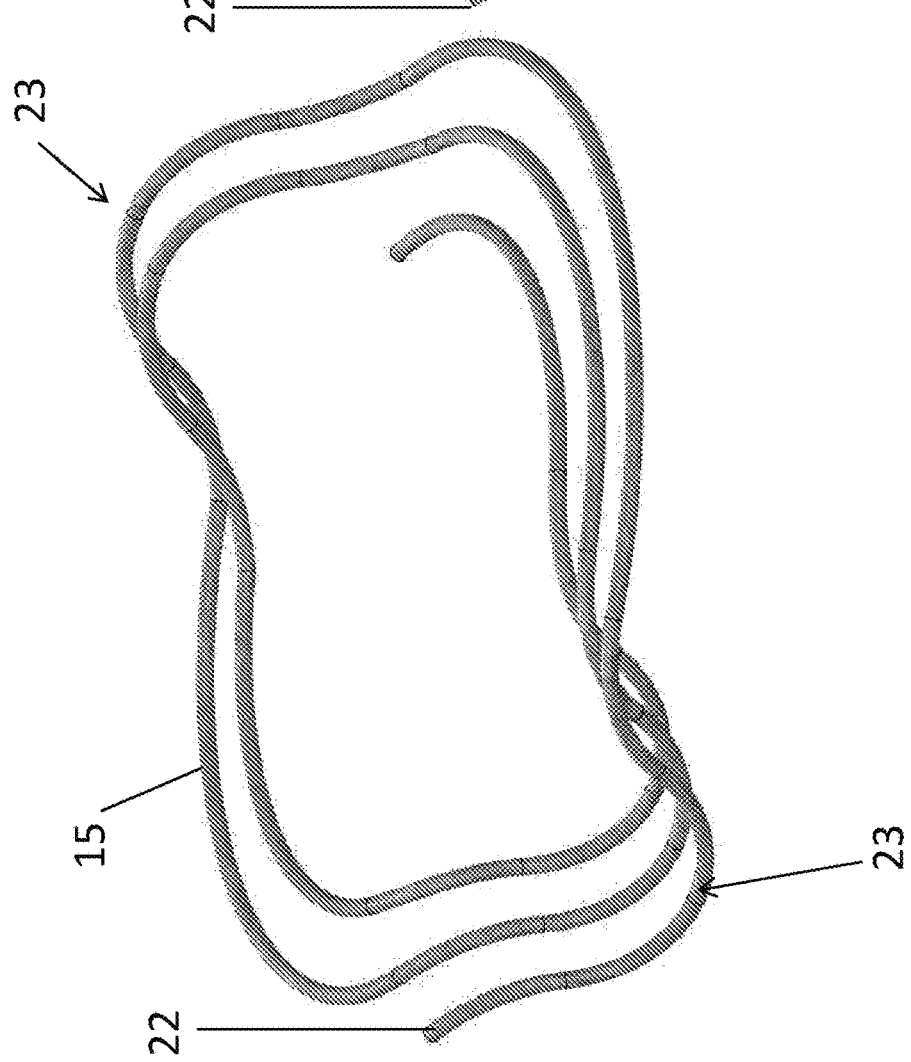

FIGS. 48-49 show various views of another anchor 15 comprising a plurality of deflection features 23. The anchor 15 may be substantially similar to any of the anchors described herein, for example a spiral wire anchor as shown. The plurality of deflection features 23 may be disposed at a plurality of locations along the length of the anchor 15 as described herein. The plurality of deflection features 23 may comprise a plurality of waves, bends, humps, or the like as described herein.

Figure 50:
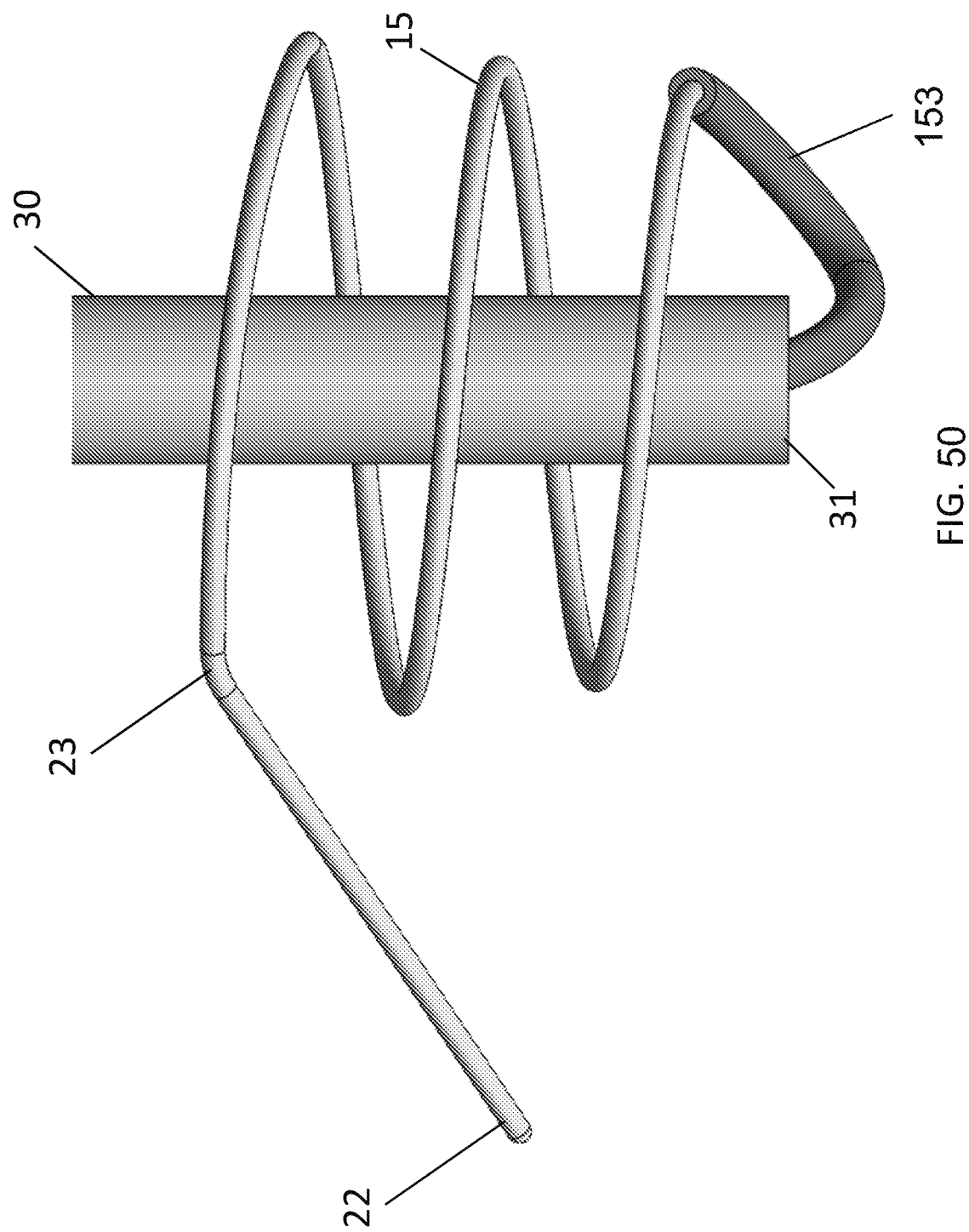
FIG. 50 shows a side view of an anchor having an optional tip orientation determined by a single deflection feature near a free end thereof, in accordance with embodiments.

FIG. 50 shows an anchor 15 having an optional tip 22 orientation determined by a single deflection feature near free end 22. The anchor 15 may be substantially similar to any of the anchors described herein, for example a helical anchor as shown. The anchor 15 may be detachably coupled to a delivery device 30 as described herein. The anchor 15 may comprise a single deflection feature 23 near the free end 22. The anchor 15 may be deployed from an aperture 31 of a delivery device 30 as described herein. Interaction of the deflection feature 23 with the aperture 31 may cause free end 22 to deflect during deployment from the elongated configuration to the deployed configuration in order to facilitate wrapping of the anchor 15 around the delivery device 30 as described herein. The free end 22 may be deflected to overlap the next turn in order to ensure that the free end wraps back around the delivery device 30. The single deflection feature 23 may, for example, comprise a bend configured to deflect the free end 22 proximally (e.g., towards a proximal portion of the anchor 15 and a distal end of the delivery device 30), distally (e.g., away from a proximal portion of the anchor 15 and towards a proximal portion of the delivery device 30), and/or radially (e.g., radially outwards or inwards from the main body of the anchor 15 and away from or towards the delivery device 30, respectively). In some embodiments, for example, the single deflection feature 23 may be configured to position the free end 22 adjacent one or more loops of the anchor 15 (i.e. the main body of the anchor 15) when the anchor 15 is in the deployed configuration. Alternatively, or in combination, the single deflection feature 23 may be configured to position the free end 22 such that it angles towards a proximal end of the anchor 15 when the anchor 15 is in the deployed configuration. Alternatively, or in combination, the single deflection feature 23 may be configured to position the free end 22 such that it angles towards a distal end of the delivery device 30 when the anchor 15 is in the deployed configuration.

In at least some instances, it may be sufficient to initially deflect the free end 22 during wrapping as described herein in order to form the first loop around the delivery device 30. Once the first loop as wrapped around the delivery device 30, the remaining loops may be more inclined or biased to wrap correctly around the delivery device 30 without additional deflection or manipulation.

In at least some instances, deflection (e.g., angling proximally, distally, and/or radially outward) of the free end 22 away from the loops of the proximal portion of the anchor 15 may aid in capture of the one or more structures by forming a "grabber" arm.

In at least some instances, the absence of additional deflection features 23 on the loops of the anchor 15 may facilitate rotation of the loops around the one or more structures as described herein. Alternatively, or in combination, the absence of additional deflection features 23 on the loops may enhance the circumferential strength of the loops of the anchor 15.

FIGS. 51-53 show various view of an anchor 15 having an optional tip 22 orientation determined by a single deflection feature 23 near free end 22. Anchor 15 may be substantially similar to the anchor 15 shown in FIG. 50 except that the handedness of the anchor may be reversed. The deflection feature 23 may deflect the free end 22 of the anchor 15 towards a distal end of the delivery device 30 and a proximal end of the anchor 15 such that it may be positioned adjacent the loops of the anchor 15 as described herein.

FIG. 54 shows a clockwise anchor 15 having an optional tip 22 orientation determined by a single deflection feature 23 near free end 22. FIG. 55 shows an anchor 15 substantially similar to the anchor in FIG. 54 but with a counter-clockwise spiral. FIG. 56 shows a clockwise anchor 15 having an optional tip 22 orientation determined by a single deflection feature 23 near free end 22. FIG. 57 shows an anchor 15 substantially similar to the anchor in FIG. 56 but with a counter-clockwise spiral. The anchor 15 may be substantially similar to any of the anchors described herein, for example a spiral band anchor as shown. The anchor 15 may be detachably coupled to a delivery device 30 as described herein. The anchor 15 may comprise a single deflection feature 23 near the free end 22. The anchor 15 may be deployed from an aperture 31 of a delivery device 30 as described herein. Interaction of the deflection feature 23 with the aperture 31 may cause free end 22 to deflect during deployment from the elongated configuration to the deployed configuration as described herein. In some embodiments, the anchor 15 may be configured not to wrap around the distal end of the delivery device 30 in the deployed configuration. The loops of the anchor 15 may instead lie entirely distal of the distal end of the delivery device 30 as shown. The single deflection feature 23 may, for example, comprise a bend configured to deflect the free end 22 proximally (for example, as shown in FIGS. 55 and 57), distally (for example, as shown in FIGS. 54 and 46), and/or radially (for example, as shown in FIG. 53). In at least some instances, deflection (e.g., angling proximally, distally, and/or radially outward) of the free end 22 away from the loops of the proximal portion of the anchor 15 may aid in capture of the one or more structures by forming a "grabber" arm.

In some embodiments, the anchor 15 may comprise a flat spiral shape in the deployed configuration as described herein. The deflection feature 23 may be comprise one or more bends or kinks along the spiral anchor which are discontinuous with the spiral shape. In some embodiments, the deflection features 23 may be attached (fixedly or detachably) to the spiral shape, for example in the form of a tab or a wing or the like. Alternatively or in combination, the deflection features 23 may comprise discontinuities in the spiral shape, for example in the form of bends, kinks, waves, humps, bumps, or the like in the spiral wire itself. In some embodiments, the deflection features 23 may position a portion of the wire radially inside, radially outside, above, below, or at an angle to the otherwise relatively continuous spiral shape of the anchor 15.

In at least some instances, the absence of additional deflection features 23 on the loops of the anchor 15 may facilitate rotation of the loops around the one or more structures as described herein. Alternatively, or in combination, the absence of additional deflection features 23 on the loops may enhance the circumferential strength of the loops of the anchor 15.

While the one or more deflection features have been described herein with reference to changing the angle of a free end of an anchor of a valve prosthesis during deployment from a delivery device, it will be understood by one of ordinary skill in the art that such features may be used in a variety of settings.

Alternatively, or in combination with, the deflection feature(s) 23 built into the anchor 15, the anchor 15 may include a movable core wire (e.g., wire or rod) therein configured to change the shape of the distal portion of the anchor assembly. For example, FIGS. 7A-25 show a movable or translatable core wire 74 configured to be translated longitudinally within and relative to the anchor 15 in order to change the shape of the distal portion of the anchor 15. The movable core element may include one or more deflecting features 33 such that, when advanced distally past the free end 22 of the anchor 15, a distal tip of the core wire 74 may be caused to "wiggle" or deflect away from the curvature of the anchor body 15 and change the deployment angle of the distal tip out of the anchor body 15 in order to facilitate wrapping of the anchor 15 around the delivery device 30 as described herein. The movable core wire 74 may be translated within the anchor 15 before, during, or after deployment of the anchor from the undeployed configuration to the deployed configuration. For example, the movable core element 74 may be translated within the anchor 15 before deployment of the anchor into a self-assembly state in order to facilitate wrapping of the anchor 15 around the delivery device (e.g., by extending past the free end 22 of the anchor and acting similarly to the anchor deflecting features 23 described herein). Alternatively, or in combination, the movable core wire 74 may be translated within the anchor 15 during deployment of the anchor 15 in order to actively or reactively "wiggle" or deflect the angle of the distal tip 22 of the anchor 15 as it deploys as described herein. Alternatively, or in combination, the movable core wire 74 may be translated with the anchor 15 into an encircling state in order to facilitate grasping of and rotation of the anchor around the one or more native structures as described herein. By utilizing a movable core wire 74 comprising one or more deflecting features 33, the anchor 15 may comprise a relatively simpler shape compared to an anchor 15 having one or more deflecting features 23 itself, which may facilitate design and fabrication of the anchor 15. For example, the anchor 15 may have a shape with a substantially continuous curvilinear shape and/or the reduction of complex bends. Alternatively, or in combination, the behavior of the free end 22 of the anchor 15 and/or core wire 74 may be optimized to facilitate various deployment and/or implantation steps of the anchor 15. The anchor 15 may be relatively stiffer than the movable core wire 74 in order to prevent or reduce deflection of the body of the anchor 15 when the movable core wire 74 is disposed in a lumen thereof. In some embodiments, the movable core wire 74 may comprise a relatively more complex shape compared to the anchor 15 in order to guide and the free end 22 of the relatively stiffer anchor 15.

In various embodiments, the anchor 15 and/or core wire 74 may have a spiral-shaped deployed configuration. In various embodiments, spiral refers to a shape with windings about a central axis. The spiral may be continuous. The windings may gradually widen (or tighten) along the length. The spiral may be formed in a flat plane perpendicular to the central axis. In various embodiments, the anchor 15 and/or core wire 74 may have a deployed configuration that is not formed in a flat plane, or in other words the deployed shape is formed in a three-dimensional and/or non-degenerate space. In various embodiments, the anchor 15 and/or core wire 74 may have a conical-shaped deployed configuration including, but not limited to, tubular, conical, frustoconical, and/or helical shapes.

In various embodiments, the core wire 74 may be configured to be removed from the valve prosthesis (e.g., translated proximally out of the body) after the anchor 15 has been deployed. The core wire 74 may be removed with the delivery device as will be understood by one of ordinary skill in the art based on the disclosure herein.

In various embodiments, the core wire 74 may be configured to remain within the anchor 15 after the anchor 15 has been deployed. A proximal end of the core wire 74 may be released from the delivery device 30 as will be understood by one of ordinary skill in the art based on the disclosure herein.

In various embodiments, a proximal end of the core wire 74 may be directly manipulated by a user outside the body in order to translate the core wire 74 within the anchor 15. In various embodiments, a proximal end of the core wire 74 may be indirectly manipulated by a user, for example, with a translatable pusher section 73 (as described elsewhere herein) disposed within the delivery device and coupled to the proximal end of the core wire 74 adjacent the anchor 15, in order to translate the core wire within the anchor.

FIG. 7A shows an exemplary straight anchor 15 core wire 74 configured to translate therethrough. The anchor 15 may comprise a lumen or channel 71 in which the core wire 74 may be disposed. The anchor 15 is shown as a straight anchor with a central channel 71, however it will be understood by one of ordinary skill in the art that the anchor 15 may have any of the configurations described herein. The core wire 74 is shown as a straight wire, however it will be understood by one of ordinary skill in the art that the core wire 74 may have any of the configurations described herein. Advancement of the distal tip 75 of the straight core wire 74 through an aperture at the free end 22 of the anchor 15 may result in the core wire 74 being deployed such that the free end 22 and/or distal tip 75 experiences no deflection and moves co-axially with the longitudinal axis of the anchor 15. When subsequently deployed out of the delivery device, the free end 22 and/or distal tip 75 may similarly experience no deflection and instead may move co-axially with the longitudinal axis of the delivery device.

FIG. 7B shows a core wire 74 comprising a deflecting feature 33. The deflecting feature 33 may, for example, comprise a pre-formed wave, bend, hump, or the like in the wire 74 (e.g., in a distal tip portion of the core wire 74). By adding a deflecting feature 33 to the core wire 74, the distal tip 75 may "wiggle" or deflect away from the longitudinal axis of the anchor 15 and/or delivery device as it exits the lumen 71 of the anchor 15 and change the deployment angle of the distal tip 75 beyond the free end 22. Deflection of the distal tip 75 of the core wire 74 may be caused by interaction of one or more changes in angle (shown here as A, B, C. and D) making up the deflecting feature 33 with the sides of lumen 71 (e.g., with an opening or aperture through which the core wire 74 is extruded). It will be understood by one of ordinary skill in the art from the teachings herein that the angle(s) of the deflecting feature 33 may be configured to deflect the distal tip 75 to any angle desired in any direction desired. The deflecting feature 33 may be positioned at a location along the core wire 74 such that deflection of the distal tip 75 is "timed" to occur with the distal tip 75 and/or free end 22 wrapping back towards the delivery device (for example as shown in FIG. 6A) such that the distal tip 75 and/or free end 22 deflects towards the correct side of the delivery device 30 as described herein. The lumen 71 of the anchor 15 may be sized and dimensioned to match or be slightly larger than the diameter of the core wire 74 in order to enable such interactions. In some embodiments, the core wire 74 may be made of a shape memory material such as nitinol in order to allow shaping of the deflection feature 33. In some embodiments, the core wire 74 may be made of a heat treatable material in order to allow shaping of the deflection feature 33.

The anchor 15 may be relatively stiffer than the core wire 74. The anchor 15 may be sufficiently stiffer than the core wire 74 such that the core wire 74 anchor 15 experiences little or no deflection itself when the core wire 74 is disposed therein.

Figure 8D:
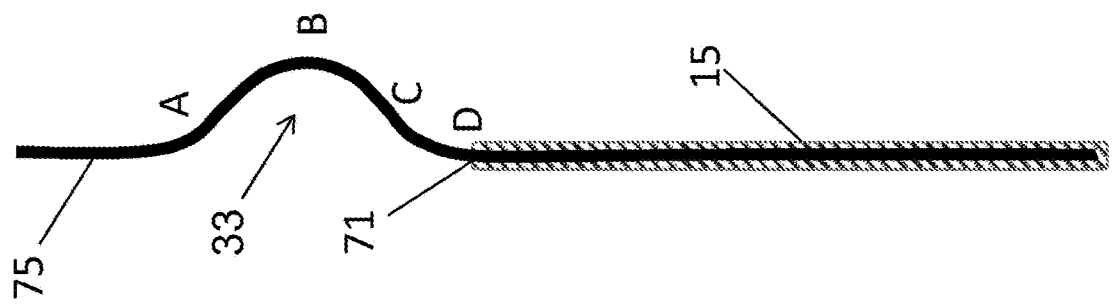
FIGS. 8A-8D show sequential cross-sectional views of a core comprising a deflecting feature during deployment from an anchor, in accordance with embodiments.
Figure 8C:
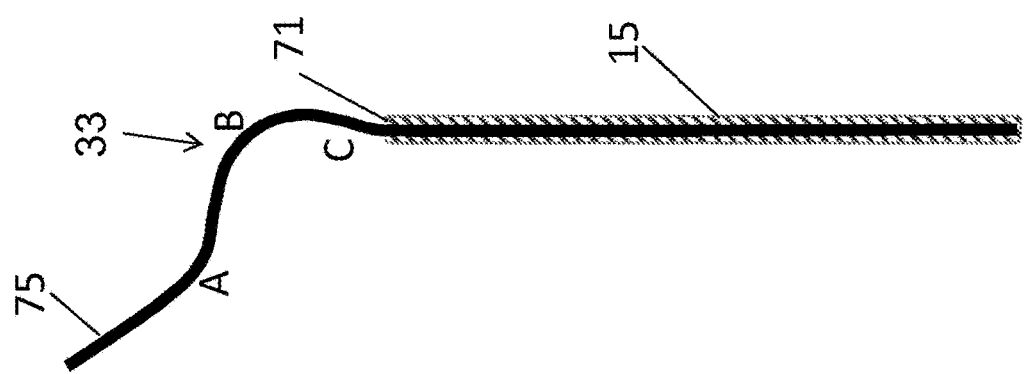
Figure 8B:
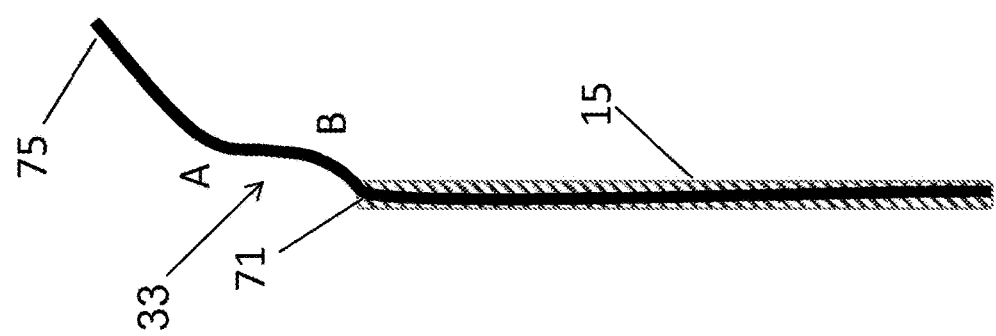
Figure 8A:
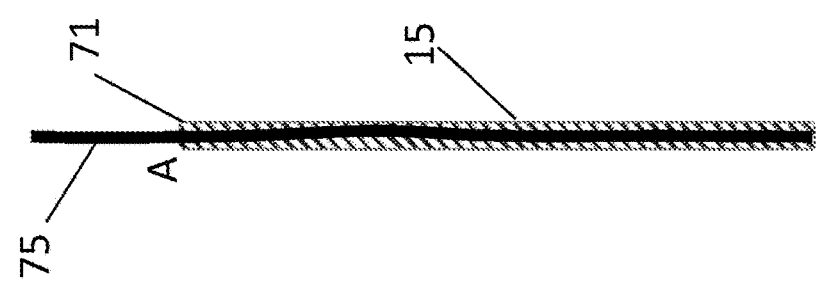

FIGS. 8A-8D show sequential cross-sectional views of a core wire 74 comprising a deflecting feature 33 during deployment from the free end 22 of an anchor 15. FIG. 8A shows the distal tip 75 as it begins advancing out of the opening in the free end 22 of the anchor 15 up to first change in angle A. As the distal tip 75 continues to be deployed (up to change in angle B), the deflection feature 33 may move past the opening in the free end 22, releasing the radial constriction of change in angle A and allowing the distal tip 75 of the core wire 74 to deflect in a first direction (shown in FIG. 8B as a deflection towards the right side of the anchor 15). Continued advancement of the core wire 74 out the opening in the free end 22 (up to change in angle C) may further deflect the distal tip 75 in second direction (shown in FIG. 8C as shown as a deflection towards the left side of the anchor 15) as change in able B is released from radially constriction. Continued advancement of the distal tip 75 out the opening of the free end 22 (up to change in angle D) may further deflect the distal tip 75 again as change in angle C is released from radial constriction, for example co-axially with the longitudinal axis of the anchor 15 (shown in FIG. 8D). Advancing the remainder of the distal tip 75 out of the anchor 15 may result in no further deflection unless and until a second deflection feature 33 is encountered at the opening to the lumen 71.

In some embodiments, the distal tip 75 may comprise an elongated delivery configuration as described herein. The deflection feature 33 may comprise one or more bends or kinks along the length of the elongated distal tip 75. The elongated distal tip 75 may be substantially straight along a longitudinal axis thereof (for example, substantially co-axial with a longitudinal axis of the delivery device 30 as described herein). The deflection feature 33 may comprise one or more bends that position at least a portion of the core wire 74 discontinuous with the rest of the core wire 74, for example along an axis other than the longitudinal axis. For example, the deflection feature 33 may comprise a bend at an angle relative to the longitudinal axis or a plurality of bends to form a portion (for example, a wave, bump, hump, or the like) which starts and ends along the longitudinal axis but which is disposed off-axis (e.g., parallel to or at an angle to the longitudinal axis) along at least a portion of the deflection feature 33. In some embodiments, the deflection features 33 may be attached (fixedly or detachably) to the distal tip 75, for example in the form of a tab or a wing or the like.

In some embodiments, at least a portion of the core wire 74 may comprise a curved shape when the anchor 15 is in the deployed configuration. The curved shape may, for example, comprise a coil a helix, or a spiral as described herein. The curved shape may be configured to encircle one or more structures of the native valve. The curved shape may correspond to the curved shape of the anchor 15 in the deployed configuration. The deflection feature 33 may be comprise one or more bends or kinks along the core wire 74 which are discontinuous with the curved shape. In some embodiments, the deflection features 33 may be attached (fixedly or detachably) or adjacent to the curved shape, for example in the form of a tab or a wing or the like. Alternatively or in combination, the deflection features 33 may comprise discontinuities in the curved shape, for example in the form of bends, kinks, waves, humps, bumps, or the like in the curved wire itself. In some embodiments, the deflection features 33 may position a portion of the wire inside, outside, above, below, or at an angle to the otherwise relatively continuous curved shape of the core wire 74.

Figure 9A:
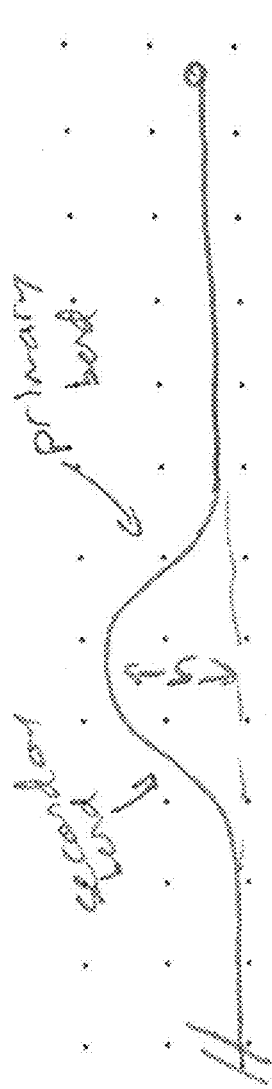
FIGS. 9A-9D show various optional, non-limiting configurations of a deflection feature, in accordance with embodiments.
Figure 9B:
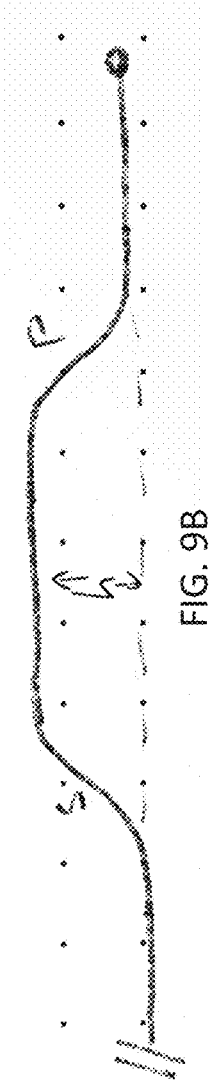
Figure 9C:
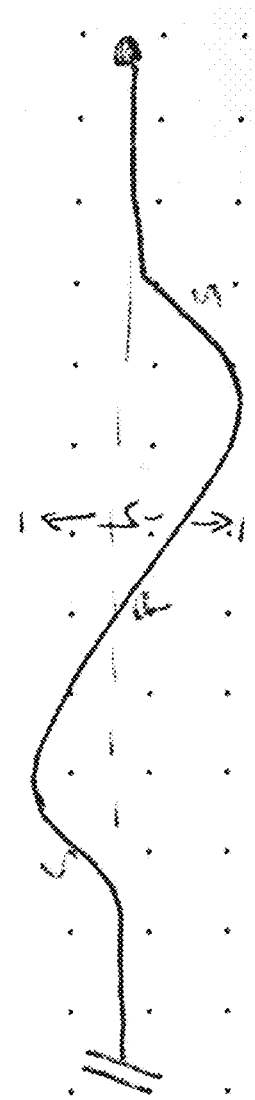
Figure 9D:
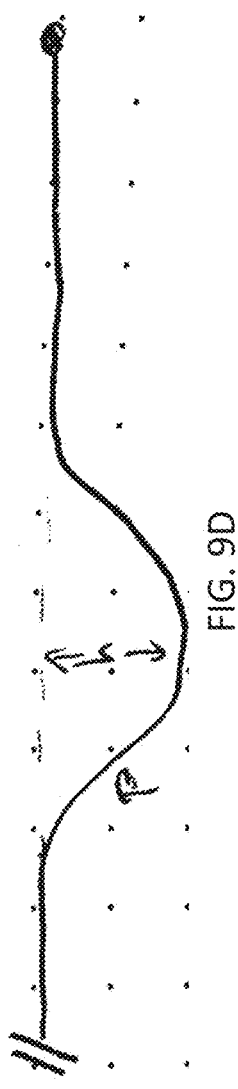

FIGS. 9A-9D show various optional, non-limiting configurations of a deflection feature 33. FIG. 9A shows a deflection feature 33 which may bend away from a longitudinal axis of the anchor 15 and/or delivery device 30 at a primary bend P and bend towards the longitudinal axis at a secondary bend S. The deflection feature 33 may comprise a height H which may correspond to the maximum orthogonal distance of the deflection feature 33 away from the longitudinal axis. FIG. 9B shows a deflection feature 33 which may be substantially similar to the deflection feature 33 shown in FIG. 9A but with a longer distance between the primary bend P and secondary bend S. FIG. 9C shows a deflection feature 33 having a primary bend P and two secondary bends S which for an "s"-like configuration about the longitudinal axis. The deflection feature 33 may comprise a maximum orthogonal distance H extending on either side of the longitudinal axis. FIG. 9D shows a deflection feature 33 substantially similar to the deflection feature 33 of FIG. 9A but the direction of deflection is down instead of up.

It will be understood by one of ordinary skill in the art that the number of bends, the angle of each bend, the length, the shape, the location, and/or the orientation of the deflection feature 33, the number of deflection features 33, and/or the diameter and/or material of the core wire 74 and/or anchor 15 may be adjusted in order to effect a desired amount and orientation of the deflection of the distal tip 75 of the core wire 74 and/or free end 22 of the anchor 15.

Figure 11:
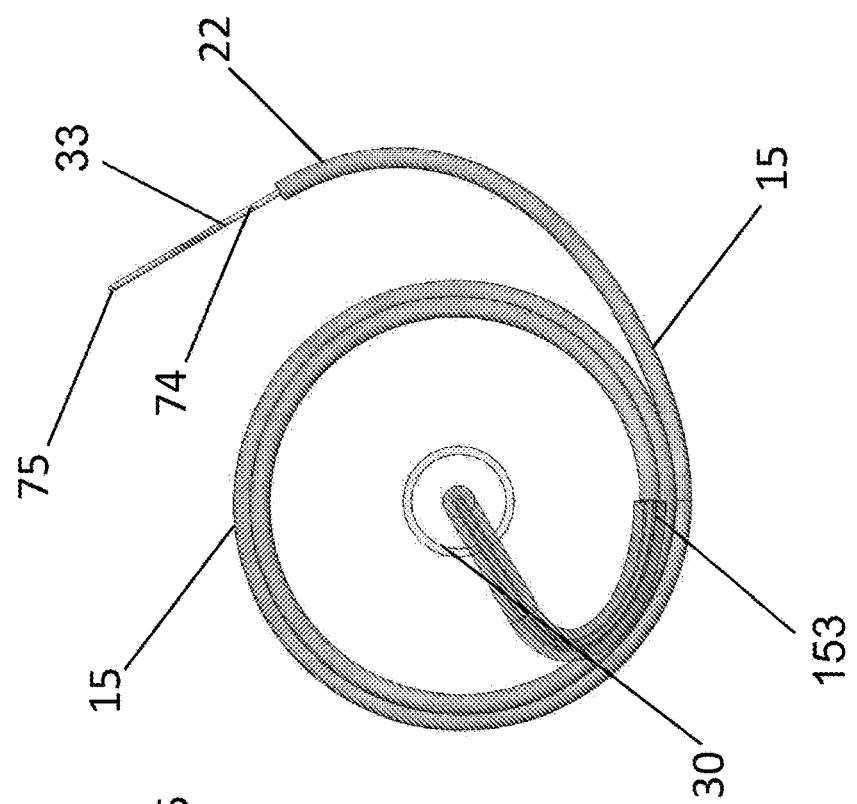
FIG. 11 shows a top view of the anchor of FIG. 10.
Figure 10:
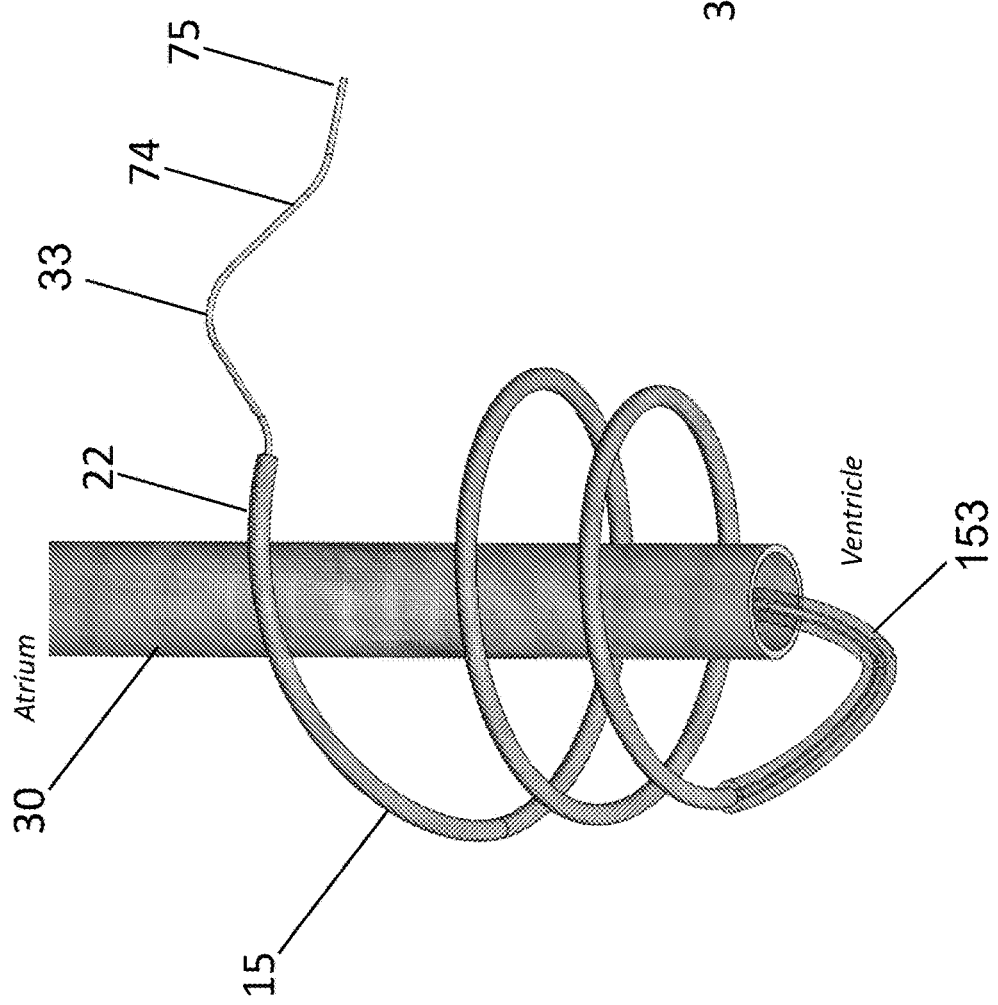
FIG. 10 shows a perspective bottom view of an exemplary anchor comprising a translatable core wire disposed therein, the core wire having a deflection feature disposed thereon and being in a nominal state relative to the anchor, in accordance with embodiments.

FIG. 10 shows a perspective bottom view of an exemplary anchor 15 comprising a translatable core wire 74 disposed therein, the core wire 74 having a deflection feature 33 disposed thereon and being in a nominal state relative to the anchor 15. FIG. 11 shows a top view of the anchor 15 of FIG. 10. The anchor 15 may be substantially similar to any of the anchors described herein, for example a helical anchor comprising a lumen or channel 71 in the deployed configuration as shown. The anchor 15 may be directly coupled to a frame structure 12, for example at a proximal or distal end thereof, as described herein. Alternatively, or in combination, the anchor 15 may be detachably coupled to the delivery device 30 prior to deployment at the native valve. The delivery device 30 may be substantially similar to any of the delivery devices described herein. For example, a proximal end 57 of the anchor 15 may be detachably coupled to the inner shaft 52 during delivery to the native valve. Alternatively, or in combination, a proximal end 57 of the anchor 15 may be coupled to a distal end of the frame structure 12 or a proximal end of the frame structure 12. The anchor 15 is shown in a deployed configuration. The anchor 15 may comprise a delivery (e.g., elongated) configuration (e.g., as shown in FIG. 1) and a deployed configuration (e.g., as shown in FIG. 2). In various embodiments, the anchor may be self-expanding and may move to the deployed configuration as it is removed from the delivery sheath as described herein. The anchor 15 may be configured to wrap at least partially around the frame structure 12 in the deployed configuration.

In various embodiments, the anchor 15 may have a generally helical shape in the deployed configuration. In various embodiments, the anchor 15 may be elongated—rather than helix-shaped—in the delivery configuration. For example, the anchor 15 may be elongated into a straight shape within the delivery device. In various embodiments, a portion of the anchor 15 may have a helical shape. In various embodiments, a substantial portion of the anchor 15 may have a helical shape. In various embodiments, the helical anchor 15 may be formed as a three-dimensional helix (in the deployed configuration) whereby the loops generally are positioned around the same axis (for example, a longitudinal axis of the delivery device 30).

Optionally, the anchor 15 may comprise a first portion comprising the helical shape and another portion. Alternatively, or in combination, the anchor 15 may comprise a plurality of helical portions. For example, the anchor 15 may comprise at least two helical portions having the same or different diameters. Alternatively, or in combination, the anchor 15 may comprise at least two helical portions having the same or different winding pitches.

The free end 22 of the anchor 15 may extend radially outward from the frame structure 12, and in particular from the remainder of the anchor 15 (for example, as shown in FIG. 11). In some embodiments, the anchor 15 may have a generally tubular shape. The free end 22 of the anchor 15 20 may extend radially outward from the tubular shape. In some embodiments, the anchor 15 may have a generally frusto-conical shape. The free end 22 of the anchor 15 may extend radially outward from the frustoconical shape. In some embodiments, the anchor 15 may have a generally cylindrical shape. The free end 22 of the anchor 15 may extend radially outward from the cylindrical shape. The free end 22 may be configured to encircle a larger radius than the main loops of the anchor 15. The larger diameter may facilitate capturing of one or more structures, for example the valve leaflets of the chordal tendineae within the sweep of the free end 22 when rotated as described herein.

The anchor 15 may comprise a movable core wire 74 disposed within a lumen or channel of the anchor 15 as described herein. A distal tip portion of the core wire 74 may comprise one or more deflection features 33 disposed thereon or therealong as described herein. For example the distal tip portion may comprise a single deflection feature 33. The core wire 74 may be translatable. The core wire 74 may translate distally and proximally within the lumen 71 of the anchor 15. Translation of the core wire 74 within the lumen 71 of the anchor 15 may cause the one or more deflection features 33 to deflect the distal tip 75 of the core wire 74 as it moves in or out of the anchor 15. For example, when advanced distally past the free end 22 of the anchor 15, a distal tip 75 of the core element 74 may be caused to "wiggle" or deflect away from the curvature of the curved anchor body 15 and change the deployment angle of the distal tip 75 of the core wire 74 out of the anchor body 15 in order to facilitate wrapping of the anchor 15 around the delivery device 30 as described herein.

Figure 13:
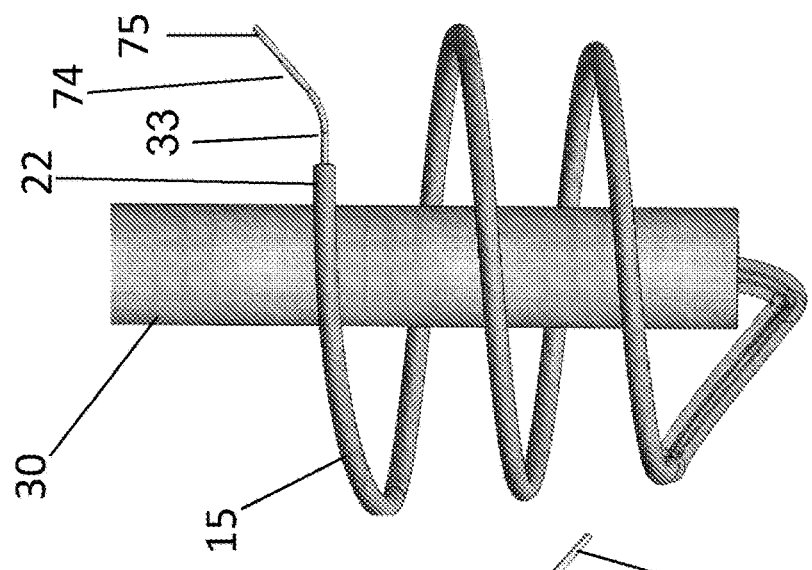
FIG. 13 shows a side view of the anchor of FIG. 10 with the core wire in an exemplary encircling state, in accordance with embodiments.
Figure 12:
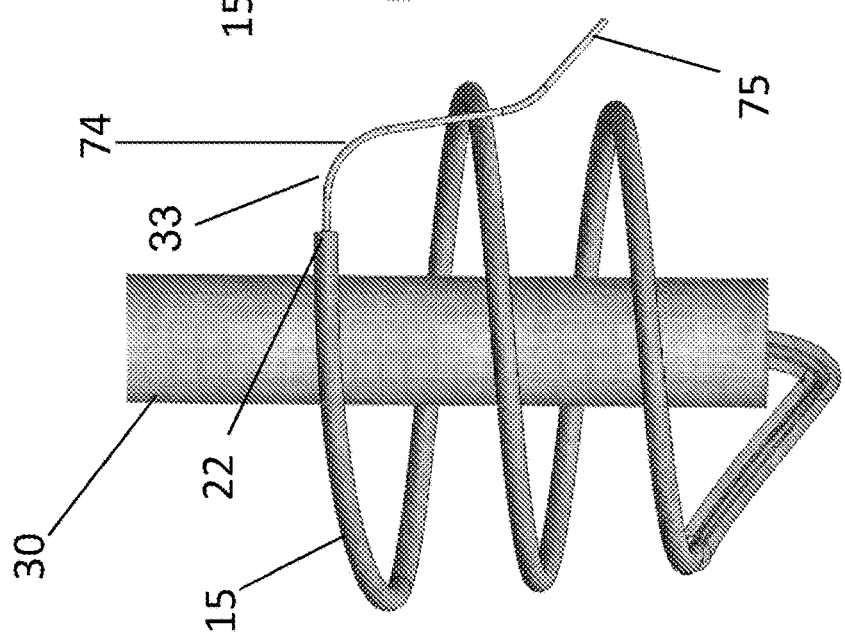
FIG. 12 shows a side view of the anchor of FIG. 10 with the core wire in a self-assembly state, in accordance with embodiments.

The movable core wire 74 may be translated within the anchor 15 before, during, or after deployment of the anchor 15 from the undeployed configuration to the deployed configuration. For example, the movable core wire 15 may be translated within the anchor 15 before deployment of the anchor 15 into a self-assembly state (e.g., as shown in FIG. 12) in order to facilitate wrapping of the anchor 15 around the delivery device (e.g., by extending past the free end 22 of the anchor 15 and acting similarly to the deflecting feature(s) 23 of the anchor 15). Alternatively, or in combination, the movable core wire 74 may be translated within the anchor 15 during deployment of the anchor 15 in order to actively or reactively "wiggle" or deflect the angle of the distal tip 75 as it deploys as described herein. Alternatively, or in combination, the movable core wire 74 may be translated with the anchor 15 into an encircling state (e.g., as shown in FIGS. 13 and/or 14) in order to facilitate grasping of and rotation of the anchor 15 around the one or more native valve structures as described herein.

FIG. 12 shows a side view of the anchor 15 of FIG. 10 with the core wire 74 in a self-assembly state. The core wire 74 may comprise a deflecting feature 33 configured to change the angle of distal tip 75 of the core wire 74 as the core wire 74 is translated distally or proximally within the lumen 71 of the anchor 15 as described herein. For example, the deflecting feature 33 may comprise a wave, bump, hump, or the like made up of a plurality of angle changes similar to the deflecting feature 33 shown in FIGS. 7A-7D. As shown in FIGS. 7A-7D, the distal tip 75 may be deflected to multiple positions (discretely or continuously) as the core wire 74 is translated out of the anchor body 15.

Deflection of the core wire 74 and distal tip 75 may be adjusted and/or optimized for various steps during deployment of the valve prosthesis 10 as described herein. For example, the distal tip 75 may be advanced into a self-assembly state prior to or during deployment of the anchor 15 from the delivery device 30 in order to facilitate wrapping of the core wire 74 and anchor 15 around the delivery device 30 into the correctly deployed configuration as described herein. In the self-assembly state, the distal tip 75 may be deflected prior to or during deployment of the anchor 15 such that the distal tip 75 overlaps with one or more turns of the anchor 15 in order to ensure that the free end 22 wraps back around the delivery device 30.

The deflection feature 33 in the self-assembly state may, for example, be configured to deflect the distal tip 15 proximally (e.g., towards a proximal portion of the anchor 15 and a distal end of the delivery device 30), distally (e.g., away from a proximal portion of the anchor 15 and towards a proximal portion of the delivery device 30), and/or radially (e.g., radially outwards or inwards from the main body of the anchor 15 and away from or towards the delivery device 30, respectively). In some embodiments, for example, the deflection feature 33 may be configured to position the distal tip 75 adjacent one or more loops of the anchor 15 when the anchor 15 is in the deployed configuration. Alternatively, or in combination, the deflection feature 33 may be configured to position the distal tip 75 such that it angles towards a proximal end of the anchor 15 when the anchor 15 is in the deployed configuration. Alternatively, or in combination, the deflection feature 33 may be configured to position the distal tip 75 such that it angles towards a distal end of the delivery device 30 when the anchor 15 is in the deployed configuration.

In at least some instances, it may be sufficient to initially deflect the distal tip 75 during wrapping as described herein in order to form the first loop of the anchor 15 around the delivery device 30. Once the first loop as wrapped around the delivery device 30, the remaining loops may be more inclined or biased to wrap correctly around the delivery device 30 without additional deflection or manipulation. The core wire 74 may remain in the self-assembly for the entirety of the deployment of the anchor 15 from the delivery device 30. Alternatively, once the free end 22 of the anchor 15 has made a first loop around the delivery device 30 facilitated by the distal tip 75 of the core wire 74, the distal tip 75 of the core wire 74 may be translated proximally and retracted at least partially back into the anchor 15 for the remainder of the deployment of the anchor 15.

FIG. 13 shows a side view of the anchor of FIG. 10 with the core wire 74 in an exemplary encircling state, in accordance with embodiments. The distal tip 75 may be advanced into an encircling state following (or during) deployment of the anchor 15 from the delivery device 30 in order to facilitate capture of the one or more structures by the anchor 15. In the encircling state, the one or more deflection features 33 of the core wire 74 may deflect the distal tip 75 such that the distal tip 75 angles away from the anchor 15.

The deflection feature 33 in the encircling state may, for example, be configured to deflect the distal tip 15 proximally (e.g., towards a proximal portion of the anchor 15 and a distal end of the delivery device 30), distally (e.g., away from a proximal portion of the anchor 15 and towards a proximal portion of the delivery device 30), and/or radially (e.g., radially outwards or inwards from the main body of the anchor 15 and away from or towards the delivery device 30, respectively).

In at least some instances, deflection (e.g., angling proximally, distally, and/or radially outward) of the distal tip 75 of the core wire 74 away from the loops of the anchor 15 may aid in capture of the one or more native valve structures by forming a "grabber" arm. For example, during rotation of the anchor 15, the grabber arm distal tip 75 of the core wire 74 may be rotated as shown to capture the one or more structures of the native valve.

The distal tip 75 of the core wire 74 may optionally rotated around one or more structures on the second side of the native valve such that the one or more structures (e.g., chordae, leaflets, and/or annulus) are pulled radially inwards towards the longitudinal axis of the anchor 15 and/or towards the longitudinal axis of the delivery device 30. The core wire 74, distal tip 75, anchor 15, and/or free end 22 may be configured such that minimal torque is applied to the one or more native valve structures. Alternatively, or in combination, the core wire 74, distal tip 75, anchor 15, and/or free end 22 may be configured such that the one or more structures are not rotated, or are minimally rotated, during rotation of the anchor 15.

Figure 14:
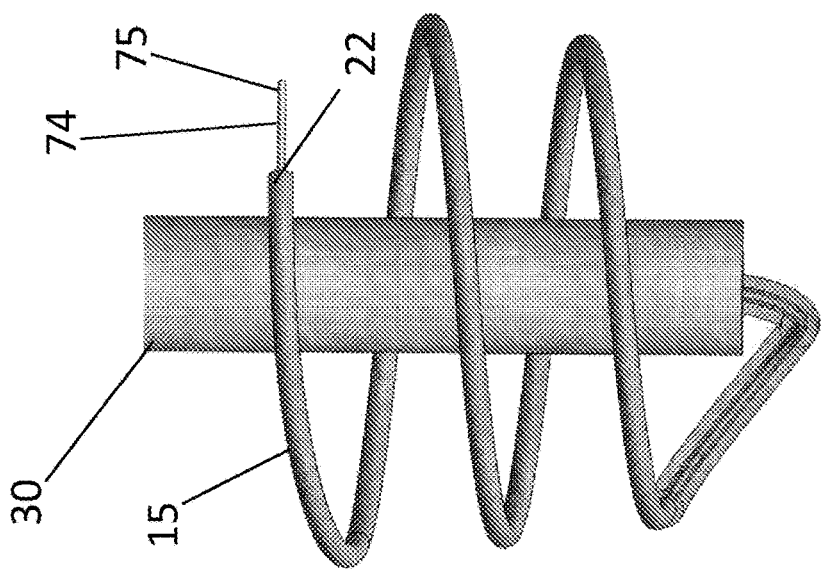
FIG. 14 shows a side view of the anchor of FIG. 10 with the core wire in another exemplary encircling state, in accordance with embodiments.

FIG. 14 shows a side view of the anchor of FIG. 10 with the core wire 74 in another exemplary encircling state, in accordance with embodiments. The distal tip 75 may be advanced into an encircling state following (or during) deployment of the anchor 15 from the delivery device 30 in order to facilitate capture of the one or more structures by the anchor 15. In the encircling state, the one or more deflection features 33 of the core wire 74 may not deflect the distal tip 75 of the core wire 74, and the distal tip 75 may be coaxial the anchor 15.

The distal tip 75 of the core wire 74 may optionally rotated around one or more structures on the second side of the native valve such that the one or more structures (e.g., chordae, leaflets, or annulus) are pulled radially inwards towards the longitudinal axis of the anchor 15 and/or towards the longitudinal axis of the delivery device 30. The core wire 74, distal tip 75, anchor 15, and/or free end 22 may be configured such that minimal torque is applied to the one or more native valve structures. Alternatively, or in combination, the core wire 74, distal tip 75, anchor 15, and/or free end 22 may be configured such that the one or more native valve structures are not rotated, or are minimally rotated, during rotation of the anchor 15.

FIG. 15 shows a perspective view of an exemplary anchor 15 comprising a lumen 71 disposed therethrough, in accordance with embodiments. The anchor 15 may be substantially similar to any of the anchors described herein, for example a helical anchor as shown. The anchor 15 may be detachably coupled to a delivery device 30 as described herein. The anchor 15 may comprise one or more lumens or channels 71 as described herein. The anchor 15 may, for example, comprise a hypotube. The anchor 15 may comprise a hollow, tubular cross-section. The one or more lumens or channels 71 may be configured to pass another component (e.g., a core wire 74, guidewire, etc.) therethrough. For example, the one or more lumens 71 may be configured to pass a core wire comprising one or more deflection features therethrough.

The anchor 15 may comprise a single lumen or channel 71. The anchor 15 may comprise a plurality of lumens or channels 71. For example, the anchor 15 may comprise one, two, three, four, five, six, seven, eight, nine, or ten lumens of channels 71 disposed therethrough. It will be understood to one of ordinary skill in the art based on the teachings herein that any number of channels may be utilized as desired. The channels 71 may for example be left as open lumens (e.g., for placement of one or more core wires 74 therethrough). Alternatively, or in combination, the channels may be filled, for example with one or more stiffening members.

The anchor 15 may comprise a round cross-section. The anchor 15 may comprise a non-round cross section. The anchor 15 may have a cross-section of any shape desired, for example a circular, tubular, hollow, square, elongated, ovoid, triangular, or any other shaped cross-section. The cross-sectional shape of the anchor 15 may, for example, be selected to facilitate deployment from the delivery device. Alternatively, or in combination, the shape of the anchor 15 may be selected to reduce pulling, torqueing, or otherwise damaging the one or more native valve structures as it is rotated therearound. Alternatively, or in combination, the shape of the anchor 15 may be selected to provide sufficient radial strength when a frame structure 12 is expanded therein to anchor the frame structure 12 to the one or more native valve structures therebetween.

The anchor 15 may comprise or more loops. For example, the anchor 15 may comprise a plurality of loops, which may increase the radial strength of the anchor by increasing friction and addition structural support. The one or more loops of the anchor 15 may be substantially cylindrical around a central axis of the anchor 15, for example along an axis which is coaxial with a longitudinal axis of a delivery device 30. The one or more loops of the anchor 15 may be substantially helical around a central axis or helical axis of the anchor 15, for example along an axis which is coaxial with a longitudinal axis of a delivery device. The one or more loops (also referred to herein as coils or turns) of the anchor 15 may comprise a curved shape that bends around back towards its origin (for example, an arc, ellipsoid, circle, or the like). In some embodiments, a loop may comprise a curved shape that bends back towards its origin but does not cross itself, making a rotation within a range of about 180 degrees to about 360 degrees, as described herein. In some embodiments, a loop may comprise a shape that bends back towards and crosses itself, making at least a 360 degree rotation, as described herein. The one or more loops may comprise any number of loops desired, for example, one, two, three, four, five, six, seven, eight, nine, or ten loops. The one or more loops may comprise a rotation within a range of about 180 degrees to about 3600 degrees as described herein. The one or more loops may comprise a rotation within a range bounded by any of the following values: 180 degrees, 270 degrees, 360 degrees, 450 degrees, 540 degrees, 630 degrees, 720 degrees, 810 degrees, 900 degrees, 990 degrees, 1080 degrees, 1170 degrees, 1260 degrees, 1350 degrees, 1440 degrees, 1530 degrees, 1620 degrees, 1710 degrees, 1800 degrees, 1890 degrees, 1980 degrees, 2070 degrees, 2160 degrees, 2250 degrees, 2340 degrees, 2430 degrees, 2520 degrees, 2610 degrees, 2700 degrees, 2790 degrees, 2880 degrees, 2970 degrees, 3060 degrees, 3150 degrees, 3240 degrees, 3330 degrees, 3420 degrees, 3510 degrees, or 3600 degrees.

Interaction of the frame structure 12 with the one or more loops of the anchor 15 may create opposing forces therebetween that provide mechanical leverage for anchoring the frame structure 12 to the one or more anatomical structures as described herein. In some embodiments, the one or more loops may comprise at least 360 degrees of rotation when deployed such that the loops wrap around one another and provide additional mechanical leverage against the frame structure 12 in order to facilitate anchoring of the frame structure as described herein. Additional loops or partial loops may provide additional mechanical strength and/or leverage.

FIG. 16 shows a side view of an exemplary core wire 74 comprising a deflection feature 33 in a distal tip section 77 of the core wire 74. The core wire 74 may comprise one or more sections of wire having the same or different preformed shapes to facilitate deployment within the lumen of the anchor. For example, the core wire 74 may comprise a distal tip section 77 comprising the distal tip 75 and one or more deflection features 33. The core wire 74 may also comprise a proximal curved section 76 proximal to the distal section 77 which comprises a curved shape. The curved shape may be substantially similar to the curved shape of the anchor 15 in order to provide robust rotational constraint to the core wire 74 so that the distal tip 75 does not rotate relative to the anchor as it is translated. Alternatively, the curved shape may be configured with a different shape or curvature that the anchor in order to induce rotation in the distal tip 75 during translation as desired. In some embodiments, the core wire 74 may comprise a proximal pusher section (e.g., proximal pusher section 73) proximal to the proximal curved section 76 which extends from the proximal curved portion 76 to a proximal end of the delivery device. The proximal pusher section may act as an actuation mechanism and facilitate longitudinal translation of the core wire 74 within the lumen 71 of the anchor 15. For example, a proximal end of the proximal pusher section may be coupled to an actuation mechanism on the delivery device in order to translate the core wire 74. Alternatively, the proximal end of the proximal pusher section may be manually manipulated by at or near a proximal end of the delivery device in order to translate the core wire 74.

In some embodiments, the core wire 74 may comprise a helical shape in the deployed configuration as described herein. The deflection feature 33 may be comprise one or more bends or kinks along the distal section 77 which are discontinuous with the helical shape of the proximal curved section 76. In some embodiments, the deflection feature 33 may be attached (fixedly or detachably) to the distal section 77, for example in the form of a tab or a wing or the like. Alternatively or in combination, the deflection feature 33 may comprise a discontinuity in the helical shape, for example in the form of bends, kinks, waves, humps, bumps, or the like in the wire itself.

In some embodiments, the core wire 74 may comprise a spiral shape in the deployed configuration as described herein (e.g., as shown in FIGS. 20-21). The deflection feature 33 may be comprise one or more bends or kinks along the distal section 77 which are discontinuous with the spiral shape of the proximal curved section 76. In some embodiments, the deflection feature 33 may be attached (fixedly or detachably) to the distal section 77, for example in the form of a tab or a wing or the like. Alternatively or in combination, the deflection feature 33 may comprise a discontinuity in the spiral shape, for example in the form of bends, kinks, waves, humps, bumps, or the like in the wire itself.

In some embodiments, one or more deflection features 33 may be positioned along the length of the distal section 77 at one or more locations such that deflection of the distal tip 75 is "timed" to occur with the distal tip 75 and/or free end 22 wrapping back towards the delivery device 30 as described herein. The distal tip 75 may, for example, be deflected each time it wraps back towards the delivery device 30 as described herein. In some embodiments, the deflection features 33 may position the distal tip portion 77 of the core wire 74 inside, outside, above, below, or at an angle to the otherwise relatively continuous curved shape of the proximal curved section 76.

The one or more deflection features 33 may be configured so as to resist straightening of the bends when the anchor is in the elongated configuration. The one or more deflection features 33 may be configured interact with the frame structure 12 to facilitate anchoring. The one or more deflection features 33 may be configured not to interact with the frame structure in order to facilitate anchoring. The one or more deflection features 33 may advantageously avoid a need for substantial circumferential compliance into the curved shape of the anchor 15.

The core wire 74 may be formed of a material having sufficient rigidity to hold a predetermined shape. The core wire 74 may, for example, be formed of a shape memory material (e.g., NiTi). It may be desirable for at least an end portion (e.g., a distal section 77 as described herein) to be relatively rigid such that it can exert a force to move chordal tendineae, while still retaining flexibility to be collapsed within the anchor 15 and/or a delivery device 30. In various embodiments, the distal section 77 only needs sufficient rigidity to hold its shape and will deform under a load. For example, the distal section 77 may be configured with a similar rigidity to a guidewire, or slightly stiffer.

FIGS. 17A-17B show side views of various optional, non-limiting configurations of a deflection feature 33 of a core wire 74. The distal section 77 of the core wire 74 may comprise one or more bends, kinks, waves, humps, bumps, or the like as described herein. For example, the distal section 77 may comprise a single bend in order to angle and deflect the distal tip 75 (e.g., distally away towards the anchor body 15 and away from the delivery device 30 or proximally away from the anchor body 15 and towards the delivery device 30) as shown in FIG. 17A. In some embodiments, the distal section 77 of the core wire 74 may comprise two bends to produce a wave-like shape in order to angle and deflect the distal tip 75 of the core wire 74 as shown in FIG. 17B. In some embodiments, the distal section 77 of the core wire 74 may comprise three bends to produce a bump-like shape in order to angle and deflect the distal tip 75 of the core wire 74 as shown in FIG. 17C. It will be understood by one of ordinary skill in the art from the teachings herein that the distal section 77 may comprise any number or shape of deflection features 33 in order to deflect the distal tip 75 as described herein.

The distal tip 75 of the core wire 74 may be sized and dimensioned for insertion through the native valve, for example through tissue at or near a commissure of the native valve or through the valve opening itself. In some embodiments, the distal tip 75 may comprise an atraumatic tip to avoid reduce risk of injury to the native valve tissue and leaflets. For example, the distal tip 75 may comprise a blunt end, a ball tip, a curved tip (e.g., J-tip or pigtail), or other atraumatic shapes. Alternatively, the distal tip 75 may be configured for piercing tissue.

In various embodiments, the distal tip 75 may be shaped and configured to reduce the risk of counter-rotation. For example, the distal tip 75 may have a curled end to cause the distal tip 75 to snag chordae if it is rotated in a direction opposite the anchoring rotation.

The distal tip 75 may optionally rotated around one or more native valve structures on the second side of the native valve such that the one or more structures (e.g., chordae, leaflets, or annulus) are pulled radially inwards towards the longitudinal axis of the anchor 15 and/or towards the longitudinal axis of the delivery device 30. The distal tip 75 and/or free end 22 may be configured such that minimal torque is applied to the one or more structures. Alternatively. or in combination, the distal tip 75 and/or free end 22 may be configured such that the one or more structures are not rotated, or are minimally rotated, during rotation of the anchor 15. For example, the anchor 15 may comprise one or more spaces between loops of the curved shape of the anchor 15 which facilitate movement of the captured tissue (e.g. chordae and/or leaflets) from the distal tip 75 and/or free end 22 to the center of the curved structure with little or no torque and/or rotation of the structures during rotation of the anchor 15 as described herein. The one or more native valve structures may sit radially inward of the loops in order to facilitate capture of the one or more native valve structures between the distal tip 75 and/or anchor 15 and the expanded frame structure 12. The one or more native valve structures may retain or nearly retain their normal anatomical position when the anchor 15 is fully deployed.

Figure 18:
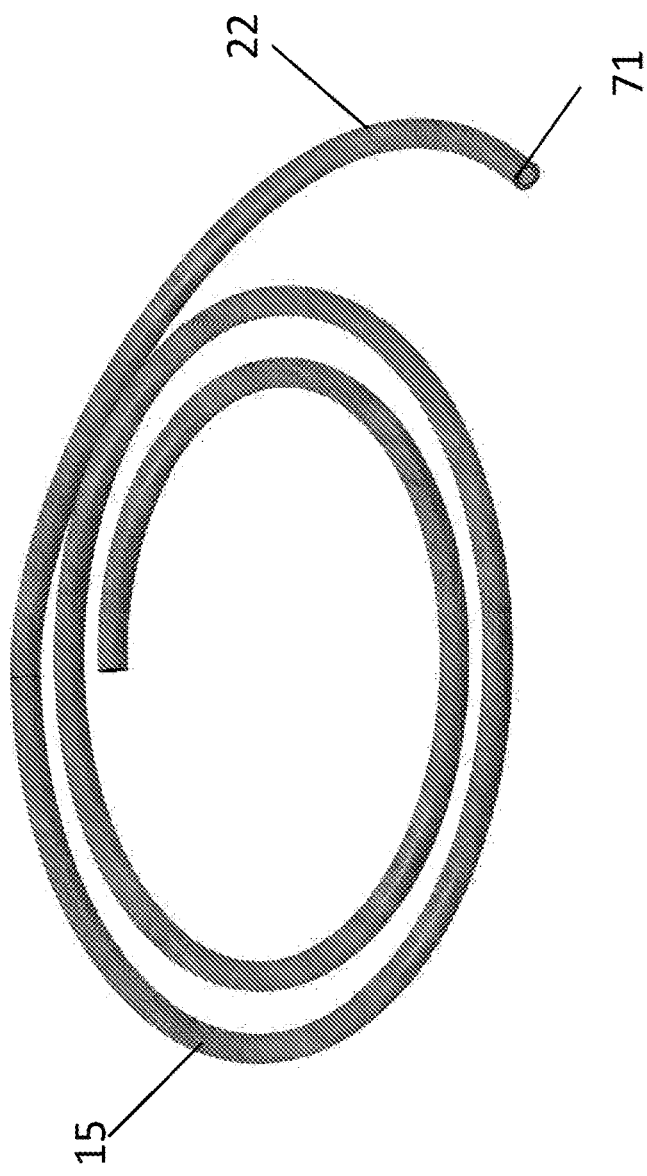
FIG. 18 shows a perspective view of another exemplary anchor comprising a lumen disposed therethrough, in accordance with embodiments.
Figure 19:
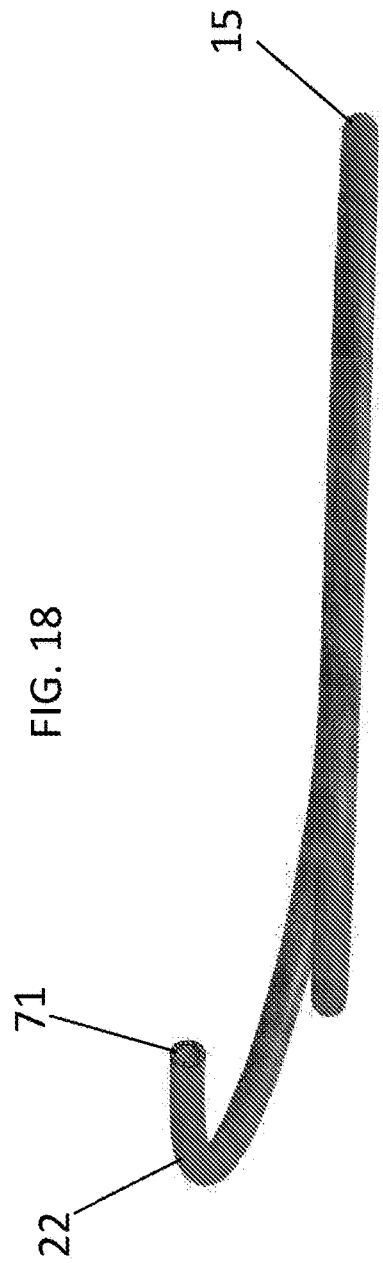
FIG. 19 shows a side view of the anchor of FIG. 18, in accordance with embodiments.

FIG. 18 shows a perspective view of another exemplary anchor 15 comprising a lumen 71 disposed therethrough. FIG. 19 shows a side view of the anchor 15 of FIG. 18. The anchor 15 may be substantially similar to the anchor shown in FIG. 15, except that the anchor may comprise a spiral shape instead of a helical shape. The anchor 15 may be detachably coupled to a delivery device as described herein. The anchor 15 may comprise one or more lumens or channels 71 as described herein. The anchor 15 may, for example, comprise a hypotube. The anchor 15 may comprise a hollow, tubular cross-section. The one or more lumens or channels 71 may be configured to pass another component (e.g., a wire, guidewire, etc.) therethrough. For example, the one or more lumens 71 may be configured to pass a core wire comprising one or more deflection features therethrough as described herein. The anchor 15 may comprise or more loops as described herein. The one or more loops of the anchor 15 may spiral radially outward from a central point or central axis of the anchor 15, for example along an axis which is coaxial with a longitudinal axis of a delivery device 30 such that the anchor 15 lies approximately along a plane perpendicular to the longitudinal axis of the delivery device 30.

The free end 22 of the anchor 15 may extend radially outward from the frame structure, and in particular from the remainder of the anchor 15. The other end of the spiral band or wire 20 may be coupled to the top or bottom of the frame structure as described herein. Alternatively, or in combination, the other end of the anchor 15 may not be attached to the frame structure 12 as described herein. The free end 22 of the anchor 15 may facilitate capturing of the valve leaflets and/or chordal tendineae within the sweep of the free end during rotation as described herein. During rotation of the anchor 15, the leaflets and/or chordae tendineae may be captured by the free end 22 and trapped between the valve frame structure and an interior surface of the anchor 15.

In various embodiments, the anchor 15 may have a generally spiral shape in the deployed configuration. In various embodiments, the anchor 15 may be elongated—rather than spiral-shaped—in the delivery configuration. For example, the anchor 15 may be elongated into a straight shape within the delivery device. In various embodiments, a portion of the anchor 15 may have a spiral shape. In various embodiments, a substantial portion of the anchor 15 may have a spiral shape. In various embodiments, the anchor 15 may be formed as a flat spiral (in the deployed configuration) whereby the loops generally are positioned within the same plane (the plane being perpendicular to a longitudinal axis).

Optionally, the anchor 15 may comprise a first portion comprising the spiral portion and another portion. Alternatively, or in combination, the anchor 15 may comprise a plurality of spiral portions. For example, the anchor 15 may comprise at least two spiral portions having the same or different diameters. Alternatively. or in combination, the anchor 15 may comprise at least two spiral portions having the same or different winding pitches.

FIGS. 20-22 show various views of the anchor 15 of FIG. 18 loaded on a delivery device 30 and having a translatable core wire 74 disposed within the its lumen 71, the core wire 74 having a deflection feature 33 disposed thereon and being in a nominal state relative to the anchor 15. FIG. 20 shows a side view. FIG. 21 shows a perspective top view. FIG. 22 shows a top view. The anchor 15 may be substantially similar to any of the anchors 15 described herein, for example a spiral-shaped anchor having a lumen or channel 71 in the deployed configuration as shown. The anchor 15 may be detachably coupled to a delivery device 30 as described herein. The anchor 15 may be directly coupled to a frame structure 12, for example at a proximal or distal end thereof, as described herein. Alternatively. or in combination, the anchor 15 may be detachably coupled to the delivery device 30 prior to deployment at the native valve. The delivery device 30 may be substantially similar to any of the delivery devices described herein. For example, a proximal end of the anchor 15 may be detachably coupled to the inner shaft 52 and/or anchor guide 153 during delivery to the native valve. Alternatively, or in combination, a proximal end of the anchor 15 may be coupled to a distal end of the frame structure 12 or a proximal end of the frame structure 12. The anchor 15 is shown in a deployed configuration. The anchor 15 may comprise a delivery (e.g., elongated) configuration (e.g., as shown in FIG. 1) and a deployed configuration (e.g., as shown in FIG. 2). In various embodiments, the anchor may be self-expanding and may move to the deployed configuration as it is removed from the delivery sheath as described herein. The anchor 15 may be configured to wrap at least partially around the frame structure 12 in the deployed configuration. In some embodiments, the anchor 15 may be configured not to wrap around the distal end of the delivery device 30 in the deployed configuration. The loops of the anchor 15 may instead lie entirely distal of the distal end of the delivery device 30 as shown.

The anchor 15 may comprise a movable core element 74 disposed within a lumen or channel 71 of the anchor 15 as described herein. A distal section 77 of the core wire 74 may comprise one or more deflection features 33 disposed thereon or therealong as described herein. For example the distal tip portion may comprise a single deflection feature 33. The core wire 74 may be translatable. The core wire 74 may translate distally and proximally within the lumen 71 of the anchor 15. Translation of the core wire 74 within the lumen 71 of the anchor 15 may cause the one or more deflection features 33 to deflect the distal tip 75 of the core wire 74 as it moves in or out of the anchor 15. For example, when advanced distally past the free end 22 of the anchor 15, a distal tip 75 of the core element 74 may be caused to "wiggle" or deflect away from the curvature of the curved anchor body 15 and change the deployment angle of the distal tip 75 out of the anchor body 15 in order to facilitate wrapping of the anchor 15 around the delivery device 30 as described herein.

The movable core wire 74 may be translated within the anchor 15 before, during, or after deployment of the anchor 15 from the undeployed configuration to the deployed configuration. For example, the movable core wire 74 be translated within the anchor 15 before deployment of the anchor 15 into a self-assembly state (e.g., as shown in FIG. 12) in order to facilitate wrapping of the anchor 15 around the delivery device 30 (e.g., by extending past the free end 22 of the anchor and acting similarly to the free end 22 comprising the deflecting feature(s) 23 described herein). Alternatively. or in combination, the movable core wire 74 may be translated within the anchor 15 during deployment of the anchor 15 in order to actively or reactively "wiggle" or deflect the angle of the distal tip as it deploys as described herein. Alternatively, or in combination, the movable core wire 74 may be translated with the anchor 15 into an encircling state (e.g., as shown in FIGS. 13 and/or 14) in order to facilitate grasping of and rotation of the anchor 15 around the one or more native valve structures as described herein. In at least some instances, deflection (e.g., angling proximally, distally, and/or radially outward) of the distal tip 75 away from the loops of the anchor 15 may aid in capture of the one or more native valve structures by forming a "grabber" arm as described herein.

While the one or more deflection features 23, 33 have been described herein with reference to changing the angle of a distal tip 75 of a core wire 74 and/or free end 22 of an anchor 14 of a valve prosthesis 10 during deployment from a delivery device 30, it will be understood by one of ordinary skill in the art that such deflection features 23, 33 may be used in a variety of settings.

Figure 23:
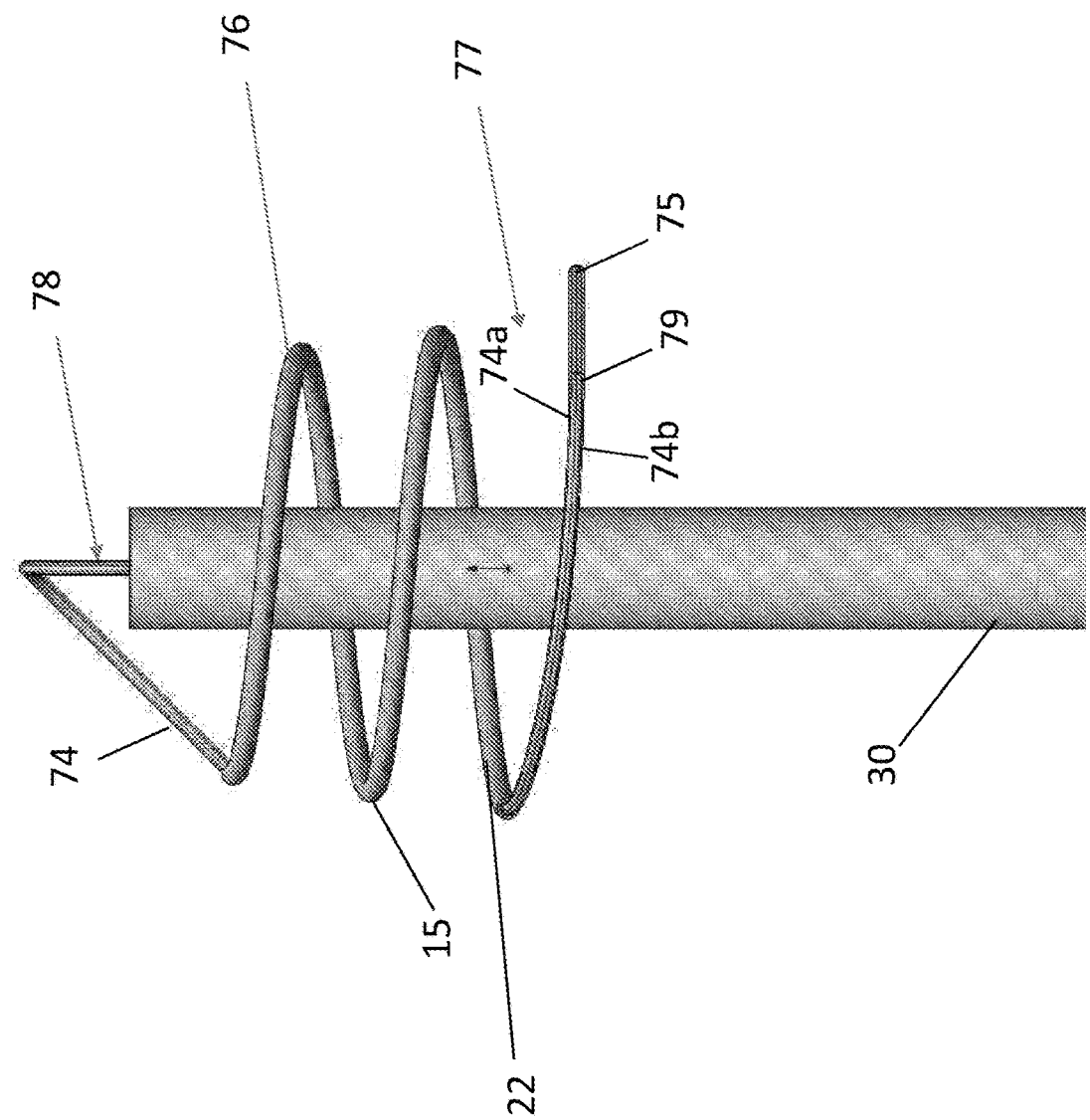
FIG. 23 shows a side view of another exemplary anchor comprising multiple translatable core wires disposed therein, in accordance with embodiments.

FIG. 23 shows a side view of another exemplary anchor 15 comprising multiple translatable core wires 74 disposed therein. The anchor 15 may be substantially similar to any of the anchors 15 described herein, for example a helix-shaped anchor 15 having a lumen or channel 71 in the deployed configuration as shown. The anchor 15 may be detachably coupled to a delivery device 30 as described herein. The anchor 15 may be directly coupled to a frame structure 12, for example at a proximal or distal end thereof, as described herein. Alternatively, or in combination, the anchor 15 may be detachably coupled to the delivery device 30 prior to deployment at the native valve. Alternatively, or in combination, the anchor 15 may be coupled to the frame structure 12 and/or delivery device 30 by a tether 78 or by a proximal pusher of the core wire 74 as described herein. The delivery device 30 may be substantially similar to any of the delivery devices 30 described herein. For example, a proximal end of the anchor 15 may be detachably coupled to the inner shaft 52 during delivery to the native valve. Alternatively, or in combination, a proximal end of the anchor 15 may be coupled to a distal end of the frame structure 12 or a proximal end of the frame structure. Alternatively, or in combination, a proximal end of the anchor 15 may be coupled to a tether 78 or a proximal pusher of the core wire 74, thereby operably coupling the anchor 15 to the delivery device 30. The anchor 15 is shown in a deployed configuration. The anchor 15 may comprise a delivery (e.g., elongated) configuration (e.g., as shown in FIG. 1) and a deployed configuration (e.g., as shown in FIG. 2). In various embodiments, the anchor 15 may be self-expanding and may move to the deployed configuration as it is removed from the delivery sheath 50 as described herein. The anchor 15 may be configured to wrap at least partially around the frame structure in the deployed configuration. The anchor 15 may be configured to wrap at least partially around a distal end of the delivery device 30 in the deployed configuration.

The core wire 74 may comprise one or more sections of wire having the same or different pre-formed shapes to facilitate deployment within the lumen of the anchor. For example, the core wire 74 may comprise a distal wire section 77 comprising the distal tip 75 and one or more deflection features as described herein. The core wire 74 may also comprise a proximal curved section 76 proximal to the distal section 77 which comprises a curved shape. The curved shape may be substantially similar to the curved shape of the anchor in order to provide robust rotational constraint to the core wire 74 so that the distal tip 75 does not rotate relative to the anchor as it is translated. Alternatively, the curved shape may be configured with a different shape or curvature that the anchor in order to induce rotation in the distal tip 75 during translation as desired. In some embodiments, the core wire 74 may comprise a tether 78 or proximal pusher section proximal to the proximal curved section 76 which extends from the proximal curved portion 76 to a proximal end of the delivery device. The proximal pusher section or tether 78 may act as an actuation mechanism and facilitate longitudinal translation of the core wire 74 within the lumen 71 of the anchor 74. For example, a proximal end of the proximal pusher section or tether 78 may be coupled to an actuation mechanism in/on the delivery device 30 in order to translate the core wire 74. Alternatively, the proximal end of the proximal pusher section or tether 78 may be manually manipulated by at or near a proximal end of the delivery device in order to translate the core wire 74.

Rather than providing a core wire 74 comprising a single wire and one or more deflection features 33 disposed thereon or therealong (e.g., as shown in FIGS. 10-22), the core wire 74 may comprise a plurality of wires which may be translated relative to one another in order to change the shape of a distal tip portion and deflect the distal tip 75 of the core wire to facilitate wrapping of the core wire 74 and/or anchor 15 around the delivery device 30 and/or one or more native valve structures as described herein. For example, the core wire 74 may comprise a first wire 74a and a second wire 74b. The first and second wires 74a. 74b may be longitudinally translatable independent of one another within the lumen 71 of the anchor 15.

In some embodiments, the first wire 74a and the second wire 74b may be disposed within a housing 79. The housing 79 may comprise a flexible material. Translation of the first and second wires 74a, 74b relative to one another may change the curvature of the housing 79, thereby deflecting the distal tip 75 of the core wire 74 in order to facilitate anchor deployment and/or wrapping of the anchor 15 around one or more structures of the native valve in a manner substantially similar to that described with respect to the deflecting features described herein. By providing two or more wires 74a, 74b within a housing 79, the distal tip 75 of the core wire 74 may be deflecting into more complex and/or varying shapes than may be possible with a deflection features disposed on or along the core wire 74. In some embodiments, the entire "grabber arm" of the distal section 77 may be made up of wires.

Figure 24:
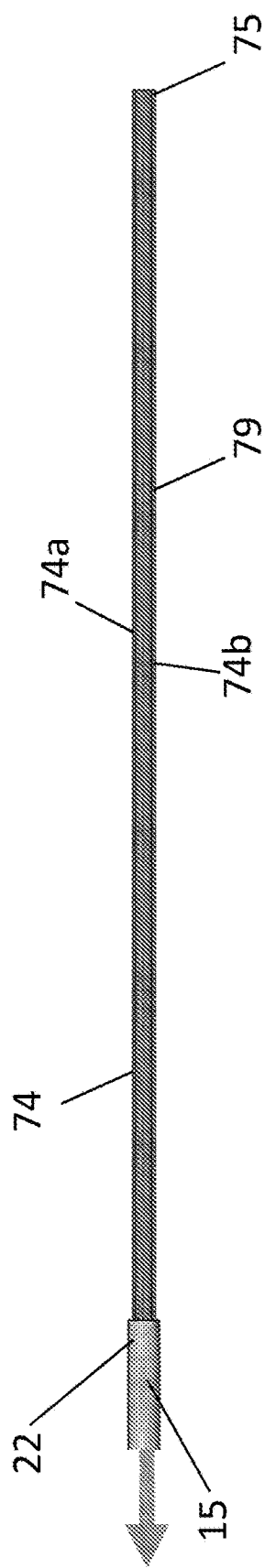
FIG. 24 shows a side view of a distal tip of the anchor and core wires of FIG. 23, in accordance with embodiments.
Figure 25:
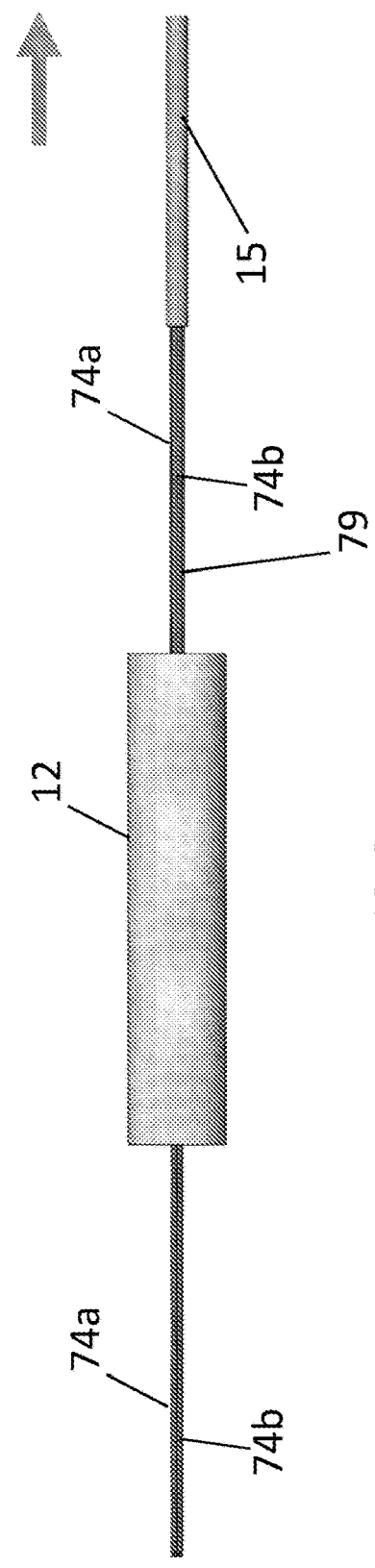
FIG. 25 shows a side view of a proximal end of the anchor and core wires of FIG. 23, in accordance with embodiments.

FIG. 24 shows a side view of a distal tip of the anchor and core wires 74a, 74b of FIG. 23. FIG. 25 shows a side view of a proximal end of the anchor and core wires 74a, 74b, of FIG. 23. The distal portions (which may include a distal tip portion 77 and, optionally, a proximal curved portion 76) of the first and second wires 74a, 74b may be disposed within a housing 79 as described herein. A proximal pusher section of the first and second wires 74a, 74b may or may not be disposed within a housing 79. For example, the proximal pusher section may be disposed within the housing 79 between the proximal end of the anchor 15 and the distal end of the frame structure 12. The frame structure 12 is shown dispose around the wires 74a, 74b in the unexpanded configuration. The wires 74a, 74b may extend through and towards a proximal end of the delivery device. The wires 74a, 74b may be coupled to one or more actuations mechanisms in/on the delivery device 30 in order to the translate the wires 74a, 74b relative to one another and/or the anchor 15. Alternatively, the wires 74a, 74b may be manually manipulated by at or near a proximal end of the delivery device in order to translate the core wires 74a, 74b. The two wires 74a, 74b may be independently translated in order to generate additive curvatures. The wires 74a, 74b may be pulled/pushed distally or proximally relative to one another to cause the housing of the distal section 77 to deflect in any number and manner of shapes or curvatures desired.

It should be understood that any feature described with respect to one embodiment may be combined with or substituted for any feature described with respect to another embodiment.

Although the method steps described herein are described sequentially in accordance with certain embodiments, a person of ordinary skill in the art will recognize many variations based on the teaching described herein. The steps may be completed in a different order. Steps may be added or deleted. Some of the steps may comprise sub-steps. Many of the steps may be repeated as often as necessary ensure correct placement of the delivery device and deployment of the valve prosthesis components.

Not necessarily all such aspects or advantages are achieved by any particular embodiment. Thus, various embodiments may be carried out in a manner that achieves or optimizes one advantage or group of advantages taught herein without necessarily achieving other aspects or advantages as may also be taught or suggested herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A delivery system for delivering a prosthesis to a diseased native valve of a heart, the delivery system comprising:
    an outer sheath;
    an inner shaft within the outer sheath, the inner shaft translatable and rotatable relative to the outer sheath;
    an anchor having an elongated delivery configuration and a deployed spiral configuration configured to encircle chordae or leaflets of the diseased native valve;
    an anchor guide attached to a distal end of the inner shaft, the anchor guide configured to house the anchor in the elongated delivery configuration, the anchor guide comprising a proximal straight section having a central axis and a distal section shape-set to bend into a tapered spiral shape extending around the central axis and distally from the proximal straight section into a distal plane orthogonal to the central axis; and
    an actuator configured to release the anchor from the delivery configuration in the anchor guide into a deployed spiral configuration within the heart;
    wherein the inner shaft and anchor guide are configured to rotate relative to the outer sheath so as to rotate the anchor in the deployed spiral configuration about the central axis to encircle chordae of the native valve.

2. The delivery system of claim 1, further comprising a tether configured to extend through the inner shaft and anchor guide, the tether configured to attach to the anchor.

3. The delivery system of claim 1, wherein the outer sheath is steerable.

4. The delivery system of claim 1, wherein the anchor guide is configured to correctly orient the anchor relative to the central axis in order to facilitate concentric wrapping of the anchor relative to the inner shaft as the anchor is deployed from the anchor guide.

5. The delivery system of claim 1, wherein the distal section is further configured to transition continuously from a high pitch, low radius curve at a proximal end to a low pitch, high radius curve at a distal end.

6. The delivery system of claim 1, wherein a curvature of the distal section is configured to match a curvature of the anchor in the deployed spiral configuration of the anchor.

7. The delivery system of claim 1, wherein the inner shaft and the anchor guide are of unitary construction.

8. The delivery system of claim 1, wherein the distal section is further configured to be coplanar with the anchor in the deployed spiral configuration of the anchor.

9. The delivery system of claim 2, wherein the tether is configured to hold the anchor while a valve frame is expanded within the spiral deployed configuration of the anchor.

10. The delivery system of claim 1, wherein the inner shaft and anchor guide are configured to rotate the anchor in the deployed spiral configuration within the plane.

11. The delivery system of claim 1, wherein the spiral shape extends greater than 360°.

12. The delivery system of claim 1, wherein the anchor guide is further configured to maintain the anchor in a deployed spiral configuration on a first side of the native valve.

13. The delivery system of claim 12, wherein the first side of the native valve is facing an atrium of the heart.

14. The delivery system of claim 1, wherein the anchor guide is configured to maintain a central axis of the anchor in the anchor's deployed configuration co-axial with the central axis of the anchor guide.

* * * * *